US012636354B2

(12) United States Patent
Russell et al.

(10) Patent No.: US 12,636,354 B2
(45) Date of Patent: *May 26, 2026

(54) HLA CLASS II DEFICIENT CELLS, HLA CLASS I DEFICIENT CELLS CAPABLE OF EXPRESSING HLA CLASS II PROTEINS, AND USES THEREOF

(71) Applicant: University of Washington through its Center for Commercialization, Seattle, WA (US)

(72) Inventors: David W. Russell, Seattle, WA (US); Roli K. Hirata, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 1262 days.

This patent is subject to a terminal disclaimer.

(21) Appl. No.: 16/441,889

(22) Filed: Jun. 14, 2019

(65) Prior Publication Data

US 2019/0365876 A1     Dec. 5, 2019

Related U.S. Application Data

(63) Continuation of application No. 14/391,328, filed as application No. PCT/US2013/032058 on Mar. 15, 2013, now abandoned.

(60) Provisional application No. 61/625,314, filed on Apr. 17, 2012.

(51) Int. Cl.

| | |
|---|---|
| *A61K 35/28* | (2015.01) |
| *A61K 35/39* | (2015.01) |
| *A61K 35/407* | (2015.01) |
| *A61K 35/545* | (2015.01) |
| *A61K 39/00* | (2006.01) |
| *A61K 40/10* | (2025.01) |
| *A61K 40/22* | (2025.01) |
| *A61K 40/41* | (2025.01) |
| *C07K 14/47* | (2006.01) |
| *C07K 14/705* | (2006.01) |
| *C07K 14/74* | (2006.01) |
| *C12N 5/10* | (2006.01) |
| *C12N 15/90* | (2006.01) |
| *A61K 48/00* | (2006.01) |

(52) U.S. Cl.
CPC .......... *A61K 39/001* (2013.01); *A61K 35/545* (2013.01); *A61K 40/10* (2025.01); *A61K 40/22* (2025.01); *A61K 40/416* (2025.01); *A61K 40/418* (2025.01); *C07K 14/4705* (2013.01); *C07K 14/70539* (2013.01); *C12N 15/907* (2013.01); *A01K 2217/075* (2013.01); *A61K 48/00* (2013.01); *C12N 2799/025* (2013.01); *C12N 2800/30* (2013.01)

(58) Field of Classification Search
None
See application file for complete search history.

(56) References Cited

U.S. PATENT DOCUMENTS

| | | | |
|---|---|---|---|
| 4,892,538 A | 1/1990 | Aebischer et al. | |
| 5,011,472 A | 4/1991 | Aebischer et al. | |
| 5,837,234 A | 11/1998 | Gentile et al. | |
| 5,869,270 A | 2/1999 | Rhode et al. | |
| 6,139,835 A | 10/2000 | Kucherlapati | |
| 6,514,752 B1 * | 2/2003 | Kucherlapati | A01K 67/0276 |
| | | | 435/325 |
| 6,750,321 B1 | 6/2004 | Chen et al. | |
| 6,986,887 B2 | 1/2006 | Lawman et al. | |
| 7,399,838 B2 | 7/2008 | Reiter | |
| 8,142,772 B2 | 3/2012 | Noessner et al. | |
| 8,945,868 B2 | 2/2015 | Collingwood et al. | |
| 2002/0156258 A1 | 10/2002 | Masternak et al. | |
| 2004/0225112 A1 | 11/2004 | Crew et al. | |
| 2005/0196404 A1 * | 9/2005 | Crew | A01K 67/0275 |
| | | | 424/185.1 |
| 2007/0020703 A1 | 1/2007 | Menier | |
| 2007/0274960 A1 | 11/2007 | Harman et al. | |
| 2008/0032941 A9 | 2/2008 | Rabbani | |
| 2008/0219956 A1 | 9/2008 | Russell et al. | |
| 2008/0299091 A1 | 12/2008 | Revazova et al. | |

(Continued)

FOREIGN PATENT DOCUMENTS

| | | |
|---|---|---|
| WO | 1991/10425 | 7/1991 |
| WO | 1991/10470 | 7/1991 |
| WO | 1992/09688 | 6/1992 |

(Continued)

OTHER PUBLICATIONS

Bradley et al (Nature, 2002, 2: 859-871) (Year: 2002).*

(Continued)

*Primary Examiner* — Misook Yu
*Assistant Examiner* — Marianne DiBrino
(74) *Attorney, Agent, or Firm* — MCDONNELL BOEHNEN HULBERT & BERGHOFF LLP

(57) ABSTRACT

The invention provides isolated primate cells preferably human cells that comprise a genetically engineered disruption in a human leukocyte antigen (HLA) class II-related gene, which results in deficiency in MHC class II expression and function. This invention also provides isolated cells further comprising a genetically engineered disruption in a beta-2 microglobulin (B2M) gene, which results in HLA class I/class II deficiency. Also provided are the method of using the cells for transplantation and treating a disease condition.

14 Claims, 2 Drawing Sheets

Specification includes a Sequence Listing.

(56) References Cited

U.S. PATENT DOCUMENTS

2012/0060230 A1* 3/2012 Collingwood .......... A61P 17/00
435/375

FOREIGN PATENT DOCUMENTS

| WO | 1993/05817 | 4/1993 |
| WO | WO 1995/017911 | 7/1995 |
| WO | WO 2001/72768 | 10/2001 |
| WO | WO 2007091078 | * 8/2007 |
| WO | WO 2009/072555 | 5/2009 |
| WO | WO 2010/052229 | 5/2010 |
| WO | 2012/012667 | 1/2012 |
| WO | 2012/145384 | 10/2012 |
| WO | WO 2014/022423 | 2/2014 |

OTHER PUBLICATIONS

Van Eggermond et al (Mol. Immunol. 2008, 45: 2920-2928) (Year: 2008).*
Khan et al.(Nat. Protocol. Apr. 2011, 6(4): 482-501).*
Munz et al (J. Repr. Immunol. , 1999, 43: 139-155) (Year: 1999).*
Borrego et al (J. Exp. Med. 1998, 187(5): 813-818) (Year: 1998).*
GenBank Accession No. NM_134440.1, Mar. 24, 2012 (Year: 2012).*
GenBank Accession No. NM_003721.2, Mar. 24, 2012 (Year: 2012).*
GenBank Accession No. NM_000449.3, Mar. 24, 2012 (Year: 2012).*
GenBank Accession No. NM_001025603.1, Mar. 24, 2012 (Year: 2012).*
GenBank Accession No. NM_000538.3, Mar. 25, 2012 (Year: 2012).*
GenBank Accession No. NM_000246.3, Mar. 25, 2012 (Year: 2012).*
Library of Congress (2022, pp. 1/6-6/6) (Year: 2022).*
Origene, 2023, pp. 1-3 (Year: 2023).*
Dulberger et al.(Immunity, 2017, 46: 1018-1029) (Year: 2017).*
Sanchez-Fueyo et al (Transplant. International, 2007, 20: 534-541) (Year: 2007).*
Iwaszko and Bogunia-Kubik (Arch. Immunol. Ther. Exp. 2011, 59: 353-367) (Year: 2011).*
Crew et al (Mol. Immunol. 2005, 42: 1205-1214) (Year: 2005).*
Braud et al (Nature, 1998, 391: 795-799) (Year: 1998).*
Biology online—definition "gene" (2016, world wide web at biology-online.org) two pages.
Brehm & Shultz, "Human allograft rejection in humanized mice: a historical perspective" Cellular & Molecular Immunology 9:225-231 (2012).
Chen et al., "DLD-1 and HCT-15 cell lines derived spearately form colorectal carcinomas have totally different chromosome changes but the same genetic origin" Cancer Genet Cytogenet. 81:103-108 (1995).
Declaration of Professor David Russell with biographical sketch, 10 pages (signed Dec. 2, 2019).
Declaration of Professor Robert Lanza with CV, 36 pages (signed Nov. 11, 2019).
De Preval & Mach, "The absence of beta 2-microglobulin in Daudi cells: active gene but inactive messenger RNA." Immunogenetics 17(2): 133-40 (1983).—Abstract only.
Dulberger et al., "Human leukocyte antigen F presents peptides and regulates immunity through interactions with NK cell receptors." Immunity 46:1018-1029 (Jun. 2017).
Gattoni-Celli et al., "beta-2 microglobulin gene is mutated in a human colon cancer cell line HCT deficient in the expression of HLA class I antigens on the cell surface," Cancer Research. 52(5):1201-04 (1992).
Gornalusse et al., "HLA-E expressing pluripotent stem cells escape allogeneic responses and lysis by NK cells" Nat Biotechnol. 35(8):765-772 (Aug. 2017).

Hoglund et al., "Recognition of beta-2 microglobulin-negative T-cell blasts by natural killer cells from normal but not from B2m negative mice: Nonresponsiveness controlled by B2m negative bone marrow in chimeric mice" PNAS 88:10332-336 (Nov. 1991).
Hull et al., "The origin and characteristics of a pig kidney cell strain, LLC-PK1" In Vitro 12:670-677 (1976).
Karre, "Natural killer cell recognition of missing self" Nature Immunology 9(5):477-480 (2008).
Karpova et al., "Combined spectral karyotyping, comparative genomice hybridization, and in vitro apoptypingof a panel of Burkitt's lymphoma derived B cell lines reveals an unexpected complexity of chromosomal aberrations and a recurrence of specific abnormalities in chemoresistant cell lines" Int. J. Oncology, 28:605-617 (2006).
Khan et al. "Engineering of human pluripotent stem cells by AAV-mediated gene targeting" Mol. Ther. 18(6):1192-99 (Jun. 2010).
Lee et al., "2B4 acts as a non-Major Histocompatibility Complex binding inhibitory receptor on mouse Natural Killer cells" J. Exp. Med. 199(9):1245-54 (May 2004).
Li et al. "In vivo genome editing restores haemostatis in a mouse model of haemophilia" Nature 475:217-223 (Jul. 2011).
Lu et al. "Generating hypoimmunogenic human embryonic stem cells by the disruption of beta 2 microglobulin" Stem Cell Rev and Rep. 9:806-813 (2013).
Marsh (2009, HLA Nomenclature, Anthony Nolan Research Institute London), 33 pages.
Murphy et al., "Acute rejection of murine bone marrow allografts by natural killer cells and T cells" J. Exp. Med. 166:1499-1509 (Nov. 1987).
Ordaz et al., "DC-expressed MHC class I single-chain trimer-based vaccines prime cytotoxic T lymphocytes against exogenous but not endogenous antigens," Cellular Immunology, 262:141-49, Feb. 2010.
Orr et al., "Natural Killer Cell Education and Tolerance," Cell, 142:847-56, Sep. 2010.
Parham, "MHC class I molecules and KIRS in human history, health and survival," Nature Reviews: immunology, 5:201-14, Mar. 2005.
Santos et al., "Non-classical human leucocyte antigens in ankylosing spondylitis: possible association with HLA-E and HLA-F" Rheumatic & Musculoskeletal Diseases Open 4(1):e000677 (2018).
Schwartz & Wesselschmidt (Human Pluripotent Stem Cells Methods and Protocols, Human Press, 2011, Chapter 2 pp. 23-24) (Year: 2011).
Wang et al., (Stem Cells Translational Medicine, 2015, 4:1234-45) (Year: 2015).
Ziljstra et al. 1989 (Nature, 1989, 342:435-38) (Year: 1989).
Jordanova et al. "Beta-2-Microglobulin Aberrations in Diffuse Large B-Cell Lymphoma of the Testis and the Central Nervous System" Int. J. Cancer 103:393-98 (2003).
Paschen et al., "Complete Loss of HLA Class I Antigen Expression on Melanoma Cells: A Result of Successive Mutational Events" Int. J. Cancer 103:759-67 (2003).
Restifo et al., Molecular Mechanisms Used by Tumors to Escape Immune Recognition: "Immunogenetherapy and the Cell Biology of Major Histocompatibility Complex Class I" J Immunother Emphasis Tumor Immunol. 14(3):182-90 (Oct. 1993).
Riolobos et al., "HLA Engineering of human pluripotent stem cells" Molecular Therapy 21(6):1232-41 (Jun. 2013).
Masternak et al., "A gene encoding a novel RFX-associated transactivator is mutated in the majority of MHC class I deficiency patients." Nature Genetics 20(3):273-7 (Nov. 1998).
Kotsiou et al. "Properties and Application of single-chain major histocompatibility complex class I molecules," Antioxidants & Redox Signalling (2011) 15(3): 645-655.
Bix, et al., "Rejection of class I MHC-deficient haemopoietic cells by irradiated MHC-matched mice," Nature, vol. 349, pp 329-331, (1991).
Chang, et al., "Definitive-like erythroid cells derived from human embryonic stem cells coexpress high levels of embryonic and fetal globins with little or no adult globin," Blood, vol. 108, No. 5, pp. 1515-1523, (2006).

(56)           References Cited

OTHER PUBLICATIONS

Deyle, et al., "Normal Collagen and Bone Production by Gene-Targeted Human Osteogenesis Imperfecta iPSCs," The American Society of Gene and Cell Therapy, vol. 20, No. 1, pp. 204-213, (2012).

DiLorenzo, et al., "Translatinal Mini-Review Series on Type 1 Diabetes: Systematic analysis of T cell epitopes in autoimmune diabetes," Clinical and Experimental Immunology, vol. 148, pp. 1-16, (2007).

Khan, "AAV-mediated gene targeting methods for human cells," Nat Protoc, vol. 6, No. 4, pp. 482-501, (2011).

Kroon, et al., "Pancreatic endoderm derived from human embryonic stem cells generates glucose-responsive insulin-secreting cells in vivo," Nature Biotechnology, vol. 26, No. 4, pp. 443-452, (2008).

Aflamme, et al., "Cardiomyocytes derived from human embryonic stem cells in pro-survival enhance function of Infarcted rat hearts," Nature Biotechnology, vol. 25, No. 9, pp. 1015-1024, (2007).

Slukvin, et al., "Directed Differentiation of Human Embryonic Stem Cells into Functional Dendritic Cells through the Meyloid Pathway," The Journal of Immunology, vol. 176, pp. 2924-2932, (2006).

International Search Report PCT/US2013/032058, mailed Aug. 28, 2013.

Van Eggermond, et al., "Trancriptional silencing of RFXAP in MHC class II-deficiency," Molecular Immunology, 45 (10): 2920-2928, 2008.

Peijnenburg, et al., "defective MHC class II expression in an MHC class II deficiency patient is caused by a novel deletion of a splice donor site in the MHC class II transactivator gene," Immunogenetics, 51(1): 42-49, 2000.

Steimle, et al., "A novel DNA-binding regulatory factor is mutated in primary MHC class II deficiency (bare lymphocyte syndrome)," Genes & Development, 9(9): 1021-1032, 1995.

Madsen, et al., "Mice lacking all conventional MHC class II genes," PNAS, 96:10338-10343, 1999.

"7th Australasian gene therapy society meeting," The Journal of Gene Medicine, 13(7-8): 410-446, 2011.

Suarez-Alvarez, et al., "Epigenetic Mechanisms regulate MHC and Antigen Processing Molecules in Human Embryonic and Induced P;uripotent Stem Cells," PLoS ONE 5(4): e10192, Apr. 2010.

Matsunga et al. (J.Immunol., 2008, 181:6635-6643).

Borrego et al. (J. Exp. Med. 1998, 187(5): 813-818).

PIR_80 Acc. No. 161856 (1996).

PIR_80 Acc. No. A28834 (1989).

Bradley et al. (Nature, 2002, 2: 859-871).

Aftab et al. (BMC Evolut. Biol. 2008, 8:226: 1-11).

Bix, et al., "Rejection of class I MHC-deficient haemopoietic cells by irradiated MHC-matched mice," Nature, vol. 349, Jan. 1991, pp. 329-331.

Crew, et al., "An HLA-E single chain trimer inhibits human NK cell reactivity towards porcine cells," Molecular Immunology, 42(2005): 1205-1214.

Jaimes, et al., "Regulation of HLA class II expression prevents allogeneic T-cell responses," Tissue Antigens (2010), 77: 36-44.

Jiang, et al., "Interaction of natural killer cells with MHC class II: reversal of HLA-DR1-mediated protection of K562 transfectant from natural killer cell-mediated cytolysis by brefeldin-A," Immunology (1996) 87: 481-486.

Storkus, et al., "Reversal of natural killing susceptibility in target cells expressing transfected class I HLA genes," Proc. Natl. Acad Sci USA (Apr. 1989) 86: 2361-2364.

Brehm MA et al.. 2010. Parameters for establishing humanized mouse models to study human immunity: analysis of human hematopoietic stem cell engraftment in three immunodeficient strains of mice bearing the IL2(gamma)mutation. Clin Immunol 135:84-98.

Campos-Martin et al. 2004. Expression of human CD1d molecules protects target cells from NK cell-mediated cytolysis. J Immunol 172:7297-7305.

Carbone et al. 2000. Inhibition of human NK cell-mediated killing by CD1 molecules. J Immunol 164:6130-6137.

Coffman et al. 1993 The Journal of Immunology vol. 151, No. 1, 425-435, "Improved Renal Function in Mouse Kidney Allografts Lacking MHC Class I Antigens".

Hillyard et al. 2007. Statins inhibit NK cell cytotoxicity by membrane raft depletion rather than inhibition of soprenylation. Atherosclerosis 191:319-325.

Huang et al. 2005. NK cells play a critical role in the regulation of class I-deficient hemopoietic stem cell engraftment: evidence for NK tolerance correlates with receptor editing. J Immunol 175:3753-3761.

King et al. 2008. A new Hu-PBL model for the study of human islet alloreactivity based on NOD-scid mice bearing a targeted mutation in the IL-2 receptor gamma chain gene. Clin Immunol 126:303-314.

Koller et al. 1990 Science vol. 248, pp. 1227-1230, "Normal Development of Mice Deficient in B2M, MHC Class I Proteins and CD8+ T Cells".

Kumar et al. 2005. A new self: MHC-class-I-independent natural-killer-cell self-tolerance. Nat Rev Immunol 5:363-374.

Li and Faustman, 1993 Transplantation vol. 55, 940-946, No. 4, "Use of Donor B2-Microglobulin-Deficient Transgenic Mouse Liver Cells for Isografts, Allografts, and Xenografts".

Pegram et al. 2011. Activating and inhibitory receptors of natural killer cells. Immunol Cell Biol 89:216-224.

Prange et al. 2001 Transplantation vol. 71, No. 7, pp. 982-985, "Transplanted MHC Class I-Deficient Nonobese Diabetic Mouse Islets Are Protected From Autoimmune Injury in Diabetic Nonobese Recipients".

Qian et al. 1996 Immunology vol. 88, 124-129, "Impact of Donor MHC Class I or Class II Antigen Deficiency on First- and Second-Set Rejection of Mouse Heart or Liver Allografts".

Raulet et al. 2006. Self-tolerance of natural killer cells. Nat Rev Immunol 6:520-531.

Yeager et al. 1995. Morphine inhibits spontaneous and cytokine-enhanced natural killer cell cytotoxicity in volunteers. Anesthesiology 83:500-508.

Zijlstra et al. 1990 Nature vol. 344, pp. 742-746, "B2-Microglobulin Deficient Mice Lack CD4-8+ Cytolytic T cells".

Tatake and Zeff (PSEBM, 1993, 203: 405-417).

Ilienfeld et al. "Transgenic expression of HLA-E single chain trimer protects porcine endothelial cells against human natural killer cell-mediated cytotoxicity," Xenotransplantation (2007) 14:126-134.

Toshitani et al. " Expression of a single chain HLA class I molecule in a human cell line: Presentation of exogenous peptide and processed antigen to cytotoxic T lymphocytes," Proc. Natl. Acad. Sci. USA (1996) 93: 236-240.

Bicknell et al. "B2-Microglobulin gene mutations: A study of established colorectal cell lines and fresh tumors," Proc. Natl. Acad. Sci. USA (1994) 91: 4751-4755.

Obermann et al. "Peptide-B2-microglobulin-major histocompatability complex expressing cells are potent antigen- presenting cells that can generate specific T cells," Immunology (2007) 122(1 ): 90-97.

Daudi cells from the American Type Culture Collection. 2016.

Greten et al. "Peptide-B2-microglobulin-MHC fusion molecules bind antigen-specific T cells and can be used for multivalent MHC-Ig complexes," Journal of Immunological Methods (2002) 271: 125-135.

Hansen et al. "Translational and basic applications of peptide-MHCI single chain trimers," Trend Immunol. (2010) 31 (10):363-369.

Quintarelli, C et al., Blood, 2007 vol. 110, pp. 2793-2802.

Pazmany, et al., "Protection from Natural Killer Cell-Mediated Lysis by HLA-G Expression in Target cells," Science (1996) vol. 274, pp. 792-795.

Arase et al., "Direct recognition of cytomegalovirus by activating and inhibitory NK cell receptors", Science, May 2002; 296(5571): 1323-1326.

Batten et al., "Immune response to stem cells and strategies to induce tolerance", Philos Trans R Soc Lond B Biol Sci. Aug. 2007; 362(1484): 1343-1356.

(56)  References Cited

OTHER PUBLICATIONS

Bonini et al., "The Suicide Gene Therapy Challenge: How to Improve a Successful Gene Therapy Approach", Mol Ther. Jul. 2007; 15(7): 1248-1252.

Deschaseaux et al., "HLA-G in organ transplantation: towards clinical applications", Cell Mol Life Sci. Feb. 2011; 68 (3): 397-404.

Kaufman, "Toward clinical therapies using hematopoietic cells derived from human pluripotent stem cells", Blood, Oct. 2009;114(17): 3513-3523.

Moscoso et al., "HLA-G, -E and -F: Allelism, function and evolution", Transplant Immunology Dec. 2006; 17(1): 61-64.

Satoh et al., "Epigenetic inactivation of class II transactivator (CIITA) is associated with the absence of interferon- gamma-induced HLADR expression in colorectal and gastric cancer cells", Oncogene, Nov. 2004; 23(55): 8876-8886.

Tiberghien, "Use of suicide gene-expressing donor T-cells to control alloreactivity after haematopoietic stem cell transplantation", J Intern Med Apr. 2001; 249(4): 369-377.

Villard et al., "MHC class II deficiency: a disease of gene regulation", Medicine (Baltimore), Nov. 2001; 80(6): 405-418.

Yan, "Human leukocyte antigen-G in cancer: are they clinically relevant?", Cancer Letters, Dec. 2011; 311(2): 123-130.

Litwin et al., "NKBI: A Natural Killer Cell Receptor Involved in the Recognition of Polymorphic HLA-B Molecules", J. Exp. Med. 180: 537-543, (1994).

* cited by examiner

1

HLA CLASS II DEFICIENT CELLS, HLA CLASS I DEFICIENT CELLS CAPABLE OF EXPRESSING HLA CLASS II PROTEINS, AND USES THEREOF

CROSS REFERENCE

This application is continuation application of U.S. patent application Ser. No. 14/391,328 filed Oct. 8, 2014, which is a U.S. national phase under 35 U.S.C. § 371 of international application PCT/US2013/032058 filed Mar. 15, 2013, which claims priority to U.S. provisional patent application Ser. No. 61/625,314 filed Apr. 17, 2012, incorporated by reference herein in their entirety.

STATEMENT OF GOVERNMENT RIGHTS

This invention was made with government support under Grant nos. R01 DK055759 and R01 GM086497 awarded by the National Institutes of Health. The government has certain rights in the invention.

REFERENCE TO SEQUENCE LISTING

A computer readable form of the Sequence Listing is filed with this application by electronic submission and is incorporated into this application by reference in its entirety. The Sequence Listing is contained in the file created on Jun. 14, 2019, having the file name "12-094-PCTUSCON_SeqList.TXT" and is 290,104 bytes in size.

BACKGROUND OF THE INVENTION

Human pluripotent stem cells have the potential to treat diseases affecting almost every organ system. However, the clinical use of human pluripotent stem cells and their derivatives has a major limitation—rejection of transplanted cells by the recipient due to differences in the major histocompatibility complex.

The major histocompatibility complex (MHC) is a cell surface multi-component molecule found in all vertebrates that mediates interactions of leukocytes with other leukocytes or other cells. The MHC gene family is divided into three groups: class I, class II and class III. In humans, MHC is referred to as human leukocyte antigen (HLA). HLA class II molecules (HLA-II) are transmembrane protein found only on professional antigen-presenting cells (APCs) including macrophages, dendritic cells and B cells. In addition, solid organ may sometimes express HLA class II genes that participate in immune rejection. The HLA class I (HLA-I) protein is expressed on all nucleated cells and consists of an HLA class I heavy chain (or α chain) and β-2 microglobulin (B2M). HLA class I protein presents peptides on the cell surface to CD8+ cytotoxic T cells. Six HLA class I α chains have been identified to date, including three classical (HLA-A, HLA-B and HLA-C) and three non-classical (HLA-E, HLA-F and HLA-G) α chains. The specificity for peptide binding on the HLA class I molecule peptide binding cleft is determined by the α chain. Recognition by CD8+ T cells of the peptides presented by the HLA class I molecule mediates cellular immunity.

HLA class II molecules and class I molecules are both heterodimers. Class I molecules consist of an alpha chain (or heavy chain) and β-2 microglobuin (B2M), whereas the class II molecules consist of two homologous subunits: the alpha subunit and beta subunit.

HLA class II (HLA-II) molecules or proteins present on the cell surface peptide antigens from extracellular proteins including proteins of an extracellular pathogen, while HLA class I proteins present peptides from intracellular proteins or pathogens. Loaded HLA class II proteins on the cell surface interact with CD4+ helper T cells. The interaction leads to recruitment of phagocytes, local inflammation, and/or humoral responses through the activation of B cells. Several HLA class II gene loci have been identified to date, including HLA-DM (HLA-DMA and HLA-DMB that encode HLA-DM α chain and HLA-DM β chain, respectively), HLA-DO (HLA-DOA and HLA-DOB that encode HLA-DO α chain and HLA-DO β chain, respectively), HLA-DP (HLA-DPA and HLA-DPB that encode HLA-DP α chain and HLA-DP β chain, respectively), HLA-DQ (HLA-DQA and HLA-DQB that encode HLA-DQ α chain and HLA-DQ β chain, respectively), and HLA-DR (HLA-DRA and HLA-DRB that encode HLA-DR α chain and HLA-DR β chain, respectively).

The HLA class I and/or class II proteins from an allogeneic source constitutes a foreign antigen in the context of transplantation. The recognition of non-self HLA class I and/or class II proteins is a major hurdle in using pluripotent cells for transplantation or replacement therapies.

Thus, although individualized stem cell preparations or HLA-diverse stem cell banks may address the current problem of transplantation, they require that multiple cell lines be characterized, differentiated into therapeutic cell products, and approved for human administration. This time-consuming, technically difficult, and expensive process is a major factor preventing stem cell-based therapies from entering clinical trials. Thus, there exists a need for a more effective and less expensive cell-based therapies that are not impeded by rejection.

SUMMARY OF THE INVENTION

In a first aspect, the present invention provides isolated cells comprising a genetically engineered disruption in a human leukocyte antigen (HLA) class II-related gene, wherein the cell is a primate cell. In one embodiment, the HLA class II-related gene is selected from the group consisting of regulatory factor X-associated ankyrin-containing protein (RFXANK), regulatory factor 5 (RFX5), regulatory factor X-associated protein (RFXAP), class II transactivator (CIITA), HLA-DPA (α chain), HLA-DPB (β chain), HLA-DQA, HLA-DQB, HLA-DRA, HLA-DRB, HLA-DMA, HLA-DMB, HLA-DOA and HLA-DOB. In another embodiment, the cell comprises genetically engineered disruptions in at least two, at least three, or in all four of the HLA class II-related genes. In a further embodiment, the HLA class II-related gene is regulatory factor X-associated ankyrin-containing protein (RFXANK). In a still further embodiment, the cell comprises genetically engineered disruptions in all copies of the HLA class II-related gene. In another embodiment the cell further comprises one or more recombinant immunomodulatory genes, each capable of expressing an immunomodulatory polypeptide in the human cell. In a further embodiment, the one or more immunomodulatory genes comprise a polynucleotide capable of encoding an HLA II protein. In another embodiment, the one or more immunomodulatory genes comprise a polynucleotide capable of encoding a single chain fusion HLA class II protein. In a further embodiment, the cell further comprises a genetically engineered disruption in the β2-microglobulin (B2M) gene.

In another aspect, the present invention provides isolated cells comprising (a) a genetically engineered disruption in a beta-2 microglobulin (B2M) gene; and (b) one or more polynucleotides capable of encoding an HLA class II protein, or a single chain fusion HLA class II protein; wherein the cell is a primate cell.

In one embodiment of either of these aspects, the cell comprises genetically engineered disruptions of all copies of the B2M gene. In a further embodiment, the HLA II gene encodes an HLA protein selected from the group consisting of an HLA-DM α chain, an HLA-DM β chain, an HLA-DO α chain, an HLA-DO β chain, an HLA-DP α chain, an HLA-DP β chain, an HLA-DQ α chain, an HLA-DQ β chain, an HLA-DR α chain and an HLA-DR β chain.

In another embodiment, the single chain fusion HLA class II protein comprises at least a portion of an HLA class II gene α chain covalently linked to at least a portion of an HLA class II gene β chain, wherein the HLA class II gene is selected from the group consisting of HLA-DP, HLA-DQ, HLA-DR, HLA-DM, and HLA-DO. In a further embodiment, the single chain fusion HLA class II protein comprises a plurality of different single chain fusion HLA class II proteins. In another embodiment, the single chain fusion HLA class II protein comprises at least a portion of HLA-DQ α chain and at least a portion of HLA-DQ β chain. In a still further embodiment, the single chain fusion HLA class II protein comprises at least a portion of HLA-DQ α chain allele HLA-DQA1*01 and at least a portion of HLA-DQ β chain allele HLA-DQB1*02.

In a further embodiment of either aspect of the cells of the invention, the HLA protein or the single chain fusion HLA class II protein presents a first target peptide antigen on the cell surface. In one such embodiment, the first target peptide antigen is covalently linked to the single chain fusion HLA class II protein.

In another embodiment the cell further comprises a polynucleotide capable of encoding a single chain fusion HLA class I protein. In one such embodiment, the single chain fusion HLA class I protein comprises at least a portion of B2M covalently linked to at least a portion of an HLA class I α chain selected from the group consisting of HLA-A, HLA-B, HLA-C, HLA-E, HLA-F and HLA-G. In another such embodiment, the single chain fusion HLA class I protein comprises at least a portion of B2M covalently linked to at least a portion of HLA-A. In a further embodiment the single chain fusion HLA class I protein comprises at least a portion of B2M covalently linked to at least a portion of HLA-A0201. In another embodiment the cell further expresses a second target peptide antigen that is presented by the single chain fusion HLA class I protein on the cell surface. For example, the second target peptide antigen may be covalently linked to the single chain fusion HLA class I protein.

In another embodiment of either aspect of the cells of the invention, the cell further comprises one or more recombinant genes capable of encoding a suicide gene product. For example, the suicide gene product may comprise a protein selected from the group consisting of thymidine kinase and an apoptotic signaling protein.

The cells of either aspect of the may have a normal karyotype and may be non-transformed cells. The cells may be stem cells, such as hematopoietic stem cells, embryonic stem cells, pluripotent stem cells, induced pluripotent stem cells, liver stem cells, neural stem cells, pancreatic stem cells or mesenchymal stem cells. The stem cell may be differentiated, such as dendritic cells, pancreatic islet cells, liver cells, muscle cells, keratinocytes, neuronal cells, hematopoietic cells, lymphocytes, red blood cells, platelets, skeletal muscle cells, ocular cells, mesenchymal cells, fibroblasts, lung cells, gastrointestinal (GI) tract cells, vascular cells, endocrine cells, adipocytes or cardiomyocytes. The cells may be human cells.

In another aspect, the present invention provides vaccines comprising the cell of any one embodiment or combinations of embodiments of the cells of the present invention that include at least one target peptide antigen on the cell surface, wherein the vaccine is capable of eliciting in a primate an immune response specific for the target peptide antigen(s).

In a further aspect, the invention provides methods of transplantation in a patient in need thereof comprising the step of administering to the patient an effective amount of the cell or vaccine of any embodiment or combination of embodiments of the cells of the invention. In one such embodiment, the patient may be immune competent. In another embodiment, the cell or vaccine may comprise a differentiated cell.

DETAILED DESCRIPTION OF THE INVENTION

Figure 1:
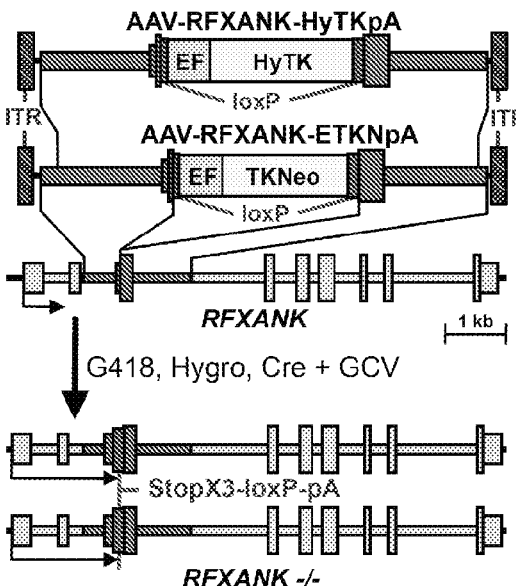
FIG. 1 shows the structure of exemplary two adeno-associated virus (AAV) gene targeting vectors, designed to insert either a TKNeo (AAV-RFXANK-ETKNpA) or HyTK (AAV-RFXANK-HyTK) gene controlled by an EF1alpha promoter (EF) into exon 3 of the RFXANK gene, which is also shown below the vectors. Selection of vector-infected cells with G418 or hygromycin (Hygro) allows one to isolate cells targeted by the TKNeo or HyTK vectors respectively. Subsequent expression of Cre recombinase and selection with gancyclovir (GCV) then allows one to isolate clones that have removed the TKNeo or HyTK genes, leaving behind two inactivated RFXANK alleles with stop codons in all 3 reading frames, a loxP site, and a polyadenylation site (StopX3-loxP-pA). LoxP is the recombination site for Cre recombinase. ITR is a vector inverted terminal repeat. Similar vectors could be designed to target other genes.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, 2nd Ed.* (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides isolated cells comprising a genetically engineered disruption in a human leukocyte antigen (HLA) class II-related gene, wherein the cell is a primate cell. The HLA class II related genes as used in the instant application broadly refer to genes that encode proteins involved in the HLA class II mediated immune responses. Thus, HLA class II related genes encompass genes that encode the HLA class II molecules such as HLA-DM (SEQ ID NO: 48, 50), HLA-DO (SEQ ID NO: 52, 54), HLA-DP (SEQ ID NO: 36, 38), HLA-DQ (SEQ ID NO: 40, 42), and HLA-DR (SEQ ID NO: 44, 46). The sequences of exemplary HLA class II genes/ proteins can be found in publicly available database under GenBank or IMGT/HLA database numbers NM_033554.3 (SEQ ID NOs:36, 37) for HLA-DPA, HLA00514 (SEQ ID NOs:38, 39) for HLA-DPB, HLA00601 (SEQ ID NOs:40, 41) for HLA-DQA, HLA00622 (SEQ ID NOs:42, 43) for HLA-DQB, NM_019111 (SEQ ID NOs:44, 45) for HLA-DRA, HLA00664 (SEQ ID NOs:46, 47) for HLA-DRB, NM_006120 (SEQ ID NOs:48, 49) for HLA-DMA, NM_002118 (SEQ ID NOs:50, 51) for HLA-DMB, NM_002119 (SEQ ID NOs:52, 53) for HLA-DOA, and NM_002120 (SEQ ID NOs:54, 55) for HLA-DOB.

In addition, HLA class II related genes also include genes that encode HLA class II regulatory proteins that regulate the expression of HLA class II molecules, including without limitation regulatory factor X-associated ankyrin-containing protein (RFXANK), regulatory factor 5 (RFX5), regulatory factor X-associated protein (RFXAP), and class II transactivator (CIITA). For example, regulatory factor X-associated ankyrin-containing protein (RFXANK) together with regulatory factor X-associated protein and regulatory factor-5 form a complex that binds to the X box motif of HLA class II gene promoters and activates transcription of the HLA class II genes. The sequences of exemplary HLA class II-related genes that regulate the expression of HLA class II molecules can be found in publicly available database under GenBank Accession Numbers NM_134440.1 (SEQ ID NOs: 24, 25) and NM_003721.2 (SEQ ID NOs:26, 27) for RFXANK, NM_000449.3 (SEQ ID NOs:28, 29) and NM_001025603.1 (SEQ ID NOs:30, 31) for RFX5, NM_000538.3 (SEQ ID NOs:32, 33) for RFXAP and NM_000246.3 (SEQ ID NOs:34, 35) for CIITA. All the sequences disclosed under these GenBank Accession Numbers are herein incorporated by reference.

In certain embodiments, the invention provides an isolated primate preferably human cell that comprises a genetically engineered disruption in at least one HLA class II-related gene as defined herein. In certain particular embodiments, the cell comprises genetically engineered disruptions of all copies of the at least one HLA class II-related gene. In certain other embodiments, the cell comprises a plurality of genetically engineered disruptions in a plurality of HLA class II-related genes.

In certain embodiments, the HLA class II-related gene is selected from the group consisting of regulatory factor X-associated ankyrin-containing protein (RFXANK), regulatory factor 5 (RFX5), regulatory factor X-associated protein (RFXAP), and class II transactivator (CIITA). In certain particular embodiments, the cell comprises at least one genetically engineered disruption in at least one, at least two, at least three, or all of the HLA class II-related genes selected from the group consisting of regulatory factor X-associated ankyrin-containing protein (RFXANK), regulatory factor 5 (RFX5), regulatory factor X-associated protein (RFXAP), and class II transactivator (CIITA). Any combinations of these four HLA class II-related genes as target for genetic disruption to create HLA class II deficient cell are within the scope of the invention.

In certain other embodiments, the cell comprises at least one genetically engineered disruption of an HLA class II-related genes selected from the group consisting of regulatory factor X-associated ankyrin-containing protein (RFXANK)(SEQ ID NO: 24-27), regulatory factor 5 (RFX5) (SEQ ID NO: 28-31), regulatory factor X-associated protein (RFXAP) (SEQ ID NO: 32, 33), class II transactivator (CIITA) (SEQ ID NO: 34, 35), HLA-DPA (α chain)(SEQ ID NO: 36, 37), HLA-DPB (β chain) (SEQ ID NO: 38, 39), HLA-DQA (SEQ ID NO: 40, 41), HLA-DQB (SEQ ID NO: 42, 43), HLA-DRA (SEQ ID NO: 44, 45), HLA-DRB (SEQ ID NO: 46-47), HLA-DMA (SEQ ID NO: 48, 49), HLA-DMB (SEQ ID NO: 50, 51), HLA-DOA (SEQ ID NO: 52, 53) and HLA-DOB (SEQ ID NO: 54, 55).

The genetically engineered disruptions include without limitation deletions, insertions, substitutions and truncations of a target HLA class II-related gene that result in no expression of the target gene or expression of a truncated or mutated protein with no function or much reduced function as compared to the wild type protein. In certain embodiments, the genetically engineered disruption of a HLA class II-related gene leads to the expression of a truncated HLA class II-related protein. In certain particular embodiments, the HLA class II-related gene is RFXANK (SEQ ID NO: 24-27). In certain other particular embodiments, the HLA-related gene is selected from the group consisting of HLA-DPA (α chain)(SEQ ID NO: 36, 37), HLA-DPB (β chain) (SEQ ID NO: 38, 39), HLA-DQA (SEQ ID NO: 40, 41), HLA-DQB (SEQ ID NO: 42, 43), HLA-DRA (SEQ ID NO: 44, 45), HLA-DRB (SEQ ID NO: 46-47), HLA-DMA (SEQ ID NO: 48, 49), HLA-DMB (SEQ ID NO: 50, 51), HLA-DOA (SEQ ID NO: 52, 53) and HLA-DOB (SEQ ID NO: 54, 55). In certain further embodiments the cell comprises genetically engineered disruptions in all copies of the HLA class II-related gene.

In another aspect, the invention provides HLA class I and HLA class II deficient cells. In certain embodiments, the invention provides a primate cell, preferably a human cell that comprises a genetically engineered disruption in an HLA class II-related gene and further comprises a genetically engineered disruption in the β2-microglobulin (B2M) gene (SEQ ID NO: 1). In other particular embodiments, the cell further comprises genetically engineered disruptions of all copies of the B2M gene (SEQ ID NO: 1). In certain embodiments, the genetic disruptions in the B2M (SEQ ID NO: 1) gene result in defective or no expression of the B2M protein (SEQ ID NO: 2). In other particular embodiments, the cell further comprises genetically engineered disruptions of all copies of the B2M gene. In certain embodiments, the genetic disruptions in the B2M gene result in defective or no expression of the B2M protein. Since B2M is a common component of all HLA class I proteins, the disruptions preclude the expression of all natural HLA class I proteins on the cell surface. Thus, in this aspect of the invention an HLA class I/class II deficient cell is provided. The B2M coding sequence is shown in SEQ ID NO:1 (GenBank Accession Number NM_004048) and the B2M protein sequence is shown in SEQ ID NO:2. There may be many single nucleotide polymorphisms (SNPs) in the gene; as will be understood by those of skill in the art, the human cells and methods of the invention are applicable to any such B2M gene and SNPs.

Any suitable technique for introducing a genetically engineered disruption (in an HLA class II-related gene, in B2M gene or any other suitable gene) can be used; exemplary techniques for gene disruptions are disclosed throughout the application and are within the level of skill in the art based on the teachings herein and the teachings known in the art. Other exemplary techniques can be found, for example, in U.S. Patent Application Publication Number US2008/ 0219956, published Sep. 11, 2008, and incorporated by reference herein in its entirety. These techniques may optionally include steps to remove non-human DNA sequences from the cells after disruption of an HLA class II-related gene and optionally disruption of B2M gene.

One such techniques employs an adeno-associated virus gene targeting vector, optionally including removing the transgene used for targeting via techniques such as those described below, or by removing the transgene used for targeting by Cre-mediated loxP recombination, or other suitable recombination techniques. See Khan et al. 2011, Protocol, 6:482-501, which is incorporated by reference in its entirety. Exemplary targeting vectors and exemplary vector diagrams are also disclosed herein. It is within the level of those of skill in the art, based on the teachings herein and known in the art, to utilize a variety of techniques for making the HLA class II, preferably human cells, of the invention.

In certain embodiments, the cell genome of HLA class II deficient cells may comprise no more than 100, no more than 50 or no more than 30 nucleotides of non-human DNA sequences. In certain other embodiments, the cell genome may comprise 6, 5, 4, 3, 2, 1, or 0 nucleotides of non-human DNA sequences. Exemplary strategy for genetically disrupting the RFXANK gene is shown in FIG. 1. The non-human DNA sequences can be removed by a second round of targeting to delete the HyTK or TKNeo transgenes in the first vectors or by the Cre-mediated loxP recombination.

In certain other embodiments, the HLA class II or HLA class I/class II deficient cells further comprise one or more recombinant immunomodulatory genes. Suitable immuno-modulatory genes include without limitation a gene encoding a viral protein that inhibits antigen presentation, a microRNA gene, a gene that encodes an HLA class II protein, or a gene that encodes a single chain (SC) fusion HLA class II protein. The term "single chain fusion HLA class II protein," "single chain fusion HLA class II molecule" or "single chain fusion HLA class II antigen" refers to a fusion protein comprising at least a portion of the HLA class II α chain covalently linked, either directly or via a linker sequence, to at least a portion of an HLA class II β chain or a class II α or β chain linked to a peptide antigen, or linked class II α and β chains also linked to a peptide antigen. On the other hand, the term "HLA class II protein," "HLA class II molecule" or "HLA class II antigen" refers to a non-covalently associated heterodimer of an HLA class II α chain and an HLA β chain expressed on the surface of a wild type cell. In embodiments wherein the gene encodes an HLA class II protein (as opposed to a single chain fusion HLA class II protein), the gene is under control of a promoter not involved in normal class II expression in the cell. In one embodiment, the gene is episomally expressed;

in another embodiment, the gene is integrated into the cell's genome. In either embodiment, the gene is operatively linked (i.e.: under transcriptional control) to a promoter not involved in normal class II expression in the cell. Any suitable promoter may be used, as may be determined by one of skill in the art based on the specific intended design and use of the constructs and cells.

In another aspect, the present invention provides isolated cells comprising (a) a genetically engineered disruption in a beta-2 microglobulin (B2M) gene; and (b) one or more polynucleotides capable of encoding an HLA II protein (alpha or beta chains) or a single chain fusion HLA class II protein; wherein the cell is a primate cell. Cells according to this aspect of the invention are HLA class I deficient cells.

HLA class II deficient cells, HLA class I deficient cells, or HLA class I/class II deficient cells can be used as universal donor cells. In certain particular embodiments, the HLA class II deficient cells, HLA class I deficient cells, or HLA class I/class II deficient cells are hematopoietic cells or dendritic cells for use in transplantation. In addition, solid organ cells may sometimes express HLA class II genes that participate in immune rejection. Thus, in certain advanta-geous embodiments, the invention provides HLA class II, HLA class I deficient cells, or HLA class I/class II deficient cells for transplantation for treatment of diseases or injuries associated with solid organs.

In certain particular embodiments of any of the cells of the present invention, the HLA α and β chains are selected from the group consisting of α and β chains of HLA-DM, HLA-DR, HLA-DP, HLA-DQ, and HLA-DO. The α and β chains can be but do not have to be from the same HLA class II gene. For example, an HLA class II protein or a single chain fusion HLA class II protein may comprise at least a portion of an HLA-DQ α chain and at least a portion of an HLA-DQ β chain (also referred to as a dimeric construct). HLA class II proteins and single chain fusion HLA class II proteins comprising mismatching HLA class II alleles are also contemplated. In certain particular embodiments, an HLA class II protein or a single chain fusion HLA class II protein may comprise at least a portion of the HLA-DQ α chain allele HLA-DQA1*01 (SEQ ID NO:41) and at least a portion of the HLA-DQ β chain allele HLA-DQB1*02 (SEQ ID NO:43). In certain preferred embodiments, the leader sequence (or signal peptide) of the second portion of the fusion protein is removed in the fusion construct. For example, in a single chain fusion HLA class II protein that comprises at least a portion of HLA-DQA1*01 (SEQ ID NO: 41) at the N-terminus covalently linked to at least a portion of HLA-DQB1*02 (SEQ ID NO: 43) at the C-ter-minus, the HLA-DQA1*01 (SEQ ID NO: 41) leader sequence is left in, and the HLA-DQB1*02 (SEQ ID NO: 43) leader sequence is removed from the construct. In certain other embodiments, the cell further expresses at least two, at least three, or at least four or more different single chain fusion HLA class II proteins. In certain particular embodiments, the HLA class II protein or single chain fusion HLA class II protein also comprises a first target peptide antigen that occupies the peptide binding site of the HLA class II protein or single chain fusion HLA class II protein, wherein the peptide antigen is covalently linked to the HLA class II protein or single chain fusion HLA class II protein (also referred to as a trimeric construct). In certain other embodiments, the covalently linked peptide antigen is cleaved via a built-in protease cleavage site, and the cleaved peptide antigen can bind to the peptide binding site of the single chain fusion HLA-II protein for presentation.

Thus, HLA class II, HLA class I deficient cells, or HLA class I/class II deficient cells also encompass cells having genetically engineered disruptions in all copies of an HLA class II gene (e.g., disruptions in all copies of HLA-DQ α and/or β chain), wherein one HLA class II allele is genetically engineered to express, instead of the wild type HLA class II protein, an HLA class II protein of interest or a single chain fusion HLA class II protein (i.e., genetically targeted knockin in one HLA-II allele). Take HLA-DQ as an example, in certain embodiments, HLA-DQ$^{-/-}$ cells express HLA-DQ protein only in the context of a single chain fusion HLA-DQ protein from an HLA-DQ genetic locus. In certain advantageous embodiments, the expression of the single chain fusion HLA class II protein is regulated by the endogenous HLA-DQ regulatory sequence located at the HLA-DQ locus.

In related embodiments, HLA class II, HLA class I deficient cells, or HLA class I/class II deficient cells further encompass cells having genetically engineered disruptions in all copies of a certain HLA-II gene, wherein all alleles of the specific HLA-II gene are genetically engineered to express, instead of the wild type HLA-II protein, single chain fusion HLA class II proteins (i.e., genetically targeted knockin in all HLA-II alleles). HLA class II, HLA class I deficient cells, or HLA class I/class II deficient cells with such genetic disruptions express a particular HLA-II protein only in the context of single chain fusion HLA class II proteins from the genetic loci of all the alleles of the particular HLA-II gene.

HLA class II proteins and single chain fusion HLA class II proteins comprising sequence variants and fragments of HLA class II α chains and β chains are contemplated by the instant invention, wherein such HLA class II proteins or single chain fusion constructs nevertheless possess normal HLA class II functions, e.g., forming proper secondary structure of the heterodimer on the cell surface, presenting peptides in the peptide binding site, interacting with CD4+ helper T cells and triggering HLA class II-mediated immune responses. In certain embodiments, the variants share at least 75%, 78%, 80%, 81%, 85%, 88%, 90%, 91%, 92%, 93%, 94%, 95%, 96%, 97%, 98%, 99%, or complete sequence homology with the naturally occurring HLA class II α or β chain sequences, wherein the variants possess normal HLA class II functions. In certain other embodiments, the variants share at least 75%, 80%, 81%, 85%, 88%, 90%, 91%, 92%, 93%, 94%, 95%, 96%, 97%, 98%, 99%, or complete sequence homology with the sequences of HLA class II α or β chains as shown in SEQ ID NOs:37, 39, 41, 43, 45, 47, 49, 51, 53 and 55.

Further, the HLA class II, HLA class I deficient cells, or HLA class I/class II deficient cells can be engineered to recombinantly express a single chain fusion HLA class I protein in a B2M−/− genetic background. The HLA class I deficient cells or HLA class I/class II deficient cells recombinantly expressing a single chain fusion HLA class I protein are nevertheless deficient in normal B2M function in that the cells do not express wild type B2M protein (SEQ ID NO:2) that can form a non-covalently associated heterodimer with any HLA class I α chain on the cell surface.

The term "single chain fusion HLA class I protein," "single chain fusion HLA class I molecule" or "single chain fusion HLA class I antigen" refers to a fusion protein comprising at least a portion of the B2M protein covalently linked, either directly or via a linker sequence, to at least a portion of an HLA-I α chain. On the other hand, the term "HLA class I protein," "HLA class I molecule" or "HLA class I antigen" refers to a non-covalently associated heterodimer of B2M and an HLA α chain expressed on the surface of a wild type cell.

As used herein, the term "HLA class I α chain" or "HLA-I heavy chain" refers to the α chain of the HLA class I heterodimer. HLA class I heavy chain includes without limitation HLA class I α chains HLA-A, HLA-B, HLA-C, HLA-E, HLA-F, and HLA-G. Representative DNA and protein sequences are provided for HLA-A (GenBank No. K02883.1, SEQ ID NO:3; UniProt No. P01892, SEQ ID NO:4), HLA-B (NM_005514, SEQ ID NO:5; NP_005505; SEQ ID NO:6), HLA-C (NM_002117, SEQ ID NO:7; NP_002108, SEQ ID NO:8), HLA-E (NM_005516, SEQ ID NO:9; NP_005507, SEQ ID NO:10), HLA-F (NM_018950, SEQ ID NO:11; NP_061823, SEQ ID NO:12), and HLA-G (NM_002127, SEQ ID NO:13; NP_002118, SEQ ID NO:14).

In addition, although the term "HLA class I or II protein/molecule" is known to refer to the MHC class I or II protein/molecule in human, the terms HLA and MHC are sometimes used interchangeably throughout this application: for example, the term HLA class I or HLA class II protein can also be used to refer to the primate equivalent to the HLA class I protein or HLA class II protein, respectively, in a primate. One of skill in the art will be able to discern the meaning of the term based on the content.

Thus, HLA class I deficient cells or HLA class I/class II deficient cells also encompass cells having genetically engineered disruptions in all copies of the B2M gene, wherein one B2M allele is genetically engineered to express, instead of the wild type B2M protein, a single chain fusion HLA class I protein (i.e., genetically targeted knockin in one B2M allele). B2M−/− cells with such genetic background express B2M only in the context of the single chain fusion HLA class I protein from a B2M genetic locus. In certain advantageous embodiments, the expression of the single chain fusion HLA class I protein is regulated by the endogenous B2M regulatory sequence located at the B2M locus.

In related embodiments, HLA class I deficient cells or HLA class I/class II deficient cells further encompass cells having genetically engineered disruptions in all copies of the B2M gene, wherein all B2M alleles are genetically engineered to express, instead of the wild type B2M protein, single chain fusion HLA class I proteins (i.e., genetically targeted knockin in all B2M alleles). HLA class I deficient cells or HLA class I/class II deficient cells with such genetic disruptions express B2M only in the context of single chain fusion HLA class I proteins from the genetic loci of all the alleles of the B2M gene. In certain embodiments, the cells are genetically engineered to express the same type of single chain fusion HLA class I protein from the genetic loci of all alleles of the B2M gene; while in other embodiments, the cells are genetically engineered to express different types of single chain fusion HLA class I proteins from different genetic loci of the B2M gene.

In certain embodiments, the single chain fusion HLA class I protein comprises at least a portion of B2M (SEQ ID NO: 2) and at least a portion of HLA-A (SEQ ID NO: 4), HLA-B (SEQ ID NO: 6), HLA-C(SEQ ID NO: 8), HLA-E (SEQ ID NO: 10), HLA-F (SEQ ID NO: 12) or HLA-G (SEQ ID NO: 14) (also referred to as a dimeric construct). In certain preferred embodiments, the HLA α chain contained in the single chain fusion HLA class I protein does not contain the leader sequence (or signal sequence) of the HLA class I α chain (leaderless HLA α chain). In certain other embodiments, the single chain fusion HLA class I protein comprises at least a portion of B2M (SEQ ID NO: 2) and at least a portion of HLA-C(SEQ ID NO: 8), HLA-E (SEQ ID NO: 10) or HLA-G (SEQ ID NO: 14). In certain further embodiments, the single chain fusion HLA class I protein comprises at least a portion of B2M (SEQ ID NO: 2) and at least a portion of HLA-A (SEQ ID NO: 4), HLA-E (SEQ ID NO: 10) or HLA-G (SEQ ID NO: 14). In certain preferred embodiments, the single chain fusion HLA class I protein comprises a leader sequence (or signal peptide) covalently linked to at least a portion of B2M and at least a portion of an HLA α chain to ensure proper folding of the single chain fusion on the cell surface. The leader sequence can be the leader sequence of the B2M protein, the leader sequence of an HLA α chain protein or the leader sequence of other secretary proteins. In certain particular embodiments, the single chain fusion HLA class I protein comprises a B2M protein with its leader sequence removed. In certain other particular embodiments, the single chain fusion HLA class I protein comprises an HLA α chain protein with its leader sequence removed. Certain HLA class I α chains are highly polymorphic. As will be understood by those of skill in the art, the human cells and methods of the invention are applicable to any such HLA α chains and polymorphism thereof.

Single chain fusion HLA class I proteins comprising sequence variants and fragments of B2M and/or HLA α chains are contemplated by the instant invention, wherein such single chain fusion constructs nevertheless possess normal HLA class I functions, e.g., forming proper secondary structure of the heterodimer on the cell surface, presenting peptides in the peptide binding cleft and engaging the inhibitory receptors on the surface of NK cells. In certain embodiments, the variants share at least 75%, 80%, 81%, 85%, 88%, 90%, 91%, 92%, 93%, 94%, 95%, 96%, 97%, 98%, 99%, or complete sequence homology with the naturally occurring HLA heavy chains and B2M sequences, wherein the variants possess normal HLA class I functions. In certain other embodiments, the variants share at least 75%, 80%, 81%, 85%, 88%, 90%, 91%, 92%, 93%, 94%, 95%, 96%, 97%, 98%, 99%, or complete sequence homology with the sequences of B2M or HLA heavy chains as shown in SEQ ID NOs:2, 4, 6, 8, 10, 12 or 14.

In certain particular embodiments, the HLA-A variants share at least 85%, 88,%, 90%, 91%, 92%, 93%, 94%, 95%, 96%, 97%, 98%, 99%, or complete sequence homology with SEQ ID NO:4. In certain other particular embodiments, the HLA-B variants share at least 81%, 83%, 85%, 88,%, 90%, 91%, 92%, 93%, 94%, 95%, 96%, 97%, 98%, 99%, or complete sequence homology with SEQ ID NO:6. In certain further embodiments, the HLA-C variants share at least 90%, 91%, 92%, 93%, 94%, 95%, 96%, 97%, 98%, 99%, or complete sequence homology with SEQ ID NO:8. In yet other embodiments, the HLA-E variants share at least 97%, 98%, 99%, or complete sequence homology with SEQ ID NO:10. In certain particular embodiments, the HLA-F variants share at least 99%, or complete sequence homology with SEQ ID NO:12. In certain other embodiments, the HLA-G variants share at least 98%, 99%, or complete sequence homology with SEQ ID NO:14.

In certain other embodiments, the single chain fusion HLA class I protein comprises full-length B2M (SEQ ID NO: 2) (including its leader sequence) and an HLA α chain without the leader sequence (leaderless HLA α chain); while in certain other embodiments, the single chain fusion HLA class I protein comprises B2M (SEQ ID NO: 2) protein without the leader sequence. It is understood that B2M–/– cells expressing two, three or more different types of single chain fusion HLA class I protein in any combination, for example, expressing SC fusion comprising HLA-A (SEQ ID NO: 4)(or a leaderless HLA-A) and SC fusion comprising HLA-C(SEQ ID NO: 8) (or a leaderless HLA-C), expressing SC fusion comprising HLA-A (SEQ ID NO: 4)(or a leaderless HLA-A) and SC fusion comprising HLA-E (SEQ ID NO: 10) (or a leaderless HLA-E), or expressing SC fusion comprising HLA-B (SEQ ID NO: 6)(or a leaderless HLA-B), SC fusion comprising HLA-E (SEQ ID NO: 10)(or a leaderless HLA-E) and SC fusion comprising HLA-G (SEQ ID NO: 14)(or a leaderless HLA-G), etc., are all contemplated by the invention and fall within the scope of the invention.

Natural killer (NK) cells are part of the innate immune response. Several pathogens can down regulate HLA class I protein expression in infected cells. The NK cells monitor infection by recognizing and inducing apoptosis in cells that do not express HLA class I proteins. The inhibitory receptors on the NK cell surface recognize HLA class I α chain alleles thereby preventing NK-medicated apoptosis in uninfected normal cells. Thus, in certain particular embodiments, the single chain fusion HLA-I protein inhibits NK cell-mediated killing of cells that do not express endogenous HLA class I proteins by binding to the inhibitory receptors on the NK cells. For example, HLA-E is a ligand for the CD94/NKG2 receptor of NK cells that inhibits NK cell-mediated apoptosis. Thus, in certain particular embodiments, the B2M–/– cell expresses the single chain fusion HLA class I protein comprising at least a portion of B2M and at least a portion of HLA-E. In addition, HLA-G is normally expressed on the surface of placental cytotrophoblasts that do not express HLA-A, B or C, and it protects these cells from NK cell-mediated lysis by interacting with the inhibitory ILT2 (LIR1) receptor on NK cells (Pazmany et al., 1996, Science 274, 792-795). Thus, in certain other preferred embodiments, the B2M–/– cell expresses the single chain fusion HLA class I protein comprising at least a portion of B2M and at least a portion of HLA-G.

In certain particular embodiments, the single chain fusion HLA class I protein comprises at least a portion of B2M and at least a portion of HLA-A0201. HLA-A0201 (SEQ ID NO:4) is a common HLA class I allele found in a large percentage of the population in the United States. Thus, in certain advantageous embodiments, the isolated cell expresses the single chain fusion HLA class I protein comprising at least a portion of B2M and at least a portion of HLA-A0201 in a B2M–/– genetic background, wherein the isolated cell is immune compatible with a large percentage of the human population in the United States. Other suitable common alleles that can be used include without limitation HLA-A0101, HLA-A0301, HLA-B0702, HLA-B0801, HLA-00401, HLA-00701, and HLA-00702. In certain preferred embodiments, the HLA allele comprises at least a portion of HLA-A0201 (SEQ ID NO:4), HLA-B0702 (SEQ ID NO:6) or HLA-00401 (SEQ ID NO:8).

Figure 2:
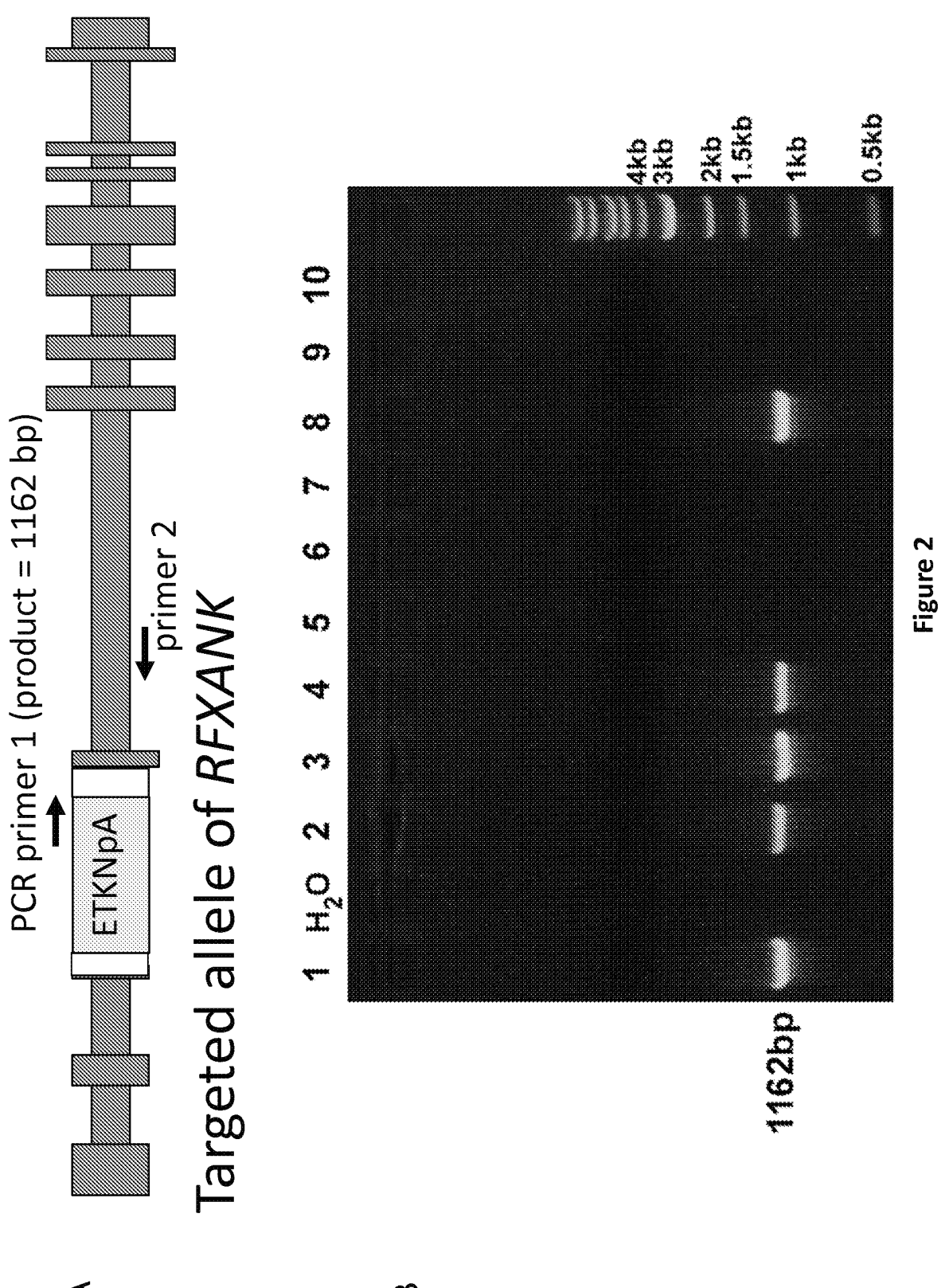
FIG. 2 (A) Schematic depiction of targeting strategy for infection of human embryonic stem cells with construct AAV-RFXANK-ETKNpA. (B) Photograph of stained gel showing polymerase chain reaction (PCR) products obtained after infection of human embryonic stem cells with AAV-RFXANK-ETKNpA and PCR using a forward primer homologous to the neomycin sequence of the selection cassette and a reverse primer homologous to the RFXANK gene which was outside the targeting homology arm, as indicated by the arrows above.

In certain further embodiments, the single chain fusion HLA class I protein also comprises a second target peptide antigen that occupies the peptide binding cleft of the single chain fusion HLA class I protein, wherein the peptide antigen is covalently linked to the single chain fusion HLA class I protein (also referred to as a trimeric construct). An example of the trimeric construct is shown in FIG. 2. The HLA-bGBE construct of FIG. 2 comprises B2M and HLA-E covalently linked to a peptide antigen (such as, but not limited to, the HLA-G signal peptide as illustrated in the figure) (SEQ ID NO:23) designed to occupy the peptide binding cleft of the single chain fusion HLA class I protein. In certain other embodiments, the covalently linked peptide antigen is cleaved via a built-in protease cleavage site, and the cleaved peptide antigen can bind to the peptide binding cleft of the single chain fusion HLA-I protein for presentation.

In certain alternative embodiments, the peptide antigen occupying the peptide binding cleft of the single chain fusion HLA class I protein is produced by the intracellular antigen processing pathway, in which the peptide antigen is produced by proteasome, transported to and loaded onto the single chain fusion HLA class I protein in the endoplasmic reticulum. In certain particular embodiments, the peptide antigen comprises a peptide of a tumor antigen. In certain other embodiments, the peptide antigen comprises a peptide of a protein from a pathogen including without limitation a bacterium, a virus, a fungus and a parasite. In further embodiments, the peptide antigen comprises a peptide of a tumor antigen. In certain particular embodiments, the HLA class I deficient cell or HLA class I/class II deficient cell expresses a single chain fusion HLA class I protein that is covalently linked to a peptide that does not comprise an auto-antigen or neo-antigen to the patient. It is within the ability of a skilled person to design the single chain fusion HLA class I protein and the peptide antigen presented thereon to modulate the immune response that may be elicited in a recipient.

The isolated HLA class II deficient cells, HLA class I deficient cells, or HLA class I/class II deficient cells expressing an HLA class II protein or a single chain fusion HLA class II protein optionally a single chain fusion HLA class I protein comprising a specific peptide antigen either covalently or non-covalently bound to the single chain fusion proteins can be used, for example, for administration to a recipient to elicit an immune response. Accordingly, in a related aspect, the invention provides a vaccine comprising the isolated cell of the invention, wherein the vaccine is capable of eliciting in a recipient an immune response specific for the target peptide antigen. The immune response includes without limitation a cellular immune response and/or a humoral immune response. The vaccine may comprise a stem cell or a differentiated cell; in certain particular embodiments, the cell is a differentiated dendritic cell. In certain other embodiments, the cell further expresses a cytokine. Any suitable cytokine can be used; in certain particular embodiments, the cytokine is IL2 or IFN-γ. In certain preferred embodiments, the cell is a human cell and the recipient is a human. Thus, in a further aspect, the invention provides kits comprising the vaccines of the invention and optionally an immune adjuvant.

The single chain fusion HLA class I protein, HLA class II protein, or single chain fusion HLA class II protein can be expressed from an expression vector that allows either transient or more preferably, stable expression of the protein in a cell. Exemplary suitable expression vectors are known in the art. One such example is a retroviral vector, which is capable of integrating into the cellular genome to provide long-term, stable expression of an exogenous gene. In certain particular embodiments, the viral vector is derived from human foamy virus, a type of retrovirus. Other suitable viral vectors include without limitation vectors derived from retrovirus, adenoviral virus, adeno-associated virus, lentivirus, herpes simplex virus, vaccinia virus, and pox virus.

In certain preferred embodiments, the polynucleotide capable of encoding a single chain fusion HLA class I or class II protein or an HLA class II protein is integrated into the chromosome of the cells, preferably into the B2M or the HLA class II loci, for stable expression. Thus, in certain preferred embodiments, the B2M loci are disrupted by inserting in the B2M loci the polynucleotide capable of encoding a single chain fusion HLA class I protein to replace the expression of the endogenous wild type B2M protein. Thus, in certain other preferred embodiments, certain HLA-II loci are disrupted by inserting in the HLA-II loci the polynucleotide capable of encoding an HLA class II protein or a single chain fusion HLA class II protein to replace the expression of the endogenous wild type HLA-II protein. The result of such gene targeting precludes formation of wild type HLA class I proteins and specific HLA class II proteins but permits expression of a predetermined HLA class II protein or single chain fusion HLA class I or class II protein of choice on the surface of the otherwise HLA class II deficient cells. Other expression vectors are also contemplated and the selection of suitable expression vector is within the ability of one ordinary skill in the art.

The "isolated cell" can be any suitable cell type for a given purpose. For example, the cell can be a pluripotent stem cell or a differentiated cell. "A stem cell" broadly encompasses any cells that are capable of further differentiation. "A pluripotent stem cell" refers to a stem cell that has the potential to differentiate into any of the three germ layers: endoderm, mesoderm or ectoderm. "An adult stem cell," on the other hand, is multipotent in that it can produce only a limited number of cell types. "An embryonic stem (ES) cell" refers to a pluripotent stem cell derived from the inner cell mass of the blastocyst, an early-stage embryo. "Induced pluripotent stem cells (iPS cells)" are pluripotent stem cell artificially derived from a non-pluripotent cell, typically an adult somatic cell, by artificially inducing expression of certain genes.

In another aspect, the invention provides a method of transplantation in a patient in need thereof comprising the step of administering to the patient an effective amount of the cells of the invention for transplantation. Because the HLA class II deficient cells and/or HLA class I deficient cells do not express wild type HLA class II protein (and optionally also HLA class I protein) on the cell surface, the cells when administered to a patient elicit minimal or no immune responses in the patient. Thus, transplantation using the HLA class II deficient cells and/or HLA class I deficient cells limits the need for taking immune suppressant therapies. Thus, in certain preferred embodiments, the patient is immune competent. In certain other embodiments, the cell is an isogeneic cell; while in other embodiments, the cell is an allogeneic cell.

In certain further embodiments, the cells of the invention are pluripotent stem cells; while in other embodiments, the cells of the invention are differentiated cells. In certain preferred embodiments, the cell is a human cell and the patient is a human patient. In certain particular embodiments, the method of transplantation comprises administering to a human an effective amount of the pluripotent stem cells or differentiated cells. In certain preferred embodiments, the cells of the invention further express one or more engineered single chain fusion HLA class II proteins and optionally also a single chain fusion HLA class I protein. In certain other embodiments, the cells are able to escape NK cell-mediated killing and elicit minimal or no immune response in the recipient after transplantation.

Transplantation therapy, replacement therapy or regenerative therapy refers to therapies for a disease condition by administering to a patient cells or tissues to replenish or replace defective cellular functions in a target organ. In certain particular embodiments, the need for transplantation arises as a result of physical or pathological injuries to a tissue or organ. In certain other particular embodiments, the need for transplantation arises as a result of one or more genetic defect or mutation in the patient and the transplantation of the cells of the invention replenishes or replaces defective cellular functions in the patient without the need for gene therapy to correct the underlying genetic mutation of the patient. In certain further embodiments, the transplantation includes without limitation hematopoietic stem cell transplantation, or transplantation of cells that are incorporated into an organ such as liver, kidney, pancreas, lung, brain, muscle, heart, gastrointestinal tract, nervous system, skin, bones, bone marrow, fat, connective tissue, immune system, or blood vessels. In certain particular embodiments, the target organ is a solid organ.

In certain particular embodiments, the cells administered to the recipient may or may not be incorporated into an organ in need of such therapy. In certain embodiments, the cells of the invention are differentiated into the desired cell type, either before or after transplantation, and provide the necessary cellular function without itself being incorporated into the tissue at the site of transplantation. For example, in certain embodiments for treating diabetes, the cells of the invention either as pluripotent stem cells or differentiated pancreatic beta islet cells are transplanted to a diabetic patient. The transplanted cells need not reconstitute a functioning pancreas: they just need to secrete insulin in response to glucose levels. In certain particular embodiments, the cells are transplanted into an ectopic location and are not fully incorporated into the pancreas. Transplantation of pluripotent cells of the invention, differentiated cells of the invention, or a tissue differentiated and developed ex vivo from the cells of the invention are all contemplated by the invention. In certain preferred embodiments, the cell is a human cell and the patient is a human patient. In certain other preferred embodiments, the cells of the invention express one or more single chain fusion HLA class II proteins and optionally also single chain fusion HLA class I proteins.

In a further aspect, the invention provides a method of treating a disease condition in a patient in need thereof comprising the step of administering to the patient an effective amount of the cell of the invention to treat the disease condition, wherein the disease condition is diabetes, an autoimmune disease, cancer, infection, anemia, cytopenia, myocardial infarction, heart failure, skeletal or joint condition, osteogenesis imperfecta or burns. In certain particular embodiments, the disease condition results from pathological or physical injuries to a tissue or organ. In certain embodiments, the cells of the invention are stem cells; while in other embodiments, the cells of the invention are differentiated cells. In certain preferred embodiments, the cell is a human cell and the patient is a human patient. In certain particular embodiments, the human cell is a differentiated cell. Transplantation of a tissue developed ex vivo from the cells of the invention is also contemplated by the invention. In certain preferred embodiments, the cells of the invention further express one or more single chain fusion HLA class II proteins and optionally also one or more single chain fusion HLA class I proteins. In certain embodiments, the cell is an isogeneic cell; while in other embodiments, the cell is an allogeneic cell.

In certain particular embodiments, the cell is a differentiated cell including without limitation a dendritic cell, lymphocyte, red blood cell, platelet, hematopoietic cell, pancreatic islet cell, liver cell, muscle cell, keratinocyte, cardiomyocyte, neuronal cell, skeletal muscle cell, ocular cell, mesenchymal cell, fibroblast, lung cell, GI tract cell, vascular cell, endocrine cell and adipocyte. In certain other particular embodiments, the invention provides a method of treating a disease condition in a solid organ. In certain embodiments, the cells of the invention used in treating a disease condition express one or more single chain fusion HLA class I proteins and optionally also one or more single chain fusion HLA class I proteins.

"Treating" a patient having a disease or disorder means accomplishing one or more of the following: (a) reducing the severity of the disease; (b) arresting the development of the disease or disorder; (c) inhibiting worsening of the disease or disorder; (d) limiting or preventing recurrence of the disease or disorder in patients that have previously had the disease or disorder; (e) causing regression of the disease or disorder; (f) improving or eliminating the symptoms of the disease or disorder; and (f) improving survival. In certain preferred embodiments, the disease or disorder is a disease or disorder that can be treated by transplantation of tissues or cells.

The effective amount of the isolated cells of the invention for transplantation or for treating a disease condition depends on a number of factors, such as the type of tissue, the severity of the disease condition, the transplantation reaction, the reason for transplantation, and the age and general health of the patient. The effective amount can be determined by a skilled researcher or clinician by routine practice. Due to the reduced immunogenicity of the transplanted cells, relative large amount of cells can be tolerated by a patient to achieve the desired therapeutic effects. Alternatively, the cells can be repeatedly transplanted at intervals until a desired therapeutic effect is achieved.

The route for administration of the cells of the invention is not limited in any particular way. Exemplary delivery routes include without limitation intravenous, intramuscular, subdermal, intraperitoneal, transcutaneous, intracutaneous, and subcutaneous route. The cells of the present invention can also be administered topically by injection. For example, the cells can be injected into an injured joint, a fractured bone, an infarct site, an ischemic site or their periphery.

In certain particular embodiments, the cells are administered via a delivery device including without limitation a syringe. For example, the cells can be suspended in a solution or a pharmaceutical composition contained in such a delivery device. The "solution" or "pharmaceutical composition" comprises a physiological compatible buffer and optionally a pharmaceutically acceptable carrier or diluent in which the cells of the invention remain viable. The use of such carriers and diluents is well known in the art. The solution includes without limitation physiologically compatible buffers such as Hank's solution, Ringer' solution, or physiologically buffered saline. The cells can be kept in the solution or pharmaceutical composition for short term storage without losing viability. In certain particular embodiments, the cells are frozen for long term storage without losing viability according to cryopreservation methods well-known in the art.

Aqueous injection suspensions may contain substances which increase the viscosity of the suspension, such as sodium carboxymethyl cellulose, sorbitol, or dextran, but still fluid to the extent that can be easily delivered by syringe injection. The solution is preferably sterile, stable under the conditions of manufacture and storage and is free of microorganism contamination through the use of, for example, parabens, chlorobutanol, phenol, ascorbic acid, thimerosal, and the like. The cells contained in the solution can be stem cells or differentiated cells as described herein, in a pharmaceutically acceptable carrier or diluent and, as required, other ingredients indicated above.

The cells may be administered systemically (e.g., intravenously) or locally (e.g., directly into a myocardial defect under the guidance of echocardiogram, or by direct application to damaged tissues or organs accessible during open surgery). For injections, the cells may be in an injectable liquid suspension preparation or in a biocompatible medium which is injectable in liquid form and becomes semi-solid at the site of damaged tissue. A syringe, a controllable endoscopic delivery device or other similar devises can be used so long as the needle lumen is of sufficient diameter (e.g. at least 30 gauge or larger) to avoid physical damages to the cells during delivery.

In certain other embodiments, the cells can be transplanted via a solid support, e.g., a planar surface or three-dimensional matrix. The matrix or planar surface is surgically implanted into the appropriate site in a patient. For example, a patient needing a pancreatic graft can have differentiated cells on a solid support surgically implanted in the pancreas tissue. Exemplary solid support includes without limitation a patch, a gel matrix (such as GELFOAM® from Pharmacia-Upjohn), polyvinyl alcohol sponge (PVA)-collagen gel implants (such as IVALON, Unipoint Industries, High Point, N.C.) and other similar or equivalent devices. A variety of other encapsulation technologies can be used with the cells of the invention, for example, WO 91/10470; WO 91/10425; U.S. Pat. Nos. 5,837,234; 5,011,472; 4,892,538).

The cells of the invention can be differentiated into various cell types of all three lineages, including without limitation hematopoietic, mesenchymal, pancreatic endoderm, cardiac and keratinocytes cells. In certain embodiments, the differentiated cell further expresses an HLA class II protein or a single chain fusion HLA class II protein and optionally also a single chain fusion HLA class I protein. In general, each cell type can be analyzed for HLA class II and optionally also class I protein expression, reactivity with human T cells and NK cells, appropriate differentiation markers, and xenotransplantation in immunodeficient mice to examine in vivo developmental potential. A brief discussion of each differentiated cell type follows.

In certain embodiments, the cells of the invention can be differentiated to hematopoietic cells for treating various hematopoietic diseases currently treated by bone marrow transplantation. Patients receiving transfusion can become refractory to platelet transfusions due to HLA mismatches. Anemic or cytopenic patients can be treated by delivering the cells of the invention-derived erythrocytes, platelets or neutrophils to treat bleeding or infection.

Further, stem cells of the invention-derived dendritic cells are antigen-presenting cells that can be used as cellular vaccines when properly engineered. In certain embodiments, the cells of the invention engineered to express an HLA class II protein or a single chain fusion HLA class II protein and optionally also a single chain fusion HLA class I protein and a unique peptide antigen are used to vaccinate against specific pathogen or tumor antigens. In certain other embodiments, differentiated HLA class II deficient, HLA class I deficient, or HLA class I/class II deficient cytotoxic lymphocytes with HLA-restricted reactivity against specific antigens are used to eliminate infected cells or tumor cells.

To obtain hematopoietic cells, the pluripotent cells are first allowed to form embryoid bodies, thereafter non-adherent cells were cultured in the presence of hematopoietic cytokines to develop into specific cell lineages. The differentiation of hematopoietic cells from the cells of the invention that express an HLA class II protein or a single chain fusion HLA class II protein and optionally also a single chain fusion HLA class I protein can be analyzed by flow cytometry and colony assays. The different cell populations are sorted based on their surface markers, and used to monitor the expression of HLA genes and reactivity with human NK cells and T cells as measured by Elispot, mixed lymphocyte reactions, and cytotoxicity assays. The effectiveness of the single chain fusion HLA constructs on suppression of NK cell-mediated killing can be examined at different stages of differentiation and transplantation. See Bix et al., 1991, Nature 349, 329-331. The hematopoietic stem cells can also be assayed using xenotransplantation models in, for example, immunodeficient mice (SCID-repopulating cells or SRCs).

The cells of the invention can be differentiated into hematopoietic cell either before or after the cells are administered to a patient. In certain preferred embodiments, the cell is a human cell and the patient is a human. In vitro hematopoietic differentiation can be performed according to established protocols. See for example, Slukvin et al., 2006, J Immunol 176:2924-32, and Chang et al., 2006, Blood 108:1515-23.

In certain other embodiments, the cells of the invention can be differentiated into mesenchymal stem cells. In certain embodiments, the cells of the invention express one or more HLA class II protein or single chain fusion HLA class II proteins and optionally also one or more single chain fusion HLA class I proteins. MSCs have the potential to form several differentiated cell types, including marrow stromal cells, adipocytes, osteoblasts, and chondrocytes. Thus, inducing pluripotent stem cells to form MSCs (iMSCs) is useful in treating skeletal and joint conditions. The iMSCs can be further differentiated into osteoblasts and formed bone in vivo. Deyle et al., 2012, Mol Ther. 20(1):204-13. Cellular responses of T cells and NK cells to ESCs, iMSCs, and their more terminally differentiated derivatives such as osteoblasts can be examined.

In certain particular embodiments, the mesenchymal stem cells are capable of differentiating into non-limiting examples of cell types such as marrow stromal cells, adipocytes, osteoblasts, osteocytes and chondrocytes. The cells of the invention are differentiated into mesenchymal stem cells either before or after the cells are administered to a patient. In certain preferred embodiments, the cell is a human cell and the patient is a human. In vitro mesenchymal differentiation can be performed according to established protocols. See for example, Deyle et al., supra.

In yet other particular embodiments, the cells of the invention can be differentiated into insulin-producing pancreatic islet cells. In certain embodiments, the cells of the invention express one or more HLA class II proteins or single chain fusion HLA class II proteins and optionally also one or more single chain fusion HLA class I proteins. The cells of the invention can be used to treat insulin-dependent diabetes mellitus. Advantageously, the transplanted cells do not need to reconstitute a functioning pancreas: they just need to secrete insulin in response to glucose levels. Therefore the treatment can succeed with different cell doses, with cells that are not perfectly differentiated into adult cell types, and when cells are transplanted into an ectopic location. Specific auto-antigens such as those derived from GAD65 or Insulin can cause autoimmune destruction of 13 cells in diabetes (Di Lorenzo et al., 2007, Clin Exp Immunol 148, 1-16). Thus, HLA class II deficient, HLA class I deficient, or HLA class I/class II deficient cells expressing single chain fusion HLA protein presenting a predetermined peptide antigen provide additional advantages in that they do not present these auto-antigens and can avoid autoimmune rejection and prevent a relapse of diabetes after transplantation.

The cells of the invention can be differentiated into pancreatic cells as described previously, which employs exposure of cells to different cytokines and drugs to promote sequential formation of mesendoderm, definitive endoderm, and pancreatic progenitors (Kroon et al., 2008, Nat Biotechnol 26, 443-452). These cells can be further cultured in implants in immunodeficient mice. The wild-type cells and cells of the invention with or without expressing one or more single chain fusion HLA class II proteins or both one or more single chain fusion HLA class II proteins and optionally also one or more single chain HLA class I proteins can be analyzed at different developmental stages for their reactivity with T cells and NK cells.

The cells of the invention are differentiated into pancreatic islet cell either before or after patient administration. In certain preferred embodiments, the cell is a human cell and the patient is a human. In vitro hematopoietic differentiation can be performed according to established protocols. See for example, Kroon et al., 2008, Nat Biotechnol 26, 443-452.

In certain other particular embodiments, the cells of the invention can be differentiated into cardiomyocytes. In certain embodiments, the cells of the invention further express one or more HLA class II proteins or single chain fusion HLA class II proteins and optionally also one or more single chain fusion HLA class I proteins. The common clinical problems of myocardial infarction and congestive heart failure can be treated by transplanting healthy stem cell-derived cardiomyocytes that engraft and re-establish functional myocardium. The cells of the invention-derived cardiomyocytes allow these treatments to proceed with pre-packaged cells and avoid the immunosuppression currently required for allogeneic heart transplants. Physiologically relevant tests can be performed on the cardiomyocytes derived from the cells of the invention, such as electrical conduction and contraction studies. HLA class II deficient, HLA class I deficient, or HLA class I/class II deficient stem cells or differentiated cardiomyocytes with or without expressing a single chain fusion HLA class I protein can be tested to determine their immunological reactivity when expressing cardiomyocyte genes, and to establish which HLA modifications minimize these immune responses.

The cells of the invention can be differentiated into cardiomyocytes either before or after the cells are administered to a patient. In certain preferred embodiments, the cell is a human cell and the patient is a human. In certain embodiments, the cells of the invention are differentiated into cardiomyocytes for treating diseases including without limitation myocardial infarction and congestive heart failure. In vitro cardiomyocyte differentiation can be performed according to established protocols. See for example, Laflamme et al., 2007, Nat Biotechnol 25, 1015-1024.

In yet other particular embodiments, the cells of the invention can be differentiated into keratinocytes. In certain embodiments, the cells of the invention used for differentiation into keratinocytes express one or more single chain fusion HLA class II proteins and optionally also one or more HLA class II proteins or single chain fusion HLA class I proteins. Severe burns and genetic skin conditions require treatment with skin grafts, and this is currently done with a variety of cell sources such as porcine skin grafts and cultured autologous human keratinocytes. Keratinocytes derived from the cells of the invention can provide a major clinical advance, since burns could be treated as an emergency with pre-packaged cells, and genetic diseases such as epidermolysis bullosum can be treated with otherwise normal HLA class II deficient, HLA class I deficient, or HLA class I/class II deficient cells that do not require correction of the responsible genetic mutations. In many cases the cells only need to engraft long enough for neighboring host cells to repopulate the affected area. For in vivo differentiation, the cells of the invention can be embedded in polyvinyl alcohol sponge (PVA)-collagen gel implants for transplantation into a recipient. The cells of the invention can be differentiated into keratinocytes either before or after transplantation. In certain preferred embodiments, the cell is a human cell and the patient is a human.

In yet another aspect, the invention provides a use of the cells of the invention for the preparation for a medicament for transplantation. In a related aspect, the invention provides a use of the cells of the invention for the preparation for a medicament for treating a disease condition.

Further, the cells of the invention can serve as a research tool to provide a system for studying the functions of immunoregulatory proteins in a HLA class II deficient, HLA class I deficient, or HLA class I/class II deficient genetic background. In certain embodiments, the cells of the invention further express one or more HLA class II proteins or single chain fusion HLA class II proteins and optionally also one or more single chain fusion HLA class I proteins. Accordingly, in a related aspect, the invention provides a method of determining the function of an immunoregulatory protein comprising the steps of introducing one or more immunoregulatory genes into the cells of the invention of the invention and assaying for the activities of the immunoregulatory genes. In certain preferred embodiments, the cell is a human cell. For example, the cells of the invention can be used to study the function of an immune regulatory gene, or to study an immune response, in the absence of unwanted HLA class II antigens or HLA class I/class II antigens. In a further related aspect, the invention provides a method of identifying a compound or molecule that modulates the function of the immunoregulatory protein comprising the steps of contacting the HLA class II deficient cells, HLA class I deficient cells, or HLA class I/class II deficient cells comprising the one or more immunoregulatory genes with a compound or molecule of interest and assaying for the activities of the immunoregulatory genes. In certain preferred embodiments, the cell is a human cell.

In a related aspect, the invention provides kits that comprise the HLA class II deficient, HLA class I deficient, or HLA class I/class II deficient cells of the invention and an implant, wherein the implant comprises the cells of the invention.

In yet another aspect, the invention provides an in vivo research tool in a mammal, particular in a non-human primate, that are administered the cells of the invention, for studying the functions of immunoregulatory genes, or identifying a compound that modulates the function of an immunoregulatory gene in the administered cells in an HLA class II deficient, HLA class I deficient, or HLA class I/class II deficient genetic background. In certain embodiments, the cells of the invention further express one or more HLA class II proteins or single chain fusion HLA class II proteins and optionally also one or more single chain fusion HLA class I proteins.

Mice, especially immune deficient mice, have been used as a model system for studying human cells in vivo. Human stem cells can behave differently in mice. In addition, the mouse and human immune systems have different HLA class II genes, NK cell receptors and non-classical MHC class I genes (e.g. HLA-E, F and G). Therefore, a *Macaca*

*nemestrina* (Mn, pigtailed macaque) model can be developed to study the cells of the invention. The *Macaca mulatta* genome has been sequenced, which is highly homologous to the nemestrina genome. Further, the organization of macaque MHC loci is similar to human HLA, including the non-classical genes. Homologs of the human HLA-E and HLA-G genes have been identified in macaques. The macaque MHC loci also contain homologs of many human NK cell receptors. Human and Mn HLA class II deficient, HLA class I deficient, or HLA class I/class II deficient ESCs can be used for transplantation in macaques.

MHC class II-deficient of MHC class I/class II-deficient macaque ESCs can be developed using the same AAV-mediated gene targeting strategy described for human cells. Mn versions of the single chain fusion HLA class II proteins and optionally single chain fusion HLA class I proteins are expressed in the HLA class II or HLA class II/class I deficient macaques ESCs using the analogous viral vectors as described above.

Cells can be expanded in vitro and labeled with a vector expressing GFP for subsequent identification of transplanted cells. The cells can be embedded in polyvinyl alcohol sponge (PVA)-collagen gel implants, and placed subdermally into macaques. The implants can be harvested, sectioned and stained to determine the cell types that are present. Specific antibodies can be used to identify the differentiated cell types formed by the transplanted cells.

Any and every embodiment described above applies to any and every aspect of the invention, unless the context clearly indicates otherwise. All embodiments within and between different aspects can be combined unless the context clearly dictates otherwise.

EXAMPLES

Example 1 Construction of Human Embryonic Stem Cells with Knockout Mutation in RFXANK Gene FIG. 1 shows the structure of exemplary two adeno-associated virus (AAV) gene targeting vectors, designed to insert either a TKNeo (AAV-RFXANK-ETKNpA) or HyTK (AAV-RFXANK-HyTK) gene controlled by an EF1alpha promoter (EF) into exon 3 of the RFXANK gene, which is also shown below the vectors. Selection of vector-infected cells with G418 or hygromycin (Hygro) allows one to isolate cells targeted by the TKNeo or HyTK vectors respectively. Subsequent expression of Cre recombinase and selection with gancyclovir (GCV) then allows one to isolate clones that have removed the TKNeo or HyTK genes, leaving behind two inactivated RFXANK alleles with stop codons in all 3 reading frames, a loxP site, and a polyadenylation site (StopX3-loxP-pA). LoxP is the recombination site for Cre recombinase. ITR is a vector inverted terminal repeat. Similar vectors could be designed to target other genes.

The AAV-RFXANK-ETKNpA vector (SEQ ID NO: 56) was used to create a knockout mutation in a first allele of the RFXANK gene. Human embryonic stem cells were infected with AAV-RFXANK-ETKNpA and screened for targeting by PCR using a forward primer homologous to the neomycin sequence of the selection cassette and a reverse primer homologous to the RFXANK gene which was outside the targeting homology arm, as indicated by the arrows above. As shown in FIG. 2, 5 positive clones of the correct size are shown above out of 40 clones screened yielding a targeting frequency of 12.5%.

---

What is claimed is:

1. An isolated cell comprising a genetically engineered disruption in all copies of a human leukocyte antigen (HLA) class II-related gene, wherein the cell is a human cell, wherein:

a) the HLA class II-related gene is selected from the group consisting of regulatory factor X-associated ankyrin-containing protein, regulatory factor 5, regulatory factor X associated protein, class II transactivator; and b) the cell further comprises one or more polynucleotides, wherein the one or more polynucleotides is capable of encoding a single chain fusion HLA class I protein, wherein the single chain fusion HLA class I protein comprises at least a portion of B2M (SEQ ID NO:2) covalently linked to at least a portion of a non-classical HLA class I α chain; and c) the cell further comprises a genetically engineered disruption in the endogenous β2-microglobulin (B2M) gene (SEQ ID NO: 1); and d) wherein the single chain fusion HLA class I protein is capable of engaging inhibitory receptors on the surface of NK cells.

2. The cell of claim 1, wherein the HLA class II-related gene is regulatory factor X associated ankyrin-containing protein.

3. The cell of claim 1, wherein the single chain fusion HLA class I protein comprises at least a portion of B2M (SEQ ID NO: 2) covalently linked to at least a portion of HLA-E (SEQ ID NO: 10), HLA-F (SEQ ID NO: 12) or HLA-G (SEQ ID NO: 14).

4. The cell of claim 1, wherein the cell comprises genetically engineered disruptions in all copies of the endogenous cell B2M gene.

5. The cell of claim 1, wherein the cell has a normal karyotype.

6. The cell of claim 1, wherein the cell is a non-transformed cell.

7. The cell of claim 1, wherein the cell is a stem cell.

8. The cell of claim 7, wherein the stem cell is selected from the group consisting of a pluripotent stem cell, a hematopoietic stem cell, an embryonic stem cell, an induced pluripotent stem cell, an adult stem cell, a liver stem cell, a neural stem cell, a pancreatic stem cell and a mesenchymal stem cell.

9. The cell of claim 7, wherein the stem cell is a pluripotent stem cell.

10. The cell of claim 1, wherein the cell is a differentiated cell.

11. The cell of claim 10, wherein the differentiated cell is selected from the group consisting of a dendritic cell, a pancreatic islet cell, a liver cell, a muscle cell, a keratinocyte, a neuronal cell, a hematopoietic cell, a lymphocyte, a red blood cell, a platelet, a skeletal muscle cell, an ocular cell, a mesenchymal cell, a fibroblast, a lung cell, a GI tract cell, a vascular cell, an endocrine cell, an adipocyte, a marrow stromal cell, an osteoblast, a chrondrocyte, and a cardiomyocyte.

12. The cell of claim 1, wherein the single chain fusion HLA class I protein comprises at least a portion of B2M (SEQ ID NO: 2) covalently linked to at least a portion of HLA-E (SEQ ID NO: 10).

13. The cell of claim 1, wherein the single chain fusion HLA class I protein comprises at least a portion of B2M (SEQ ID NO: 2) covalently linked to at least a portion of HLA-F (SEQ ID NO: 12).

14. The cell of claim 1, wherein the single chain fusion HLA class I protein comprises at least a portion of B2M (SEQ ID NO: 2) covalently linked to at least a portion of HLA-G (SEQ ID NO: 14).

* * * * *

SEQUENCE LISTING

```
<160> NUMBER OF SEQ ID NOS: 56

<210> SEQ ID NO 1
<211> LENGTH: 987
<212> TYPE: DNA
<213> ORGANISM: Homo sapiens
<220> FEATURE:
<221> NAME/KEY: CDS
<222> LOCATION: (61)..(420)

<400> SEQUENCE: 1
aatataagtg gaggcgtcgc gctggcgggc attcctgaag ctgacagcat tcgggccgag        60 atg tct cgc tcc gtg gcc tta gct gtg ctc gcg cta ctc tct ctt tct       108
Met Ser Arg Ser Val Ala Leu Ala Val Leu Ala Leu Leu Ser Leu Ser
1               5                   10                  15 ggc ctg gag gct atc cag cgt act cca aag att cag gtt tac tca cgt       156
Gly Leu Glu Ala Ile Gln Arg Thr Pro Lys Ile Gln Val Tyr Ser Arg
                20                  25                  30 cat cca gca gag aat gga aag tca aat ttc ctg aat tgc tat gtg tct       204
His Pro Ala Glu Asn Gly Lys Ser Asn Phe Leu Asn Cys Tyr Val Ser
            35                  40                  45 ggg ttt cat cca tcc gac att gaa gtt gac tta ctg aag aat gga gag       252
Gly Phe His Pro Ser Asp Ile Glu Val Asp Leu Leu Lys Asn Gly Glu
        50                  55                  60 aga att gaa aaa gtg gag cat tca gac ttg tct ttc agc aag gac tgg       300
Arg Ile Glu Lys Val Glu His Ser Asp Leu Ser Phe Ser Lys Asp Trp
65                  70                  75                  80 tct ttc tat ctc ttg tac tac act gaa ttc acc ccc act gaa aaa gat       348
Ser Phe Tyr Leu Leu Tyr Tyr Thr Glu Phe Thr Pro Thr Glu Lys Asp
                85                  90                  95
```

```
gag tat gcc tgc cgt gtg aac cat gtg act ttg tca cag ccc aag ata        396
Glu Tyr Ala Cys Arg Val Asn His Val Thr Leu Ser Gln Pro Lys Ile
            100                 105                 110 gtt aag tgg gat cga gac atg taa gcagcatcat ggaggtttga agatgccgca       450
Val Lys Trp Asp Arg Asp Met
        115 tttggattgg atgaattcca aattctgctt gcttgctttt taatattgat atgcttatac      510 acttacactt tatgcacaaa atgtaggggtt ataataatgt taacatggac atgatcttct     570 ttataattct actttgagtg ctgtctccat gtttgatgta tctgagcagg ttgctccaca      630 ggtagctcta ggagggctgg caacttagag gtggggagca gagaattctc ttatccaaca      690 tcaacatctt ggtcagattt gaactcttca atctcttgca ctcaaagctt gttaagatag      750 ttaagcgtgc ataagttaac ttccaattta catactctgc ttagaatttg ggggaaaatt      810 tagaaatata attgacagga ttattggaaa tttgttataa tgaatgaaac attttgtcat      870 ataagattca tatttacttc ttatacattt gataaagtaa ggcatggttg tggttaatct      930 ggtttatttt tgttccacaa gttaaataaa tcataaaact tgatgtgtta tctctta        987
```

```
<210> SEQ ID NO 2
<211> LENGTH: 119
<212> TYPE: PRT
<213> ORGANISM: Homo sapiens

<400> SEQUENCE: 2

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115
```

```
<210> SEQ ID NO 3
<211> LENGTH: 1611
<212> TYPE: DNA
<213> ORGANISM: Homo sapiens
<220> FEATURE:
<221> NAME/KEY: CDS
<222> LOCATION: (85)..(1182)

<400> SEQUENCE: 3
gagaagccaa tcagtgtcgt cgcggtcgct gttctaaagt ccgcacgcac ccaccgggac        60
tcagattctc cccagacgcc gagg atg gcc gtc atg gcg ccc cga acc ctc          111
                          Met Ala Val Met Ala Pro Arg Thr Leu
                           1               5 ctc ctg cta ctc tcg ggg gcc ctg gcc ctg acc cag acc tgg gcg ggc         159
Leu Leu Leu Leu Ser Gly Ala Leu Ala Leu Thr Gln Thr Trp Ala Gly
10                  15                  20                  25
```

-continued

```
tcc cac tcc atg agg tat ttc ttc aca tcc gtg tcc cgg ccc ggc cgc       207
Ser His Ser Met Arg Tyr Phe Phe Thr Ser Val Ser Arg Pro Gly Arg
                30                  35                  40 ggg gag ccc cgc ttc atc gcc gtg ggc tac gtg gac gac acg cag ttc       255
Gly Glu Pro Arg Phe Ile Ala Val Gly Tyr Val Asp Asp Thr Gln Phe
            45                  50                  55 gtg cgg ttc gac agc gac gcc gcg agc cag aag atg gag ccg cgg gcg       303
Val Arg Phe Asp Ser Asp Ala Ala Ser Gln Lys Met Glu Pro Arg Ala
            60                  65                  70 ccg tgg ata gag cag gag ggg ccg gag tat tgg gac cag gag aca cgg       351
Pro Trp Ile Glu Gln Glu Gly Pro Glu Tyr Trp Asp Gln Glu Thr Arg
        75                  80                  85 aat atg aag gcc cac tca cag act gac cga gcg aac ctg ggg acc ctg       399
Asn Met Lys Ala His Ser Gln Thr Asp Arg Ala Asn Leu Gly Thr Leu
90                  95                  100                 105 cgc ggc tac tac aac cag agc gag gac ggt tct cac acc atc cag ata       447
Arg Gly Tyr Tyr Asn Gln Ser Glu Asp Gly Ser His Thr Ile Gln Ile
                110                 115                 120 atg tat ggc tgc gac gtg ggg ccg gac ggg cgc ttc ctc cgc ggg tac       495
Met Tyr Gly Cys Asp Val Gly Pro Asp Gly Arg Phe Leu Arg Gly Tyr
                125                 130                 135 cgg cag gac gcc tac gac ggc aag gat tac atc gcc ctg aac gag gac       543
Arg Gln Asp Ala Tyr Asp Gly Lys Asp Tyr Ile Ala Leu Asn Glu Asp
            140                 145                 150 ctg cgc tct tgg acc gcg gcg gac atg gca gct cag atc acc aag cgc       591
Leu Arg Ser Trp Thr Ala Ala Asp Met Ala Ala Gln Ile Thr Lys Arg
        155                 160                 165 aag tgg gag gcg gtc cat gcg gcg gag cag cgg aga gtc tac ctg gag       639
Lys Trp Glu Ala Val His Ala Ala Glu Gln Arg Arg Val Tyr Leu Glu
170                 175                 180                 185 ggc cgg tgc gtg gac ggg ctc cgc aga tac ctg gag aac ggg aag gag       687
Gly Arg Cys Val Asp Gly Leu Arg Arg Tyr Leu Glu Asn Gly Lys Glu
                190                 195                 200 acg ctg cag cgc acg gac ccc ccc aag aca cat atg acc cac cac ccc       735
Thr Leu Gln Arg Thr Asp Pro Pro Lys Thr His Met Thr His His Pro
                205                 210                 215 atc tct gac cat gag gcc acc ctg agg tgc tgg gcc ctg ggc ttc tac       783
Ile Ser Asp His Glu Ala Thr Leu Arg Cys Trp Ala Leu Gly Phe Tyr
                220                 225                 230 cct gcg gag atc aca ctg acc tgg cag cgg gat ggg gag gac cag acc       831
Pro Ala Glu Ile Thr Leu Thr Trp Gln Arg Asp Gly Glu Asp Gln Thr
        235                 240                 245 cag gac acg gag ctc gtg gag acc agg cct gca ggg gat gga acc ttc       879
Gln Asp Thr Glu Leu Val Glu Thr Arg Pro Ala Gly Asp Gly Thr Phe
250                 255                 260                 265 cag aag tgg gcg gct gtg gtg gtg cct tct gga gag gag cag aga tac       927
Gln Lys Trp Ala Ala Val Val Val Pro Ser Gly Glu Glu Gln Arg Tyr
                270                 275                 280 acc tgc cat gtg cag cat gag ggt ctg ccc aag ccc ctc acc ctg aga       975
Thr Cys His Val Gln His Glu Gly Leu Pro Lys Pro Leu Thr Leu Arg
                285                 290                 295 tgg gag ctg tct tcc cag ccc acc atc ccc atc gtg ggc atc att gct      1023
Trp Glu Leu Ser Ser Gln Pro Thr Ile Pro Ile Val Gly Ile Ile Ala
                300                 305                 310 ggc ctg gtt ctc ctt gga gct gtg atc act gga gct gtg gtc gct gcc      1071
Gly Leu Val Leu Leu Gly Ala Val Ile Thr Gly Ala Val Val Ala Ala
                315                 320                 325 gtg atg tgg agg agg aag agc tca gat aga aaa gga ggg agt tac act      1119
Val Met Trp Arg Arg Lys Ser Ser Asp Arg Lys Gly Gly Ser Tyr Thr
```

-continued

```
      330              335              340              345 cag gct gca agc agt gac agt gcc cag ggc tct gat gtg tct ctc aca    1167
Gln Ala Ala Ser Ser Asp Ser Ala Gln Gly Ser Asp Val Ser Leu Thr
                350              355              360 gct tgt aaa gtg tga gacagctgcc ttgtgtggga ctgagaggca agagttgttc    1222
Ala Cys Lys Val
            365 ctgcccttcc ctttgtgact tgaagaaccc tgactttgtt tctgcaaagg cacctgcatg    1282 tgtctgtgtt cgtgtaggca taatgtgagg aggtggggag agcaccccac ccccatgtcc    1342 accatgaccc tcttcccacg ctgacctgtg ctccctctcc aatcatcttt cctgttccag    1402 agaggtgggg ctgaggtgtc tccatctctg tctcaacttc atggtgcact gagctgtaac    1462 ttcttccttc cctattaaaa ttagaacctg agtataaatt tactttctca aattcttgcc    1522 atgagaggtt gatgagttaa ttaaaggaga agattcctaa aatttgagag acaaaattaa    1582 tggaacgcat gagaaccttc cagagtcca                                       1611

<210> SEQ ID NO 4
<211> LENGTH: 365
<212> TYPE: PRT
<213> ORGANISM: Homo sapiens

<400> SEQUENCE: 4

Met Ala Val Met Ala Pro Arg Thr Leu Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Lys Met Glu Pro Arg Ala Pro Trp Ile Glu Gln Glu Gly
65                  70                  75                  80

Pro Glu Tyr Trp Asp Gln Glu Thr Arg Asn Met Lys Ala His Ser Gln
                85                  90                  95

Thr Asp Arg Ala Asn Leu Gly Thr Leu Arg Gly Tyr Tyr Asn Gln Ser
            100                 105                 110

Glu Asp Gly Ser His Thr Ile Gln Ile Met Tyr Gly Cys Asp Val Gly
        115                 120                 125

Pro Asp Gly Arg Phe Leu Arg Gly Tyr Arg Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Lys Arg Lys Trp Glu Ala Val His Ala
                165                 170                 175

Ala Glu Gln Arg Arg Val Tyr Leu Glu Gly Arg Cys Val Asp Gly Leu
            180                 185                 190

Arg Arg Tyr Leu Glu Asn Gly Lys Glu Thr Leu Gln Arg Thr Asp Pro
        195                 200                 205

Pro Lys Thr His Met Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255
```

-continued

```
Thr Arg Pro Ala Gly Asp Gly Thr Phe Gln Lys Trp Ala Ala Val Val
            260                 265             270

Val Pro Ser Gly Glu Glu Gln Arg Tyr Thr Cys His Val Gln His Glu
            275                 280             285

Gly Leu Pro Lys Pro Leu Thr Leu Arg Trp Glu Leu Ser Ser Gln Pro
            290                 295             300

Thr Ile Pro Ile Val Gly Ile Ile Ala Gly Leu Val Leu Leu Gly Ala
305                 310             315                 320

Val Ile Thr Gly Ala Val Val Ala Ala Val Met Trp Arg Arg Lys Ser
            325                 330             335

Ser Asp Arg Lys Gly Gly Ser Tyr Thr Gln Ala Ala Ser Ser Asp Ser
            340                 345             350

Ala Gln Gly Ser Asp Val Ser Leu Thr Ala Cys Lys Val
            355                 360             365
```

```
<210> SEQ ID NO 5
<211> LENGTH: 1578
<212> TYPE: DNA
<213> ORGANISM: Homo sapiens
<220> FEATURE:
<221> NAME/KEY: CDS
<222> LOCATION: (55)..(1143)

<400> SEQUENCE: 5
agttctaaag tccccacgca cccacccgga ctcagagtct cctcagacgc cgag atg        57
                                                              Met
                                                              1 ctg gtc atg gcg ccc cga acc gtc ctc ctg ctg ctc tcg gcg gcc ctg       105
Leu Val Met Ala Pro Arg Thr Val Leu Leu Leu Leu Ser Ala Ala Leu
            5                  10                  15 gcc ctg acc gag acc tgg gcc ggc tcc cac tcc atg agg tat ttc tac       153
Ala Leu Thr Glu Thr Trp Ala Gly Ser His Ser Met Arg Tyr Phe Tyr
            20                  25                  30 acc tcc gtg tcc cgg ccc ggc cgc ggg gag ccc cgc ttc atc tca gtg       201
Thr Ser Val Ser Arg Pro Gly Arg Gly Glu Pro Arg Phe Ile Ser Val
        35                  40                  45 ggc tac gtg gac gac acc cag ttc gtg agg ttc gac agc gac gcc gcg       249
Gly Tyr Val Asp Asp Thr Gln Phe Val Arg Phe Asp Ser Asp Ala Ala
50                  55                  60                  65 agt ccg aga gag gag ccg cgg gcg ccg tgg ata gag cag gag ggg ccg       297
Ser Pro Arg Glu Glu Pro Arg Ala Pro Trp Ile Glu Gln Glu Gly Pro
                70                  75                  80 gag tat tgg gac cgg aac aca cag atc tac aag gcc cag gca cag act       345
Glu Tyr Trp Asp Arg Asn Thr Gln Ile Tyr Lys Ala Gln Ala Gln Thr
            85                  90                  95 gac cga gag agc ctg cgg aac ctg cgc ggc tac tac aac cag agc gag       393
Asp Arg Glu Ser Leu Arg Asn Leu Arg Gly Tyr Tyr Asn Gln Ser Glu
            100                 105             110 gcc ggg tct cac acc ctc cag agc atg tac ggc tgc gac gtg ggg ccg       441
Ala Gly Ser His Thr Leu Gln Ser Met Tyr Gly Cys Asp Val Gly Pro
            115                 120             125 gac ggg cgc ctc ctc cgc ggg cat gac cag tac gcc tac gac ggc aag       489
Asp Gly Arg Leu Leu Arg Gly His Asp Gln Tyr Ala Tyr Asp Gly Lys
130                 135             140                 145 gat tac atc gcc ctg aac gag gac ctg cgc tcc tgg acc gcc gcg gac       537
Asp Tyr Ile Ala Leu Asn Glu Asp Leu Arg Ser Trp Thr Ala Ala Asp
                150                 155             160 acg gcg gct cag atc acc cag cgc aag tgg gag gcg gcc cgt gag gcg       585
Thr Ala Ala Gln Ile Thr Gln Arg Lys Trp Glu Ala Ala Arg Glu Ala
```

```
                165                 170                 175 gag cag cgg aga gcc tac ctg gag ggc gag tgc gtg gag tgg ctc cgc    633
Glu Gln Arg Arg Ala Tyr Leu Glu Gly Glu Cys Val Glu Trp Leu Arg
        180                 185                 190 aga tac ctg gag aac ggg aag gac aag ctg gag cgc gct gac ccc cca    681
Arg Tyr Leu Glu Asn Gly Lys Asp Lys Leu Glu Arg Ala Asp Pro Pro
    195                 200                 205 aag aca cac gtg acc cac cac ccc atc tct gac cat gag gcc acc ctg    729
Lys Thr His Val Thr His His Pro Ile Ser Asp His Glu Ala Thr Leu
210                 215                 220                 225 agg tgc tgg gcc ctg ggt ttc tac cct gcg gag atc aca ctg acc tgg    777
Arg Cys Trp Ala Leu Gly Phe Tyr Pro Ala Glu Ile Thr Leu Thr Trp
            230                 235                 240 cag cgg gat ggc gag gac caa act cag gac act gag ctt gtg gag acc    825
Gln Arg Asp Gly Glu Asp Gln Thr Gln Asp Thr Glu Leu Val Glu Thr
            245                 250                 255 aga cca gca gga gat aga acc ttc cag aag tgg gca gct gtg gtg gtg    873
Arg Pro Ala Gly Asp Arg Thr Phe Gln Lys Trp Ala Ala Val Val Val
        260                 265                 270 cct tct gga gaa gag cag aga tac aca tgc cat gta cag cat gag ggg    921
Pro Ser Gly Glu Glu Gln Arg Tyr Thr Cys His Val Gln His Glu Gly
    275                 280                 285 ctg ccg aag ccc ctc acc ctg aga tgg gag ccg tct tcc cag tcc acc    969
Leu Pro Lys Pro Leu Thr Leu Arg Trp Glu Pro Ser Ser Gln Ser Thr
290                 295                 300                 305 gtc ccc atc gtg ggc att gtt gct ggc ctg gct gtc cta gca gtt gtg    1017
Val Pro Ile Val Gly Ile Val Ala Gly Leu Ala Val Leu Ala Val Val
            310                 315                 320 gtc atc gga gct gtg gtc gct gct gtg atg tgt agg agg aag agt tca    1065
Val Ile Gly Ala Val Val Ala Ala Val Met Cys Arg Arg Lys Ser Ser
        325                 330                 335 ggt gga aaa gga ggg agc tac tct cag gct gcg tgc agc gac agt gcc    1113
Gly Gly Lys Gly Gly Ser Tyr Ser Gln Ala Ala Cys Ser Asp Ser Ala
        340                 345                 350 cag ggc tct gat gtg tct ctc aca gct tga aaagcctgag acagctgtct    1163
Gln Gly Ser Asp Val Ser Leu Thr Ala
    355                 360 tgtgagggac tgagatgcag gatttcttca cgcctcccct ttgtgacttc aagagcctct    1223
ggcatctctt tctgcaaagg cacctgaatg tgtctgcgtc cctgttagca taatgtgagg    1283
aggtggagag acagcccacc cttgtgtcca ctgtgacccc tgttcccatg ctgacctgtg    1343
tttcctcccc agtcatcttt cttgttccag agaggtgggg ctggatgtct ccatctctgt    1403
ctcaacttta cgtgcactga gctgcaactt cttacttccc tactgaaaat aagaatctga    1463
atataaattt gttttctcaa atatttgcta tgagaggttg atggattaat taaataagtc    1523
aattcctgga atttgagaga gcaaataaag acctgagaac cttccagaaa aaaaa    1578

<210> SEQ ID NO 6
<211> LENGTH: 362
<212> TYPE: PRT
<213> ORGANISM: Homo sapiens

<400> SEQUENCE: 6

Met Leu Val Met Ala Pro Arg Thr Val Leu Leu Leu Leu Ser Ala Ala
1               5                   10                  15

Leu Ala Leu Thr Glu Thr Trp Ala Gly Ser His Ser Met Arg Tyr Phe
            20                  25                  30

Tyr Thr Ser Val Ser Arg Pro Gly Arg Gly Glu Pro Arg Phe Ile Ser
```

-continued

```
                35                    40                    45
Val Gly Tyr Val Asp Asp Thr Gln Phe Val Arg Phe Asp Ser Asp Ala
    50                    55                    60
Ala Ser Pro Arg Glu Glu Pro Arg Ala Pro Trp Ile Glu Gln Glu Gly
65                    70                    75                    80
Pro Glu Tyr Trp Asp Arg Asn Thr Gln Ile Tyr Lys Ala Gln Ala Gln
                85                    90                    95
Thr Asp Arg Glu Ser Leu Arg Asn Leu Arg Gly Tyr Tyr Asn Gln Ser
            100                   105                   110
Glu Ala Gly Ser His Thr Leu Gln Ser Met Tyr Gly Cys Asp Val Gly
            115                   120                   125
Pro Asp Gly Arg Leu Leu Arg Gly His Asp Gln Tyr Ala Tyr Asp Gly
    130                   135                   140
Lys Asp Tyr Ile Ala Leu Asn Glu Asp Leu Arg Ser Trp Thr Ala Ala
145                   150                   155                   160
Asp Thr Ala Ala Gln Ile Thr Gln Arg Lys Trp Glu Ala Ala Arg Glu
                165                   170                   175
Ala Glu Gln Arg Arg Ala Tyr Leu Glu Gly Glu Cys Val Glu Trp Leu
            180                   185                   190
Arg Arg Tyr Leu Glu Asn Gly Lys Asp Lys Leu Glu Arg Ala Asp Pro
            195                   200                   205
Pro Lys Thr His Val Thr His His Pro Ile Ser Asp His Glu Ala Thr
    210                   215                   220
Leu Arg Cys Trp Ala Leu Gly Phe Tyr Pro Ala Glu Ile Thr Leu Thr
225                   230                   235                   240
Trp Gln Arg Asp Gly Glu Asp Gln Thr Gln Asp Thr Glu Leu Val Glu
                245                   250                   255
Thr Arg Pro Ala Gly Asp Arg Thr Phe Gln Lys Trp Ala Ala Val Val
            260                   265                   270
Val Pro Ser Gly Glu Glu Gln Arg Tyr Thr Cys His Val Gln His Glu
            275                   280                   285
Gly Leu Pro Lys Pro Leu Thr Leu Arg Trp Glu Pro Ser Ser Gln Ser
    290                   295                   300
Thr Val Pro Ile Val Gly Ile Val Ala Gly Leu Ala Val Leu Ala Val
305                   310                   315                   320
Val Val Ile Gly Ala Val Val Ala Ala Val Met Cys Arg Arg Lys Ser
                325                   330                   335
Ser Gly Gly Lys Gly Gly Ser Tyr Ser Gln Ala Ala Cys Ser Asp Ser
            340                   345                   350
Ala Gln Gly Ser Asp Val Ser Leu Thr Ala
        355                   360
```

<210> SEQ ID NO 7
<211> LENGTH: 1586
<212> TYPE: DNA
<213> ORGANISM: Homo sapiens
<220> FEATURE:
<221> NAME/KEY: CDS
<222> LOCATION: (66)..(1166)

<400> SEQUENCE: 7

```
tccgcagtcc cggttctaaa gtccccagtc acccacccgg actcacattc tccccagagg     60 ccgag atg cgg gtc atg gcg ccc cga gcc ctc ctc ctg ctg ctc tcg gga    110
      Met Arg Val Met Ala Pro Arg Ala Leu Leu Leu Leu Leu Ser Gly
      1               5                   10                  15
```

-continued

```
ggc ctg gcc ctg acc gag acc tgg gcc tgc tcc cac tcc atg agg tat     158
Gly Leu Ala Leu Thr Glu Thr Trp Ala Cys Ser His Ser Met Arg Tyr
         20                  25                  30 ttc gac acc gcc gtg tcc cgg ccc ggc cgc gga gag ccc cgc ttc atc     206
Phe Asp Thr Ala Val Ser Arg Pro Gly Arg Gly Glu Pro Arg Phe Ile
         35                  40                  45 tca gtg ggc tac gtg gac gac acg cag ttc gtg cgg ttc gac agc gac     254
Ser Val Gly Tyr Val Asp Asp Thr Gln Phe Val Arg Phe Asp Ser Asp
         50                  55                  60 gcc gcg agt ccg aga ggg gag ccg cgg gcg ccg tgg gtg gag cag gag     302
Ala Ala Ser Pro Arg Gly Glu Pro Arg Ala Pro Trp Val Glu Gln Glu
65                  70                  75 ggg ccg gag tat tgg gac cgg gag aca cag aag tac aag cgc cag gca     350
Gly Pro Glu Tyr Trp Asp Arg Glu Thr Gln Lys Tyr Lys Arg Gln Ala
80                  85                  90                  95 cag gct gac cga gtg agc ctg cgg aac ctg cgc ggc tac tac aac cag     398
Gln Ala Asp Arg Val Ser Leu Arg Asn Leu Arg Gly Tyr Tyr Asn Gln
                100                 105                 110 agc gag gac ggg tct cac acc ctc cag agg atg tct ggc tgc gac ctg     446
Ser Glu Asp Gly Ser His Thr Leu Gln Arg Met Ser Gly Cys Asp Leu
             115                 120                 125 ggg ccc gac ggg cgc ctc ctc cgc ggg tat gac cag tcc gcc tac gac     494
Gly Pro Asp Gly Arg Leu Leu Arg Gly Tyr Asp Gln Ser Ala Tyr Asp
         130                 135                 140 ggc aag gat tac atc gcc ctg aac gag gac ctg cgc tcc tgg acc gcc     542
Gly Lys Asp Tyr Ile Ala Leu Asn Glu Asp Leu Arg Ser Trp Thr Ala
         145                 150                 155 gcg gac acc gcg gct cag atc acc cag cgc aag ttg gag gcg gcc cgt     590
Ala Asp Thr Ala Ala Gln Ile Thr Gln Arg Lys Leu Glu Ala Ala Arg
160                 165                 170                 175 gcg gcg gag cag ctg aga gcc tac ctg gag ggc acg tgc gtg gag tgg     638
Ala Ala Glu Gln Leu Arg Ala Tyr Leu Glu Gly Thr Cys Val Glu Trp
                180                 185                 190 ctc cgc aga tac ctg gag aac ggg aag gag acg ctg cag cgc gca gaa     686
Leu Arg Arg Tyr Leu Glu Asn Gly Lys Glu Thr Leu Gln Arg Ala Glu
             195                 200                 205 ccc cca aag aca cac gtg acc cac cac ccc ctc tct gac cat gag gcc     734
Pro Pro Lys Thr His Val Thr His His Pro Leu Ser Asp His Glu Ala
         210                 215                 220 acc ctg agg tgc tgg gcc ctg ggc ttc tac cct gcg gag atc aca ctg     782
Thr Leu Arg Cys Trp Ala Leu Gly Phe Tyr Pro Ala Glu Ile Thr Leu
         225                 230                 235 acc tgg cag cgg gat ggg gag gac cag acc cag gac acc gag ctt gtg     830
Thr Trp Gln Arg Asp Gly Glu Asp Gln Thr Gln Asp Thr Glu Leu Val
240                 245                 250                 255 gag acc agg cca gca gga gat gga acc ttc cag aag tgg gca gct gtg     878
Glu Thr Arg Pro Ala Gly Asp Gly Thr Phe Gln Lys Trp Ala Ala Val
                260                 265                 270 gtg gtg cct tct gga caa gag cag aga tac acg tgc cat atg cag cac     926
Val Val Pro Ser Gly Gln Glu Gln Arg Tyr Thr Cys His Met Gln His
             275                 280                 285 gag ggg ctg caa gag ccc ctc acc ctg agc tgg gag cca tct tcc cag     974
Glu Gly Leu Gln Glu Pro Leu Thr Leu Ser Trp Glu Pro Ser Ser Gln
         290                 295                 300 ccc acc atc ccc atc atg ggc atc gtt gct ggc ctg gct gtc ctg gtt    1022
Pro Thr Ile Pro Ile Met Gly Ile Val Ala Gly Leu Ala Val Leu Val
         305                 310                 315 gtc cta gct gtc ctt gga gct gtg gtc acc gct atg atg tgt agg agg    1070
Val Leu Ala Val Leu Gly Ala Val Val Thr Ala Met Met Cys Arg Arg
320                 325                 330                 335
```

-continued

```
aag agc tca ggt gga aaa gga ggg agc tgc tct cag gct gcg tgc agc      1118
Lys Ser Ser Gly Gly Lys Gly Gly Ser Cys Ser Gln Ala Ala Cys Ser
            340                 345                 350 aac agt gcc cag ggc tct gat gag tct ctc atc act tgt aaa gcc tga      1166
Asn Ser Ala Gln Gly Ser Asp Glu Ser Leu Ile Thr Cys Lys Ala
            355                 360                 365 gacagctgcc tgtgtgggac tgagatgcag gatttcttca cacctctcct ttgtgacttc    1226
aagagcctct ggcatctctt tctgcaaagg cacctgaatg tgtctgcgtt cctgttagca    1286
taatgtgagg aggtggagag acagcccacc cccgtgtcca ccgtgacccc tgtccccaca    1346
ctgacctgtg ttccctcccc gatcatcttt cctgttccag agaggtgggg ctggatgtct    1406
ccatctctgt ctcaaattca tggtgcactg agctgcaact tcttacttcc ctaatgaagt    1466
taagaacctg aatataaatt tgtgttctca aatatttgct atgaagcgtt gatggattaa    1526
ttaaataagt caattcctag aagttgagag agcaaataaa gacctgagaa ccttccagaa    1586
```

```
<210> SEQ ID NO 8
<211> LENGTH: 366
<212> TYPE: PRT
<213> ORGANISM: Homo sapiens

<400> SEQUENCE: 8

Met Arg Val Met Ala Pro Arg Ala Leu Leu Leu Leu Leu Ser Gly Gly
1               5                   10                  15

Leu Ala Leu Thr Glu Thr Trp Ala Cys Ser His Ser Met Arg Tyr Phe
                20                  25                  30

Asp Thr Ala Val Ser Arg Pro Gly Arg Gly Glu Pro Arg Phe Ile Ser
            35                  40                  45

Val Gly Tyr Val Asp Asp Thr Gln Phe Val Arg Phe Asp Ser Asp Ala
        50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Ala Asp Arg Val Ser Leu Arg Asn Leu Arg Gly Tyr Tyr Asn Gln Ser
            100                 105                 110

Glu Asp Gly Ser His Thr Leu Gln Arg Met Ser Gly Cys Asp Leu Gly
            115                 120                 125

Pro Asp Gly Arg Leu Leu Arg Gly Tyr Asp Gln Ser Ala Tyr Asp Gly
        130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Leu Glu Ala Ala Arg Ala
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Ala Glu Pro
            195                 200                 205

Pro Lys Thr His Val Thr His His Pro Leu Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255
```

-continued

```
Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Met Gln His Glu
        275                 280                 285

Gly Leu Gln Glu Pro Leu Thr Leu Ser Trp Glu Pro Ser Ser Gln Pro
    290                 295                 300

Thr Ile Pro Ile Met Gly Ile Val Ala Gly Leu Ala Val Leu Val Val
305                 310                 315                 320

Leu Ala Val Leu Gly Ala Val Val Thr Ala Met Met Cys Arg Arg Lys
                325                 330                 335

Ser Ser Gly Gly Lys Gly Gly Ser Cys Ser Gln Ala Ala Cys Ser Asn
            340                 345                 350

Ser Ala Gln Gly Ser Asp Glu Ser Leu Ile Thr Cys Lys Ala
        355                 360                 365
```

```
<210> SEQ ID NO 9
<211> LENGTH: 2679
<212> TYPE: DNA
<213> ORGANISM: Homo sapiens
<220> FEATURE:
<221> NAME/KEY: CDS
<222> LOCATION: (127)..(1203)

<400> SEQUENCE: 9
gcagactcag ttctcattcc caatgggtgt cgggtttcta gagaagccaa tcagcgtcgc      60
cacgactccc gactataaag tccccatccg gactcaagaa gttctcagga ctcagaggct     120 gggatc atg gta gat gga acc ctc ctt tta ctc ctc tcg gag gcc ctg        168
       Met Val Asp Gly Thr Leu Leu Leu Leu Leu Ser Glu Ala Leu
       1               5                   10 gcc ctt acc cag acc tgg gcg ggc tcc cac tcc ttg aag tat ttc cac      216
Ala Leu Thr Gln Thr Trp Ala Gly Ser His Ser Leu Lys Tyr Phe His
15                  20                  25                  30 act tcc gtg tcc cgg ccc ggc cgc ggg gag ccc cgc ttc atc tct gtg      264
Thr Ser Val Ser Arg Pro Gly Arg Gly Glu Pro Arg Phe Ile Ser Val
                35                  40                  45 ggc tac gtg gac gac acc cag ttc gtg cgc ttc gac aac gac gcc gcg      312
Gly Tyr Val Asp Asp Thr Gln Phe Val Arg Phe Asp Asn Asp Ala Ala
            50                  55                  60 agt ccg agg atg gtg ccg cgg gcg ccg tgg atg gag cag gag ggg tca      360
Ser Pro Arg Met Val Pro Arg Ala Pro Trp Met Glu Gln Glu Gly Ser
        65                  70                  75 gag tat tgg gac cgg gag aca cgg agc gcc agg gac acc gca cag att      408
Glu Tyr Trp Asp Arg Glu Thr Arg Ser Ala Arg Asp Thr Ala Gln Ile
    80                  85                  90 ttc cga gtg aat ctg cgg acg ctg cgc ggc tac tac aat cag agc gag      456
Phe Arg Val Asn Leu Arg Thr Leu Arg Gly Tyr Tyr Asn Gln Ser Glu
95                  100                 105                 110 gcc ggg tct cac acc ctg cag tgg atg cat ggc tgc gag ctg ggg ccc      504
Ala Gly Ser His Thr Leu Gln Trp Met His Gly Cys Glu Leu Gly Pro
                115                 120                 125 gac ggg cgc ttc ctc cgc ggg tat gaa cag ttc gcc tac gac ggc aag      552
Asp Gly Arg Phe Leu Arg Gly Tyr Glu Gln Phe Ala Tyr Asp Gly Lys
            130                 135                 140 gat tat ctc acc ctg aat gag gac ctg cgc tcc tgg acc gcg gtg gac      600
Asp Tyr Leu Thr Leu Asn Glu Asp Leu Arg Ser Trp Thr Ala Val Asp
        145                 150                 155 acg gcg gct cag atc tcc gag caa aag tca aat gat gcc tct gag gcg      648
Thr Ala Ala Gln Ile Ser Glu Gln Lys Ser Asn Asp Ala Ser Glu Ala
    160                 165                 170
```

-continued

```
gag cac cag aga gcc tac ctg gaa gac aca tgc gtg gag tgg ctc cac       696
Glu His Gln Arg Ala Tyr Leu Glu Asp Thr Cys Val Glu Trp Leu His
175                 180                 185                 190 aaa tac ctg gag aag ggg aag gag acg ctg ctt cac ctg gag ccc cca       744
Lys Tyr Leu Glu Lys Gly Lys Glu Thr Leu Leu His Leu Glu Pro Pro
                195                 200                 205 aag aca cac gtg act cac cac ccc atc tct gac cat gag gcc acc ctg       792
Lys Thr His Val Thr His His Pro Ile Ser Asp His Glu Ala Thr Leu
            210                 215                 220 agg tgc tgg gcc ctg ggc ttc tac cct gcg gag atc aca ctg acc tgg       840
Arg Cys Trp Ala Leu Gly Phe Tyr Pro Ala Glu Ile Thr Leu Thr Trp
        225                 230                 235 cag cag gat ggg gag ggc cat acc cag gac acg gag ctc gtg gag acc       888
Gln Gln Asp Gly Glu Gly His Thr Gln Asp Thr Glu Leu Val Glu Thr
    240                 245                 250 agg cct gca ggg gat gga acc ttc cag aag tgg gca gct gtg gtg gtg       936
Arg Pro Ala Gly Asp Gly Thr Phe Gln Lys Trp Ala Ala Val Val Val
255                 260                 265                 270 cct tct gga gag gag cag aga tac acg tgc cat gtg cag cat gag ggg       984
Pro Ser Gly Glu Glu Gln Arg Tyr Thr Cys His Val Gln His Glu Gly
                275                 280                 285 cta ccc gag ccc gtc acc ctg aga tgg aag ccg gct tcc cag ccc acc      1032
Leu Pro Glu Pro Val Thr Leu Arg Trp Lys Pro Ala Ser Gln Pro Thr
                290                 295                 300 atc ccc atc gtg ggc atc att gct ggc ctg gtt ctc ctt gga tct gtg      1080
Ile Pro Ile Val Gly Ile Ile Ala Gly Leu Val Leu Leu Gly Ser Val
            305                 310                 315 gtc tct gga gct gtg gtt gct gct gtg ata tgg agg aag aag agc tca      1128
Val Ser Gly Ala Val Val Ala Ala Val Ile Trp Arg Lys Lys Ser Ser
        320                 325                 330 ggt gga aaa gga ggg agc tac tct aag gct gag tgg agc gac agt gcc      1176
Gly Gly Lys Gly Gly Ser Tyr Ser Lys Ala Glu Trp Ser Asp Ser Ala
335                 340                 345                 350 cag ggg tct gag tct cac agc ttg taa agcctgagac agctgccttg            1223
Gln Gly Ser Glu Ser His Ser Leu
                355 tgtgcgactg agatgcacag ctgccttgtg tgcgactgag atgcaggatt tcctcacgcc   1283 tcccctatgt gtcttagggg actctggctt ctcttttttgc aagggcctct gaatctgtct  1343 gtgtccctgt tagcacaatg tgaggaggta gagaaacagt ccacctctgt gtctaccatg   1403 accccccttcc tcacactgac ctgtgttcct tccctgttct cttttctatt aaaaataaga  1463 acctgggcag agtgcggcag ctcatgcctg taatcccagc acttagggag gccgaggagg   1523 gcagatcacg aggtcaggag atcgaaacca tcctggctaa cacggtgaaa ccccgtctct   1583 actaaaaaat acaaaaaatt agctgggcgc agaggcacgg gcctgtagtc ccagctactc   1643 aggaggcgga ggcaggagaa tggcgtcaac ccgggaggcg gaggttgcag tgagccagga   1703 ttgtgcgact gcactccagc ctgggtgaca gggtgaaacg ccatctcaaa aaataaaaat   1763 tgaaaaataa aaaaagaacc tggatctcaa tttaattttt catattcttg caatgaaatg   1823 gacttgagga agctaagatc atagctagaa atacagataa ttccacagca catctctagc   1883 aaatttagcc tattcctatt ctctagccta ttccttacca cctgtaatct tgaccatata   1943 ccttggagtt gaatattgtt ttcatactgc tgtggtttga atgttccctc caacactcat   2003 gttgagactt aatccctaat gtggcaatac tgaaaggtgg ggcctttgag atgtgattgg   2063 atcgtaaggc tgtgccttca ttcatgggtt aatggattaa tgggttatca caggaatggg   2123
```

-continued

```
actggtggct ttataagaag aggaaaagag aactgagcta gcatgcccag cccacagaga    2183
gcctccacta gagtgatgct aagtggaaat gtgaggtgca gctgccacag agggcccca     2243 ccagggaaat gtctagtgtc tagtggatcc aggccacagg agagagtgcc ttgtggagcg    2303
ctgggagcag gacctgacca ccaccaggac cccagaactg tggagtcagt ggcagcatgc    2363 agcgcccct tgggaaagct ttaggcacca gcctgcaacc cattcgagca gccacgtagg     2423
ctgcacccag caaagccaca ggcacgggc tacctgaggc cttgggggcc caatccctgc     2483
tccagtgtgt ccgtgaggca gcacacgaag tcaaaagaga ttattctctt cccacagata    2543 cctttctct cccatgaccc tttaacagca tctgcttcat tccctcacc ttcccaggct      2603 gatctgaggt aaactttgaa gtaaataaa agctgtgttt gagcatcatt tgtatttcaa     2663
aaaaaaaaaa aaaaaa                                                    2679
```

```
<210> SEQ ID NO 10
<211> LENGTH: 358
<212> TYPE: PRT
<213> ORGANISM: Homo sapiens

<400> SEQUENCE: 10

Met Val Asp Gly Thr Leu Leu Leu Leu Leu Ser Glu Ala Leu Ala Leu
1               5                   10                  15

Thr Gln Thr Trp Ala Gly Ser His Ser Leu Lys Tyr Phe His Thr Ser
            20                  25                  30

Val Ser Arg Pro Gly Arg Gly Glu Pro Arg Phe Ile Ser Val Gly Tyr
        35                  40                  45

Val Asp Asp Thr Gln Phe Val Arg Phe Asp Asn Asp Ala Ala Ser Pro
    50                  55                  60

Arg Met Val Pro Arg Ala Pro Trp Met Glu Gln Glu Gly Ser Glu Tyr
65                  70                  75                  80

Trp Asp Arg Glu Thr Arg Ser Ala Arg Asp Thr Ala Gln Ile Phe Arg
                85                  90                  95

Val Asn Leu Arg Thr Leu Arg Gly Tyr Tyr Asn Gln Ser Glu Ala Gly
            100                 105                 110

Ser His Thr Leu Gln Trp Met His Gly Cys Glu Leu Gly Pro Asp Gly
        115                 120                 125

Arg Phe Leu Arg Gly Tyr Glu Gln Phe Ala Tyr Asp Gly Lys Asp Tyr
    130                 135                 140

Leu Thr Leu Asn Glu Asp Leu Arg Ser Trp Thr Ala Val Asp Thr Ala
145                 150                 155                 160

Ala Gln Ile Ser Glu Gln Lys Ser Asn Asp Ala Ser Glu Ala Glu His
                165                 170                 175

Gln Arg Ala Tyr Leu Glu Asp Thr Cys Val Glu Trp Leu His Lys Tyr
            180                 185                 190

Leu Glu Lys Gly Lys Glu Thr Leu Leu His Leu Glu Pro Pro Lys Thr
        195                 200                 205

His Val Thr His His Pro Ile Ser Asp His Glu Ala Thr Leu Arg Cys
    210                 215                 220

Trp Ala Leu Gly Phe Tyr Pro Ala Glu Ile Thr Leu Thr Trp Gln Gln
225                 230                 235                 240

Asp Gly Glu Gly His Thr Gln Asp Thr Glu Leu Val Glu Thr Arg Pro
                245                 250                 255

Ala Gly Asp Gly Thr Phe Gln Lys Trp Ala Ala Val Val Val Pro Ser
            260                 265                 270
```

-continued

```
Gly Glu Glu Gln Arg Tyr Thr Cys His Val Gln His Glu Gly Leu Pro
        275                 280                 285

Glu Pro Val Thr Leu Arg Trp Lys Pro Ala Ser Gln Pro Thr Ile Pro
        290                 295                 300

Ile Val Gly Ile Ile Ala Gly Leu Val Leu Leu Gly Ser Val Val Ser
305                 310                 315                 320

Gly Ala Val Val Ala Ala Val Ile Trp Arg Lys Lys Ser Ser Gly Gly
                325                 330                 335

Lys Gly Gly Ser Tyr Ser Lys Ala Glu Trp Ser Asp Ser Ala Gln Gly
        340                 345                 350

Ser Glu Ser His Ser Leu
        355

<210> SEQ ID NO 11
<211> LENGTH: 1301
<212> TYPE: DNA
<213> ORGANISM: Homo sapiens
<220> FEATURE:
<221> NAME/KEY: CDS
<222> LOCATION: (125)..(1165)

<400> SEQUENCE: 11
tttctcactc ccattgggcg tcgcgtttct agagaagcca atcagtgtcg ccgcagttcc        60
caggttctaa agtcccacgc accccgcggg actcatattt ttcccagacg cggaggttgg       120 ggtc atg gcg ccc cga agc ctc ctc ctg ctg ctc tca ggg gcc ctg gcc       169
     Met Ala Pro Arg Ser Leu Leu Leu Leu Leu Ser Gly Ala Leu Ala
     1               5                  10                  15 ctg acc gat act tgg gcg ggc tcc cac tcc ttg agg tat ttc agc acc       217
Leu Thr Asp Thr Trp Ala Gly Ser His Ser Leu Arg Tyr Phe Ser Thr
            20                  25                  30 gct gtg tcg cgg ccc ggc cgc ggg gag ccc cgc tac atc gcc gtg gag       265
Ala Val Ser Arg Pro Gly Arg Gly Glu Pro Arg Tyr Ile Ala Val Glu
        35                  40                  45 tac gta gac gac acg caa ttc ctg cgg ttc gac agc gac gcc gcg att       313
Tyr Val Asp Asp Thr Gln Phe Leu Arg Phe Asp Ser Asp Ala Ala Ile
        50                  55                  60 ccg agg atg gag ccg cgg gag ccg tgg gtg gag caa gag ggg ccg cag       361
Pro Arg Met Glu Pro Arg Glu Pro Trp Val Glu Gln Glu Gly Pro Gln
65                  70                  75 tat tgg gag tgg acc aca ggg tac gcc aag gcc aac gca cag act gac       409
Tyr Trp Glu Trp Thr Thr Gly Tyr Ala Lys Ala Asn Ala Gln Thr Asp
80                  85                  90                  95 cga gtg gcc ctg agg aac ctg ctc cgc cgc tac aac cag agc gag gct       457
Arg Val Ala Leu Arg Asn Leu Leu Arg Arg Tyr Asn Gln Ser Glu Ala
                100                 105                 110 ggg tct cac acc ctc cag gga atg aat ggc tgc gac atg ggg ccc gac       505
Gly Ser His Thr Leu Gln Gly Met Asn Gly Cys Asp Met Gly Pro Asp
            115                 120                 125 gga cgc ctc ctc cgc ggg tat cac cag cac gcg tac gac ggc aag gat       553
Gly Arg Leu Leu Arg Gly Tyr His Gln His Ala Tyr Asp Gly Lys Asp
        130                 135                 140 tac atc tcc ctg aac gag gac ctg cgc tcc tgg acc gcg gcg gac acc       601
Tyr Ile Ser Leu Asn Glu Asp Leu Arg Ser Trp Thr Ala Ala Asp Thr
        145                 150                 155 gtg gct cag atc acc cag cgc ttc tat gag gca gag gaa tat gca gag       649
Val Ala Gln Ile Thr Gln Arg Phe Tyr Glu Ala Glu Glu Tyr Ala Glu
160                 165                 170                 175 gag ttc agg acc tac ctg gag ggc gag tgc ctg gag ttg ctc cgc aga       697
Glu Phe Arg Thr Tyr Leu Glu Gly Glu Cys Leu Glu Leu Leu Arg Arg
```

-continued

```
                    180              185              190 tac ttg gag aat ggg aag gag acg cta cag cgc gca gat cct cca aag      745
Tyr Leu Glu Asn Gly Lys Glu Thr Leu Gln Arg Ala Asp Pro Pro Lys
            195              200              205 gca cac gtt gcc cac cac ccc atc tct gac cat gag gcc acc ctg agg      793
Ala His Val Ala His His Pro Ile Ser Asp His Glu Ala Thr Leu Arg
        210              215              220 tgc tgg gcc ctg ggc ttc tac cct gcg gag atc acg ctg acc tgg cag      841
Cys Trp Ala Leu Gly Phe Tyr Pro Ala Glu Ile Thr Leu Thr Trp Gln
    225              230              235 cgg gat ggg gag gaa cag acc cag gac aca gag ctt gtg gag acc agg      889
Arg Asp Gly Glu Glu Gln Thr Gln Asp Thr Glu Leu Val Glu Thr Arg
240              245              250              255 cct gca ggg gat gga acc ttc cag aag tgg gcc gct gtg gtg gtg cct      937
Pro Ala Gly Asp Gly Thr Phe Gln Lys Trp Ala Ala Val Val Val Pro
                260              265              270 cct gga gag gaa cag aga tac aca tgc cat gtg cag cac gag ggg ctg      985
Pro Gly Glu Glu Gln Arg Tyr Thr Cys His Val Gln His Glu Gly Leu
            275              280              285 ccc cag ccc ctc atc ctg aga tgg gag cag tct ccc cag ccc acc atc     1033
Pro Gln Pro Leu Ile Leu Arg Trp Glu Gln Ser Pro Gln Pro Thr Ile
        290              295              300 ccc atc gtg ggc atc gtt gct ggc ctt gtt gtc ctt gga gct gtg gtc     1081
Pro Ile Val Gly Ile Val Ala Gly Leu Val Val Leu Gly Ala Val Val
    305              310              315 act gga gct gtg gtc gct gct gtg atg tgg agg aag aag agc tca gat     1129
Thr Gly Ala Val Val Ala Ala Val Met Trp Arg Lys Lys Ser Ser Asp
320              325              330              335 aga aac aga ggg agc tac tct cag gct gca gtg tga gacagcttcc          1175
Arg Asn Arg Gly Ser Tyr Ser Gln Ala Ala Val
            340              345 ttgtgtggga ctgagaagca agatatcaat gtagcagaat tgcacttgtg cctcacgaac   1235
atacataaat tttaaaaata aagaataaaa atatatcttt ttatagataa aaaaaaaaaa   1295
aaaaaa                                                             1301
```

```
<210> SEQ ID NO 12
<211> LENGTH: 346
<212> TYPE: PRT
<213> ORGANISM: Homo sapiens

<400> SEQUENCE: 12
```

```
Met Ala Pro Arg Ser Leu Leu Leu Leu Ser Gly Ala Leu Ala Leu
1               5                   10                  15

Thr Asp Thr Trp Ala Gly Ser His Ser Leu Arg Tyr Phe Ser Thr Ala
            20                  25                  30

Val Ser Arg Pro Gly Arg Gly Glu Pro Arg Tyr Ile Ala Val Glu Tyr
        35                  40                  45

Val Asp Asp Thr Gln Phe Leu Arg Phe Asp Ser Asp Ala Ala Ile Pro
        50                  55                  60

Arg Met Glu Pro Arg Glu Pro Trp Val Glu Gln Glu Gly Pro Gln Tyr
65                  70                  75                  80

Trp Glu Trp Thr Thr Gly Tyr Ala Lys Ala Asn Ala Gln Thr Asp Arg
                85                  90                  95

Val Ala Leu Arg Asn Leu Leu Arg Arg Tyr Asn Gln Ser Glu Ala Gly
            100                 105                 110

Ser His Thr Leu Gln Gly Met Asn Gly Cys Asp Met Gly Pro Asp Gly
            115                 120                 125
```

-continued

```
Arg Leu Leu Arg Gly Tyr His Gln His Ala Tyr Asp Gly Lys Asp Tyr
    130                 135                 140

Ile Ser Leu Asn Glu Asp Leu Arg Ser Trp Thr Ala Ala Asp Thr Val
145                 150                 155                 160

Ala Gln Ile Thr Gln Arg Phe Tyr Glu Ala Glu Glu Tyr Ala Glu Glu
                165                 170                 175

Phe Arg Thr Tyr Leu Glu Gly Glu Cys Leu Glu Leu Leu Arg Arg Tyr
            180                 185                 190

Leu Glu Asn Gly Lys Glu Thr Leu Gln Arg Ala Asp Pro Pro Lys Ala
            195                 200                 205

His Val Ala His His Pro Ile Ser Asp His Glu Ala Thr Leu Arg Cys
    210                 215                 220

Trp Ala Leu Gly Phe Tyr Pro Ala Glu Ile Thr Leu Thr Trp Gln Arg
225                 230                 235                 240

Asp Gly Glu Glu Gln Thr Gln Asp Thr Glu Leu Val Glu Thr Arg Pro
                245                 250                 255

Ala Gly Asp Gly Thr Phe Gln Lys Trp Ala Ala Val Val Val Pro Pro
            260                 265                 270

Gly Glu Glu Gln Arg Tyr Thr Cys His Val Gln His Glu Gly Leu Pro
            275                 280                 285

Gln Pro Leu Ile Leu Arg Trp Glu Gln Ser Pro Gln Pro Thr Ile Pro
    290                 295                 300

Ile Val Gly Ile Val Ala Gly Leu Val Val Leu Gly Ala Val Val Thr
305                 310                 315                 320

Gly Ala Val Val Ala Ala Val Met Trp Arg Lys Lys Ser Ser Asp Arg
                325                 330                 335

Asn Arg Gly Ser Tyr Ser Gln Ala Ala Val
            340                 345
```

```
<210> SEQ ID NO 13
<211> LENGTH: 1578
<212> TYPE: DNA
<213> ORGANISM: Homo sapiens
<220> FEATURE:
<221> NAME/KEY: CDS
<222> LOCATION: (179)..(1195)

<400> SEQUENCE: 13
agtgtggtac tttgtcttga ggagatgtcc tggactcaca cggaaactta gggctacgga      60
atgaagttct cactcccatt aggtgacagg tttttagaga agccaatcag cgtcgccgcg     120
gtcctggttc taaagtcctc gctcacccac ccggactcat tctccccaga cgccaagg      178 atg gtg gtc atg gcg ccc cga acc ctc ttc ctg ctg ctc tcg ggg gcc     226
Met Val Val Met Ala Pro Arg Thr Leu Phe Leu Leu Leu Ser Gly Ala
1               5                   10                  15 ctg acc ctg acc gag acc tgg gcg ggc tcc cac tcc atg agg tat ttc     274
Leu Thr Leu Thr Glu Thr Trp Ala Gly Ser His Ser Met Arg Tyr Phe
            20                  25                  30 agc gcc gcc gtg tcc cgg ccc ggc cgc ggg gag ccc cgc ttc atc gcc     322
Ser Ala Ala Val Ser Arg Pro Gly Arg Gly Glu Pro Arg Phe Ile Ala
        35                  40                  45 atg ggc tac gtg gac gac acg cag ttc gtg cgg ttc gac agc gac tcg     370
Met Gly Tyr Val Asp Asp Thr Gln Phe Val Arg Phe Asp Ser Asp Ser
    50                  55                  60 gcg tgt ccg agg atg gag ccg cgg gcg ccg tgg gtg gag cag gag ggg     418
Ala Cys Pro Arg Met Glu Pro Arg Ala Pro Trp Val Glu Gln Glu Gly
65                  70                  75                  80
```

```
ccg gag tat tgg gaa gag gag aca cgg aac acc aag gcc cac gca cag        466
Pro Glu Tyr Trp Glu Glu Glu Thr Arg Asn Thr Lys Ala His Ala Gln
                85                  90                  95 act gac aga atg aac ctg cag acc ctg cgc ggc tac tac aac cag agc        514
Thr Asp Arg Met Asn Leu Gln Thr Leu Arg Gly Tyr Tyr Asn Gln Ser
            100                 105                 110 gag gcc agt tct cac acc ctc cag tgg atg att ggc tgc gac ctg ggg        562
Glu Ala Ser Ser His Thr Leu Gln Trp Met Ile Gly Cys Asp Leu Gly
            115                 120                 125 tcc gac gga cgc ctc ctc cgc ggg tat gaa cag tat gcc tac gat ggc        610
Ser Asp Gly Arg Leu Leu Arg Gly Tyr Glu Gln Tyr Ala Tyr Asp Gly
        130                 135                 140 aag gat tac ctc gcc ctg aac gag gac ctg cgc tcc tgg acc gca gcg        658
Lys Asp Tyr Leu Ala Leu Asn Glu Asp Leu Arg Ser Trp Thr Ala Ala
145                 150                 155                 160 gac act gcg gct cag atc tcc aag cgc aag tgt gag gcg gcc aat gtg        706
Asp Thr Ala Ala Gln Ile Ser Lys Arg Lys Cys Glu Ala Ala Asn Val
                165                 170                 175 gct gaa caa agg aga gcc tac ctg gag ggc acg tgc gtg gag tgg ctc        754
Ala Glu Gln Arg Arg Ala Tyr Leu Glu Gly Thr Cys Val Glu Trp Leu
            180                 185                 190 cac aga tac ctg gag aac ggg aag gag atg ctg cag cgc gcg gac ccc        802
His Arg Tyr Leu Glu Asn Gly Lys Glu Met Leu Gln Arg Ala Asp Pro
            195                 200                 205 ccc aag aca cac gtg acc cac cac cct gtc ttt gac tat gag gcc acc        850
Pro Lys Thr His Val Thr His His Pro Val Phe Asp Tyr Glu Ala Thr
        210                 215                 220 ctg agg tgc tgg gcc ctg ggc ttc tac cct gcg gag atc ata ctg acc        898
Leu Arg Cys Trp Ala Leu Gly Phe Tyr Pro Ala Glu Ile Ile Leu Thr
225                 230                 235                 240 tgg cag cgg gat ggg gag gac cag acc cag gac gtg gag ctc gtg gag        946
Trp Gln Arg Asp Gly Glu Asp Gln Thr Gln Asp Val Glu Leu Val Glu
                245                 250                 255 acc agg cct gca ggg gat gga acc ttc cag aag tgg gca gct gtg gtg        994
Thr Arg Pro Ala Gly Asp Gly Thr Phe Gln Lys Trp Ala Ala Val Val
            260                 265                 270 gtg cct tct gga gag gag cag aga tac acg tgc cat gtg cag cat gag       1042
Val Pro Ser Gly Glu Glu Gln Arg Tyr Thr Cys His Val Gln His Glu
            275                 280                 285 ggg ctg ccg gag ccc ctc atg ctg aga tgg aag cag tct tcc ctg ccc       1090
Gly Leu Pro Glu Pro Leu Met Leu Arg Trp Lys Gln Ser Ser Leu Pro
        290                 295                 300 acc atc ccc atc atg ggt atc gtt gct ggc ctg gtt gtc ctt gca gct       1138
Thr Ile Pro Ile Met Gly Ile Val Ala Gly Leu Val Val Leu Ala Ala
305                 310                 315                 320 gta gtc act gga gct gcg gtc gct gct gtg ctg tgg aga aag aag agc       1186
Val Val Thr Gly Ala Ala Val Ala Ala Val Leu Trp Arg Lys Lys Ser
                325                 330                 335 tca gat tga aaaggaggga gctactctca ggctgcaatg tgaaacagct              1235
Ser Asp gccctgtgtg ggactgagtg gcaagtccct ttgtgacttc aagaaccctg actcctcttt   1295
gtgcagagac cagcccaccc ctgtgcccac catgaccctc ttcctcatgc tgaactgcat   1355
tccttcccca atcacctttc ctgttccaga aaaggggctg ggatgtctcc gtctctgtct   1415
caaatttgtg gtccactgag ctataactta cttctgtatt aaaattagaa tctgagtata   1475
aatttacttt ttcaaattat ttccaagaga gattgatggg ttaattaaag gagaagattc   1535
ctgaaatttg agagacaaaa taaatggaag acatgagaac ttt                     1578
```

-continued

<210> SEQ ID NO 14
<211> LENGTH: 338
<212> TYPE: PRT
<213> ORGANISM: Homo sapiens

<400> SEQUENCE: 14

```
Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
        115                 120                 125

Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
            165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
            195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Lys Gln Ser Ser Leu Pro
    290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
            325                 330                 335

Ser Asp
```

<210> SEQ ID NO 15
<211> LENGTH: 9232
<212> TYPE: DNA
<213> ORGANISM: Artificial Sequence

```
<220> FEATURE:
<223> OTHER INFORMATION: Vector sequence for human B2M-HLA-A0201 fusion
      protein

<400> SEQUENCE: 15
ctcgaggagc ttggcccatt gcatacgttg tatccatatc ataatatgta catttatatt      60
ggctcatgtc caacattacc gccatgttga cattgattat tgactagtta ttaatagtaa     120
tcaattacgg ggtcattagt tcatagccca tatatggagt tccgcgttac ataacttacg     180
gtaaatggcc cgcctggctg accgcccaac gacccccgcc cattgacgtc aataatgacg     240
tatgttccca gtaacgcc aatagggact ttccattgac gtcaatgggt ggagtattta     300
cgctaaactg cccacttggc agtacatcaa gtgtatcata tgccaagtac gccccctatt     360
gacgtcaatg acggtaaatg gcccgcctgg cattatgccc agtacatgac cttatgggac     420
tttcctactt ggcagtacat ctacgtatta gtcatcgcta ttaccatggt gatgcggttt     480
tggcagtaca tcaatgggcg tggatagcgg tttgactcac ggggatttcc aagtctccac     540
cccattgacg tcaatgggag tttgttttgg caccaaaatc aacgggactt tccaaaatgt     600
cgtaacaact ccgccccatt gacgcaaatg ggcggtaggc gtgtacggtg ggaggtctat     660
ataagcagag cttctagatt gtacgggagc tcttcactac tcgctgcgtc gagagtgtac     720
gagactctcc aggtttggta agaaatattt tatattgtta taatgttact atgatccatt     780
aacactctgc ttatagattg taagggtgat tgcaatgctt tctgcataaa actttggttt     840
tcttgttaat caataaaccg acttgattcg agaacctact catatattat tgtctctttt     900
atactttatt aagtaaaagg atttgtatat tagccttgct aagggagaca tctagtgata     960
taagtgtgaa ctacacttat cttaaatgat gtaactcctt aggataatca atatacaaaa    1020
ttccatgaca attggcgccc aacgtggggc tcgaatataa gtcgggttta tttgtaaatt    1080
atccctaggg acctccgagc aagcgagcat agcgggaggc atataaaagc caatagacaa    1140
tggctagcag gaagtaatgt tgaagaatat gaacttgatg ttgaagctct ggttgtaatt    1200
ttaagagata gaaatatacc aagaaatcct ttacatggag aagttatagg tcttcgcctt    1260
actgaaggat ggtggggaca aattgagaga tttcagatgg tacgttgatc taaggctatg    1320
gatttggcca tgggacaaga aatattagtt tatagtccca ttgtatctat gactaaaata    1380
caaaaaactc cactaccaga aagaaaagct ttacccatta gatggataac atggatgact    1440
tatttagaag atccaagaat ccaatttcat tatgataaaa ccttaccaga acttaagcat    1500
attccagatg tatatacatc tagtcagtct cctgttaaac atccttctca atatgaagga    1560 gtgtttata ctgatggctc ggccatcaaa agtcctgatc ctacaaaaag caataatgct    1620
ggcatgggaa tagtacatgc cacatacaaa cctgaatatc aagttttgaa tcaatggtca    1680
ataccactag gtaatcatac tgctcagatg gctgaaatag ctgcagttga atttgcctgt    1740
aaaaaagctt taaaaatacc tggtcctgta ttagttataa ctgatagttt ctatgtagca    1800
gaaagtgcta ataagaatt accatactgg aaatctaatg ggtttgttaa taataagaaa    1860
aagcctctta aacatatctc caaatggaaa tctattgctg agtgtttatc tatgaaacca    1920
gacattacta ttcaacatga aaaaggcatc agcctacaaa taccagtatt catactgaaa    1980
ggcaatgccc tagcagataa gcttgccacc caaggaagtt atgtggttaa ttgtaatacc    2040
aaaaaaccaa acctggatgc agagttggat caattattac agggtcatta tataaaagga    2100
tatcccaaac aatatacata ttttttagaa gatggcaaag taaaagtttc cagacctgaa    2160
ggggttaaaa ttattccccc tcagtcagac agacaaaaaa ttgtgcttca agcccacaat    2220
```

-continued

```
ttggctcaca ccggacgtga agccactctt ttaaaaattg ccaaccttta ttggtggcca    2280
aatatgagaa aggatgtggt taaacaacta ggacgctgtc aacagtgttt aatcacaaat    2340
gcttccaaca aagcctctgg tcctattcta agaccagata ggcctcaaaa accttttgat    2400
aaattcttta ttgactatat tggacctttg ccaccttcac agggatacct atatgtatta    2460
gtagttgttg atggaatgac aggattcact tggttatacc ccactaaggc tccttctact    2520
agcgcaactg ttaaatctct caatgtactc actagtattg caattccaaa ggtgattcac    2580
tctgatcaag gtgcagcatt cacttcttca acctttgctg aatgggcaaa ggaaagaggt    2640
atacatttgg aattcagtac tccttatcac ccccaaagtg gtagtaaggt ggaaaggaaa    2700
aatagtgata taaaacgact tttaactaaa ctgctagtag gaagacccac aaagtggtat    2760
gacctattgc ctgttgtaca acttgcttta aacaacacct atagccctgt attaaaatat    2820
actccacatc aactcttatt tggtatagat tcaaatactc catttgcaaa tcaagataca    2880
cttgacttga ccagagaaga agaactttct cttttacagg aaattcgtac ttctttatac    2940
catccatcca cccctccagc ctcctctcgt tcctggtctc ctgttgttgg ccaattggtc    3000
caggagaggt ggctaggccc tgcttctttg agacctcgtt ggcataaacc gtctactgta    3060
cttaaggtgt tgaatccaag gactgttgtt attttggacc atcttggcaa caacagaact    3120
gtaagtatag ataatttaaa acctacttct catcagaatg gcaccaccaa tgacactgca    3180
acaatggatc atttggaaaa aaatgaataa agcgcatgag gcacttcaaa atacaacaac    3240
tgtgactgaa cagcagaagg aacaaattat actggacatt caaaatgaag aagtacaacc    3300
aactaggaga gataaattta gatatctgct ttatacttgt tgtgctacta gctcaagagt    3360
attggcctgg atgttttttag tttgtatatt gttaatcatt gttttggttt catgctttgt    3420
gactatatcc agaatacaat ggaataagga tattcaggta ttaggacctg taatagactg    3480
gaatgttact caaagagctg tttatcaacc cttacagact agaaggattg cacgttccct    3540
tagaatgcag catcctgttc caaaatatgt ggaggtaaat atgactagta ttccacaagg    3600
tgtatactat gaaccccatc cggcctcgac ggtatcgatg gtaccggtat cgataagctt    3660
gataacctcg agagatctaa ttctaccggg taggggaggc gcttttccca aggcagtctg    3720
gagcatgcgc tttagcagcc ccgctggcac ttggcgctac acaagtggcc tctggcctcg    3780
cacacattcc acatccaccg gtagcgccaa ccggctccgt tctttggtgg ccccttcgcg    3840
ccacttctac tcctcccta gtcaggaagt ttcccccagc aagctcgcgt cgtgcaggac    3900
gtgacaaatg gaagtagcac gtctcactag tctcgtgcag atggacagca ccgctgagca    3960
atggaagcgg gtaggccttt ggggcagcgg ccaatagcag ctttgttcct tcgctttctg    4020
ggctcagagg ctgggaaggg gtgggtccgg gggcgggctc aggggcgggc tcaggggcgg    4080
gcgggcgccc gaaggtcctc ccgaggcccg gcattctgca cgcttcaaaa gcgcacgtct    4140
gccgcgctgt tctcctcttc ctcatctccg ggcctttcga cctgcagccc gggggatcga    4200
tcctaggtga tttaaatcca ccatgaccga gtacaagccc acggtgcgcc tcgccacccg    4260
cgacgacgtc cccgggccg tacgcaccct cgccgccgcg ttcgccgact accccgccac    4320
gcgccacacc gtcgacccgg accgccacat cgagcgggtc accgagctgc aagaactctt    4380
cctcacgcgc gtcgggctcg acatcggcaa ggtgtgggtc gcggacgacg gcgccgcggt    4440
ggcggtctgg accacgccgg agagcgtcga agcggggggcg gtgttcgccg agatcggccc    4500
gcgcatggcc gagttgagcg gttcccggct ggccgcgcag caacagatgg aaggcctcct    4560
```

-continued

```
ggcgccgcac cggcccaagg agcccgcgtg gttcctggcc accgtcggcg tctcgcccga    4620
ccaccagggc aagggtctgg gcagcgccgt cgtgctcccc ggagtggagg cggccgagcg    4680
cgccggggtg cccgccttcc tggagacctc cgcgccccgc aacctcccct tctacgagcg    4740
gctcggcttc accgtcaccg ccgacgtcga gtgcccgaag gaccgcgcga cctggtgcat    4800
gacccgcaag cccggtgcct gacggatcca tcgctccggt gcccgtcagt gggcagagcg    4860
cacatcgccc acagtccccg agaagttggg gggaggggtc ggcaattgaa ccggtgccta    4920
gagaaggtgg cgcggggtaa actgggaaag tgatgtcgtg tactggctcc gccttttttcc    4980 cgagggtggg ggagaaccgt atataagtgc agtagtcgcc gtgaacgttc tttttcgcaa    5040
cgggtttgcc gccagaacac agctgcggcc gcgccgccac catgtctcgc tccgtggcct    5100
tagctgtgct cgcgctactc tctctttctg gcctggaggc tatccagcgt actccaaaga    5160
ttcaggttta ctcacgtcat ccagcagaga atggaaagtc aaatttcctg aattgctatg    5220
tgtctgggtt tcatccatcc gacattgaag ttgacttact gaagaatgga gagagaattg    5280
aaaaagtgga gcattcagac ttgtctttca gcaaggactg gtctttctat ctcttgtact    5340
acactgaatt cacccccact gaaaaagatg agtatgcctg ccgtgtgaac catgtgactt    5400
tgtcacagcc caagatagtt aagtgggatc gagacatggg cggaggcgga agcggggggcg    5460 gcggatccgg cggaggcgga agcggcggcg ggggaagcgg ctctcactcc atgaggtatt    5520
tcttcacatc cgtgtcccgg cccggccgcg gggagccccg cttcatcgca gtgggctacg    5580
tggacgacac gcagttcgtg cggttcgaca gcgacgccgc gagccagagg atggagccgc    5640
gggcgccgtg gatagagcag gagggtccgg agtattggga cggggagaca cggaaagtga    5700
aggcccactc acagactcac cgagtggacc tggggaccct gcgcggctac tacaaccaga    5760
gcgaggccgg ttctcacacc gtccagagga tgtatggctg cgacgtgggg tcggactggc    5820
gcttcctccg cgggtaccac cagtacgcct acgacggcaa ggattacatc gccctgaaag    5880
aggacctgcg ctcttggacc gcggcggaca tggcagctca gaccaccaag cacaagtggg    5940
aggcggccca tgtggcggag cagttgagag cctacctgga gggcacgtgc gtggagtggc    6000
tccgcagata cctggagaac gggaaggaga cgctgcagcg cacggacgcc cccaaaacgc    6060
atatgactca ccacgctgtc tctgaccatg aagccaccct gaggtgctgg gccctgagct    6120
tctaccctgc ggagatcaca ctgacctggc agcgggatgg ggaggaccag acccaggaca    6180
cggagctcgt ggagaccagg cctgcagggg atggaacctt ccagaagtgg cggctgtgg    6240 tggtgccttc tggacaggag cagagataca cctgccatgt gcagcatgag ggtttgccca    6300
agcccctcac cctgagatgg gagccgtctt cccagcccac catccccatc gtgggcatca    6360
ttgctggcct ggttctcttt ggagctgtga tcactggagc tgtggtcgct gctgtgatgt    6420
ggaggaggaa gagctcagat agaaaaggag ggagctactc tcaggctgca agcagtgaca    6480
gtgcccaggg ctctgatgtg tctctcacag cttgtaaagt gtgagcggcc gcgactctag    6540
atcaggcgcg ccgttaccaa gcagctatgg aagcttatgg acctcagaga ggaagtaacg    6600
aggagagggt gtggtggaat gtcactagaa accaggggaaa acaaggagga gagtattaca    6660
gggaaggagg tgaagaacct cattacccaa atactcctgc tcctcataga cgtacctggg    6720
atgagagaca caaggttctt aaattgtcct cattcgctac tccctctgac atccaacgct    6780
gggctactaa ctctagattg tacgggagct ctcttcacta ctcgctgcgt cgagagtgta    6840
cgagactctc caggtttggt aagaaatatt ttatattgtt ataatgttac tatgatccat    6900
taacactctg cttatagatt gtaagggtga ttgcaatgct ttctgcataa aactttggtt    6960
```

-continued

```
ttcttgttaa tcaataaacc gacttgattc gagaacctac tcatatatta ttgtctcttt    7020
tatactttat taagtaaaag gatttgtata ttagccttgc taagggagac atctagtgat    7080
ataagtgtga actacactta tcttaaatga tgtaactcct taggataatc aatatacaaa    7140
attccatgac aattggcgat accgtcgacc gttcagctgc attaatgaat cggccaacgc    7200
gcggggagag gcggtttgcg tattgggcgc tcttccgctt cctcgctcac tgactcgctg    7260
cgctcggtcg ttcggctgcg gcgagcggta tcagctcact caaaggcggt aatacggtta    7320
tccacagaat caggggataa cgcaggaaag aacatgtgag caaaaggcca gcaaaaggcc    7380
aggaaccgta aaaaggccgc gttgctggcg ttttttccata ggctccgccc ccctgacgag    7440
catcacaaaa atcgacgctc aagtcagagg tggcgaaacc cgacaggact ataaagatac    7500
caggcgtttc ccctggaag ctccctcgtg cgctctcctg ttccgaccct gccgcttacc    7560
ggatacctgt ccgcctttct cccttcggga agcgtggcgc tttctcaatg ctcacgctgt    7620
aggtatctca gttcggtgta ggtcgttcgc tccaagctgg gctgtgtgca cgaacccccc    7680
gttcagcccg accgctgcgc cttatccggt aactatcgtc ttgagtccaa cccggtaaga    7740
cacgacttat cgccactggc agcagccact ggtaacagga ttagcagagc gaggtatgta    7800
ggcggtgcta cagagttctt gaagtggtgg cctaactacg gctacactag aaggacagta    7860
tttggtatct gcgctctgct gaagccagtt accttcggaa aaagagttgg tagctcttga    7920
tccggcaaac aaaccaccgc tggtagcggt ggtttttttg tttgcaagca gcagattacg    7980
cgcagaaaaa aaggatctca agaagatcct ttgatctttt ctacggggtc tgacgctcag    8040
tggaacgaaa actcacgtta agggattttg gtcatgagat tatcaaaaag gatcttcacc    8100
tagatccttt taaattaaaa atgaagtttt aaatcaatct aaagtatata tgagtaaact    8160
tggtctgaca gttaccaatg cttaatcagt gaggcaccta tctcagcgat ctgtctattt    8220
cgttcatcca tagttgcctg actccccgtc gtgtagataa ctacgatacg ggagggctta    8280
ccatctggcc ccagtgctgc aatgataccg cgagacccac gctcaccggc tccagattta    8340
tcagcaataa accagccagc cggaagggcc gagcgcagaa gtggtcctgc aactttatcc    8400
gcctccatcc agtctattaa ttgttgccgg gaagctagag taagtagttc gccagttaat    8460
agtttgcgca acgttgttgc cattgctaca ggcatcgtgg tgtcacgctc gtcgtttggt    8520
atggcttcat tcagctccgg ttcccaacga tcaaggcgag ttacatgatc ccccatgttg    8580
tgcaaaaaag cggttagctc cttcggtcct ccgatcgttg tcagaagtaa gttggccgca    8640
gtgttatcac tcatggttat ggcagcactg cataattctc ttactgtcat gccatccgta    8700
agatgctttt ctgtgactgg tgagtactca accaagtcat tctgagaata gtgtatgcgg    8760
cgaccgagtt gctcttgccc ggcgtcaata cgggataata ccgcgccaca tagcagaact    8820
ttaaaagtgc tcatcattgg aaaacgttct cgggggcgaa aactctcaag gatcttaccg    8880
ctgttgagat ccagttcgat gtaacccact cgtgcaccca actgatcttc agcatctttt    8940
actttcacca gcgtttctgg gtgagcaaaa acaggaaggc aaaatgccgc aaaaaaggga    9000
ataagggcga cacggaaatg ttgaatactc atactcttcc ttttcaata ttattgaagc    9060 atttatcagg gttattgtct catgagcgga tacatatttg aatgtattta gaaaaataaa    9120 caaataggggg ttccgcgcac atttccccga aaagtgccac ctgacgtcta agaaaccatt    9180
attatcatga cattaaccta taaaaatagg cgtatcacga ggccctttcg tc    9232
```

<210> SEQ ID NO 16

```
<211> LENGTH: 480
<212> TYPE: PRT
<213> ORGANISM: Artificial Sequence
<220> FEATURE:
<223> OTHER INFORMATION: HLA-bBA0201 (human B2M-HLA-A0201 fusion
      peptide)

<400> SEQUENCE: 16

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met Gly Gly Gly Gly Ser Gly Gly Gly Gly
            115                 120                 125

Ser Gly Gly Gly Gly Ser Gly Gly Gly Ser Gly Ser His Ser Met
    130                 135                 140

Arg Tyr Phe Phe Thr Ser Val Ser Arg Pro Gly Arg Gly Glu Pro Arg
145                 150                 155                 160

Phe Ile Ala Val Gly Tyr Val Asp Asp Thr Gln Phe Val Arg Phe Asp
                165                 170                 175

Ser Asp Ala Ala Ser Gln Arg Met Glu Pro Arg Ala Pro Trp Ile Glu
            180                 185                 190

Gln Glu Gly Pro Glu Tyr Trp Asp Gly Glu Thr Arg Lys Val Lys Ala
            195                 200                 205

His Ser Gln Thr His Arg Val Asp Leu Gly Thr Leu Arg Gly Tyr Tyr
    210                 215                 220

Asn Gln Ser Glu Ala Gly Ser His Thr Val Gln Arg Met Tyr Gly Cys
225                 230                 235                 240

Asp Val Gly Ser Asp Trp Arg Phe Leu Arg Gly Tyr His Gln Tyr Ala
                245                 250                 255

Tyr Asp Gly Lys Asp Tyr Ile Ala Leu Lys Glu Asp Leu Arg Ser Trp
            260                 265                 270

Thr Ala Ala Asp Met Ala Ala Gln Thr Thr Lys His Lys Trp Glu Ala
            275                 280                 285

Ala His Val Ala Glu Gln Leu Arg Ala Tyr Leu Glu Gly Thr Cys Val
    290                 295                 300

Glu Trp Leu Arg Arg Tyr Leu Glu Asn Gly Lys Glu Thr Leu Gln Arg
305                 310                 315                 320

Thr Asp Ala Pro Lys Thr His Met Thr His His Ala Val Ser Asp His
                325                 330                 335

Glu Ala Thr Leu Arg Cys Trp Ala Leu Ser Phe Tyr Pro Ala Glu Ile
            340                 345                 350

Thr Leu Thr Trp Gln Arg Asp Gly Glu Asp Gln Thr Gln Asp Thr Glu
            355                 360                 365

Leu Val Glu Thr Arg Pro Ala Gly Asp Gly Thr Phe Gln Lys Trp Ala
```

-continued

```
        370             375             380
Ala Val Val Val Pro Ser Gly Gln Glu Gln Arg Tyr Thr Cys His Val
385             390             395             400

Gln His Glu Gly Leu Pro Lys Pro Leu Thr Leu Arg Trp Glu Pro Ser
            405             410             415

Ser Gln Pro Thr Ile Pro Ile Val Gly Ile Ile Ala Gly Leu Val Leu
            420             425             430

Phe Gly Ala Val Ile Thr Gly Ala Val Val Ala Ala Val Met Trp Arg
        435             440             445

Arg Lys Ser Ser Asp Arg Lys Gly Gly Ser Tyr Ser Gln Ala Ala Ser
        450             455             460

Ser Asp Ser Ala Gln Gly Ser Asp Val Ser Leu Thr Ala Cys Lys Val
465             470             475             480
```

```
<210> SEQ ID NO 17
<211> LENGTH: 9224
<212> TYPE: DNA
<213> ORGANISM: Artificial Sequence
<220> FEATURE:
<223> OTHER INFORMATION: Vector sequence for HLA-gBE

<400> SEQUENCE: 17
ctcgaggagc ttggcccatt gcatacgttg tatccatatc ataatatgta catttatatt      60
ggctcatgtc caacattacc gccatgttga cattgattat tgactagtta ttaatagtaa     120
tcaattacgg ggtcattagt tcatagccca tatatggagt tccgcgttac ataacttacg     180
gtaaatggcc cgcctggctg accgcccaac gacccccgcc cattgacgtc aataatgacg     240
tatgttccca gtaacgcc  aatagggact ttccattgac gtcaatgggt ggagtattta     300
cgctaaactg cccacttggc agtacatcaa gtgtatcata tgccaagtac gccccctatt     360
gacgtcaatg acggtaaatg gcccgcctgg cattatgccc agtacatgac cttatgggac     420
tttcctactt ggcagtacat ctacgtatta gtcatcgcta ttaccatggt gatgcggttt     480
tggcagtaca tcaatgggcg tggatagcgg tttgactcac ggggatttcc aagtctccac     540
cccattgacg tcaatgggag tttgttttgg caccaaaatc aacgggactt tccaaaatgt     600
cgtaacaact ccgccccatt gacgcaaatg ggcggtaggc gtgtacggtg ggaggtctat     660
ataagcagag cttctagatt gtacgggagc tcttcactac tcgctgcgtc gagagtgtac     720
gagactctcc aggtttggta agaaatattt tatattgtta taatgttact atgatccatt     780
aacactctgc ttatagattg taagggtgat tgcaatgctt tctgcataaa actttggttt     840
tcttgttaat caataaaccg acttgattcg agaacctact catatattat tgtctctttt     900
atactttatt aagtaaaagg atttgtatat tagccttgct aagggagaca tctagtgata     960
taagtgtgaa ctacacttat cttaaatgat gtaactcctt aggataatca atatacaaaa    1020
ttccatgaca attggcgccc aacgtggggc tcgaatataa gtcgggttta tttgtaaatt    1080
atccctaggg acctccgagc atagcgggag gcatataaaa gccaatagac aatggctagc    1140
aggaagtaat gttgaagaat atgaacttga tgttgaagct ctggttgtaa ttttaagaga    1200
tagaaatata ccaagaaatc ctttacatgg agaagttata ggtcttcgcc ttactgaagg    1260
atggtgggga caaattgaga gatttcagat ggtacgttga tctaaggcta tggatttggc    1320
catgggacaa gaaatattag tttatagtcc cattgtatct atgactaaaa tacaaaaaac    1380
tccactacca gaaagaaaag ctttacccat tagatggata acatggatga cttatttaga    1440
agatccaaga atccaatttc attatgataa aaccttacca gaacttaagc atattccaga    1500
```

```
tgtatataca tctagtcagt ctcctgttaa acatccttct caatatgaag gagtgtttta      1560
tactgatggc tcggccatca aaagtcctga tcctacaaaa agcaataatg ctggcatggg      1620
aatagtacat gccacataca aacctgaata tcaagttttg aatcaatggt caataccact      1680
aggtaatcat actgctcaga tggctgaaat agctgcagtt gaatttgcct gtaaaaaagc      1740
tttaaaaata cctggtcctg tattagttat aactgatagt ttctatgtag cagaaagtgc      1800
taataaagaa ttaccatact ggaaatctaa tgggtttgtt aataataaga aaaagcctct      1860
taaacatatc tccaaatgga aatctattgc tgagtgttta tctatgaaac cagacattac      1920
tattcaacat gaaaaaggca tcagcctaca aataccagta ttcatactga aaggcaatgc      1980
cctagcagat aagcttgcca cccaaggaag ttatgtggtt aattgtaata ccaaaaaacc      2040
aaacctggat gcagagttgg atcaattatt acagggtcat tatataaaag gatatcccaa      2100
acaatataca tattttttag aagatggcaa agtaaaagtt tccagacctg aaggggttaa      2160
aattattccc cctcagtcag acagacaaaa aattgtgctt caagcccaca atttggctca      2220
caccggacgt gaagccactc tttttaaaaat tgccaacctt tattggtggc caaatatgag      2280
aaaggatgtg gttaaacaac taggacgctg tcaacagtgt ttaatcacaa atgcttccaa      2340
caaagcctct ggtcctattc taagaccaga taggcctcaa aaaccttttg ataaattctt      2400
tattgactat attggacctt tgccaccttc acagggatac ctatatgtat tagtagttgt      2460
tgatggaatg acaggattca cttggttata ccccactaag gctccttcta ctagcgcaac      2520
tgttaaatct ctcaatgtac tcactagtat tgcaattcca aaggtgattc actctgatca      2580
aggtgcagca ttcacttctt caacctttgc tgaatgggca aaggaaagag gtatacattt      2640
ggaattcagt actccttatc acccccaaag tggtagtaag gtggaaagga aaaatagtga      2700
tataaaacga cttttaacta aactgctagt aggaagaccc acaaagtggt atgacctatt      2760
gcctgttgta caacttgctt taaacaacac ctatagccct gtattaaaat atactccaca      2820
tcaactctta tttggtatag attcaaatac tccatttgca aatcaagata cacttgactt      2880
gaccagagaa gaagaacttt ctctttacca ggaaattcgt acttctttat accatccatc      2940
cacccctcca gcctcctctc gttcctggtc tcctgttgtt ggccaattgg tccaggagag      3000
ggtggctagg cctgcttctt tgagacctcg ttggcataaa ccgtctactg tacttaaggt      3060
gttgaatcca aggactgttg ttattttgga ccatcttggc aacaacagaa ctgtaagtat      3120
agataattta aaacctactt ctcatcagaa tggcaccacc aatgacactg caacaatgga      3180
tcatttggaa aaaaatgaat aaagcgcatg aggcacttca aaatacaaca actgtgactg      3240
aacagcagaa ggaacaaatt atactggaca ttcaaaatga agaagtacaa ccaactagga      3300
gagataaatt tagatatctg ctttatactt gttgtgctac tagctcaaga gtattggcct      3360
ggatgttttt agtttgtata ttgttaatca ttgttttggt ttcatgcttt gtgactatat      3420
ccagaataca atggaataag gatattcagg tattaggacc tgtaatagac tggaatgtta      3480
ctcaaagagc tgtttatcaa cccttacaga ctagaaggat tgcacgttcc cttagaatgc      3540
agcatcctgt tccaaaatat gtggaggtaa atatgactag tattccacaa ggtgtatact      3600
atgaacccca tccggcctcg acggtatcga tggtaccggt atcgataagc ttgataacct      3660
cgagagatct aattctaccg ggtaggggag gcgcttttcc caaggcagtc tggagcatgc      3720
gctttagcag ccccgctggc acttggcgct acacaagtgg cctctggcct cgcacacatt      3780
ccacatccac cggtagcgcc aaccggctcc gttctttggt ggccccttcg cgccacttct      3840
```

```
actcctcccc tagtcaggaa gtttcccca gcaagctcgc gtcgtgcagg acgtgacaaa    3900
tggaagtagc acgtctcact agtctcgtgc agatggacag caccgctgag caatggaagc    3960
gggtaggcct ttggggcagc ggccaatagc agctttgttc cttcgctttc tgggctcaga    4020
ggctgggaag gggtgggtcc gggggcgggc tcaggggcgg gctcaggggc gggcgggcgc    4080
ccgaaggtcc tcccgaggcc cggcattctg cacgcttcaa aagcgcacgt ctgccgcgct    4140
gttctcctct tcctcatctc cgggcctttc gacctgcagc ccgggggatc gatcctaggt    4200
gatttaaatc caccatgacc gagtacaagc ccacggtgcg cctcgccacc cgcgacgacg    4260
tcccccgggc cgtacgcacc ctcgccgccg cgttcgccga ctaccccgcc acgcgccaca    4320
ccgtcgaccc ggaccgccac atcgagcggg tcaccgagct gcaagaactc ttcctcacgc    4380
gcgtcgggct cgacatcggc aaggtgtggg tcgcggacga cggcgccgcg gtggcggtct    4440
ggaccacgcc ggagagcgtc gaagcggggg cggtgttcgc cgagatcggc ccgcgcatgg    4500
ccgagttgag cggttcccgg ctggccgcgc agcaacagat ggaaggcctc ctggcgccgc    4560
accggcccaa ggagcccgcg tggttcctgg ccaccgtcgg cgtctcgccc gaccaccagg    4620
gcaagggtct gggcagcgcc gtcgtgctcc cggagtgga ggcggccgag cgcgccgggg    4680
tgcccgcctt cctggagacc tccgcgcccc gcaacctccc cttctacgag cggctcggct    4740
tcaccgtcac cgccgacgtc gagtgcccga aggaccgcgc gacctggtgc atgacccgca    4800
agcccggtgc ctgacggatc catcgctccg gtgcccgtca gtgggcagag cgcacatcgc    4860
ccacagtccc cgagaagttg gggggagggg tcggcaattg aaccggtgcc tagagaaggt    4920
ggcgcggggt aaactgggaa agtgatgtcg tgtactggct ccgcctttt cccgagggtg    4980 ggggagaacc gtatataagt gcagtagtcg ccgtgaacgt tctttttcgc aacgggtttg    5040
ccgccagaac acagctgcgg ccgcgttaac catggtggtc atggcccctc gaactctgtt    5100
cctgctgctg agtggggctc tgaccctgac agagtccgga atccagcgga cccccaagat    5160
tcaggtgtac agcagacacc ctgcagagaa cggcaaatcc aacttcctga attgctatgt    5220
gtctgggttt catcccagtg acatcgaagt cgatctgctg aagaatggcg agagaattga    5280
aaaagtcgag cactctgacc tgagcttctc caaggattgg tccttttacc tgctgtacta    5340
taccgagttt actccaaccg aaaaagacga gtatgcctgt agggtgaacc atgtcacact    5400
gagccagccc aagatcgtga atgggaccg cgatatgggc gggggaggct cagggggagg    5460
cgggagcgga ggcggggggct ccggcggggg aggatccggt tctcactcct tgaagtattt    5520
ccacacttcc gtgtcccggc ccggccgcgg ggagccccgc ttcatctctg tgggctacgt    5580
ggacgacacc cagttcgtgc gcttcgacaa cgacgccgcg agtccgagga tggtgccgcg    5640
ggcgccgtgg atggagcagg aggggtcaga gtattgggac cgggagacac ggagcgccag    5700
ggacaccgca cagattttcc gagtgaatct gcggacgctg cgcggctact acaatcagag    5760
cgaggccggg tctcacaccc tgcagtggat gcatggctgc gagctggggc cgacgggcg    5820 cttcctccgc gggtatgaac agttcgccta cgacggcaag gattatctca ccctgaatga    5880
ggacctgcgc tcctggaccg cggtggacac ggcggctcag atctccgagc aaaagtcaaa    5940
tgatgcctct gaggcggagc accagagagc ctacctggaa gacacatgcg tggagtggct    6000
ccacaaatac ctggagaagg ggaaggagac gctgcttcac ctggagcccc caaagacaca    6060
cgtgactcac caccccatct ctgaccatga ggccaccctg aggtgctggg ccctgggctt    6120
ctaccctgcg gagatcacac tgacctggca gcaggatggg gagggccata cccaggacac    6180
ggagctcgtg gagaccaggc ctgcagggga tggaaccttc cagaagtggg cagctgtggt    6240
```

```
ggtgccttct ggagaggagc agagatacac gtgccatgtg cagcatgagg ggctacccga   6300
gcccgtcacc ctgagatgga agccggcttc ccagcccacc atccccatcg tgggcatcat   6360
tgctggcctg gttctccttg gatctgtggt ctctggagct gtggttgctg ctgtgatatg   6420
gaggaagaag agctcaggtg gaaaaggagg gagctactct aaggctgagt ggagcgacag   6480
tgcccagggg tctgagtctc acagcttgta atctagagcg gccgcgactc tagatcaggc   6540
gcgccgttac caagcagcta tggaagctta tggacctcag agaggaagta acgaggagag   6600
ggtgtggtgg aatgtcacta gaaaccaggg aaaacaagga ggagagtatt acagggaagg   6660
aggtgaagaa cctcattacc caaatactcc tgctcctcat agacgtacct gggatgagag   6720
acacaaggtt cttaaattgt cctcattcgc tactccctct gacatccaac gctggactac   6780
taactctaga ttgtacggga ggctcttcac tactcgctgc gtcgagagtg tacgagactc   6840
tccaggtttg gtaagaaata ttttatattg ttataatgtt actatgatcc attaacactc   6900
tgcttataga ttgtaagggt gattgcaatg ctttctgcat aaaactttgg ttttcttgtt   6960
aatcaataaa ccgacttgat tcgagaacca actcctatat tattgtctct tttatacttt   7020
attaagtaaa aggatttgta tattagcctt gctaagggag acatctagtg atataagtgt   7080
gaactacact tatcttaaat gatgtaactc cttaggataa tcaatataca aaattccatg   7140
acaattggcg ataccgtcga ccgttcagct gcattaatga atcggccaac gcgcggggag   7200
aggcggtttg cgtattgggc gctcttccgc ttcctcgctc actgactcgc tgcgctcggt   7260
cgttcggctg cggcgagcgg tatcagctca ctcaaaggcg gtaatacggt tatccacaga   7320
atcaggggat aacgcaggaa agaacatgtg agcaaaaggc cagcaaaagg ccaggaaccg   7380
taaaaaggcc gcgttgctgg cgtttttcca taggctccgc ccccctgacg agcatcacaa   7440
aaatcgacgc tcaagtcaga ggtggcgaaa cccgacagga ctataaagat accaggcgtt   7500
tccccctgga agctccctcg tgcgctctcc tgttccgacc ctgccgctta ccggatacct   7560
gtccgccttt ctcccttcgg gaagcgtggc gctttctcaa tgctcacgct gtaggtatct   7620
cagttcggtg taggtcgttc gctccaagct gggctgtgtg cacgaacccc ccgttcagcc   7680
cgaccgctgc gccttatccg gtaactatcg tcttgagtcc aacccggtaa gacacgactt   7740
atcgccactg gcagcagcca ctggtaacag gattagcaga gcgaggtatg taggcggtgc   7800
tacagagttc ttgaagtggt ggcctaacta cggctacact agaaggacag tatttggtat   7860
ctgcgctctg ctgaagccag ttaccttcgg aaaaagagtt ggtagctctt gatccggcaa   7920
acaaaccacc gctggtagcg gtggtttttt tgtttgcaag cagcagatta cgcgcagaaa   7980
aaaaggatct caagaagatc ctttgatctt ttctacgggg tctgacgctc agtggaacga   8040
aaactcacgt taagggattt ggtcatgag attatcaaaa aggatcttca cctagatcct   8100
tttaaattaa aaatgaagtt ttaaatcaat ctaaagtata tatgagtaaa cttggtctga   8160
cagttaccaa tgcttaatca gtgaggcacc tatctcagcg atctgtctat ttcgttcatc   8220
catagttgcc tgactccccg tcgtgtagat aactacgata cgggagggct taccatctgg   8280
ccccagtgct gcaatgatac cgcgagaccc acgctcaccg gctccagatt tatcagcaat   8340
aaaccagcca gccggaaggg ccgagcgcag aagtggtcct gcaactttat ccgcctccat   8400
ccagtctatt aattgttgcc gggaagctag agtaagtagt tcgccagtta atagtttgcg   8460
caacgttgtt gccattgcta caggcatcgt ggtgtcacgc tcgtcgtttg gtatggcttc   8520
attcagctcc ggttcccaac gatcaaggcg agttacatga tcccccatgt tgtgcaaaaa   8580
```

-continued

---

```
agcggttagc tccttcggtc ctccgatcgt tgtcagaagt aagttggccg cagtgttatc      8640
actcatggtt atggcagcac tgcataattc tcttactgtc atgccatccg taagatgctt      8700
ttctgtgact ggtgagtact caaccaagtc attctgagaa tagtgtatgc ggcgaccgag      8760
ttgctcttgc ccggcgtcaa tacgggataa taccgcgcca catagcagaa ctttaaaagt      8820
gctcatcatt ggaaaacgtt cttcggggcg aaaactctca aggatcttac cgctgttgag      8880
atccagttcg atgtaaccca ctcgtgcacc caactgatct tcagcatctt ttactttcac      8940
cagcgtttct gggtgagcaa aaacaggaag gcaaaatgcc gcaaaaaagg gaataagggc      9000
gacacggaaa tgttgaatac tcatactctt cctttttcaa tattattgaa gcatttatca      9060
gggttattgt ctcatgagcg gatacatatt tgaatgtatt tagaaaaata aacaaatagg      9120
ggttccgcgc acatttcccc gaaaagtgcc acctgacgtc taagaaacca ttattatcat      9180
gacattaacc tataaaaata ggcgtatcac gaggcccttt cgtc                        9224
```

```
<210> SEQ ID NO 18
<211> LENGTH: 476
<212> TYPE: PRT
<213> ORGANISM: Artificial Sequence
<220> FEATURE:
<223> OTHER INFORMATION: HLA-gBE

<400> SEQUENCE: 18

Met Ala Pro Arg Thr Leu Phe Leu Leu Leu Ser Gly Ala Leu Thr Leu
1               5                   10                  15

Thr Glu Ser Gly Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met Gly Gly Gly Gly Ser Gly Gly Gly Gly
            115                 120                 125

Ser Gly Gly Gly Gly Ser Gly Gly Gly Gly Ser Gly Ser His Ser Leu
        130                 135                 140

Lys Tyr Phe His Thr Ser Val Ser Arg Pro Gly Arg Gly Glu Pro Arg
145                 150                 155                 160

Phe Ile Ser Val Gly Tyr Val Asp Asp Thr Gln Phe Val Arg Phe Asp
                165                 170                 175

Asn Asp Ala Ala Ser Pro Arg Met Val Pro Arg Ala Pro Trp Met Glu
            180                 185                 190

Gln Glu Gly Ser Glu Tyr Trp Asp Arg Glu Thr Arg Ser Ala Arg Asp
        195                 200                 205

Thr Ala Gln Ile Phe Arg Val Asn Leu Arg Thr Leu Arg Gly Tyr Tyr
    210                 215                 220

Asn Gln Ser Glu Ala Gly Ser His Thr Leu Gln Trp Met His Gly Cys
225                 230                 235                 240

Glu Leu Gly Pro Asp Gly Arg Phe Leu Arg Gly Tyr Glu Gln Phe Ala
                245                 250                 255
```

-continued

```
Tyr Asp Gly Lys Asp Tyr Leu Thr Leu Asn Glu Asp Leu Arg Ser Trp
            260                 265                 270

Thr Ala Val Asp Thr Ala Ala Gln Ile Ser Glu Gln Lys Ser Asn Asp
            275                 280                 285

Ala Ser Glu Ala Glu His Gln Arg Ala Tyr Leu Glu Asp Thr Cys Val
            290                 295                 300

Glu Trp Leu His Lys Tyr Leu Glu Lys Gly Lys Glu Thr Leu Leu His
305                 310                 315                 320

Leu Glu Pro Pro Lys Thr His Val Thr His His Pro Ile Ser Asp His
                    325                 330                 335

Glu Ala Thr Leu Arg Cys Trp Ala Leu Gly Phe Tyr Pro Ala Glu Ile
                    340                 345                 350

Thr Leu Thr Trp Gln Gln Asp Gly Glu Gly His Thr Gln Asp Thr Glu
                    355                 360                 365

Leu Val Glu Thr Arg Pro Ala Gly Asp Gly Thr Phe Gln Lys Trp Ala
            370                 375                 380

Ala Val Val Val Pro Ser Gly Glu Glu Gln Arg Tyr Thr Cys His Val
385                 390                 395                 400

Gln His Glu Gly Leu Pro Glu Pro Val Thr Leu Arg Trp Lys Pro Ala
                    405                 410                 415

Ser Gln Pro Thr Ile Pro Ile Val Gly Ile Ile Ala Gly Leu Val Leu
                    420                 425                 430

Leu Gly Ser Val Val Ser Gly Ala Val Val Ala Ala Val Ile Trp Arg
            435                 440                 445

Lys Lys Ser Ser Gly Gly Lys Gly Gly Ser Tyr Ser Lys Ala Glu Trp
            450                 455                 460

Ser Asp Ser Ala Gln Gly Ser Glu Ser His Ser Leu
465                 470                 475
```

<210> SEQ ID NO 19
<211> LENGTH: 9287
<212> TYPE: DNA
<213> ORGANISM: Artificial Sequence
<220> FEATURE:
<223> OTHER INFORMATION: Vector sequence for HLA-bGBE

<400> SEQUENCE: 19

```
ctcgaggagc ttggcccatt gcatacgttg tatccatatc ataatatgta catttatatt      60
ggctcatgtc caacattacc gccatgttga cattgattat tgactagtta ttaatagtaa     120
tcaattacgg ggtcattagt tcatagccca tatatggagt tccgcgttac ataacttacg     180
gtaaatggcc cgcctggctg accgcccaac gacccccgcc cattgacgtc aataatgacg     240
tatgttccca gtaacgcc aatagggact ttccattgac gtcaatgggt ggagtattta     300
cgctaaactg cccacttggc agtacatcaa gtgtatcata tgccaagtac gccccctatt     360
gacgtcaatg acggtaaatg gcccgcctgg cattatgccc agtacatgac cttatgggac     420
tttcctactt ggcagtacat ctacgtatta gtcatcgcta ttaccatggt gatgcggttt     480
tggcagtaca tcaatgggcg tggatagcgg tttgactcac ggggatttcc aagtctccac     540
cccattgacg tcaatgggag tttgttttgg caccaaaatc aacgggactt tccaaaatgt     600
cgtaacaact ccgccccatt gacgcaaatg ggcggtaggc gtgtacggtg ggaggtctat     660
ataagcagag cttctagatt gtacgggagc tcttcactac tcgctgcgtc gagagtgtac     720
gagactctcc aggtttggta agaaatattt tatattgtta taatgttact atgatccatt     780
```

-continued

```
aacactctgc ttatagattg taagggtgat tgcaatgctt tctgcataaa actttggttt      840
tcttgttaat caataaaccg acttgattcg agaacctact catatattat tgtctctttt      900
atactttatt aagtaaaagg atttgtatat tagccttgct aagggagaca tctagtgata      960
taagtgtgaa ctacacttat cttaaatgat gtaactcctt aggataatca atatacaaaa     1020
ttccatgaca attggcgccc aacgtggggc tcgaatataa gtcgggttta tttgtaaatt     1080
atccctaggg acctccgagc atagcgggag gcatataaaa gccaatagac aatggctagc     1140
aggaagtaat gttgaagaat atgaacttga tgttgaagct ctggttgtaa ttttaagaga     1200
tagaaatata ccaagaaatc ctttacatgg agaagttata ggtcttcgcc ttactgaagg     1260
atggtgggga caaattgaga gatttcagat ggtacgttga tctaaggcta tggatttggc     1320
catgggacaa gaaatattag tttatagtcc cattgtatct atgactaaaa tacaaaaaac     1380
tccactacca gaaagaaaag ctttacccat tagatggata acatggatga cttatttaga     1440
agatccaaga atccaatttc attatgataa aaccttacca gaacttaagc atattccaga     1500
tgtatataca tctagtcagt ctcctgttaa acatccttct caatatgaag gagtgtttta     1560
tactgatggc tcggccatca aaagtcctga tcctacaaaa agcaataatg ctggcatggg     1620
aatagtacat gccacataca aacctgaata tcaagttttg aatcaatggt caataccact     1680
aggtaatcat actgctcaga tggctgaaat agctgcagtt gaatttgcct gtaaaaaagc     1740
tttaaaaata cctggtcctg tattagttat aactgatagt ttctatgtag cagaaagtgc     1800
taataaagaa ttaccatact ggaaatctaa tgggtttgtt aataataaga aaaagcctct     1860
taaacatatc tccaaatgga aatctattgc tgagtgttta tctatgaaac cagacattac     1920
tattcaacat gaaaaaggca tcagcctaca ataccagta ttcatactga aaggcaatgc      1980
cctagcagat aagcttgcca cccaaggaag ttatgtggtt aattgtaata ccaaaaaacc     2040
aaacctggat gcagagttgg atcaattatt acagggtcat tatataaaag gatatcccaa     2100
acaatataca tatttttag aagatggcaa agtaaaagtt tccagacctg aaggggttaa      2160
aattattccc cctcagtcag acagacaaaa aattgtgctt caagcccaca atttggctca     2220
caccggacgt gaagccactc tttttaaaaat tgccaacctt tattggtggc caaatatgag     2280
aaaggatgtg gttaaacaac taggacgctg tcaacagtgt ttaatcacaa atgcttccaa     2340
caaagcctct ggtcctattc taagaccaga taggcctcaa aaaccttttg ataaaattctt     2400 tattgactat attggacctt tgccaccttc acagggatac ctatatgtat tagtagttgt     2460
tgatggaatg acaggattca cttggttata ccccactaag gctccttcta ctagcgcaac     2520
tgttaaatct ctcaatgtac tcactagtat tgcaattcca aaggtgattc actctgatca     2580
aggtgcagca ttcacttctt caacctttgc tgaatgggca aaggaaagag gtataacattt     2640 ggaattcagt actccttatc accccaaag tggtagtaag gtggaaagga aaaatagtga     2700
tataaaacga cttttaacta aactgctagt aggaagaccc acaaagtggt atgacctatt     2760
gcctgttgta caacttgctt taaacaacac ctatagccct gtattaaaat atactccaca     2820
tcaactctta tttggtatag attcaaatac tccatttgca aatcaagata cacttgactt     2880
gaccagagaa gaagaacttt ctcttttaca ggaaattcgt acttctttat accatccatc     2940 caccctcca gcctcctctc gttcctggtc tcctgttgtt ggccaattgg tccaggagag      3000
ggtggctagg cctgcttctt tgagacctcg ttggcataaa ccgtctactg tacttaaggt     3060
gttgaatcca aggactgttg ttattttgga ccatcttggc aacaacagaa ctgtaagtat     3120 agataatttta aaacctactt ctcatcagaa tggcaccacc aatgacactg caacaatgga     3180
```

```
tcatttggaa aaaaatgaat aaagcgcatg aggcacttca aaatacaaca actgtgactg     3240
aacagcagaa ggaacaaatt atactggaca ttcaaaatga agaagtacaa ccaactagga     3300
gagataaatt tagatatctg ctttatactt gttgtgctac tagctcaaga gtattggcct     3360
ggatgttttt agtttgtata ttgttaatca ttgtttttggt ttcatgcttt gtgactatat     3420
ccagaataca atggaataag gatattcagg tattaggacc tgtaatagac tggaatgtta     3480
ctcaaagagc tgtttatcaa cccttacaga ctagaaggat tgcacgttcc cttagaatgc     3540
agcatcctgt tccaaaatat gtggaggtaa atatgactag tattccacaa ggtgtatact     3600
atgaacccca tccggcctcg acggtatcga tggtaccggt atcgataagc ttgataacct     3660
cgagagatct aattctaccg ggtaggggag gcgcttttcc caaggcagtc tggagcatgc     3720
gctttagcag ccccgctggc acttggcgct acacaagtgg cctctggcct cgcacacatt     3780
ccacatccac cggtagcgcc aaccggctcc gttctttggt ggcccccttcg cgccacttct     3840 actcctcccc tagtcaggaa gtttcccccca gcaagctcgc gtcgtgcagg acgtgacaaa     3900
tggaagtagc acgtctcact agtctcgtgc agatggacag caccgctgag caatggaagc     3960
gggtaggcct ttggggcagc ggccaatagc agctttgttc cttcgctttc tgggctcaga     4020
ggctgggaag gggtgggtcc ggggggcgggc tcaggggcgg gctcaggggc gggcgggcgc     4080
ccgaaggtcc tcccgaggcc cggcattctg cacgcttcaa aagcgcacgt ctgccgcgct     4140
gttctcctct tcctcatctc cgggccttttc gacctgcagc ccgggggatc gatcctaggt     4200
gatttaaatc caccatgacc gagtacaagc ccacggtgcg cctcgccacc cgcgacgacg     4260
tcccccgggc cgtacgcacc ctcgccgccg cgttcgccga ctaccccgcc acgcgccaca     4320
ccgtcgaccc ggaccgccac atcgagcggg tcaccgagct gcaagaactc ttcctcacgc     4380
gcgtcgggct cgacatcggc aaggtgtggg tcgcggacga cggcgccgcg gtggcggtct     4440
ggaccacgcc ggagagcgtc gaagcggggg cggtgttcgc cgagatcggc ccgcgcatgg     4500
ccgagttgag cggttcccgg ctggccgcgc agcaacagat ggaaggcctc ctggcgccgc     4560
accggcccaa ggagcccgcg tggttcctgg ccaccgtcgg cgtctcgccc gaccaccagg     4620
gcaagggtct gggcagcgcc gtcgtgctcc cggagtgga ggcggccgag cgcgccgggg     4680
tgcccgcctt cctggagacc tccgcgcccc gcaacctccc cttctacgag cggctcggct     4740
tcaccgtcac cgccgacgtc gagtgcccga aggaccgcgc gacctggtgc atgacccgca     4800
agcccggtgc ctgacggatc catcgctccg gtgcccgtca gtgggcagag cgcacatcgc     4860
ccacagtccc cgagaagttg ggggggaggg tcggcaattg aaccggtgcc tagagaaggt     4920
ggcgcggggt aaactgggaa agtgatgtcg tgtactggct ccgcctttttt cccgagggtg     4980 ggggagaacc gtatataagt gcagtagtcg ccgtgaacgt tctttttcgc aacgggtttg     5040
ccgccagaac acagctgcgg ccgcgttaac catgagccga tccgtggcac tggctgtcct     5100
ggctctgctg tctctgagtg gcctggaagc agtgatggcc cctagaacac tgttcctggg     5160
cggaggcggc tccggaggag gagggtctgg aggcggggga agtatccagc ggactcccaa     5220
gattcaggtc tacagcagac accctgccga aaacgggaaa tccaacttcc tgaattgcta     5280
tgtgtcaggc tttcatccca gcgacatcga ggtcgatctg ctgaagaatg gcgagcggat     5340
tgaaaaagtg gagcactctg acctgtcatt cagcaaggat tggagctttt acctgctgta     5400
ctatactgag tttaccccaa cagaaaaaga cgagtatgcc gtagggtga accatgtcac     5460 cctgagtcag cccaagatcg tgaaatggga ccgcgatatg ggcggggagc gctccggggg     5520
```

-continued

```
aggcggctcc ggcggcgggg gaagtggcgg gggaggatcc ggttctcact ccttgaagta    5580
tttccacact tccgtgtccc ggcccggccg cggggagccc cgcttcatct ctgtgggcta    5640
cgtggacgac acccagttcg tgcgcttcga caacgacgcc gcgagtccga ggatggtgcc    5700
gcgggcgccg tggatggagc aggaggggtc agagtattgg gaccgggaga cacggagcgc    5760
cagggacacc gcacagattt tccgagtgaa tctgcggacg ctgcgcggct actacaatca    5820
gagcgaggcc gggtctcaca ccctgcagtg gatgcatggc tgcgagctgg ggcccgacgg    5880
gcgcttcctc cgcgggtatg aacagttcgc ctacgacggc aaggattatc tcaccctgaa    5940
tgaggacctg cgctcctgga ccgcggtgga cacggcggct cagatctccg agcaaaagtc    6000
aaatgatgcc tctgaggcgg agcaccagag agcctacctg gaagacacat gcgtggagtg    6060
gctccacaaa tacctggaga aggggaagga gacgctgctt cacctggagc ccccaaagac    6120
acacgtgact caccacccca tctctgacca tgaggccacc ctgaggtgct gggccctggg    6180
cttctaccct gcggagatca cactgacctg gcagcaggat ggggagggcc atacccagga    6240
cacggagctc gtggagacca ggcctgcagg ggatggaacc ttccagaagt gggcagctgt    6300
ggtggtgcct tctggagagg agcagagata cacgtgccat gtgcagcatg aggggctacc    6360
cgagcccgtc accctgagat ggaagccggc ttcccagccc accatcccca tcgtgggcat    6420
cattgctggc ctggttctcc ttggatctgt ggtctctgga gctgtggttg ctgctgtgat    6480
atggaggaag aagagctcag gtggaaaagg agggagctac tctaaggctg agtggagcga    6540
cagtgcccag gggtctgagt ctcacagctt gtaatctaga gcggccgcga ctctagatca    6600
ggcgcgccgt taccaagcag ctatggaagc ttatggacct cagagaggaa gtaacgagga    6660
gagggtgtgg tggaatgtca ctagaaacca gggaaaacaa ggaggagagt attacaggga    6720
aggaggtgaa gaacctcatt acccaaatac tcctgctcct catagacgta cctgggatga    6780
gagacacaag gttcttaaat tgtcctcatt cgctactccc tctgacatcc aacgctggac    6840
tactaactct agattgtacg ggaggctctt cactactcgc tgcgtcgaga gtgtacgaga    6900
ctctccaggt ttggtaagaa atattttata ttgttataat gttactatga tccattaaca    6960
ctctgcttat agattgtaag ggtgattgca atgctttctg cataaaactt tggttttctt    7020
gttaatcaat aaaccgactt gattcgagaa ccaactccta tattattgtc tcttttatac    7080
tttattaagt aaaaggattt gtatattagc cttgctaagg gagacatcta gtgatataag    7140
tgtgaactac acttatctta aatgatgtaa ctccttagga taatcaatat acaaaattcc    7200
atgacaattg gcgataccgt cgaccgttca gctgcattaa tgaatcggcc aacgcgcggg    7260
gagaggcggt ttgcgtattg ggcgctcttc cgcttcctcg ctcactgact cgctgcgctc    7320
ggtcgttcgg ctgcggcgag cggtatcagc tcactcaaag gcggtaatac ggttatccac    7380
agaatcaggg gataacgcag gaaagaacat gtgagcaaaa ggccagcaaa aggccaggaa    7440
ccgtaaaaag gccgcgttgc tggcgttttt ccataggctc cgcccccctg acgagcatca    7500
caaaaatcga cgctcaagtc agaggtggcg aaacccgaca ggactataaa gataccaggc    7560
gtttccccct ggaagctccc tcgtgcgctc tcctgttccg accctgccgc ttaccggata    7620
cctgtccgcc tttctccctt cgggaagcgt ggcgctttct caatgctcac gctgtaggta    7680
tctcagttcg gtgtaggtcg ttcgctccaa gctgggctgt gtgcacgaac cccccgttca    7740
gcccgaccgc tgcgccttat ccggtaacta tcgtcttgag tccaacccgg taagacacga    7800
cttatcgcca ctggcagcag ccactggtaa caggattagc agagcgaggt atgtaggcgg    7860
tgctacagag ttcttgaagt ggtggcctaa ctacggctac actagaagga cagtatttgg    7920
```

-continued

```
tatctgcgct ctgctgaagc cagttacctt cggaaaaaga gttggtagct cttgatccgg    7980
caaacaaacc accgctggta gcggtggttt ttttgtttgc aagcagcaga ttacgcgcag    8040
aaaaaaagga tctcaagaag atcctttgat cttttctacg gggtctgacg ctcagtggaa    8100
cgaaaactca cgttaaggga ttttggtcat gagattatca aaaaggatct tcacctagat    8160 cctttttaaat taaaaatgaa gttttaaatc aatctaaagt atatatgagt aaacttggtc    8220
tgacagttac caatgcttaa tcagtgaggc acctatctca gcgatctgtc tatttcgttc    8280
atccatagtt gcctgactcc ccgtcgtgta dataactacg atacgggagg gcttaccatc    8340
tggccccagt gctgcaatga taccgcgaga cccacgctca ccggctccag atttatcagc    8400
aataaaccag ccagccggaa gggccgagcg cagaagtggt cctgcaactt tatccgcctc    8460
catccagtct attaattgtt gccgggaagc tagagtaagt agttcgccag ttaatagttt    8520
gcgcaacgtt gttgccattg ctacaggcat cgtggtgtca cgctcgtcgt ttggtatggc    8580
ttcattcagc tccggttccc aacgatcaag gcgagttaca tgatccccca tgttgtgcaa    8640
aaaagcggtt agctccttcg gtcctccgat cgttgtcaga agtaagttgg ccgcagtgtt    8700
atcactcatg gttatggcag cactgcataa ttctcttact gtcatgccat ccgtaagatg    8760
cttttctgtg actggtgagt actcaaccaa gtcattctga gaatagtgta tgcggcgacc    8820
gagttgctct tgcccggcgt caatacggga taataccgcg ccacatagca gaactttaaa    8880
agtgctcatc attggaaaac gttcttcggg gcgaaaactc tcaaggatct taccgctgtt    8940
gagatccagt tcgatgtaac ccactcgtgc acccaactga tcttcagcat cttttacttt    9000
caccagcgtt tctgggtgag caaaaacagg aaggcaaaat gccgcaaaaa agggaataag    9060
ggcgacacgg aaatgttgaa tactcatact cttccttttt caatattatt gaagcattta    9120
tcagggttat tgtctcatga gcggatacat atttgaatgt atttagaaaa ataaacaaat    9180
aggggttccg cgcacatttc cccgaaaagt gccacctgac gtctaagaaa ccattattat    9240
catgacatta acctataaaa ataggcgtat cacgaggccc tttcgtc                  9287
```

```
<210> SEQ ID NO 20
<211> LENGTH: 500
<212> TYPE: PRT
<213> ORGANISM: Artificial Sequence
<220> FEATURE:
<223> OTHER INFORMATION: HLA-bGBE

<400> SEQUENCE: 20

Met Ser Arg Ser Val Ala Leu Ala Val Leu Ala Leu Leu Ser Leu Ser
1               5                   10                  15

Gly Leu Glu Ala Val Met Ala Pro Arg Thr Leu Phe Leu Gly Gly Gly
            20                  25                  30

Gly Ser Gly Gly Gly Gly Ser Gly Gly Gly Gly Ser Ile Gln Arg Thr
        35                  40                  45

Pro Lys Ile Gln Val Tyr Ser Arg His Pro Ala Glu Asn Gly Lys Ser
    50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
            100                 105                 110

Glu Phe Thr Pro Thr Glu Lys Asp Glu Tyr Ala Cys Arg Val Asn His
```

-continued

```
                115              120              125
Val Thr Leu Ser Gln Pro Lys Ile Val Lys Trp Asp Arg Asp Met Gly
    130              135              140

Gly Gly Gly Ser Gly Gly Gly Gly Ser Gly Gly Gly Ser Gly Gly
145              150              155              160

Gly Gly Ser Gly Ser His Ser Leu Lys Tyr Phe His Thr Ser Val Ser
            165              170              175

Arg Pro Gly Arg Gly Glu Pro Arg Phe Ile Ser Val Gly Tyr Val Asp
            180              185              190

Asp Thr Gln Phe Val Arg Phe Asp Asn Asp Ala Ala Ser Pro Arg Met
            195              200              205

Val Pro Arg Ala Pro Trp Met Glu Gln Glu Gly Ser Glu Tyr Trp Asp
    210              215              220

Arg Glu Thr Arg Ser Ala Arg Asp Thr Ala Gln Ile Phe Arg Val Asn
225              230              235              240

Leu Arg Thr Leu Arg Gly Tyr Tyr Asn Gln Ser Glu Ala Gly Ser His
            245              250              255

Thr Leu Gln Trp Met His Gly Cys Glu Leu Gly Pro Asp Gly Arg Phe
            260              265              270

Leu Arg Gly Tyr Glu Gln Phe Ala Tyr Asp Gly Lys Asp Tyr Leu Thr
            275              280              285

Leu Asn Glu Asp Leu Arg Ser Trp Thr Ala Val Asp Thr Ala Ala Gln
    290              295              300

Ile Ser Glu Gln Lys Ser Asn Asp Ala Ser Glu Ala Glu His Gln Arg
305              310              315              320

Ala Tyr Leu Glu Asp Thr Cys Val Glu Trp Leu His Lys Tyr Leu Glu
            325              330              335

Lys Gly Lys Glu Thr Leu Leu His Leu Glu Pro Pro Lys Thr His Val
            340              345              350

Thr His His Pro Ile Ser Asp His Glu Ala Thr Leu Arg Cys Trp Ala
            355              360              365

Leu Gly Phe Tyr Pro Ala Glu Ile Thr Leu Thr Trp Gln Gln Asp Gly
    370              375              380

Glu Gly His Thr Gln Asp Thr Glu Leu Val Glu Thr Arg Pro Ala Gly
385              390              395              400

Asp Gly Thr Phe Gln Lys Trp Ala Ala Val Val Val Pro Ser Gly Glu
            405              410              415

Glu Gln Arg Tyr Thr Cys His Val Gln His Glu Gly Leu Pro Glu Pro
            420              425              430

Val Thr Leu Arg Trp Lys Pro Ala Ser Gln Pro Thr Ile Pro Ile Val
    435              440              445

Gly Ile Ile Ala Gly Leu Val Leu Leu Gly Ser Val Val Ser Gly Ala
    450              455              460

Val Val Ala Ala Val Ile Trp Arg Lys Lys Ser Ser Gly Gly Lys Gly
465              470              475              480

Gly Ser Tyr Ser Lys Ala Glu Trp Ser Asp Ser Ala Gln Gly Ser Glu
            485              490              495

Ser His Ser Leu
            500
```

```
<210> SEQ ID NO 21
<211> LENGTH: 7159
<212> TYPE: DNA
<213> ORGANISM: Artificial Sequence
```

-continued

```
<220> FEATURE:
<223> OTHER INFORMATION: Vector sequence for pA2-B2METKNpA

<400> SEQUENCE: 21
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct gcggccgcga tgcagtccaa actctcacta aaattgccga gccctttgtc     180
ttccagtgtc taaaatatta atgtcaatgg aatcaggcca gagtttgaat tctagtctct     240
tagcctttgt ttcccctgtc cataaaatga atgggggtaa ttctttcctc ctacagttta     300
tttatatatt cactaattca ttcattcatc catccattcg ttcattcggt ttactgagta     360
cctactatgt gccagcccct gttctagggt ggaaactaag agaatgatgt acctagaggg     420
cgctggaagc tctaaagccc tagcagttac tgcttttact attagtggtc gttttttttct     480 cccccccgcc ccccgacaaa tcaacagaac aaagaaaatt acctaaacag caaggacata     540
gggaggaact tcttggcaca gaactttcca aacactttt cctgaaggga tacaagaagc     600
aagaaaggta ctctttcact aggaccttct ctgagctgtc ctcaggatgc ttttgggact     660
atttttctta cccagagaat ggagaaaccc tgcagggaat tcccaagctg tagttataaa     720
cagaagttct ccttctgcta ggtagcattc aaagatctta atcttctggg tttccgtttt     780
ctcgaatgaa aaatgcaggt ccgagcagtt aactggctgg ggcaccatta gcaagtcact     840
tagcatctct ggggccagtc tgcaaagcga ggggggcagcc ttaatgtgcc tccagcctga     900
agtcctagaa tgagcgcccg gtgtcccaag ctggggcgcg cacccccagat cggagggcgc     960 cgatgtacag acagcaaact cacccagtct agtgcatgcc ttcttaaaca tcacgagact    1020
ctaagaaaag gaaactgaaa acgggaaagt ccctctctct aacctggcac tgcgtcgctg    1080
gcttggagac aggtgacggt ccctgcgggc cttgtcctga ttggctgggc acgcgtttaa    1140
tataagtgga ggcgtcgcgc tggcgggcat tcctgaagct gacagcattc gggccgagat    1200
ctagataact tcgtataatg tatgctatac gaagttatgg atccatcgat tctgcgatcg    1260
ctccggtgcc cgtcagtggg cagagcgcac atcgcccaca gtccccgaga agttgggggg    1320
aggggtcggc aattgaaccg gtgcctagag aaggtggcgc ggggtaaact gggaaagtga    1380
tgtcgtgtac tggctccgcc ttttttccga gggtggggga gaaccgtata taagtgcagt    1440
agtcgccgtg aacgttcttt ttcgcaacgg gtttgccgcc agaacacagc tgaagcttcc    1500
accatgccca cgctactgcg ggtttatata gacggtcccc acgggatggg gaaaaccacc    1560
accacgcaac tgctggtggc cctgggttcg cgcgacgata tcgtctacgt acccgagccg    1620
atgacttact ggcgggtgct gggggcttcc gagacaatcg cgaacatcta caccacacaa    1680
caccgcctcg accagggtga gatatcggcc ggggacgcgg cggtggtaat gacaagcgcc    1740
cagataacaa tgggcatgcc ttatgccgtg accgacgccg ttctggctcc tcatatcggg    1800
ggggaggctg ggagctcaca tgccccgccc ccggccctca ccctcatctt cgaccgccat    1860
cccatcgccg ccctcctgtg ctacccggcc gcgcggtacc ttatgggcag catgacccc    1920 caggccgtgc tggcgttcgt ggccctcatc ccgccgacct gcccggcac caacatcgtg    1980 cttgggccc ttccggagga cagacacatc gaccgcctgg ccaaacgcca gcgccccggc    2040
gagcggctgg acctggctat gctggctgcg attcgccgcg tttacgggct acttgccaat    2100
acggtgcggt atctgcagtg cggcgggtcg tggcgggagg actggggaca gcttcgggg    2160 acggccgtgc cgccccaggg tgccgagccc cagagcaacg cgggcccacg accccatatc    2220
```

-continued

```
ggggacacgt tatttaccct gtttcgggcc cccgagttgc tggccccaa cggcgacctg    2280 tataacgtgt ttgcctgggc cttggacgtc ttggccaaac gcctccgttc catgcacgtc    2340
tttatcctgg attacgacca atcgcccgcc ggctgccggg acgccctgct gcaacttacc    2400
tccgggatgg tccagaccca cgtcaccacc cccggctcca taccgacgat atgcgacctg    2460
gcgcgcacgt ttgcccggga gatgggatcg gccattgaac aagatggatt gcacgcaggt    2520
tctccggccg cttgggtgga gaggctattc ggctatgact gggcacaaca gacaatcggc    2580
tgctctgatg ccgccgtgtt ccggctgtca gcgcaggggc gcccggttct ttttgtcaag    2640
accgacctgt ccggtgccct gaatgaactg caggacgagg cagcgcggct atcgtggctg    2700
gccacgacgg gcgttccttg cgcagctgtg ctcgacgttg tcactgaagc gggaagggac    2760
tggctgctat tgggcgaagt gccggggcag gatctcctgt catctcacct tgctcctgcc    2820
gagaaagtat ccatcatggc tgatgcaatg cggcggctgc atacgcttga tccggctacc    2880
tgcccattcg accaccaagc gaaacatcgc atcgagcgag cacgtactcg gatggaagcc    2940
ggtcttgtcg atcaggatga tctggacgaa gagcatcagg gctcgcgcc agccgaactg    3000 ttcgccaggc tcaaggcgcg catgcccgac ggcgaggatc tcgtcgtgac ccatggcgat    3060
gcctgcttgc cgaatatcat ggtggaaaat ggccgctttt ctggattcat cgactgtggc    3120
cggctgggtg tggcggaccg ctatcaggac atagcgttgg ctacccgtga tattgctgaa    3180
gagcttggcg gcgaatgggc tgaccgcttc ctcgtgcttt acggtatcgc cgctcccgat    3240
tcgcagcgca tcgccttcta tcgccttctt gacgagttct tctgagggtc tctagcataa    3300
cttcgtataa tgtatgctat acgaagttat aataaaagat ccttatttc attggatctg    3360 tgtgttggtt ttttgtgtgg gatccgtcga taccgtcgac tgtctcgctc cgtggcctta    3420
gctgtgctcg cgctactctc tctttctggc ctggaggcta tccagcgtga gtctctccta    3480
ccctcccgct ctggtccttc tctcccgct ctgcaccctc tgtggccctc gctgtgctct    3540
ctcgctccgt gacttccctt ctccaagttc tccttggtgg cccgccgtgg ggctagtcca    3600
gggctggatc tcggggaagc ggcggggtgg cctgggagtg gggaaggggg tgcgcacccg    3660
ggacgcgcgc tacttgcccc tttcggcggg gagcagggga gacctttggc ctacggcgac    3720
gggagggtcg ggacaaagtt tagggcgtcg ataagcgtca gagcgccgag gttgggggag    3780
ggtttctctt ccgctctttc gcggggcctc tggctccccc agcgcagctg gagtggggga    3840
cgggtaggct cgtcccaaag gcgcggcgct gaggtttgtg aacgcgtgga ggggcgcttg    3900
gggtctgggg gaggcgtcgc ccgggtaagc ctgtctgctg cggctctgct tcccttagac    3960
tggagagctg tggacttcgt ctaggcgccc gctaagttcg catgtcctag cacctctggg    4020
tctatgtggg gccacaccgt ggggaggaaa cagcacgcga cgtttgtaga atgcttggct    4080
gtgatacaaa gcggtttcga ataattaact tatttgttcc catcacatgt cacttttaaa    4140
aaattataag aactacccgt tattgacatc tttctgtgtg ccaaggactt tatgtgcttt    4200
gcgtcattta attttgaaaa cagttatctt ccgccataga taactactat ggttatcttc    4260
tgcctctcac agatgaagaa actaaggcac cgagatttta agaaacttaa ttacacaggg    4320
gataaatggc agcaatcgag attgaagtca agcctaacca gggcttttgc gggagcgcat    4380
gccttttggc tgtaattcgt gcgcggccgc aggaacccct agtgatggag ttggccactc    4440
cctctctgcg cgctcgctcg ctcactgagg ccgggcgacc aaaggtcgcc cgacgcccgg    4500
gctttgcccg ggcggcctca gtgagcgagc gagcgcgcag ctgcctgcag gggcgcctga    4560
tgcggtattt tctccttacg catctgtgcg gtatttcaca ccgcatacgt caaagcaacc    4620
```

```
atagtacgcg ccctgtagcg gcgcattaag cgcggcgggt gtggtggtta cgcgcagcgt    4680
gaccgctaca cttgccagcg ccctagcgcc cgctcctttc gctttcttcc cttcctttct    4740
cgccacgttc gccggctttc cccgtcaagc tctaaatcgg gggctccctt tagggttccg    4800
atttagtgct ttacggcacc tcgacccaa aaaacttgat ttgggtgatg gttcacgtag    4860
tgggccatcg ccctgataga cggttttttcg ccctttgacg ttggagtcca cgttctttaa    4920
tagtggactc ttgttccaaa ctggaacaac actcaaccct atctcgggct attctttga    4980 tttataaggg attttgccga tttcggccta ttggttaaaa aatgagctga tttaacaaaa    5040
atttaacgcg aattttaaca aaatattaac gtttacaatt ttatggtgca ctctcagtac    5100
aatctgctct gatgccgcat agttaagcca gccccgacac ccgccaacac ccgctgacgc    5160
gccctgacgg gcttgtctgc tcccggcatc cgcttacaga caagctgtga ccgtctccgg    5220
gagctgcatg tgtcagaggt tttcaccgtc atcaccgaaa cgcgcgagac gaaagggcct    5280
cgtgatacgc ctatttttat aggttaatgt catgataata atggtttctt agacgtcagg    5340 tggcacttttt cggggaaatg tgcgcggaac ccctatttgt ttatttttct aaatacattc    5400
aaatatgtat ccgctcatga gacaataacc ctgataaatg cttcaataat attgaaaaag    5460
gaagagtatg agtattcaac atttccgtgt cgcccttatt ccctttttttg cggcattttg    5520 ccttcctgtt tttgctcacc cagaaacgct ggtgaaagta aaagatgctg aagatcagtt    5580
gggtgcacga gtgggttaca tcgaactgga tctcaacagc ggtaagatcc ttgagagttt    5640
tcgccccgaa gaacgttttc caatgatgag cactttttaaa gttctgctat gtggcgcggt    5700
attatcccgt attgacgccg ggcaagagca actcggtcgc cgcatacact attctcagaa    5760
tgacttggtt gagtactcac cagtcacaga aaagcatctt acggatggca tgacagtaag    5820
agaattatgc agtgctgcca taaccatgag tgataacact gcggccaact tacttctgac    5880
aacgatcgga ggaccgaagg agctaaccgc tttttttgcac aacatggggg atcatgtaac    5940
tcgccttgat cgttgggaac cggagctgaa tgaagccata ccaaacgacg agcgtgacac    6000
cacgatgcct gtagcaatgg caacaacgtt gcgcaaacta ttaactggcg aactacttac    6060
tctagcttcc cggcaacaat taatagactg gatggaggcg gataaagttg caggaccact    6120
tctgcgctcg gcccttccgg ctggctggtt tattgctgat aaatctggag ccggtgagcg    6180
tgggtctcgc ggtatcattg cagcactggg gccagatggt aagccctccc gtatcgtagt    6240
tatctacacg acggggagtc aggcaactat ggatgaacga aatagacaga tcgctgagat    6300
aggtgcctca ctgattaagc attggtaact gtcagaccaa gtttactcat atatacttta    6360
gattgattta aaacttcatt tttaatttaa aaggatctag gtgaagatcc tttttgataa    6420
tctcatgacc aaaatccctt aacgtgagtt ttcgttccac tgagcgtcag accccgtaga    6480
aaagatcaaa ggatcttctt gagatccttt ttttctgcgc gtaatctgct gcttgcaaac    6540
aaaaaaacca ccgctaccag cggtggtttg tttgccggat caagagctac caactctttt    6600
tccgaaggta actggcttca gcagagcgca gataccaaat actgtccttc tagtgtagcc    6660
gtagttaggc caccacttca agaactctgt agcaccgcct acatacctcg ctctgctaat    6720
cctgttacca gtggctgctg ccagtggcga taagtcgtgt cttaccgggt tggactcaag    6780
acgatagtta ccggataagg cgcagcggtc gggctgaacg gggggttcgt gcacacagcc    6840
cagcttggag cgaacgacct acaccgaact gagatacctb cagcgtgagc tatgagaaag    6900
cgccacgctt cccgaaggga gaaaggcgga caggtatccg gtaagcggca gggtcggaac    6960
```

-continued

```
aggagagcgc acgagggagc ttccagggggg aaacgcctgg tatctttata gtcctgtcgg   7020
gtttcgccac ctctgacttg agcgtcgatt tttgtgatgc tcgtcagggg ggcggagcct   7080
atggaaaaac gccagcaacg cggccttttt acggttcctg gccttttgct ggccttttgc   7140
tcacatgtcc tgcaggcag                                                  7159

<210> SEQ ID NO 22
<211> LENGTH: 7199
<212> TYPE: DNA
<213> ORGANISM: Artificial Sequence
<220> FEATURE:
<223> OTHER INFORMATION: Vector sequence for  pA2-B2MEHyTKpA

<400> SEQUENCE: 22
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc tgcggccgcg aaactaagag aatgatgtac ctagagggcg    180
ctggaagctc taaagcccta gcagttactg cttttactat tagtggtcgt ttttttctcc    240 ccccgcccc ccgacaaatc aacagaacaa agaaaattac ctaaacagca aggacatagg    300
gaggaacttc ttggcacaga actttccaaa cacttttttcc tgaagggata caagaagcaa    360
gaaaggtact ctttcactag gaccttctct gagctgtcct caggatgctt ttgggactat    420
ttttcttacc cagagaatgg agaaaccctg caggagaattc ccaagctgta gttataaaca    480
gaagttctcc ttctgctagg tagcattcaa agatcttaat cttctgggtt tccgttttct    540
cgaatgaaaa atgcaggtcc gagcagttaa ctggctgggg caccattagc aagtcactta    600
gcatctctgg ggccagtctg caaagcgagg gggcagcctt aatgtgcctc cagcctgaag    660
tcctagaatg agcgcccggt gtcccaagct ggggcgcgca ccccagatcg gagggcgccg    720
atgtacagac agcaaactca cccagtctag tgcatgcctt cttaaacatc acgagactct    780
aagaaaagga aactgaaaac gggaaagtcc ctctctctaa cctggcactg cgtcgctggc    840
ttggagacag gtgacggtcc ctgcgggcct tgtcctgatt ggctgggcac gcgtttaata    900
taagtggagg cgtcgcgctg gcgggcattc ctgaagctga cagcattcgg gccgagatct    960
agataacttc gtataatgta tgctatacga agttatggat ccatcgattc tgcgatcgct   1020
ccggtgcccg tcagtgggca gagcgcacat cgcccacagt ccccgagaag ttgggggggag   1080 gggtcggcaa ttgaaccggt gcctagagaa ggtggcgcgg ggtaaactgg gaaagtgatg   1140
tcgtgtactg gctccgcctt tttcccgagg gtgggggaga accgtatata agtgcagtag   1200
tcgccgtgaa cgttcttttt cgcaacgggt ttgccgccag aacacagctg aagcttccac   1260
catgaaaaag cctgaactca ccgcgacgtc tgtcgagaag tttctgatcg aaaagttcga   1320
cagcgtctcc gacctgatgc agctctcgga gggcgaagaa tctcgtgctt tcagcttcga   1380
tgtaggaggg cgtggatatg tcctgcgggt aaatagctgc gccgatggtt tctacaaaga   1440
tcgttatgtt tatcggcact ttgcatcggc cgcgctcccg attccggaag tgcttgacat   1500
tggggaattc agcgagagcc tgacctattg catctcccgc cgtgcacagg gtgtcacgtt   1560
gcaagacctg cctgaaaccg aactgcccgc tgttctgcag ccggtcgcgg aggccatgga   1620
tgcgatcgct gcggccgatc ttagccagac gagcgggttc ggcccattcg gaccgcaagg   1680
aatcggtcaa tacactacat ggcgtgattt catatgcgcg attgctgatc cccatgtgta   1740
tcactggcaa actgtgatgg acgacaccgt cagtgcgtcc gtcgcgcagg ctctcgatga   1800
gctgatgctt tgggccgagg actgccccga agtccggcac ctcgtgcacg cggatttcgg   1860
```

-continued

```
ctccaacaat gtcctgacgg acaatggccg cataacagcg gtcattgact ggagcgaggc   1920
gatgttcggg gattcccaat acgaggtcgc caacatcttc ttctggaggc cgtggttggc   1980
ttgtatggag cagcagacgc gctacttcga gcggaggcat ccggagcttg caggatcgcc   2040
gcggctccgg gcgtatatgc tccgcattgg tcttgaccaa ctctatcaga gcttggttga   2100
cggcaatttc gatgatgcag cttgggcgca gggtcgatgc gacgcaatcg tccgatccgg   2160
agccgggact gtcgggcgta cacaaatcgc ccgcagaagc gcggccgtct ggaccgatgg   2220
ctgtgtagaa gtcgcgtctg cgttcgacca ggctgcgcgt tctcgcggcc atagcaaccg   2280
acgtacggcg ttgcgccctc gccggcagca agaagccacg gaagtccgcc cggagcagaa   2340
aatgcccacg ctactgcggg tttatataga cggtccccac gggatgggga aaaccaccac   2400
cacgcaactg ctggtggccc tgggttcgcg cgacgatatc gtctacgtac ccgagccgat   2460
gacttactgg cgggtgctgg gggcttccga dacaatcgcg aacatctaca ccacacaaca   2520
ccgcctcgac cagggtgaga tatcggccgg ggacgcggcg gtggtaatga caagcgccca   2580
gataacaatg ggcatgcctt atgccgtgac cgacgccgtt ctggctcctc atatcggggg   2640
ggaggctggg agctcacatg ccccgccccc ggccctcacc ctcatcttcg accgccatcc   2700
catcgccgcc ctcctgtgct acccggccgc gcggtacctt atgggcagca tgacccccca   2760
ggccgtgctg gcgttcgtgg ccctcatccc gccgaccttg cccggcacca acatcgtgct   2820 tggggcccctt ccggaggaca gacacatcga ccgcctggcc aaacgccagc gccccggcga   2880
gcggctggac ctggctatgc tggctgcgat tcgccgcgtt tacgggctac ttgccaatac   2940
ggtgcggtat ctgcagtgcg gcgggtcgtg gcgggaggac tggggacagc tttcggggac   3000
ggccgtgccg ccccagggtg ccgagcccca gagcaacgcg ggcccacgac cccatatcgg   3060
ggacacgtta tttaccctgt ttcgggcccc cgagttgctg gcccccaacg gcgacctgta   3120
taacgtgttt gcctgggcct tggacgtctt ggccaaacgc ctccgttcca tgcacgtctt   3180
tatcctggat tacgaccaat cgcccgccgg ctgccgggac gccctgctgc aacttacctc   3240
cgggatggtc cagacccacg tcaccacccc cggctccata ccgacgatat gcgacctggc   3300
gcgcacgttt gcccgggaga tggggaaggc taactgaggt ctctagcata acttcgtata   3360
atgtatgcta tacgaagtta taataaaaga tccttatttt cattggatct gtgtgttggt   3420
tttttgtgtg ggatccgtcg ataccgtcga ctgtctcgct ccgtggcctt agctgtgctc   3480
gcgctactct ctctttctgg cctggaggct atccagcgtg agtctctcct accctcccgc   3540
tctggtcctt cctctcccgc tctgcaccct ctgtggccct cgctgtgctc tctcgctccg   3600
tgacttccct tctccaagtt ctccttggtg gcccgccgtg gggctagtcc agggctggat   3660
ctcggggaag cggcggggtg gcctgggagt ggggaagggg gtgcgcaccc gggacgcgcg   3720
ctacttgccc cttttcggcgg ggagcagggg agacctttgg cctacggcga cgggagggtc   3780
gggacaaagt ttagggcgtc gataagcgtc agagcgccga ggttggggga gggtttctct   3840
tccgctcttt cgcggggcct ctggctcccc cagcgcagct ggagtggggg acgggtaggc   3900
tcgtcccaaa ggcgcggcgc tgaggtttgt gaacgcgtgg aggggcgctt ggggtctggg   3960
ggaggcgtcg cccgggtaag cctgtctgct gcggctctgc ttcccttaga ctggagagct   4020
gtggacttcg tctaggcgcc cgctaagttc gcatgtccta gcacctctgg gtctatgtgg   4080
ggccacaccg tggggaggaa acagcacgcg acgtttgtag aatgcttggc tgtgatacaa   4140
agcggtttcg aataattaac ttatttgttc ccatcacatg tcacttttaa aaaattataa   4200
```

-continued

```
gaactacccg ttattgacat ctttctgtgt gccaaggact ttatgtgctt tgcgtcattt    4260
aattttgaaa acagttatct tccgccatag ataactacta tggttatctt ctgcctctca    4320
cagatgaaga aactaaggca ccgagatttt aagaaactta attacacagg ggataaatgg    4380
cagcaatcga gattgaagtc aagcctaacc agggctttg cgggagcgca tgccttttgg    4440
ctgtaattcg tgcgcggccg caggaacccc tagtgatgga gttggccact ccctctctgc    4500
gcgctcgctc gctcactgag gccgggcgac caaaggtcgc ccgacgcccg ggctttgccc    4560
gggcggcctc agtgagcgag cgagcgcgca gctgcctgca ggggcgcctg atgcggtatt    4620
ttctccttac gcatctgtgc ggtatttcac accgcatacg tcaaagcaac catagtacgc    4680
gccctgtagc ggcgcattaa gcgcggcggg tgtggtggtt acgcgcagcg tgaccgctac    4740
acttgccagc gccctagcgc ccgctccttt cgctttcttc ccttcctttc tcgccacgtt    4800
cgccggcttt ccccgtcaag ctctaaatcg ggggctccct ttagggttcc gatttagtgc    4860
tttacggcac ctcgacccca aaaaacttga tttgggtgat ggttcacgta gtgggccatc    4920
gccctgatag acggtttttc gccctttgac gttggagtcc acgttcttta atagtggact    4980
cttgttccaa actggaacaa cactcaaccc tatctcgggc tattcttttg atttataagg    5040
gattttgccg atttcggcct attggttaaa aaatgagctg atttaacaaa aatttaacgc    5100
gaattttaac aaaatattaa cgtttacaat tttatggtgc actctcagta caatctgctc    5160
tgatgccgca tagttaagcc agccccgaca cccgccaaca cccgctgacg cgccctgacg    5220
ggcttgtctg ctcccggcat ccgcttacag acaagctgtg accgtctccg ggagctgcat    5280
gtgtcagagg ttttcaccgt catcaccgaa acgcgcgaga cgaaagggcc tcgtgatacg    5340
cctattttta taggttaatg tcatgataat aatggtttct tagacgtcag gtggcacttt    5400
tcggggaaat gtgcgcggaa cccctatttg tttattttc taaatacatt caaatatgta    5460
tccgctcatg agacaataac cctgataaat gcttcaataa tattgaaaaa ggaagagtat    5520
gagtattcaa catttccgtg tcgcccttat tcccttttt gcggcatttt gccttcctgt    5580
ttttgctcac ccagaaacgc tggtgaaagt aaaagatgct gaagatcagt tgggtgcacg    5640
agtgggttac atcgaactgg atctcaacag cggtaagatc cttgagagtt ttcgccccga    5700
agaacgtttt ccaatgatga gcacttttaa agttctgcta tgtggcgcgg tattatcccg    5760
tattgacgcc gggcaagagc aactcggtcg ccgcatacac tattctcaga atgacttggt    5820
tgagtactca ccagtcacag aaaagcatct tacggatggc atgacagtaa gagaattatg    5880
cagtgctgcc ataaccatga gtgataacac tgcggccaac ttacttctga caacgatcgg    5940
aggaccgaag gagctaaccg ctttttttgca caacatgggg gatcatgtaa ctcgccttga    6000
tcgttgggaa ccggagctga atgaagccat accaaacgac gagcgtgaca ccacgatgcc    6060
tgtagcaatg gcaacaacgt tgcgcaaact attaactggc gaactactta ctctagcttc    6120
ccggcaacaa ttaatagact ggatggaggc ggataaagtt gcaggaccac ttctgcgctc    6180
ggcccttccg gctggctggt ttattgctga taaatctgga gccggtgagc gtgggtctcg    6240
cggtatcatt gcagcactgg ggccagatgg taagccctcc cgtatcgtag ttatctacac    6300
gacggggagt caggcaacta tggatgaacg aaatagacag atcgctgaga taggtgcctc    6360
actgattaag cattggtaac tgtcagacca agtttactca tatatacttt agattgattt    6420
aaaacttcat ttttaattta aaaggatcta ggtgaagatc cttttttgata atctcatgac    6480 caaaatccct taacgtgagt tttcgttcca ctgagcgtca gaccccgtag aaaagatcaa    6540
aggatcttct tgagatcctt tttttctgcg cgtaatctgc tgcttgcaaa caaaaaaacc    6600
```

-continued

```
accgctacca gcggtggttt gtttgccgga tcaagagcta ccaactcttt ttccgaaggt     6660
aactggcttc agcagagcgc agataccaaa tactgtcctt ctagtgtagc cgtagttagg     6720
ccaccacttc aagaactctg tagcaccgcc tacatacctc gctctgctaa tcctgttacc     6780
agtggctgct gccagtggcg ataagtcgtg tcttaccggg ttggactcaa gacgatagtt     6840
accggataag gcgcagcggt cgggctgaac ggggggttcg tgcacacagc ccagcttgga     6900
gcgaacgacc tacaccgaac tgagatacct acagcgtgag ctatgagaaa gcgccacgct     6960
tcccgaaggg agaaaggcgg acaggtatcc ggtaagcggc agggtcggaa caggagagcg     7020
cacgagggag cttccagggg gaaacgcctg gtatctttat agtcctgtcg ggtttcgcca     7080
cctctgactt gagcgtcgat ttttgtgatg ctcgtcaggg gggcggagcc tatggaaaaa     7140
cgccagcaac gcggcctttt tacggttcct ggccttttgc tggccttttg ctcacatgt      7199
```

```
<210> SEQ ID NO 23
<211> LENGTH: 29
<212> TYPE: PRT
<213> ORGANISM: Artificial Sequence
<220> FEATURE:
<223> OTHER INFORMATION: HLA-G peptide

<400> SEQUENCE: 23

Met Ala Pro Arg Thr Leu Phe Leu Gly Gly Gly Gly Ser Gly Gly Gly
1               5                   10                  15

Gly Ser Gly Gly Gly Gly Ser Ile Gln Arg Thr Pro Lys
            20                  25
```

```
<210> SEQ ID NO 24
<211> LENGTH: 1369
<212> TYPE: DNA
<213> ORGANISM: Homo sapiens
<220> FEATURE:
<221> NAME/KEY: CDS
<222> LOCATION: (506)..(1219)

<400> SEQUENCE: 24
ccggacgccg cacggctcct gttccggtgt cagagggccc gccctccccg ctcctcagtc      60
tttgcggaca agaaaggggc tgtgtgagac gcagggaagg aggcacaccc gggggtggcg     120
cagtgaggag ggggcgcgac ggccaggagg ctggtggagc gacacccagg caggagaggg     180
ggaagaactc tctcccttc tgaacccct tttccttgag agacgagttg ggggagtcct      240
ccacgcatta cccactcggg ccgcaaaaac tcccttcttt agccctctgc ccccgccctt     300
gcttataagc ctttgagacc gcagaaggga ccttgttgtg aacgggacg gccaagagga      360 agccagatcg ctgagggtcc ggtctccagt ttgcctcctg ctatatccat ggaagagaa      420 aagtttgtga cttgggcccc caagtttga gagaactggg ctttcggcgc ggggggacag      480
aggaggctcg tggggagctt ccccc atg gag ctt acc cag cct gca gaa gac       532
                             Met Glu Leu Thr Gln Pro Ala Glu Asp
                             1               5 ctc atc cag acc cag cag acc cct gcc tca gaa ctt ggg gac cct gaa       580
Leu Ile Gln Thr Gln Gln Thr Pro Ala Ser Glu Leu Gly Asp Pro Glu
10              15                  20                  25 gac ccc gga gag gag gct gca gat ggc tca gac act gtg gtc ctc agt       628
Asp Pro Gly Glu Glu Ala Ala Asp Gly Ser Asp Thr Val Val Leu Ser
                30                  35                  40 ctc ttt ccc tgc acc cct gag cct gtg aat cct gaa ccg gat gcc agt       676
Leu Phe Pro Cys Thr Pro Glu Pro Val Asn Pro Glu Pro Asp Ala Ser
            45                  50                  55
```

-continued

```
gtt tcc tct cca cag ggc agc tcc ctg aag cac tcc acc act ctc acc      724
Val Ser Ser Pro Gln Gly Ser Ser Leu Lys His Ser Thr Thr Leu Thr
        60              65                  70 aac cgg cag cga ggg aac gag gtg tca gct ctg ccg gcc acc cta gac      772
Asn Arg Gln Arg Gly Asn Glu Val Ser Ala Leu Pro Ala Thr Leu Asp
    75              80                  85 tgt gac aac ctc gtc aac aag cca gac gag cgc ggc ttc acc ccc ctc      820
Cys Asp Asn Leu Val Asn Lys Pro Asp Glu Arg Gly Phe Thr Pro Leu
90              95                  100                 105 atc tgg gcc tcc gcc ttt gga gag att gag acc gtt cgc ttc ctg ctg      868
Ile Trp Ala Ser Ala Phe Gly Glu Ile Glu Thr Val Arg Phe Leu Leu
            110             115                 120 gag tgg ggt gcc gac ccc cac atc ctg gca aaa gag cga gag agc gcc      916
Glu Trp Gly Ala Asp Pro His Ile Leu Ala Lys Glu Arg Glu Ser Ala
            125             130                 135 ctg tcg ctg gcc agc aca ggc ggc tac aca gac att gtg ggg ctg ctg      964
Leu Ser Leu Ala Ser Thr Gly Gly Tyr Thr Asp Ile Val Gly Leu Leu
            140             145                 150 ctg gag cgt gac gtg gac atc aac atc tat gat tgg aat gga ggg acg     1012
Leu Glu Arg Asp Val Asp Ile Asn Ile Tyr Asp Trp Asn Gly Gly Thr
    155             160                 165 cca ctg ctg tac gct gtg cgc ggg aac cac gtg aaa tgc gtt gag gcc     1060
Pro Leu Leu Tyr Ala Val Arg Gly Asn His Val Lys Cys Val Glu Ala
170             175                 180                 185 ttg ctg gcc cga ggc gct gac ctc acc acc gaa gcc gac tct ggc tac     1108
Leu Leu Ala Arg Gly Ala Asp Leu Thr Thr Glu Ala Asp Ser Gly Tyr
            190             195                 200 acc ccg atg gac ctt gcc gtg gcc ctg gga tac cgg aaa gtg caa cag     1156
Thr Pro Met Asp Leu Ala Val Ala Leu Gly Tyr Arg Lys Val Gln Gln
            205             210                 215 gtg atc gag aac cac atc ctc aag ctc ttc cag agc aac ctg gtg ccc     1204
Val Ile Glu Asn His Ile Leu Lys Leu Phe Gln Ser Asn Leu Val Pro
            220             225                 230 gct gac cct gag tga aggccgcctg ccggggactc agacactcag ggaacaaat     1259
Ala Asp Pro Glu
        235 ggtcagccag agctgggaa acccagaact gacttcaaag gcagcttctg dacaggtggt    1319 gggagggggac ccttcccaag aggaaccaat aaaccttctg tgcagaatga             1369
```

```
<210> SEQ ID NO 25
<211> LENGTH: 237
<212> TYPE: PRT
<213> ORGANISM: Homo sapiens

<400> SEQUENCE: 25

Met Glu Leu Thr Gln Pro Ala Glu Asp Leu Ile Gln Thr Gln Gln Thr
1               5                   10                  15

Pro Ala Ser Glu Leu Gly Asp Pro Glu Asp Pro Gly Glu Glu Ala Ala
            20                  25                  30

Asp Gly Ser Asp Thr Val Val Leu Ser Leu Phe Pro Cys Thr Pro Glu
            35                  40                  45

Pro Val Asn Pro Glu Pro Asp Ala Ser Val Ser Ser Pro Gln Gly Ser
    50                  55                  60

Ser Leu Lys His Ser Thr Thr Leu Thr Asn Arg Gln Arg Gly Asn Glu
65                  70                  75                  80

Val Ser Ala Leu Pro Ala Thr Leu Asp Cys Asp Asn Leu Val Asn Lys
            85                  90                  95
```

-continued

```
Pro Asp Glu Arg Gly Phe Thr Pro Leu Ile Trp Ala Ser Ala Phe Gly
            100                 105                 110

Glu Ile Glu Thr Val Arg Phe Leu Leu Glu Trp Gly Ala Asp Pro His
            115                 120                 125

Ile Leu Ala Lys Glu Arg Glu Ser Ala Leu Ser Leu Ala Ser Thr Gly
            130                 135                 140

Gly Tyr Thr Asp Ile Val Gly Leu Leu Leu Glu Arg Asp Val Asp Ile
145                 150                 155                 160

Asn Ile Tyr Asp Trp Asn Gly Gly Thr Pro Leu Leu Tyr Ala Val Arg
                165                 170                 175

Gly Asn His Val Lys Cys Val Glu Ala Leu Leu Ala Arg Gly Ala Asp
            180                 185                 190

Leu Thr Thr Glu Ala Asp Ser Gly Tyr Thr Pro Met Asp Leu Ala Val
            195                 200                 205

Ala Leu Gly Tyr Arg Lys Val Gln Gln Val Ile Glu Asn His Ile Leu
            210                 215                 220

Lys Leu Phe Gln Ser Asn Leu Val Pro Ala Asp Pro Glu
225                 230                 235
```

```
<210> SEQ ID NO 26
<211> LENGTH: 1438
<212> TYPE: DNA
<213> ORGANISM: Homo sapiens
<220> FEATURE:
<221> NAME/KEY: CDS
<222> LOCATION: (506)..(1288)

<400> SEQUENCE: 26
ccggacgccg cacggctcct gttccggtgt cagagggccc gccctccccg ctcctcagtc        60
tttgcggaca agaaaggggc tgtgtgagac gcagggaagg aggcacaccc gggggtggcg       120
cagtgaggag ggggcgcgac ggccaggagg ctggtggagc gacacccagg caggagaggg       180
ggaagaactc tctcccttc tgaaccccct tttccttgag agacgagttg ggggagtcct       240
ccacgcatta cccactcggg ccgcaaaaac tcccttcttt agccctctgc ccccgccctt       300
gcttataagc ctttgagacc gcagaaggga ccttgttgtg aacgggacg ccaagagga        360 agccagatcg ctgagggtcc ggtctccagt ttgcctcctg ctatatccat tggaagagaa       420
aagtttgtga cttgggcccc caagtttga gagaactggg ctttcggcgc ggggggacag       480
```

```
aggaggctcg tggggagctt ccccc atg gag ctt acc cag cct gca gaa gac       532
                              Met Glu Leu Thr Gln Pro Ala Glu Asp
                                1               5 ctc atc cag acc cag cag acc cct gcc tca gaa ctt ggg gac cct gaa       580
Leu Ile Gln Thr Gln Gln Thr Pro Ala Ser Glu Leu Gly Asp Pro Glu
10                  15                  20                  25 gac ccc gga gag gag gct gca gat ggc tca gac act gtg gtc ctc agt       628
Asp Pro Gly Glu Glu Ala Ala Asp Gly Ser Asp Thr Val Val Leu Ser
                30                  35                  40 ctc ttt ccc tgc acc cct gag cct gtg aat cct gaa ccg gat gcc agt       676
Leu Phe Pro Cys Thr Pro Glu Pro Val Asn Pro Glu Pro Asp Ala Ser
            45                  50                  55 gtt tcc tct cca cag gca ggc agc tcc ctg aag cac tcc acc act ctc       724
Val Ser Ser Pro Gln Ala Gly Ser Ser Leu Lys His Ser Thr Thr Leu
            60                  65                  70 acc aac cgg cag cga ggg aac gag gtg tca gct ctg ccg gcc acc cta       772
Thr Asn Arg Gln Arg Gly Asn Glu Val Ser Ala Leu Pro Ala Thr Leu
            75                  80                  85 gac tcc ctg tcc atc cac cag ctc gca gca cag ggg gag ctg gac cag       820
```

```
Asp Ser Leu Ser Ile His Gln Leu Ala Ala Gln Gly Glu Leu Asp Gln
90              95              100             105 ctg aag gag cat ttg cgg aaa ggt gac aac ctc gtc aac aag cca gac      868
Leu Lys Glu His Leu Arg Lys Gly Asp Asn Leu Val Asn Lys Pro Asp
            110             115             120 gag cgc ggc ttc acc ccc ctc atc tgg gcc tcc gcc ttt gga gag att      916
Glu Arg Gly Phe Thr Pro Leu Ile Trp Ala Ser Ala Phe Gly Glu Ile
            125             130             135 gag acc gtt cgc ttc ctg ctg gag tgg ggt gcc gac ccc cac atc ctg      964
Glu Thr Val Arg Phe Leu Leu Glu Trp Gly Ala Asp Pro His Ile Leu
        140             145             150 gca aaa gag cga gag agc gcc ctg tcg ctg gcc agc aca ggc ggc tac      1012
Ala Lys Glu Arg Glu Ser Ala Leu Ser Leu Ala Ser Thr Gly Gly Tyr
        155             160             165 aca gac att gtg ggg ctg ctg ctg gag cgt gac gtg gac atc aac atc      1060
Thr Asp Ile Val Gly Leu Leu Leu Glu Arg Asp Val Asp Ile Asn Ile
170             175             180             185 tat gat tgg aat gga ggg acg cca ctg ctg tac gct gtg cgc ggg aac      1108
Tyr Asp Trp Asn Gly Gly Thr Pro Leu Leu Tyr Ala Val Arg Gly Asn
            190             195             200 cac gtg aaa tgc gtt gag gcc ttg ctg gcc cga ggc gct gac ctc acc      1156
His Val Lys Cys Val Glu Ala Leu Leu Ala Arg Gly Ala Asp Leu Thr
            205             210             215 acc gaa gcc gac tct ggc tac acc ccg atg gac ctt gcc gtg gcc ctg      1204
Thr Glu Ala Asp Ser Gly Tyr Thr Pro Met Asp Leu Ala Val Ala Leu
        220             225             230 gga tac cgg aaa gtg caa cag gtg atc gag aac cac atc ctc aag ctc      1252
Gly Tyr Arg Lys Val Gln Gln Val Ile Glu Asn His Ile Leu Lys Leu
        235             240             245 ttc cag agc aac ctg gtg ccc gct gac cct gag tga aggccgcctg          1298
Phe Gln Ser Asn Leu Val Pro Ala Asp Pro Glu
250             255             260 ccggggactc agacactcag ggaacaaaat ggtcagccag agctggggaa acccagaact   1358
gacttcaaag gcagcttctg acaggtggt gggaggggac ccttcccaag aggaaccaat    1418
aaaccttctg tgcagaatga                                               1438
```

<210> SEQ ID NO 27
<211> LENGTH: 260
<212> TYPE: PRT
<213> ORGANISM: Homo sapiens

<400> SEQUENCE: 27

```
Met Glu Leu Thr Gln Pro Ala Glu Asp Leu Ile Gln Thr Gln Gln Thr
1               5               10              15

Pro Ala Ser Glu Leu Gly Asp Pro Glu Asp Pro Gly Glu Glu Ala Ala
            20              25              30

Asp Gly Ser Asp Thr Val Val Leu Ser Leu Phe Pro Cys Thr Pro Glu
            35              40              45

Pro Val Asn Pro Glu Pro Asp Ala Ser Val Ser Ser Pro Gln Ala Gly
        50              55              60

Ser Ser Leu Lys His Ser Thr Thr Leu Thr Asn Arg Gln Arg Gly Asn
65              70              75              80

Glu Val Ser Ala Leu Pro Ala Thr Leu Asp Ser Leu Ser Ile His Gln
            85              90              95

Leu Ala Ala Gln Gly Glu Leu Asp Gln Leu Lys Glu His Leu Arg Lys
            100             105             110

Gly Asp Asn Leu Val Asn Lys Pro Asp Glu Arg Gly Phe Thr Pro Leu
```

```
              115                   120                   125
Ile Trp Ala Ser Ala Phe Gly Glu Ile Glu Thr Val Arg Phe Leu Leu
    130                   135                   140

Glu Trp Gly Ala Asp Pro His Ile Leu Ala Lys Glu Arg Glu Ser Ala
145                   150                   155                   160

Leu Ser Leu Ala Ser Thr Gly Gly Tyr Thr Asp Ile Val Gly Leu Leu
                  165                   170                   175

Leu Glu Arg Asp Val Asp Ile Asn Ile Tyr Asp Trp Asn Gly Gly Thr
              180                   185                   190

Pro Leu Leu Tyr Ala Val Arg Gly Asn His Val Lys Cys Val Glu Ala
              195                   200                   205

Leu Leu Ala Arg Gly Ala Asp Leu Thr Thr Glu Ala Asp Ser Gly Tyr
          210                   215                   220

Thr Pro Met Asp Leu Ala Val Ala Leu Gly Tyr Arg Lys Val Gln Gln
225                   230                   235                   240

Val Ile Glu Asn His Ile Leu Lys Leu Phe Gln Ser Asn Leu Val Pro
                  245                   250                   255

Ala Asp Pro Glu
              260

<210> SEQ ID NO 28
<211> LENGTH: 3618
<212> TYPE: DNA
<213> ORGANISM: Homo sapiens
<220> FEATURE:
<221> NAME/KEY: CDS
<222> LOCATION: (222)..(2072)

<400> SEQUENCE: 28
attcagaaaa aggaaaataa agcaacgcac gagccggctg ggccaggacc ttggggctgg       60
gctggagtga aggtggctac gagtttttcca gatttaggag acttcagaaa ggtggggcag      120
atagaatgga gatggcaaag atctctttgg gcatatatgg gcctggcgaa gtaatggaat      180
aatttctaat tttcggagaa ggcaagtgcc ctcatgccgg g atg gca gaa gat gag      236
                                            Met Ala Glu Asp Glu
                                              1               5 cct gat gct aag agc ccc aag act ggg gga agg gcc ccc cca ggt ggt      284
Pro Asp Ala Lys Ser Pro Lys Thr Gly Gly Arg Ala Pro Pro Gly Gly
                  10                  15                  20 gct gag gct ggg gaa cct acc acc ctt ctt cag agg ctc cga ggt acc      332
Ala Glu Ala Gly Glu Pro Thr Thr Leu Leu Gln Arg Leu Arg Gly Thr
              25                  30                  35 att tcc aag gcc gtg cag aac aaa gta gag ggg atc ctg caa gat gta      380
Ile Ser Lys Ala Val Gln Asn Lys Val Glu Gly Ile Leu Gln Asp Val
          40                  45                  50 cag aaa ttt tct gac aat gac aag ctg tat ctc tac ctt cag ctc ccc      428
Gln Lys Phe Ser Asp Asn Asp Lys Leu Tyr Leu Tyr Leu Gln Leu Pro
      55                  60                  65 tca gga ccc acc act gga gac aaa agc tca gag cca agt aca ctg agc      476
Ser Gly Pro Thr Thr Gly Asp Lys Ser Ser Glu Pro Ser Thr Leu Ser
70                  75                  80                  85 aat gag gag tac atg tat gcc tat agg tgg atc cgc aac cac ctg gaa      524
Asn Glu Glu Tyr Met Tyr Ala Tyr Arg Trp Ile Arg Asn His Leu Glu
                  90                  95                  100 gag cac act gac acc tgt ctg cca aag caa agt gtt tat gat gcc tat      572
Glu His Thr Asp Thr Cys Leu Pro Lys Gln Ser Val Tyr Asp Ala Tyr
              105                 110                 115 cgg aag tac tgt gag agt ctt gcc tgt tgc cgc cca ctc agc aca gcc      620
```

```
Arg Lys Tyr Cys Glu Ser Leu Ala Cys Cys Arg Pro Leu Ser Thr Ala
    120                 125                 130 aac ttt ggc aag atc atc aga gag atc ttc cct gac atc aaa gct cga      668
Asn Phe Gly Lys Ile Ile Arg Glu Ile Phe Pro Asp Ile Lys Ala Arg
    135                 140                 145 agg ctt ggt ggc cgg ggc cag tcc aaa tat tgc tac agt ggc ata agg      716
Arg Leu Gly Gly Arg Gly Gln Ser Lys Tyr Cys Tyr Ser Gly Ile Arg
150                 155                 160                 165 agg aag acc ttg gtg tct atg cca ccc ctg cct gga ctt gac cta aag      764
Arg Lys Thr Leu Val Ser Met Pro Pro Leu Pro Gly Leu Asp Leu Lys
            170                 175                 180 ggt tct gag agt cca gaa atg ggc cca gaa gta acc cca gca cct cga      812
Gly Ser Glu Ser Pro Glu Met Gly Pro Glu Val Thr Pro Ala Pro Arg
                185                 190                 195 gat gaa ctg gtg gag gca gcg tgt gcc ctg acc tgt gac tgg gca gag      860
Asp Glu Leu Val Glu Ala Ala Cys Ala Leu Thr Cys Asp Trp Ala Glu
            200                 205                 210 cgg atc ctg aaa cgg tcc ttc agt tcc atc gtt gag gtc gcc cgc ttc      908
Arg Ile Leu Lys Arg Ser Phe Ser Ser Ile Val Glu Val Ala Arg Phe
    215                 220                 225 ctg cta cag cag cat ctc atc tct gcc cga tct gca cat gcc cat gtg      956
Leu Leu Gln Gln His Leu Ile Ser Ala Arg Ser Ala His Ala His Val
230                 235                 240                 245 ctt aag gcc atg ggg ctt gct gaa gag gac gaa cat gca cct cgg gaa     1004
Leu Lys Ala Met Gly Leu Ala Glu Glu Asp Glu His Ala Pro Arg Glu
                250                 255                 260 cgg tca tct aaa cca aag aat ggt tta gag aac cca gag ggt gga gcc     1052
Arg Ser Ser Lys Pro Lys Asn Gly Leu Glu Asn Pro Glu Gly Gly Ala
                265                 270                 275 cac aag aag cca gag aga ctg gcc cag cct cct aag gat ctg gaa gcc     1100
His Lys Lys Pro Glu Arg Leu Ala Gln Pro Pro Lys Asp Leu Glu Ala
            280                 285                 290 cga act ggg gcc ggt cct ctc gca cgt gga gag cgg aag aag agt gta     1148
Arg Thr Gly Ala Gly Pro Leu Ala Arg Gly Glu Arg Lys Lys Ser Val
    295                 300                 305 gtt gag agc tcg gcc cca gga gcc aat aac ctg cag gtt aat gcc cta     1196
Val Glu Ser Ser Ala Pro Gly Ala Asn Asn Leu Gln Val Asn Ala Leu
310                 315                 320                 325 gtg gct cgg ctg cct ctg ctc ctt ccc cgg gcc cct cgc tca cta att     1244
Val Ala Arg Leu Pro Leu Leu Leu Pro Arg Ala Pro Arg Ser Leu Ile
                330                 335                 340 ccg cca atc cca gtc tct cca cct att ctg gcc ccc agg ctt tct tca     1292
Pro Pro Ile Pro Val Ser Pro Pro Ile Leu Ala Pro Arg Leu Ser Ser
                345                 350                 355 ggt gcc ctg aaa gtg gct aca ctg cct ctg tct agt agg gcc ggg gca     1340
Gly Ala Leu Lys Val Ala Thr Leu Pro Leu Ser Ser Arg Ala Gly Ala
            360                 365                 370 ccc cca gca gct gtg ccc atc att aac atg atc tta cca act gtt cct     1388
Pro Pro Ala Ala Val Pro Ile Ile Asn Met Ile Leu Pro Thr Val Pro
    375                 380                 385 gct ttg cct gga cct gga cct ggg cct ggg cga gct cca cct ggg gga     1436
Ala Leu Pro Gly Pro Gly Pro Gly Pro Gly Arg Ala Pro Pro Gly Gly
390                 395                 400                 405 ctc act cag ccc cgg ggc aca gag aac aga gag gta ggc ata ggt ggt     1484
Leu Thr Gln Pro Arg Gly Thr Glu Asn Arg Glu Val Gly Ile Gly Gly
                410                 415                 420 gac caa gga cca cat gac aag ggt gtc aag agg aca gct gaa gta cct     1532
Asp Gln Gly Pro His Asp Lys Gly Val Lys Arg Thr Ala Glu Val Pro
                425                 430                 435
```

-continued

```
gtg agt gag gcc agt ggg cag gct cca cca gct aaa gca gca aag cag       1580
Val Ser Glu Ala Ser Gly Gln Ala Pro Pro Ala Lys Ala Ala Lys Gln
        440             445             450 gat ata gag gat aca gca agt gat gcc aaa agg aaa cgg ggg cgc cct       1628
Asp Ile Glu Asp Thr Ala Ser Asp Ala Lys Arg Lys Arg Gly Arg Pro
    455             460             465 cga aaa aag tca ggt gga agt ggg gaa agg aat tct acc cct ctc aag       1676
Arg Lys Lys Ser Gly Gly Ser Gly Glu Arg Asn Ser Thr Pro Leu Lys
470             475             480             485 tca gca gct gcc atg gaa tct gcc cag tcc tca agg tta cca tgg gag       1724
Ser Ala Ala Ala Met Glu Ser Ala Gln Ser Ser Arg Leu Pro Trp Glu
                490             495             500 aca tgg ggc tca gga ggg gaa ggc aac tca gct gga ggg gca gag agg       1772
Thr Trp Gly Ser Gly Gly Glu Gly Asn Ser Ala Gly Gly Ala Glu Arg
            505             510             515 cca ggg cca atg gga gag gct gaa aag ggg gca gta ctt gcc cag ggt       1820
Pro Gly Pro Met Gly Glu Ala Glu Lys Gly Ala Val Leu Ala Gln Gly
        520             525             530 cag gga gat ggt act gtt tcc aaa gga gga agg ggc ccc ggt tcc cag       1868
Gln Gly Asp Gly Thr Val Ser Lys Gly Gly Arg Gly Pro Gly Ser Gln
        535             540             545 cat acc aaa gaa gca gaa gat aaa att ccc ttg gtc ccc tca aaa gtg       1916
His Thr Lys Glu Ala Glu Asp Lys Ile Pro Leu Val Pro Ser Lys Val
550             555             560             565 agt gtc atc aag ggc agc aga agc caa aag gag gct ttt cct ttg gca       1964
Ser Val Ile Lys Gly Ser Arg Ser Gln Lys Glu Ala Phe Pro Leu Ala
                570             575             580 aag gga gag gta gac act gca cca cag ggt aat aaa gac tta aag gag       2012
Lys Gly Glu Val Asp Thr Ala Pro Gln Gly Asn Lys Asp Leu Lys Glu
                585             590             595 cat gtg ctt caa agt tcc tta tcc cag gag cat aaa gac cca aaa gca       2060
His Val Leu Gln Ser Ser Leu Ser Gln Glu His Lys Asp Pro Lys Ala
            600             605             610 aca ccc cca tga tacaggtctg tggggaagag tgtttatatc cctacgttaa          2112
Thr Pro Pro
        615 ctttgcctag tagaggccct tctttgcact tgcttctcat ttggctattc ttttcctaag     2172 gaagtccatt ctcctctgta cagacagctg agtcacccag tctacttagt acctggttgc     2232 tgcctctgac cttttcagct tgataccctg ggctttagtg taaccaataa atctgtagtg     2292 accttacctg tattccctgt gctatcctgt gggaaggtag gaatgggcta agtatgatga     2352 atatataggt tagggatctt ttggttttaa atcacagaaa acctaattca aactggctta     2412 aaataaaaag gatttattgg ttcatgtaac tagaaagtcc ataggtagtg ctggctccag     2472 gtgaagactt gacccagtag ttcagtatgt ctctaaatac cggactgact tttttctcac     2532 tgttgcatct tctgtaggac catttaagtc tgggccactt aatggctgcc agcattccta     2592 agattacact tttccccatt tatgtccaat cagaaaaaga aggcatcttt gtaccagaaa     2652 tctcagcaaa agccctaata ttcacactga ttaggcctgg gtcacatgtc caccctgacc     2712 aatcactgtg gccaggagga tgatacatgc taatttgctt attctatatc atggacaaca     2772 cctttgggga aaagggtggg ggtcagcctc cccaaaatca catggattcc ccaagtggaa     2832 actaggagca gggagttgct tgggtggccg ctaacaccag gctactctta ttttagcttg     2892 ctaagttgag atcagctaga cctgctttct tttctcctca gtcttgcatt tccctcaata     2952 caagctgtag cctctttcct cgtttctagt ctcagaagga aggagaggga agccattctc     3012 ctctagggac tcttcagtct catttagatg atagtccctt tttttctacc tccatattag     3072
```

```
agatggagct ccttcctttt cctgtttctt aatttttgtc ttctcattcc tgcttccctc      3132
tcaccctatt gccagttcca ccaactagag tgaaagactt cctagccatt tcattaaatc      3192
tattctgtat ccaccaggtg gcagcatctt gtcatacgtg tcaggactta ggactgcggg      3252
gtttaggtta gatgtcacgg aaaaagctag ttctgtggtc aggcggcacc aatgagaaag      3312
gaatgcagac cctccagatg tatccttggg aaaagcagta aaccaactaa tatttattga      3372
agacctactt tgtcctctac ataggatagc ttctgtcagg gaatcttggt tcttcccaag      3432
aaacactgat tttctttcag ggagacttca tgtgttcatt tatttccacc acagcagatt      3492
ttaagaaatt ataatatgta atatttgata tctataaaga gtatatctaa cgtgaataaa      3552
ttatgaagca tactaatgag tacctatgac ccataacaca tatacattaa aacattttaa      3612
atacca                                                                  3618
```

<210> SEQ ID NO 29
<211> LENGTH: 616
<212> TYPE: PRT
<213> ORGANISM: Homo sapiens

<400> SEQUENCE: 29

```
Met Ala Glu Asp Glu Pro Asp Ala Lys Ser Pro Lys Thr Gly Gly Arg
1               5                   10                  15

Ala Pro Pro Gly Gly Ala Glu Ala Gly Glu Pro Thr Thr Leu Leu Gln
            20                  25                  30

Arg Leu Arg Gly Thr Ile Ser Lys Ala Val Gln Asn Lys Val Glu Gly
        35                  40                  45

Ile Leu Gln Asp Val Gln Lys Phe Ser Asp Asn Asp Lys Leu Tyr Leu
    50                  55                  60

Tyr Leu Gln Leu Pro Ser Gly Pro Thr Thr Gly Asp Lys Ser Ser Glu
65                  70                  75                  80

Pro Ser Thr Leu Ser Asn Glu Glu Tyr Met Tyr Ala Tyr Arg Trp Ile
                85                  90                  95

Arg Asn His Leu Glu Glu His Thr Asp Thr Cys Leu Pro Lys Gln Ser
            100                 105                 110

Val Tyr Asp Ala Tyr Arg Lys Tyr Cys Glu Ser Leu Ala Cys Cys Arg
        115                 120                 125

Pro Leu Ser Thr Ala Asn Phe Gly Lys Ile Ile Arg Glu Ile Phe Pro
    130                 135                 140

Asp Ile Lys Ala Arg Arg Leu Gly Gly Arg Gly Gln Ser Lys Tyr Cys
145                 150                 155                 160

Tyr Ser Gly Ile Arg Arg Lys Thr Leu Val Ser Met Pro Pro Leu Pro
                165                 170                 175

Gly Leu Asp Leu Lys Gly Ser Glu Ser Pro Glu Met Gly Pro Glu Val
            180                 185                 190

Thr Pro Ala Pro Arg Asp Glu Leu Val Glu Ala Ala Cys Ala Leu Thr
        195                 200                 205

Cys Asp Trp Ala Glu Arg Ile Leu Lys Arg Ser Phe Ser Ser Ile Val
    210                 215                 220

Glu Val Ala Arg Phe Leu Leu Gln Gln His Leu Ile Ser Ala Arg Ser
225                 230                 235                 240

Ala His Ala His Val Leu Lys Ala Met Gly Leu Ala Glu Glu Asp Glu
                245                 250                 255

His Ala Pro Arg Glu Arg Ser Ser Lys Pro Lys Asn Gly Leu Glu Asn
            260                 265                 270
```

-continued

```
Pro Glu Gly Gly Ala His Lys Lys Pro Glu Arg Leu Ala Gln Pro Pro
        275                 280                 285

Lys Asp Leu Glu Ala Arg Thr Gly Ala Gly Pro Leu Ala Arg Gly Glu
        290                 295                 300

Arg Lys Lys Ser Val Val Glu Ser Ser Ala Pro Gly Ala Asn Asn Leu
305                 310                 315                 320

Gln Val Asn Ala Leu Val Ala Arg Leu Pro Leu Leu Leu Pro Arg Ala
                325                 330                 335

Pro Arg Ser Leu Ile Pro Pro Ile Pro Val Ser Pro Pro Ile Leu Ala
                340                 345                 350

Pro Arg Leu Ser Ser Gly Ala Leu Lys Val Ala Thr Leu Pro Leu Ser
                355                 360                 365

Ser Arg Ala Gly Ala Pro Pro Ala Ala Val Pro Ile Ile Asn Met Ile
        370                 375                 380

Leu Pro Thr Val Pro Ala Leu Pro Gly Pro Gly Pro Gly Pro Gly Arg
385                 390                 395                 400

Ala Pro Pro Gly Gly Leu Thr Gln Pro Arg Gly Thr Glu Asn Arg Glu
                405                 410                 415

Val Gly Ile Gly Gly Asp Gln Gly Pro His Asp Lys Gly Val Lys Arg
                420                 425                 430

Thr Ala Glu Val Pro Val Ser Glu Ala Ser Gly Gln Ala Pro Pro Ala
                435                 440                 445

Lys Ala Ala Lys Gln Asp Ile Glu Asp Thr Ala Ser Asp Ala Lys Arg
        450                 455                 460

Lys Arg Gly Arg Pro Arg Lys Lys Ser Gly Gly Ser Gly Glu Arg Asn
465                 470                 475                 480

Ser Thr Pro Leu Lys Ser Ala Ala Ala Met Glu Ser Ala Gln Ser Ser
                485                 490                 495

Arg Leu Pro Trp Glu Thr Trp Gly Ser Gly Gly Glu Gly Asn Ser Ala
                500                 505                 510

Gly Gly Ala Glu Arg Pro Gly Pro Met Gly Glu Ala Glu Lys Gly Ala
                515                 520                 525

Val Leu Ala Gln Gly Gln Gly Asp Gly Thr Val Ser Lys Gly Gly Arg
        530                 535                 540

Gly Pro Gly Ser Gln His Thr Lys Glu Ala Glu Asp Lys Ile Pro Leu
545                 550                 555                 560

Val Pro Ser Lys Val Ser Val Ile Lys Gly Ser Arg Ser Gln Lys Glu
                565                 570                 575

Ala Phe Pro Leu Ala Lys Gly Glu Val Asp Thr Ala Pro Gln Gly Asn
                580                 585                 590

Lys Asp Leu Lys Glu His Val Leu Gln Ser Ser Leu Ser Gln Glu His
        595                 600                 605

Lys Asp Pro Lys Ala Thr Pro Pro
    610                 615
```

<210> SEQ ID NO 30
<211> LENGTH: 3611
<212> TYPE: DNA
<213> ORGANISM: Homo sapiens
<220> FEATURE:
<221> NAME/KEY: CDS
<222> LOCATION: (215)..(2065)

<400> SEQUENCE: 30
attcagaaaa aggaaaataa agcaacgcac gagccggctg ggccaggacc ttggggctgg        60

```
gctggagtga aggtggctac gagtttccca gatttaggag acttcagaaa ggtggggcag          120
atagaatgga gatggcaaag atctctttgg gcatatatgg gcctggcgaa gtaatggaat          180
aatttctaat tttcggagaa gccctcatgc cggg atg gca gaa gat gag cct gat          235
                                        Met Ala Glu Asp Glu Pro Asp
                                         1               5 gct aag agc ccc aag act ggg gga agg gcc ccc cca ggt ggt gct gag          283
Ala Lys Ser Pro Lys Thr Gly Gly Arg Ala Pro Pro Gly Gly Ala Glu
         10              15                  20 gct ggg gaa cct acc acc ctt ctt cag agg ctc cga ggt acc att tcc          331
Ala Gly Glu Pro Thr Thr Leu Leu Gln Arg Leu Arg Gly Thr Ile Ser
     25              30                  35 aag gcc gtg cag aac aaa gta gag ggg atc ctg caa gat gta cag aaa          379
Lys Ala Val Gln Asn Lys Val Glu Gly Ile Leu Gln Asp Val Gln Lys
40                  45                  50                  55 ttt tct gac aat gac aag ctg tat ctc tac ctt cag ctc ccc tca gga          427
Phe Ser Asp Asn Asp Lys Leu Tyr Leu Tyr Leu Gln Leu Pro Ser Gly
             60                  65                  70 ccc acc act gga gac aaa agc tca gag cca agt aca ctg agc aat gag          475
Pro Thr Thr Gly Asp Lys Ser Ser Glu Pro Ser Thr Leu Ser Asn Glu
             75                  80                  85 gag tac atg tat gcc tat agg tgg atc cgc aac cac ctg gaa gag cac          523
Glu Tyr Met Tyr Ala Tyr Arg Trp Ile Arg Asn His Leu Glu Glu His
             90                  95                  100 act gac acc tgt ctg cca aag caa agt gtt tat gat gcc tat cgg aag          571
Thr Asp Thr Cys Leu Pro Lys Gln Ser Val Tyr Asp Ala Tyr Arg Lys
     105                 110                 115 tac tgt gag agt ctt gcc tgt tgc cgc cca ctc agc aca gcc aac ttt          619
Tyr Cys Glu Ser Leu Ala Cys Cys Arg Pro Leu Ser Thr Ala Asn Phe
120                 125                 130                 135 ggc aag atc atc aga gag atc ttc cct gac atc aaa gct cga agg ctt          667
Gly Lys Ile Ile Arg Glu Ile Phe Pro Asp Ile Lys Ala Arg Arg Leu
             140                 145                 150 ggt ggc cgg ggc cag tcc aaa tat tgc tac agt ggc ata agg agg aag          715
Gly Gly Arg Gly Gln Ser Lys Tyr Cys Tyr Ser Gly Ile Arg Arg Lys
         155                 160                 165 acc ttg gtg tct atg cca ccc ctg cct gga ctt gac cta aag ggt tct          763
Thr Leu Val Ser Met Pro Pro Leu Pro Gly Leu Asp Leu Lys Gly Ser
         170                 175                 180 gag agt cca gaa atg ggc cca gaa gta acc cca gca cct cga gat gaa          811
Glu Ser Pro Glu Met Gly Pro Glu Val Thr Pro Ala Pro Arg Asp Glu
         185                 190                 195 ctg gtg gag gca gcg tgt gcc ctg acc tgt gac tgg gca gag cgg atc          859
Leu Val Glu Ala Ala Cys Ala Leu Thr Cys Asp Trp Ala Glu Arg Ile
200                 205                 210                 215 ctg aaa cgg tcc ttc agt tcc atc gtt gag gtc gcc cgc ttc ctg cta          907
Leu Lys Arg Ser Phe Ser Ser Ile Val Glu Val Ala Arg Phe Leu Leu
             220                 225                 230 cag cag cat ctc atc tct gcc cga tct gca cat gcc cat gtg ctt aag          955
Gln Gln His Leu Ile Ser Ala Arg Ser Ala His Ala His Val Leu Lys
             235                 240                 245 gcc atg ggg ctt gct gaa gag gac gaa cat gca cct cgg gaa cgg tca          1003
Ala Met Gly Leu Ala Glu Glu Asp Glu His Ala Pro Arg Glu Arg Ser
         250                 255                 260 tct aaa cca aag aat ggt tta gag aac cca gag ggt gga gcc cac aag          1051
Ser Lys Pro Lys Asn Gly Leu Glu Asn Pro Glu Gly Gly Ala His Lys
         265                 270                 275 aag cca gag aga ctg gcc cag cct cct aag gat ctg gaa gcc cga act          1099
Lys Pro Glu Arg Leu Ala Gln Pro Pro Lys Asp Leu Glu Ala Arg Thr
```

-continued

```
        280              285              290              295 ggg gcc ggt cct ctc gca cgt gga gag cgg aag aag agt gta gtt gag    1147
Gly Ala Gly Pro Leu Ala Arg Gly Glu Arg Lys Lys Ser Val Val Glu
            300              305              310 agc tcg gcc cca gga gcc aat aac ctg cag gtt aat gcc cta gtg gct    1195
Ser Ser Ala Pro Gly Ala Asn Asn Leu Gln Val Asn Ala Leu Val Ala
            315              320              325 cgg ctg cct ctg ctc ctt ccc cgg gcc cct cgc tca cta att ccg cca    1243
Arg Leu Pro Leu Leu Leu Pro Arg Ala Pro Arg Ser Leu Ile Pro Pro
            330              335              340 atc cca gtc tct cca cct att ctg gcc ccc agg ctt tct tca ggt gcc    1291
Ile Pro Val Ser Pro Pro Ile Leu Ala Pro Arg Leu Ser Ser Gly Ala
    345              350              355 ctg aaa gtg gct aca ctg cct ctg tct agt agg gcc ggg gca ccc cca    1339
Leu Lys Val Ala Thr Leu Pro Leu Ser Ser Arg Ala Gly Ala Pro Pro
360              365              370              375 gca gct gtg ccc atc att aac atg atc tta cca act gtt cct gct ttg    1387
Ala Ala Val Pro Ile Ile Asn Met Ile Leu Pro Thr Val Pro Ala Leu
            380              385              390 cct gga cct gga cct ggg cct ggg cga gct cca cct ggg gga ctc act    1435
Pro Gly Pro Gly Pro Gly Pro Gly Arg Ala Pro Pro Gly Gly Leu Thr
            395              400              405 cag ccc cgg ggc aca gag aac aga gag gta ggc ata ggt ggt gac caa    1483
Gln Pro Arg Gly Thr Glu Asn Arg Glu Val Gly Ile Gly Gly Asp Gln
            410              415              420 gga cca cat gac aag ggt gtc aag agg aca gct gaa gta cct gtg agt    1531
Gly Pro His Asp Lys Gly Val Lys Arg Thr Ala Glu Val Pro Val Ser
    425              430              435 gag gcc agt ggg cag gct cca cca gct aaa gca gca aag cag gat ata    1579
Glu Ala Ser Gly Gln Ala Pro Pro Ala Lys Ala Ala Lys Gln Asp Ile
440              445              450              455 gag gat aca gca agt gat gcc aaa agg aaa cgg ggg cgc cct cga aaa    1627
Glu Asp Thr Ala Ser Asp Ala Lys Arg Lys Arg Gly Arg Pro Arg Lys
            460              465              470 aag tca ggt gga agt ggg gaa agg aat tct acc cct ctc aag tca gca    1675
Lys Ser Gly Gly Ser Gly Glu Arg Asn Ser Thr Pro Leu Lys Ser Ala
            475              480              485 gct gcc atg gaa tct gcc cag tcc tca agg tta cca tgg gag aca tgg    1723
Ala Ala Met Glu Ser Ala Gln Ser Ser Arg Leu Pro Trp Glu Thr Trp
            490              495              500 ggc tca gga ggg gaa ggc aac tca gct gga ggg gca gag agg cca ggg    1771
Gly Ser Gly Gly Glu Gly Asn Ser Ala Gly Gly Ala Glu Arg Pro Gly
    505              510              515 cca atg gga gag gct gaa aag ggg gca gta ctt gcc cag ggt cag gga    1819
Pro Met Gly Glu Ala Glu Lys Gly Ala Val Leu Ala Gln Gly Gln Gly
520              525              530              535 gat ggt act gtt tcc aaa gga gga agg ggc ccc ggt tcc cag cat acc    1867
Asp Gly Thr Val Ser Lys Gly Gly Arg Gly Pro Gly Ser Gln His Thr
            540              545              550 aaa gaa gca gaa gat aaa att ccc ttg gtc ccc tca aaa gtg agt gtc    1915
Lys Glu Ala Glu Asp Lys Ile Pro Leu Val Pro Ser Lys Val Ser Val
            555              560              565 atc aag ggc agc aga agc caa aag gag gct ttt cct ttg gca aag gga    1963
Ile Lys Gly Ser Arg Ser Gln Lys Glu Ala Phe Pro Leu Ala Lys Gly
            570              575              580 gag gta gac act gca cca cag ggt aat aaa gac tta aag gag cat gtg    2011
Glu Val Asp Thr Ala Pro Gln Gly Asn Lys Asp Leu Lys Glu His Val
    585              590              595 ctt caa agt tcc tta tcc cag gag cat aaa gac cca aaa gca aca ccc    2059
```

-continued

```
Leu Gln Ser Ser Leu Ser Gln Glu His Lys Asp Pro Lys Ala Thr Pro
600             605                 610                 615 cca tga tacaggtctg tggggaagag tgtttatatc cctacgttaa ctttgcctag     2115
Pro tagaggccct tctttgcact tgcttctcat ttggctattc ttttcctaag gaagtccatt     2175
ctcctctgta cagacagctg agtcacccag tctacttagt acctggttgc tgcctctgac     2235
cttttcagct tgataccctg ggctttagtg taaccaataa atctgtagtg accttacctg     2295
tattccctgt gctatcctgt gggaaggtag gaatgggcta agtatgatga atatataggt     2355
tagggatctt ttggttttaa atcacagaaa acctaattca aactggctta aaataaaaag     2415
gatttattgg ttcatgtaac tagaaagtcc ataggtagtg ctggctccag gtgaagactt     2475
gacccagtag ttcagtatgt ctctaaatac cggactgact tttttctcac tgttgcatct     2535
tctgtaggac catttaagtc tgggccactt aatggctgcc agcattccta agattacact     2595
tttccccatt tatgtccaat cagaaaaaga aggcatcttt gtaccagaaa tctcagcaaa     2655
agccctaata ttcacactga ttaggcctgg gtcacatgtc caccctgacc aatcactgtg     2715
gccaggagga tgatacatgc taatttgctt attctatatc atggacaaca cctttggga     2775 aaagggtggg ggtcagcctc cccaaaatca catggattcc ccaagtggaa actaggagca     2835
gggagttgct tgggtggccg ctaacaccag gctactctta ttttagcttg ctaagttgag     2895
atcagctaga cctgctttct tttctcctca gtcttgcatt tccctcaata caagctgtag     2955
cctctttcct cgtttctagt ctcagaagga aggagaggga agccattctc ctctagggac     3015
tcttcagtct catttagatg atagtccctt tttttctacc tccatattag agatggagct     3075
ccttcctttt cctgtttctt aatttttgtc ttctcattcc tgcttccctc tcaccctatt     3135
gccagttcca ccaactagag tgaaagactt cctagccatt tcattaaatc tattctgtat     3195
ccaccaggtg gcagcatctt gtcatacgtg tcaggactta ggactgcggg gtttaggtta     3255
gatgtcacgg aaaaagctag ttctgtggtc aggcggcacc aatgagaaag gaatgcagac     3315
cctccagatg tatccttggg aaaagcagta aaccaactaa tatttattga agacctactt     3375
tgtcctctac atagggtagc ttctgtcagg gaatcttggt tcttcccaag aaacactgat     3435
tttctttcag ggagacttca tgtgttcatt tatttccacc acagcagatt ttaagaaatt     3495
ataatatgta atatttgata tctataaaga gtatatctaa cgtgaataaa ttatgaagca     3555
tactaatgag tacctatgac ccataacaca tatacattaa aacattttaa atacca     3611
```

```
<210> SEQ ID NO 31
<211> LENGTH: 616
<212> TYPE: PRT
<213> ORGANISM: Homo sapiens

<400> SEQUENCE: 31

Met Ala Glu Asp Glu Pro Asp Ala Lys Ser Pro Lys Thr Gly Gly Arg
1               5                   10                  15

Ala Pro Pro Gly Gly Ala Glu Ala Gly Glu Pro Thr Thr Leu Leu Gln
            20                  25                  30

Arg Leu Arg Gly Thr Ile Ser Lys Ala Val Gln Asn Lys Val Glu Gly
        35                  40                  45

Ile Leu Gln Asp Val Gln Lys Phe Ser Asp Asn Asp Lys Leu Tyr Leu
    50                  55                  60

Tyr Leu Gln Leu Pro Ser Gly Pro Thr Thr Gly Asp Lys Ser Ser Glu
65                  70                  75                  80
```

-continued

```
Pro Ser Thr Leu Ser Asn Glu Glu Tyr Met Tyr Ala Tyr Arg Trp Ile
            85               90               95

Arg Asn His Leu Glu Glu His Thr Asp Thr Cys Leu Pro Lys Gln Ser
            100              105              110

Val Tyr Asp Ala Tyr Arg Lys Tyr Cys Glu Ser Leu Ala Cys Cys Arg
            115              120              125

Pro Leu Ser Thr Ala Asn Phe Gly Lys Ile Ile Arg Glu Ile Phe Pro
    130              135              140

Asp Ile Lys Ala Arg Arg Leu Gly Gly Arg Gly Gln Ser Lys Tyr Cys
145              150              155              160

Tyr Ser Gly Ile Arg Arg Lys Thr Leu Val Ser Met Pro Pro Leu Pro
                165              170              175

Gly Leu Asp Leu Lys Gly Ser Glu Ser Pro Glu Met Gly Pro Glu Val
            180              185              190

Thr Pro Ala Pro Arg Asp Glu Leu Val Glu Ala Ala Cys Ala Leu Thr
            195              200              205

Cys Asp Trp Ala Glu Arg Ile Leu Lys Arg Ser Phe Ser Ser Ile Val
    210              215              220

Glu Val Ala Arg Phe Leu Leu Gln Gln His Leu Ile Ser Ala Arg Ser
225              230              235              240

Ala His Ala His Val Leu Lys Ala Met Gly Leu Ala Glu Glu Asp Glu
            245              250              255

His Ala Pro Arg Glu Arg Ser Ser Lys Pro Lys Asn Gly Leu Glu Asn
            260              265              270

Pro Glu Gly Gly Ala His Lys Lys Pro Glu Arg Leu Ala Gln Pro Pro
            275              280              285

Lys Asp Leu Glu Ala Arg Thr Gly Ala Gly Pro Leu Ala Arg Gly Glu
    290              295              300

Arg Lys Lys Ser Val Val Glu Ser Ser Ala Pro Gly Ala Asn Asn Leu
305              310              315              320

Gln Val Asn Ala Leu Val Ala Arg Leu Pro Leu Leu Leu Pro Arg Ala
            325              330              335

Pro Arg Ser Leu Ile Pro Pro Ile Pro Val Ser Pro Pro Ile Leu Ala
            340              345              350

Pro Arg Leu Ser Ser Gly Ala Leu Lys Val Ala Thr Leu Pro Leu Ser
            355              360              365

Ser Arg Ala Gly Ala Pro Pro Ala Ala Val Pro Ile Ile Asn Met Ile
    370              375              380

Leu Pro Thr Val Pro Ala Leu Pro Gly Pro Gly Pro Gly Pro Gly Arg
385              390              395              400

Ala Pro Pro Gly Gly Leu Thr Gln Pro Arg Gly Thr Glu Asn Arg Glu
            405              410              415

Val Gly Ile Gly Gly Asp Gln Gly Pro His Asp Lys Gly Val Lys Arg
            420              425              430

Thr Ala Glu Val Pro Val Ser Glu Ala Ser Gly Gln Ala Pro Pro Ala
            435              440              445

Lys Ala Ala Lys Gln Asp Ile Glu Asp Thr Ala Ser Asp Ala Lys Arg
    450              455              460

Lys Arg Gly Arg Pro Arg Lys Lys Ser Gly Gly Ser Gly Glu Arg Asn
465              470              475              480

Ser Thr Pro Leu Lys Ser Ala Ala Ala Met Glu Ser Ala Gln Ser Ser
            485              490              495

Arg Leu Pro Trp Glu Thr Trp Gly Ser Gly Gly Glu Gly Asn Ser Ala
```

-continued

```
              500              505              510
Gly Gly Ala Glu Arg Pro Gly Pro Met Gly Glu Ala Glu Lys Gly Ala
         515              520              525

Val Leu Ala Gln Gly Gln Gly Asp Gly Thr Val Ser Lys Gly Gly Arg
     530              535              540

Gly Pro Gly Ser Gln His Thr Lys Glu Ala Glu Asp Lys Ile Pro Leu
545              550              555              560

Val Pro Ser Lys Val Ser Val Ile Lys Gly Ser Arg Ser Gln Lys Glu
                 565              570              575

Ala Phe Pro Leu Ala Lys Gly Glu Val Asp Thr Ala Pro Gln Gly Asn
             580              585              590

Lys Asp Leu Lys Glu His Val Leu Gln Ser Ser Leu Ser Gln Glu His
         595              600              605

Lys Asp Pro Lys Ala Thr Pro Pro
     610              615

<210> SEQ ID NO 32
<211> LENGTH: 2825
<212> TYPE: DNA
<213> ORGANISM: Homo sapiens
<220> FEATURE:
<221> NAME/KEY: CDS
<222> LOCATION: (157)..(975)

<400> SEQUENCE: 32
cgcgcaggct gcggtcgcgc aggcgcagtc ggggcgcctt cccggtatag gcgccttta      60 ccccagcgtg tcctgagtct ttggttcgcg aagtgccgtt aggccaagca ggtgctaaaa     120 gcccgggggtc gtggacccg gccaggtctt agcagc atg gag gcg cag ggt gta     174
                                       Met Glu Ala Gln Gly Val
                                         1               5 gcg gag ggc gcg ggg ccg ggc gcc gcc agc ggc gtg ccc cac ccc gcg     222
Ala Glu Gly Ala Gly Pro Gly Ala Ala Ser Gly Val Pro His Pro Ala
             10              15              20 gcc cta gcc ccg gct gcg gct ccc acc ttg gcg cca gcc tcg gtg gcg     270
Ala Leu Ala Pro Ala Ala Ala Pro Thr Leu Ala Pro Ala Ser Val Ala
         25              30              35 gcc gcg gcc tct caa ttc acc ctg cta gtg atg caa ccc tgt gct ggg     318
Ala Ala Ala Ser Gln Phe Thr Leu Leu Val Met Gln Pro Cys Ala Gly
     40              45              50 cag gac gag gct gcg gcc ccc ggg ggc agc gtt ggg gcg ggc aag ccc     366
Gln Asp Glu Ala Ala Ala Pro Gly Gly Ser Val Gly Ala Gly Lys Pro
55              60              65              70 gtt agg tac ctg tgc gaa ggg gcc ggg gat ggc gaa gag gag gct ggg     414
Val Arg Tyr Leu Cys Glu Gly Ala Gly Asp Gly Glu Glu Glu Ala Gly
                 75              80              85 gag gac gag gcg gac ctg tta gac act tcg gac cct ccg ggg gga ggc     462
Glu Asp Glu Ala Asp Leu Leu Asp Thr Ser Asp Pro Pro Gly Gly Gly
             90              95              100 gag agc gcg gct agt ttg gag gat cta gag gac gag gag act cac tcg     510
Glu Ser Ala Ala Ser Leu Glu Asp Leu Glu Asp Glu Glu Thr His Ser
         105              110              115 ggg ggc gag ggc agc agc ggg ggc gcc cgg agg cgg ggc agc ggt ggg     558
Gly Gly Glu Gly Ser Ser Gly Gly Ala Arg Arg Arg Gly Ser Gly Gly
         120              125              130 ggc agc atg agc aag acc tgc acc tac gaa ggc tgc agc gag acc acg     606
Gly Ser Met Ser Lys Thr Cys Thr Tyr Glu Gly Cys Ser Glu Thr Thr
135              140              145              150 agc cag gtg gcc aag cag cgc aaa ccg tgg atg tgc aag aaa cac cgc     654
```

-continued

```
                                  Ser Gln Val Ala Lys Gln Arg Lys Pro Trp Met Cys Lys Lys His Arg
                                                  155                 160                 165 aac aag atg tac aag gac aag tat aaa aag aag aag agc gac cag gcc       702
Asn Lys Met Tyr Lys Asp Lys Tyr Lys Lys Lys Lys Ser Asp Gln Ala
                170                 175                 180 ctg aac tgc ggt ggg act gcc tcg act ggc agc gcg gga aac gtc aaa       750
Leu Asn Cys Gly Gly Thr Ala Ser Thr Gly Ser Ala Gly Asn Val Lys
            185                 190                 195 ctc gag gaa agt gca gat aac ata ctc tcc att gtt aaa caa aga aca       798
Leu Glu Glu Ser Ala Asp Asn Ile Leu Ser Ile Val Lys Gln Arg Thr
        200                 205                 210 gga tct ttt ggg gat cgt cct gca aga cct act ctt tta gaa caa gtg       846
Gly Ser Phe Gly Asp Arg Pro Ala Arg Pro Thr Leu Leu Glu Gln Val
215                 220                 225                 230 tta aat caa aaa aga ctg tcg tta cta aga agt cca gaa gta gtg caa       894
Leu Asn Gln Lys Arg Leu Ser Leu Leu Arg Ser Pro Glu Val Val Gln
                235                 240                 245 ttt tta cag aaa cag caa cag cta tta aat cag caa gtt ttg gag caa       942
Phe Leu Gln Lys Gln Gln Gln Leu Leu Asn Gln Gln Val Leu Glu Gln
                250                 255                 260 aga caa cag cag ttt cca gga aca tca atg tga gggaacttac caagaacatc     995
Arg Gln Gln Gln Phe Pro Gly Thr Ser Met
                265                 270 tacatggttt tttatcttat tgtaatagat gagcatattt ttttaccaga cataaatggg     1055
gtaataatct atgcctgtag aacataaaca tttttcctgta aatgtatgtg tgcatttggg    1115
gataagtaag tattgcactt tgtgcatcta atctttcaga ttactgtgag tttgaagaag     1175
tcagcttatc tttccaaata acatttaatt ataatgtttt ttaaaaaata tattcctctt     1235
cagtcattgt tactgaaggt aatgaagcag ttactttctg tggaagtcat aaagttaata     1295
gatattaatc ttgactcatc tagctcagtg gttctcatca agggtcaatt tgattgtcat     1355
agtgaccttg aaaaccactg gctttttagtg agtggccagg aatgctaaat gttctgcagt    1415
gtcaggggta gtcccacata ctaaagattg tctcacccgc agtgccaata acactcctaa     1475
gaaatgttga tggctatttt gtggtgctaa catgtagttg gggcacctat aattgggttc     1535
tcttaataac ctttctttgc agttaagact gaagctgtca aagaggtaag cacattttat     1595
atagacgtaa ggaaagtgat tattgtttaa tatctgtgaa tttaggatgt gcatctcttt     1655
tcagaggtgt gttagtaaaa cctgacggat taactaagca cactgggatg tgtctcctac     1715
agttggcttc tctctttgat gttacctgtt agtgctgatc tcttaaagca gacatttctt     1775
gtttgttgaa tttgtgaaca gtatagatct cagcccacca atgccaagac aaaattattt     1835
ttcttatact tattttttat taaacaaaat gaaaagatc cttttcaaaa aggtgatcct      1895
gaaaataaaa ctaacactcc agtattttgt cattgttttt cgcaattgag ctatctgaaa     1955
actgttattc ctaagtaatg ttcaaaaatg ataagtaatc tggatacctt tttcttatac     2015
tttctcctag gaaaacttta aaactttaaa aaggcaaacc taccaatagg aataacaaat     2075
taaatgtcaa gagagtatat ccaatattag gatataaatg tatgtgtctc aagtttaact     2135
ctacaaaaat ttgttacttg ttttttaaac tctatatata aagttcgact taatcatggc     2195
tgttctaaga agtacttatg gagagcaaga acgttttgt tcatttctta atgtgtgtgt      2255
ttttacttgc atatctgttc aaaacacttt taacaaaatt aattcattaa agtccagttg     2315
ttgacctttg agttagctga tttctttatt ctgttcttta gttattctt actagatgca      2375 gaggaattca tctactgtct gttattaact gttagtttat tctcatactt acgatgttga     2435
```

```
gagttttttt gaagcttaag ttacccttta tggtggaaaa cattagctta tgcttcttta   2495
gatggaataa tgggaaagga gggaaatggg aaatggatgg aaatgggaaa ggagggaaaa   2555
taatagccca gtgagagctg aatgaaaagg gactgaattt aaatatttgt aagaactttg   2615
tgatgatgag taattgtcag acgtgggata gataactgag aggctcagaa tctttaccaa   2675 ggatatttt taggataagg tagctgcctg ttcatgaatt tggataagaa tagtaggaca   2735
atattcaaca caatttaatt tttgtctgcc acattagaca tttttttacc ttataaaatg   2795
atcaataaag caataaggtt tattttgggt                                     2825
```

```
<210> SEQ ID NO 33
<211> LENGTH: 272
<212> TYPE: PRT
<213> ORGANISM: Homo sapiens

<400> SEQUENCE: 33

Met Glu Ala Gln Gly Val Ala Glu Gly Ala Gly Pro Gly Ala Ala Ser
1               5                   10                  15

Gly Val Pro His Pro Ala Ala Leu Ala Pro Ala Ala Ala Pro Thr Leu
            20                  25                  30

Ala Pro Ala Ser Val Ala Ala Ala Ala Ser Gln Phe Thr Leu Leu Val
        35                  40                  45

Met Gln Pro Cys Ala Gly Gln Asp Glu Ala Ala Ala Pro Gly Gly Ser
        50                  55                  60

Val Gly Ala Gly Lys Pro Val Arg Tyr Leu Cys Glu Gly Ala Gly Asp
65                  70                  75                  80

Gly Glu Glu Glu Ala Gly Glu Asp Glu Ala Asp Leu Leu Asp Thr Ser
                85                  90                  95

Asp Pro Pro Gly Gly Gly Glu Ser Ala Ala Ser Leu Glu Asp Leu Glu
            100                 105                 110

Asp Glu Glu Thr His Ser Gly Gly Glu Gly Ser Ser Gly Gly Ala Arg
            115                 120                 125

Arg Arg Gly Ser Gly Gly Gly Ser Met Ser Lys Thr Cys Thr Tyr Glu
        130                 135                 140

Gly Cys Ser Glu Thr Thr Ser Gln Val Ala Lys Gln Arg Lys Pro Trp
145                 150                 155                 160

Met Cys Lys Lys His Arg Asn Lys Met Tyr Lys Asp Lys Tyr Lys Lys
                165                 170                 175

Lys Lys Ser Asp Gln Ala Leu Asn Cys Gly Gly Thr Ala Ser Thr Gly
            180                 185                 190

Ser Ala Gly Asn Val Lys Leu Glu Glu Ser Ala Asp Asn Ile Leu Ser
            195                 200                 205

Ile Val Lys Gln Arg Thr Gly Ser Phe Gly Asp Arg Pro Ala Arg Pro
        210                 215                 220

Thr Leu Leu Glu Gln Val Leu Asn Gln Lys Arg Leu Ser Leu Leu Arg
225                 230                 235                 240

Ser Pro Glu Val Val Gln Phe Leu Gln Lys Gln Gln Gln Leu Leu Asn
                245                 250                 255

Gln Gln Val Leu Glu Gln Arg Gln Gln Gln Phe Pro Gly Thr Ser Met
            260                 265                 270
```

```
<210> SEQ ID NO 34
<211> LENGTH: 4654
<212> TYPE: DNA
<213> ORGANISM: Homo sapiens
<220> FEATURE:
```

```
<221> NAME/KEY: CDS
<222> LOCATION: (134)..(3526)

<400> SEQUENCE: 34
ggttagtgat gaggctagtg atgaggctgt gtgcttctga gctgggcatc cgaaggcatc      60
cttgggaaag ctgagggcac gaggaggggc tgccagactc cgggagctgc tgcctggctg     120
ggattcctac aca atg cgt tgc ctg gct cca cgc cct gct ggg tcc tac        169
               Met Arg Cys Leu Ala Pro Arg Pro Ala Gly Ser Tyr
                1               5                  10 ctg tca gag ccc caa ggc agc tca cag tgt gcc acc atg gag ttg ggg      217
Leu Ser Glu Pro Gln Gly Ser Ser Gln Cys Ala Thr Met Glu Leu Gly
            15                  20                  25 ccc cta gaa ggt ggc tac ctg gag ctt ctt aac agc gat gct gac ccc      265
Pro Leu Glu Gly Gly Tyr Leu Glu Leu Leu Asn Ser Asp Ala Asp Pro
        30                  35                  40 ctg tgc ctc tac cac ttc tat gac cag atg gac ctg gct gga gaa gaa      313
Leu Cys Leu Tyr His Phe Tyr Asp Gln Met Asp Leu Ala Gly Glu Glu
45                  50                  55                  60 gag att gag ctc tac tca gaa ccc gac aca gac acc atc aac tgc gac      361
Glu Ile Glu Leu Tyr Ser Glu Pro Asp Thr Asp Thr Ile Asn Cys Asp
                65                  70                  75 cag ttc agc agg ctg ttg tgt gac atg gaa ggt gat gaa gag acc agg      409
Gln Phe Ser Arg Leu Leu Cys Asp Met Glu Gly Asp Glu Glu Thr Arg
            80                  85                  90 gag gct tat gcc aat atc gcg gaa ctg gac cag tat gtc ttc cag gac      457
Glu Ala Tyr Ala Asn Ile Ala Glu Leu Asp Gln Tyr Val Phe Gln Asp
        95                  100                 105 tcc cag ctg gag ggc ctg agc aag gac att ttc aag cac ata gga cca      505
Ser Gln Leu Glu Gly Leu Ser Lys Asp Ile Phe Lys His Ile Gly Pro
    110                 115                 120 gat gaa gtg atc ggt gag agt atg gag atg cca gca gaa gtt ggg cag      553
Asp Glu Val Ile Gly Glu Ser Met Glu Met Pro Ala Glu Val Gly Gln
125                 130                 135                 140 aaa agt cag aaa aga ccc ttc cca gag gag ctt ccg gca gac ctg aag      601
Lys Ser Gln Lys Arg Pro Phe Pro Glu Glu Leu Pro Ala Asp Leu Lys
                145                 150                 155 cac tgg aag cca gct gag ccc ccc act gtg gtg act ggc agt ctc cta      649
His Trp Lys Pro Ala Glu Pro Pro Thr Val Val Thr Gly Ser Leu Leu
            160                 165                 170 gtg gga cca gtg agc gac tgc tcc acc ctg ccc tgc ctg cca ctg cct      697
Val Gly Pro Val Ser Asp Cys Ser Thr Leu Pro Cys Leu Pro Leu Pro
        175                 180                 185 gcg ctg ttc aac cag gag cca gcc tcc ggc cag atg cgc ctg gag aaa      745
Ala Leu Phe Asn Gln Glu Pro Ala Ser Gly Gln Met Arg Leu Glu Lys
    190                 195                 200 acc gac cag att ccc atg cct ttc tcc agt tcc tcg ttg agc tgc ctg      793
Thr Asp Gln Ile Pro Met Pro Phe Ser Ser Ser Ser Leu Ser Cys Leu
205                 210                 215                 220 aat ctc cct gag gga ccc atc cag ttt gtc ccc acc atc tcc act ctg      841
Asn Leu Pro Glu Gly Pro Ile Gln Phe Val Pro Thr Ile Ser Thr Leu
                225                 230                 235 ccc cat ggg ctc tgg caa atc tct gag gct gga aca ggg gtc tcc agt      889
Pro His Gly Leu Trp Gln Ile Ser Glu Ala Gly Thr Gly Val Ser Ser
            240                 245                 250 ata ttc atc tac cat ggt gag gtg ccc cag gcc agc caa gta ccc cct      937
Ile Phe Ile Tyr His Gly Glu Val Pro Gln Ala Ser Gln Val Pro Pro
        255                 260                 265 ccc agt gga ttc act gtc cac ggc ctc cca aca tct cca gac cgg cca      985
Pro Ser Gly Phe Thr Val His Gly Leu Pro Thr Ser Pro Asp Arg Pro
```

-continued

```
             270                   275                   280 ggc tcc acc agc ccc ttc gct cca tca gcc act gac ctg ccc agc atg      1033
Gly Ser Thr Ser Pro Phe Ala Pro Ser Ala Thr Asp Leu Pro Ser Met
285                 290                 295                 300 cct gaa cct gcc ctg acc tcc cga gca aac atg aca gag cac aag acg      1081
Pro Glu Pro Ala Leu Thr Ser Arg Ala Asn Met Thr Glu His Lys Thr
                305                 310                 315 tcc ccc acc caa tgc ccg gca gct gga gag gtc tcc aac aag ctt cca      1129
Ser Pro Thr Gln Cys Pro Ala Ala Gly Glu Val Ser Asn Lys Leu Pro
            320                 325                 330 aaa tgg cct gag ccg gtg gag cag ttc tac cgc tca ctg cag gac acg      1177
Lys Trp Pro Glu Pro Val Glu Gln Phe Tyr Arg Ser Leu Gln Asp Thr
            335                 340                 345 tat ggt gcc gag ccc gca ggc ccg gat ggc atc cta gtg gag gtg gat      1225
Tyr Gly Ala Glu Pro Ala Gly Pro Asp Gly Ile Leu Val Glu Val Asp
350                 355                 360 ctg gtg cag gcc agg ctg gag agg agc agc agc aag agc ctg gag cgg      1273
Leu Val Gln Ala Arg Leu Glu Arg Ser Ser Ser Lys Ser Leu Glu Arg
365                 370                 375                 380 gaa ctg gcc acc ccg gac tgg gca gaa cgg cag ctg gcc caa gga ggc      1321
Glu Leu Ala Thr Pro Asp Trp Ala Glu Arg Gln Leu Ala Gln Gly Gly
                385                 390                 395 ctg gct gag gtg ctg ttg gct gcc aag gag cac cgg cgg ccg cgt gag      1369
Leu Ala Glu Val Leu Leu Ala Ala Lys Glu His Arg Arg Pro Arg Glu
                400                 405                 410 aca cga gtg att gct gtg ctg ggc aaa gct ggt cag ggc aag agc tat      1417
Thr Arg Val Ile Ala Val Leu Gly Lys Ala Gly Gln Gly Lys Ser Tyr
            415                 420                 425 tgg gct ggg gca gtg agc cgg gcc tgg gct tgt ggc cgg ctt ccc cag      1465
Trp Ala Gly Ala Val Ser Arg Ala Trp Ala Cys Gly Arg Leu Pro Gln
            430                 435                 440 tac gac ttt gtc ttc tct gtc ccc tgc cat tgc ttg aac cgt ccg ggg      1513
Tyr Asp Phe Val Phe Ser Val Pro Cys His Cys Leu Asn Arg Pro Gly
445                 450                 455                 460 gat gcc tat ggc ctg cag gat ctg ctc ttc tcc ctg ggc cca cag cca      1561
Asp Ala Tyr Gly Leu Gln Asp Leu Leu Phe Ser Leu Gly Pro Gln Pro
                465                 470                 475 ctc gtg gcg gcc gat gag gtt ttc agc cac atc ttg aag aga cct gac      1609
Leu Val Ala Ala Asp Glu Val Phe Ser His Ile Leu Lys Arg Pro Asp
                480                 485                 490 cgc gtt ctg ctc atc cta gac ggc ttc gag gag ctg gaa gcg caa gat      1657
Arg Val Leu Leu Ile Leu Asp Gly Phe Glu Glu Leu Glu Ala Gln Asp
            495                 500                 505 ggc ttc ctg cac agc acg tgc gga ccg gca ccg gcg gag ccc tgc tcc      1705
Gly Phe Leu His Ser Thr Cys Gly Pro Ala Pro Ala Glu Pro Cys Ser
            510                 515                 520 ctc cgg ggg ctg ctg gcc ggc ctt ttc cag aag aag ctg ctc cga ggt      1753
Leu Arg Gly Leu Leu Ala Gly Leu Phe Gln Lys Lys Leu Leu Arg Gly
525                 530                 535                 540 tgc acc ctc ctc ctc aca gcc cgg ccc cgg ggc cgc ctg gtc cag agc      1801
Cys Thr Leu Leu Leu Thr Ala Arg Pro Arg Gly Arg Leu Val Gln Ser
                545                 550                 555 ctg agc aag gcc gac gcc cta ttt gag ctg tcc ggc ttc tcc atg gag      1849
Leu Ser Lys Ala Asp Ala Leu Phe Glu Leu Ser Gly Phe Ser Met Glu
                560                 565                 570 cag gcc cag gca tac gtg atg cgc tac ttt gag agc tca ggg atg aca      1897
Gln Ala Gln Ala Tyr Val Met Arg Tyr Phe Glu Ser Ser Gly Met Thr
                575                 580                 585 gag cac caa gac aga gcc ctg acg ctc ctc cgg gac cgg cca ctt ctt      1945
```

-continued

```
    Glu His Gln Asp Arg Ala Leu Thr Leu Leu Arg Asp Arg Pro Leu Leu
        590                 595                 600 ctc agt cac agc cac agc cct act ttg tgc cgg gca gtg tgc cag ctc      1993
Leu Ser His Ser His Ser Pro Thr Leu Cys Arg Ala Val Cys Gln Leu
605                 610                 615                 620 tca gag gcc ctg ctg gag ctt ggg gag gac gcc aag ctg ccc tcc acg      2041
Ser Glu Ala Leu Leu Glu Leu Gly Glu Asp Ala Lys Leu Pro Ser Thr
                625                 630                 635 ctc acg gga ctc tat gtc ggc ctg ctg ggc cgt gca gcc ctc gac agc      2089
Leu Thr Gly Leu Tyr Val Gly Leu Leu Gly Arg Ala Ala Leu Asp Ser
                640                 645                 650 ccc ccc ggg gcc ctg gca gag ctg gcc aag ctg gcc tgg gag ctg ggc      2137
Pro Pro Gly Ala Leu Ala Glu Leu Ala Lys Leu Ala Trp Glu Leu Gly
                655                 660                 665 cgc aga cat caa agt acc cta cag gag gac cag ttc cca tcc gca gac      2185
Arg Arg His Gln Ser Thr Leu Gln Glu Asp Gln Phe Pro Ser Ala Asp
        670                 675                 680 gtg agg acc tgg gcg atg gcc aaa ggc tta gtc caa cac cca ccg cgg      2233
Val Arg Thr Trp Ala Met Ala Lys Gly Leu Val Gln His Pro Pro Arg
685                 690                 695                 700 gcc gca gag tcc gag ctg gcc ttc ccc agc ttc ctc ctg caa tgc ttc      2281
Ala Ala Glu Ser Glu Leu Ala Phe Pro Ser Phe Leu Leu Gln Cys Phe
                705                 710                 715 ctg ggg gcc ctg tgg ctg gct ctg agt ggc gaa atc aag gac aag gag      2329
Leu Gly Ala Leu Trp Leu Ala Leu Ser Gly Glu Ile Lys Asp Lys Glu
                720                 725                 730 ctc ccg cag tac cta gca ttg acc cca agg aag aag agg ccc tat gac      2377
Leu Pro Gln Tyr Leu Ala Leu Thr Pro Arg Lys Lys Arg Pro Tyr Asp
                735                 740                 745 aac tgg ctg gag ggc gtg cca cgc ttt ctg gct ggg ctg atc ttc cag      2425
Asn Trp Leu Glu Gly Val Pro Arg Phe Leu Ala Gly Leu Ile Phe Gln
        750                 755                 760 cct ccc gcc cgc tgc ctg gga gcc cta ctc ggg cca tcg gcg gct gcc      2473
Pro Pro Ala Arg Cys Leu Gly Ala Leu Leu Gly Pro Ser Ala Ala Ala
765                 770                 775                 780 tcg gtg gac agg aag cag aag gtg ctt gcg agg tac ctg aag cgg ctg      2521
Ser Val Asp Arg Lys Gln Lys Val Leu Ala Arg Tyr Leu Lys Arg Leu
                785                 790                 795 cag ccg ggg aca ctg cgg gcg cgg cag ctg ctg gag ctg ctg cac tgc      2569
Gln Pro Gly Thr Leu Arg Ala Arg Gln Leu Leu Glu Leu Leu His Cys
                800                 805                 810 gcc cac gag gcc gag gag gct gga att tgg cag cac gtg gta cag gag      2617
Ala His Glu Ala Glu Glu Ala Gly Ile Trp Gln His Val Val Gln Glu
                815                 820                 825 ctc ccc ggc cgc ctc tct ttt ctg ggc acc cgc ctc acg cct cct gat      2665
Leu Pro Gly Arg Leu Ser Phe Leu Gly Thr Arg Leu Thr Pro Pro Asp
        830                 835                 840 gca cat gta ctg ggc aag gcc ttg gag gcg gcg ggc caa gac ttc tcc      2713
Ala His Val Leu Gly Lys Ala Leu Glu Ala Ala Gly Gln Asp Phe Ser
845                 850                 855                 860 ctg gac ctc cgc agc act ggg att tgc ccc tct gga ttg ggg agc ctc      2761
Leu Asp Leu Arg Ser Thr Gly Ile Cys Pro Ser Gly Leu Gly Ser Leu
                865                 870                 875 gtg gga ctc agc tgt gtc acc cgt ttc agg gct gcc ttg agc gac acg      2809
Val Gly Leu Ser Cys Val Thr Arg Phe Arg Ala Ala Leu Ser Asp Thr
                880                 885                 890 gtg gcg ctg tgg gag tcc ctg cag cag cat ggg gag acc aag cta ctt      2857
Val Ala Leu Trp Glu Ser Leu Gln Gln His Gly Glu Thr Lys Leu Leu
                895                 900                 905
```

-continued

```
cag gca gca gag gag aag ttc acc atc gag cct ttc aaa gcc aag tcc     2905
Gln Ala Ala Glu Glu Lys Phe Thr Ile Glu Pro Phe Lys Ala Lys Ser
    910             915                 920 ctg aag gat gtg gaa gac ctg gga aag ctt gtg cag act cag agg acg     2953
Leu Lys Asp Val Glu Asp Leu Gly Lys Leu Val Gln Thr Gln Arg Thr
925             930                 935                 940 aga agt tcc tcg gaa gac aca gct ggg gag ctc cct gct gtt cgg gac     3001
Arg Ser Ser Ser Glu Asp Thr Ala Gly Glu Leu Pro Ala Val Arg Asp
                945                 950                 955 cta aag aaa ctg gag ttt gcg ctg ggc cct gtc tca ggc ccc cag gct     3049
Leu Lys Lys Leu Glu Phe Ala Leu Gly Pro Val Ser Gly Pro Gln Ala
                960                 965                 970 ttc ccc aaa ctg gtg cgg atc ctc acg gcc ttt tcc tcc ctg cag cat     3097
Phe Pro Lys Leu Val Arg Ile Leu Thr Ala Phe Ser Ser Leu Gln His
            975                 980                 985 ctg gac ctg gat gcg ctg agt gag aac aag atc ggg  gac gag ggt gtc    3145
Leu Asp Leu Asp Ala Leu Ser Glu Asn Lys Ile Gly  Asp Glu Gly Val
        990                 995                 1000 tcg cag ctc tca gcc acc ttc ccc cag ctg aag tcc ttg gaa acc         3190
Ser Gln Leu Ser Ala Thr Phe Pro Gln Leu Lys Ser Leu Glu Thr
1005            1010                1015 ctc aat ctg tcc cag aac aac atc act gac ctg ggt gcc tac aaa         3235
Leu Asn Leu Ser Gln Asn Asn Ile Thr Asp Leu Gly Ala Tyr Lys
1020            1025                1030 ctc gcc gag gcc ctg cct tcg ctc gct gca tcc ctg ctc agg cta         3280
Leu Ala Glu Ala Leu Pro Ser Leu Ala Ala Ser Leu Leu Arg Leu
1035            1040                1045 agc ttg tac aat aac tgc atc tgc gac gtg gga gcc gag agc ttg         3325
Ser Leu Tyr Asn Asn Cys Ile Cys Asp Val Gly Ala Glu Ser Leu
1050            1055                1060 gct cgt gtg ctt ccg gac atg gtg tcc ctc cgg gtg atg gac gtc         3370
Ala Arg Val Leu Pro Asp Met Val Ser Leu Arg Val Met Asp Val
1065            1070                1075 cag tac aac aag ttc acg gct gcc ggg gcc cag cag ctc gct gcc         3415
Gln Tyr Asn Lys Phe Thr Ala Ala Gly Ala Gln Gln Leu Ala Ala
1080            1085                1090 agc ctt cgg agg tgt cct cat gtg gag acg ctg gcg atg tgg acg         3460
Ser Leu Arg Arg Cys Pro His Val Glu Thr Leu Ala Met Trp Thr
1095            1100                1105 ccc acc atc cca ttc agt gtc cag gaa cac ctg caa caa cag gat         3505
Pro Thr Ile Pro Phe Ser Val Gln Glu His Leu Gln Gln Gln Asp
1110            1115                1120 tca cgg atc agc ctg aga tga tcccagctgt gctctggaca ggcatgttct        3556
Ser Arg Ile Ser Leu Arg
1125            1130 ctgaggacac taaccacgct ggaccttgaa ctgggtactt gtggacacag ctcttctcca   3616
ggctgtatcc catgagcctc agcatcctgg cacccggccc ctgctggttc agggttggcc   3676
cctgcccggc tgcggaatga accacatctt gctctgctga cagacacagg cccggctcca   3736
ggctccttta gcgcccagtt gggtggatgc ctggtggcag ctgcggtcca cccaggagcc   3796
ccgaggcctt ctctgaagga cattgcggac agccacggcc aggccagagg gagtgacaga   3856
ggcagcccca ttctgcctgc ccaggcccct gccaccctgg ggagaaagta cttctttttt   3916 tttatttta gacagagtct cactgttgcc caggctggcg tgcagtggtg cgatctgggt    3976
tcactgcaac ctccgcctct ggggttcaag cgattcttct gcttcagcct cccgagtagc   4036
tgggactaca ggcacccacc atcatgtctg gctaattttt catttttagt agagacaggg   4096
ttttgccatg ttggccaggc tggtctcaaa ctcttgacct caggtgatcc acccacctca   4156
```

-continued

```
gcctcccaaa gtgctgggat tacaagcgtg agccactgca ccgggccaca gagaaagtac   4216
ttctccaccc tgctctccga ccagacacct tgacagggca caccgggcac tcagaagaca   4276
ctgatgggca acccccagcc tgctaattcc ccagattgca acaggctggg cttcagtggc   4336
agctgctttt gtctatggga ctcaatgcac tgacattgtt ggccaaagcc aaagctaggc   4396
ctggccagat gcaccagccc ttagcaggga aacagctaat gggacactaa tggggcggtg   4456
agaggggaac agactggaag cacagcttca tttcctgtgt cttttttcac tacattataa   4516
atgtctcttt aatgtcacag gcaggtccag ggtttgagtt cataccctgt taccattttg   4576
gggtacccac tgctctggtt atctaatatg taacaagcca ccccaaatca tagtggctta   4636
aaacaacact cacattta                                                 4654
```

<210> SEQ ID NO 35
<211> LENGTH: 1130
<212> TYPE: PRT
<213> ORGANISM: Homo sapiens

<400> SEQUENCE: 35

```
Met Arg Cys Leu Ala Pro Arg Pro Ala Gly Ser Tyr Leu Ser Glu Pro
1               5                   10                  15

Gln Gly Ser Ser Gln Cys Ala Thr Met Glu Leu Gly Pro Leu Glu Gly
            20                  25                  30

Gly Tyr Leu Glu Leu Leu Asn Ser Asp Ala Asp Pro Leu Cys Leu Tyr
        35                  40                  45

His Phe Tyr Asp Gln Met Asp Leu Ala Gly Glu Glu Glu Ile Glu Leu
    50                  55                  60

Tyr Ser Glu Pro Asp Thr Asp Thr Ile Asn Cys Asp Gln Phe Ser Arg
65                  70                  75                  80

Leu Leu Cys Asp Met Glu Gly Asp Glu Glu Thr Arg Glu Ala Tyr Ala
                85                  90                  95

Asn Ile Ala Glu Leu Asp Gln Tyr Val Phe Gln Asp Ser Gln Leu Glu
            100                 105                 110

Gly Leu Ser Lys Asp Ile Phe Lys His Ile Gly Pro Asp Glu Val Ile
        115                 120                 125

Gly Glu Ser Met Glu Met Pro Ala Glu Val Gly Gln Lys Ser Gln Lys
    130                 135                 140

Arg Pro Phe Pro Glu Glu Leu Pro Ala Asp Leu Lys His Trp Lys Pro
145                 150                 155                 160

Ala Glu Pro Pro Thr Val Val Thr Gly Ser Leu Leu Val Gly Pro Val
                165                 170                 175

Ser Asp Cys Ser Thr Leu Pro Cys Leu Pro Leu Pro Ala Leu Phe Asn
            180                 185                 190

Gln Glu Pro Ala Ser Gly Gln Met Arg Leu Glu Lys Thr Asp Gln Ile
        195                 200                 205

Pro Met Pro Phe Ser Ser Ser Ser Leu Ser Cys Leu Asn Leu Pro Glu
    210                 215                 220

Gly Pro Ile Gln Phe Val Pro Thr Ile Ser Thr Leu Pro His Gly Leu
225                 230                 235                 240

Trp Gln Ile Ser Glu Ala Gly Thr Gly Val Ser Ser Ile Phe Ile Tyr
                245                 250                 255

His Gly Glu Val Pro Gln Ala Ser Gln Val Pro Pro Pro Ser Gly Phe
            260                 265                 270

Thr Val His Gly Leu Pro Thr Ser Pro Asp Arg Pro Gly Ser Thr Ser
```

```
              275                280                285
Pro Phe Ala Pro Ser Ala Thr Asp Leu Pro Ser Met Pro Glu Pro Ala
    290                295                300
Leu Thr Ser Arg Ala Asn Met Thr Glu His Lys Thr Ser Pro Thr Gln
305                310                315                320
Cys Pro Ala Ala Gly Glu Val Ser Asn Lys Leu Pro Lys Trp Pro Glu
            325                330                335
Pro Val Glu Gln Phe Tyr Arg Ser Leu Gln Asp Thr Tyr Gly Ala Glu
            340                345                350
Pro Ala Gly Pro Asp Gly Ile Leu Val Glu Val Asp Leu Val Gln Ala
            355                360                365
Arg Leu Glu Arg Ser Ser Ser Lys Ser Leu Glu Arg Glu Leu Ala Thr
    370                375                380
Pro Asp Trp Ala Glu Arg Gln Leu Ala Gln Gly Gly Leu Ala Glu Val
385                390                395                400
Leu Leu Ala Ala Lys Glu His Arg Arg Pro Arg Glu Thr Arg Val Ile
            405                410                415
Ala Val Leu Gly Lys Ala Gly Gln Gly Lys Ser Tyr Trp Ala Gly Ala
            420                425                430
Val Ser Arg Ala Trp Ala Cys Gly Arg Leu Pro Gln Tyr Asp Phe Val
            435                440                445
Phe Ser Val Pro Cys His Cys Leu Asn Arg Pro Gly Asp Ala Tyr Gly
    450                455                460
Leu Gln Asp Leu Leu Phe Ser Leu Gly Pro Gln Pro Leu Val Ala Ala
465                470                475                480
Asp Glu Val Phe Ser His Ile Leu Lys Arg Pro Asp Arg Val Leu Leu
            485                490                495
Ile Leu Asp Gly Phe Glu Glu Leu Glu Ala Gln Asp Gly Phe Leu His
            500                505                510
Ser Thr Cys Gly Pro Ala Pro Ala Glu Pro Cys Ser Leu Arg Gly Leu
            515                520                525
Leu Ala Gly Leu Phe Gln Lys Lys Leu Leu Arg Gly Cys Thr Leu Leu
    530                535                540
Leu Thr Ala Arg Pro Arg Gly Arg Leu Val Gln Ser Leu Ser Lys Ala
545                550                555                560
Asp Ala Leu Phe Glu Leu Ser Gly Phe Ser Met Glu Gln Ala Gln Ala
            565                570                575
Tyr Val Met Arg Tyr Phe Glu Ser Ser Gly Met Thr Glu His Gln Asp
            580                585                590
Arg Ala Leu Thr Leu Leu Arg Asp Arg Pro Leu Leu Leu Ser His Ser
            595                600                605
His Ser Pro Thr Leu Cys Arg Ala Val Cys Gln Leu Ser Glu Ala Leu
    610                615                620
Leu Glu Leu Gly Glu Asp Ala Lys Leu Pro Ser Thr Leu Thr Gly Leu
625                630                635                640
Tyr Val Gly Leu Leu Gly Arg Ala Ala Leu Asp Ser Pro Pro Gly Ala
            645                650                655
Leu Ala Glu Leu Ala Lys Leu Ala Trp Glu Leu Gly Arg Arg His Gln
            660                665                670
Ser Thr Leu Gln Glu Asp Gln Phe Pro Ser Ala Asp Val Arg Thr Trp
            675                680                685
Ala Met Ala Lys Gly Leu Val Gln His Pro Pro Arg Ala Ala Glu Ser
    690                695                700
```

-continued

```
Glu Leu Ala Phe Pro Ser Phe Leu Leu Gln Cys Phe Leu Gly Ala Leu
705                 710                 715                 720

Trp Leu Ala Leu Ser Gly Glu Ile Lys Asp Lys Glu Leu Pro Gln Tyr
                725                 730                 735

Leu Ala Leu Thr Pro Arg Lys Lys Arg Pro Tyr Asp Asn Trp Leu Glu
            740                 745                 750

Gly Val Pro Arg Phe Leu Ala Gly Leu Ile Phe Gln Pro Pro Ala Arg
            755                 760                 765

Cys Leu Gly Ala Leu Leu Gly Pro Ser Ala Ala Ala Ser Val Asp Arg
            770                 775                 780

Lys Gln Lys Val Leu Ala Arg Tyr Leu Lys Arg Leu Gln Pro Gly Thr
785                 790                 795                 800

Leu Arg Ala Arg Gln Leu Leu Glu Leu Leu His Cys Ala His Glu Ala
                805                 810                 815

Glu Glu Ala Gly Ile Trp Gln His Val Val Gln Glu Leu Pro Gly Arg
                820                 825                 830

Leu Ser Phe Leu Gly Thr Arg Leu Thr Pro Pro Asp Ala His Val Leu
            835                 840                 845

Gly Lys Ala Leu Glu Ala Ala Gly Gln Asp Phe Ser Leu Asp Leu Arg
            850                 855                 860

Ser Thr Gly Ile Cys Pro Ser Gly Leu Gly Ser Leu Val Gly Leu Ser
865                 870                 875                 880

Cys Val Thr Arg Phe Arg Ala Ala Leu Ser Asp Thr Val Ala Leu Trp
                885                 890                 895

Glu Ser Leu Gln Gln His Gly Glu Thr Lys Leu Leu Gln Ala Ala Glu
            900                 905                 910

Glu Lys Phe Thr Ile Glu Pro Phe Lys Ala Lys Ser Leu Lys Asp Val
            915                 920                 925

Glu Asp Leu Gly Lys Leu Val Gln Thr Gln Arg Thr Arg Ser Ser Ser
    930                 935                 940

Glu Asp Thr Ala Gly Glu Leu Pro Ala Val Arg Asp Leu Lys Lys Leu
945                 950                 955                 960

Glu Phe Ala Leu Gly Pro Val Ser Gly Pro Gln Ala Phe Pro Lys Leu
                965                 970                 975

Val Arg Ile Leu Thr Ala Phe Ser Ser Leu Gln His Leu Asp Leu Asp
            980                 985                 990

Ala Leu Ser Glu Asn Lys Ile Gly  Asp Glu Gly Val Ser  Gln Leu Ser
            995                 1000                1005

Ala Thr  Phe Pro Gln Leu Lys  Ser Leu Glu Thr Leu  Asn Leu Ser
    1010                1015                1020

Gln Asn  Asn Ile Thr Asp Leu  Gly Ala Tyr Lys Leu  Ala Glu Ala
    1025                1030                1035

Leu Pro  Ser Leu Ala Ala Ser  Leu Leu Arg Leu Ser  Leu Tyr Asn
    1040                1045                1050

Asn Cys  Ile Cys Asp Val Gly  Ala Glu Ser Leu Ala  Arg Val Leu
    1055                1060                1065

Pro Asp  Met Val Ser Leu Arg  Val Met Asp Val Gln  Tyr Asn Lys
    1070                1075                1080

Phe Thr  Ala Ala Gly Ala Gln  Gln Leu Ala Ala Ser  Leu Arg Arg
    1085                1090                1095

Cys Pro  His Val Glu Thr Leu  Ala Met Trp Thr Pro  Thr Ile Pro
    1100                1105                1110
```

-continued

```
Phe Ser  Val Gln Glu His Leu  Gln Gln Gln Asp Ser  Arg Ile Ser
    1115                 1120                 1125

Leu Arg
    1130

<210> SEQ ID NO 36
<211> LENGTH: 1697
<212> TYPE: DNA
<213> ORGANISM: Homo sapiens
<220> FEATURE:
<221> NAME/KEY: CDS
<222> LOCATION: (108)..(890)

<400> SEQUENCE: 36
atttccagtg ctagaggccc acagtttcag tctcatctgc ctccactcgg cctcagttcc        60
tcatcactgt tcctgtgctc acagtcatca attatagacc ccacaac atg cgc cct       116
                                                    Met Arg Pro
                                                      1 gaa gac aga atg ttc cat atc aga gct gtg atc ttg aga gcc ctc tcc       164
Glu Asp Arg Met Phe His Ile Arg Ala Val Ile Leu Arg Ala Leu Ser
    5                  10                 15 ttg gct ttc ctg ctg agt ctc cga gga gct ggg gcc atc aag gcg gac       212
Leu Ala Phe Leu Leu Ser Leu Arg Gly Ala Gly Ala Ile Lys Ala Asp
20                  25                 30                 35 cat gtg tca act tat gcc gcg ttt gta cag acg cat aga cca aca ggg       260
His Val Ser Thr Tyr Ala Ala Phe Val Gln Thr His Arg Pro Thr Gly
                40                 45                 50 gag ttt atg ttt gaa ttt gat gaa gat gag atg ttc tat gtg gat ctg       308
Glu Phe Met Phe Glu Phe Asp Glu Asp Glu Met Phe Tyr Val Asp Leu
                55                 60                 65 gac aag aag gag acc gtc tgg cat ctg gag gag ttt ggc caa gcc ttt       356
Asp Lys Lys Glu Thr Val Trp His Leu Glu Glu Phe Gly Gln Ala Phe
            70                 75                 80 tcc ttt gag gct cag ggc ggg ctg gct aac att gct ata ttg aac aac       404
Ser Phe Glu Ala Gln Gly Gly Leu Ala Asn Ile Ala Ile Leu Asn Asn
        85                 90                 95 aac ttg aat acc ttg atc cag cgt tcc aac cac act cag gcc acc aac       452
Asn Leu Asn Thr Leu Ile Gln Arg Ser Asn His Thr Gln Ala Thr Asn
100                105                110                115 gat ccc cct gag gtg acc gtg ttt ccc aag gag cct gtg gag ctg ggc       500
Asp Pro Pro Glu Val Thr Val Phe Pro Lys Glu Pro Val Glu Leu Gly
                120                125                130 cag ccc aac acc ctc atc tgc cac att gac aag ttc ttc cca cca gtg       548
Gln Pro Asn Thr Leu Ile Cys His Ile Asp Lys Phe Phe Pro Pro Val
                135                140                145 ctc aac gtc acg tgg ctg tgc aac ggg gag ctg gtc act gag ggt gtc       596
Leu Asn Val Thr Trp Leu Cys Asn Gly Glu Leu Val Thr Glu Gly Val
            150                155                160 gct gag agc ctc ttc ctg ccc aga aca gat tac agc ttc cac aag ttc       644
Ala Glu Ser Leu Phe Leu Pro Arg Thr Asp Tyr Ser Phe His Lys Phe
        165                170                175 cat tac ctg acc ttt gtg ccc tca gca gag gac ttc tat gac tgc agg       692
His Tyr Leu Thr Phe Val Pro Ser Ala Glu Asp Phe Tyr Asp Cys Arg
180                185                190                195 gtg gag cac tgg ggc ttg gac cag ccg ctc ctc aag cac tgg gag gcc       740
Val Glu His Trp Gly Leu Asp Gln Pro Leu Leu Lys His Trp Glu Ala
                200                205                210 caa gag cca atc cag atg cct gag aca acg gag act gtg ctc tgt gcc       788
Gln Glu Pro Ile Gln Met Pro Glu Thr Thr Glu Thr Val Leu Cys Ala
                215                220                225
```

```
ctg ggc ctg gtg ctg ggc cta gtc ggc atc atc gtg ggc acc gtc ctc        836
Leu Gly Leu Val Leu Gly Leu Val Gly Ile Ile Val Gly Thr Val Leu
        230             235             240 atc ata aag tct ctg cgt tct ggc cat gac ccc cgg gcc cag ggg acc        884
Ile Ile Lys Ser Leu Arg Ser Gly His Asp Pro Arg Ala Gln Gly Thr
        245             250             255 ctg tga aatactgtaa aggtgacaaa atatctgaac agaagaggac ttaggagaga        940
Leu
260 tctgaactcc agctgcccta caaactccat ctcagctttt cttctcactt catgtgaaaa       1000 ctactccagt ggctgactga attgctgacc cttcaagctc tgtccttatc cattacctca       1060 aagcagtcat tccttagtaa agtttccaac aaatagaaat taatgacact ttggtagcac       1120 taatatggag attatccttt cattgagcct tttatcctct gttctccttt gaagaacccc       1180 tcactgtcac cttcccgaga ataccctaag accaataaat acttcagtat ttcagagcgg       1240 ggagactctg agtcattctt actggaagtc taggaccagg tcacatgtga atactatttc       1300 ttgaaggtgt ggtttcaacc tctgttgccg atgtggttac taaaggttct gatcccactt       1360 gaacggaaag gtctgaggat attgattcag tcctgggttt ttccctaact acaggatagg       1420 gtggggtaga gaaaggatat ttggggggaaa ttttacttgg atgaagattt tcttggatgt       1480 agtttgaaga ctgcagtgtt tgaagtctct gagggaagag atttggtctg tctggatcaa       1540 gatttcaggc agattaggat tccattcaca gcccctgagc ttccttccca aggctgtatt       1600 gtaattatag caatatttca tggaggattt ttctacatga taaactaaga gccaagaaat       1660 aaaattttta aaatgccta aaaaaaaaaa aaaaaaa                                 1697

<210> SEQ ID NO 37
<211> LENGTH: 260
<212> TYPE: PRT
<213> ORGANISM: Homo sapiens

<400> SEQUENCE: 37

Met Arg Pro Glu Asp Arg Met Phe His Ile Arg Ala Val Ile Leu Arg
1               5                   10                  15

Ala Leu Ser Leu Ala Phe Leu Leu Ser Leu Arg Gly Ala Gly Ala Ile
            20                  25                  30

Lys Ala Asp His Val Ser Thr Tyr Ala Ala Phe Val Gln Thr His Arg
        35                  40                  45

Pro Thr Gly Glu Phe Met Phe Glu Phe Asp Glu Asp Glu Met Phe Tyr
    50                  55                  60

Val Asp Leu Asp Lys Lys Glu Thr Val Trp His Leu Glu Glu Phe Gly
65                  70                  75                  80

Gln Ala Phe Ser Phe Glu Ala Gln Gly Gly Leu Ala Asn Ile Ala Ile
                85                  90                  95

Leu Asn Asn Asn Leu Asn Thr Leu Ile Gln Arg Ser Asn His Thr Gln
            100                 105                 110

Ala Thr Asn Asp Pro Pro Glu Val Thr Val Phe Pro Lys Glu Pro Val
        115                 120                 125

Glu Leu Gly Gln Pro Asn Thr Leu Ile Cys His Ile Asp Lys Phe Phe
    130                 135                 140

Pro Pro Val Leu Asn Val Thr Trp Leu Cys Asn Gly Glu Leu Val Thr
145                 150                 155                 160

Glu Gly Val Ala Glu Ser Leu Phe Leu Pro Arg Thr Asp Tyr Ser Phe
                165                 170                 175
```

-continued

```
His Lys Phe His Tyr Leu Thr Phe Val Pro Ser Ala Glu Asp Phe Tyr
            180                 185                 190

Asp Cys Arg Val Glu His Trp Gly Leu Asp Gln Pro Leu Leu Lys His
        195                 200                 205

Trp Glu Ala Gln Glu Pro Ile Gln Met Pro Glu Thr Thr Glu Thr Val
    210                 215                 220

Leu Cys Ala Leu Gly Leu Val Leu Gly Leu Val Gly Ile Ile Val Gly
225                 230                 235                 240

Thr Val Leu Ile Ile Lys Ser Leu Arg Ser Gly His Asp Pro Arg Ala
                245                 250                 255

Gln Gly Thr Leu
            260

<210> SEQ ID NO 38
<211> LENGTH: 777
<212> TYPE: DNA
<213> ORGANISM: Homo sapiens
<220> FEATURE:
<221> NAME/KEY: CDS
<222> LOCATION: (1)..(777)

<400> SEQUENCE: 38 atg atg gtt ctg cag gtt tct gcg gcc ccc cgg aca gtg gct ctg acg      48
Met Met Val Leu Gln Val Ser Ala Ala Pro Arg Thr Val Ala Leu Thr
1               5                   10                  15 gcg tta ctg atg gtg ctg ctc aca tct gtg gtc cag ggc agg gcc act      96
Ala Leu Leu Met Val Leu Leu Thr Ser Val Val Gln Gly Arg Ala Thr
                20                  25                  30 cca gag aat tac gtg tac cag gga cgg cag gaa tgc tac gcg ttt aat     144
Pro Glu Asn Tyr Val Tyr Gln Gly Arg Gln Glu Cys Tyr Ala Phe Asn
            35                  40                  45 ggg aca cag cgc ttc ctg gag aga tac atc tac aac cgg gag gag tac     192
Gly Thr Gln Arg Phe Leu Glu Arg Tyr Ile Tyr Asn Arg Glu Glu Tyr
        50                  55                  60 gcg cgc ttc gac agc gac gtg ggg gag ttc cgg gcg gtg acg gag ctg     240
Ala Arg Phe Asp Ser Asp Val Gly Glu Phe Arg Ala Val Thr Glu Leu
65                  70                  75                  80 ggg cgg cct gct gcg gag tac tgg aac agc cag aag gac atc ctg gag     288
Gly Arg Pro Ala Ala Glu Tyr Trp Asn Ser Gln Lys Asp Ile Leu Glu
                85                  90                  95 gag aag cgg gca gtg ccg gac agg gta tgc aga cac aac tac gag ctg     336
Glu Lys Arg Ala Val Pro Asp Arg Val Cys Arg His Asn Tyr Glu Leu
            100                 105                 110 gac gag gcc gtg acc ctg cag cgc cga gtc cag cct aag gtg aac gtt     384
Asp Glu Ala Val Thr Leu Gln Arg Arg Val Gln Pro Lys Val Asn Val
        115                 120                 125 tcc ccc tcc aag aag ggg ccc ctg cag cac cac aac ctg ctt gtc tgc     432
Ser Pro Ser Lys Lys Gly Pro Leu Gln His His Asn Leu Leu Val Cys
    130                 135                 140 cac gtg aca gat ttc tac cca ggc agc att caa gtc cga tgg ttc ctg     480
His Val Thr Asp Phe Tyr Pro Gly Ser Ile Gln Val Arg Trp Phe Leu
145                 150                 155                 160 aat gga cag gag gaa aca gct ggg gtc gtg tcc acc aac ctg atc cgt     528
Asn Gly Gln Glu Glu Thr Ala Gly Val Val Ser Thr Asn Leu Ile Arg
                165                 170                 175 aat gga gac tgg acc ttc cag atc ctg gtg atg ctg gaa atg acc ccc     576
Asn Gly Asp Trp Thr Phe Gln Ile Leu Val Met Leu Glu Met Thr Pro
            180                 185                 190 cag cag gga gac gtc tac atc tgc caa gtg gag cac acc agc ctg gac     624
Gln Gln Gly Asp Val Tyr Ile Cys Gln Val Glu His Thr Ser Leu Asp
```

-continued

```
          195                200                205 agt cct gtc acc gtg gag tgg aag gca cag tct gat tct gcc cag agt   672
Ser Pro Val Thr Val Glu Trp Lys Ala Gln Ser Asp Ser Ala Gln Ser
    210                215                220 aag aca ttg acg gga gct ggg ggc ttc gtg ctg ggg ctc atc atc tgt   720
Lys Thr Leu Thr Gly Ala Gly Gly Phe Val Leu Gly Leu Ile Ile Cys
225                230                235                240 gga gtg ggc atc ttc atg cac agg agg agc aag aaa gtt caa cga gga   768
Gly Val Gly Ile Phe Met His Arg Arg Ser Lys Lys Val Gln Arg Gly
                245                250                255 tct gca taa                                                        777
Ser Ala
```

<210> SEQ ID NO 39
<211> LENGTH: 258
<212> TYPE: PRT
<213> ORGANISM: Homo sapiens

<400> SEQUENCE: 39

```
Met Met Val Leu Gln Val Ser Ala Ala Pro Arg Thr Val Ala Leu Thr
1               5                10                15

Ala Leu Leu Met Val Leu Leu Thr Ser Val Val Gln Gly Arg Ala Thr
                20                25                30

Pro Glu Asn Tyr Val Tyr Gln Gly Arg Gln Glu Cys Tyr Ala Phe Asn
            35                40                45

Gly Thr Gln Arg Phe Leu Glu Arg Tyr Ile Tyr Asn Arg Glu Glu Tyr
    50                55                60

Ala Arg Phe Asp Ser Asp Val Gly Glu Phe Arg Ala Val Thr Glu Leu
65                70                75                80

Gly Arg Pro Ala Ala Glu Tyr Trp Asn Ser Gln Lys Asp Ile Leu Glu
                85                90                95

Glu Lys Arg Ala Val Pro Asp Arg Val Cys Arg His Asn Tyr Glu Leu
            100                105                110

Asp Glu Ala Val Thr Leu Gln Arg Arg Val Gln Pro Lys Val Asn Val
        115                120                125

Ser Pro Ser Lys Lys Gly Pro Leu Gln His His Asn Leu Leu Val Cys
    130                135                140

His Val Thr Asp Phe Tyr Pro Gly Ser Ile Gln Val Arg Trp Phe Leu
145                150                155                160

Asn Gly Gln Glu Glu Thr Ala Gly Val Val Ser Thr Asn Leu Ile Arg
                165                170                175

Asn Gly Asp Trp Thr Phe Gln Ile Leu Val Met Leu Glu Met Thr Pro
            180                185                190

Gln Gln Gly Asp Val Tyr Ile Cys Gln Val Glu His Thr Ser Leu Asp
        195                200                205

Ser Pro Val Thr Val Glu Trp Lys Ala Gln Ser Asp Ser Ala Gln Ser
    210                215                220

Lys Thr Leu Thr Gly Ala Gly Gly Phe Val Leu Gly Leu Ile Ile Cys
225                230                235                240

Gly Val Gly Ile Phe Met His Arg Arg Ser Lys Lys Val Gln Arg Gly
                245                250                255

Ser Ala
```

<210> SEQ ID NO 40
<211> LENGTH: 768
<212> TYPE: DNA

-continued

<213> ORGANISM: Homo sapiens
<220> FEATURE:
<221> NAME/KEY: CDS
<222> LOCATION: (1)..(768)

<400> SEQUENCE: 40

```
atg atc cta aac aaa gct ctg ctg ctg ggg gcc ctc gct ctg acc acc        48
Met Ile Leu Asn Lys Ala Leu Leu Leu Gly Ala Leu Ala Leu Thr Thr
1               5                   10                  15 gtg atg agc ccc tgt gga ggt gaa gac att gtg gct gac cac gtt gcc        96
Val Met Ser Pro Cys Gly Gly Glu Asp Ile Val Ala Asp His Val Ala
            20                  25                  30 tct tgt ggt gta aac ttg tac cag ttt tac ggt ccc tct ggc cag tac       144
Ser Cys Gly Val Asn Leu Tyr Gln Phe Tyr Gly Pro Ser Gly Gln Tyr
        35                  40                  45 acc cat gaa ttt gat gga gat gag gag ttc tac gtg gac ctg gag agg       192
Thr His Glu Phe Asp Gly Asp Glu Glu Phe Tyr Val Asp Leu Glu Arg
        50                  55                  60 aag gag act gcc tgg cgg tgg cct gag ttc agc aaa ttt gga ggt ttt       240
Lys Glu Thr Ala Trp Arg Trp Pro Glu Phe Ser Lys Phe Gly Gly Phe
65                  70                  75                  80 gac ccg cag ggt gca ctg aga aac atg gct gtg gca aaa cac aac ttg       288
Asp Pro Gln Gly Ala Leu Arg Asn Met Ala Val Ala Lys His Asn Leu
                85                  90                  95 aac atc atg att aaa cgc tac aac tct acc gct gct acc aat gag gtt       336
Asn Ile Met Ile Lys Arg Tyr Asn Ser Thr Ala Ala Thr Asn Glu Val
            100                 105                 110 cct gag gtc aca gtg ttt tcc aag tct ccc gtg aca ctg ggt cag ccc       384
Pro Glu Val Thr Val Phe Ser Lys Ser Pro Val Thr Leu Gly Gln Pro
            115                 120                 125 aac acc ctc att tgt ctt gtg gac aac atc ttt cct cct gtg gtc aac       432
Asn Thr Leu Ile Cys Leu Val Asp Asn Ile Phe Pro Pro Val Val Asn
        130                 135                 140 atc aca tgg ctg agc aat ggg cag tca gtc aca gaa ggt gtt tct gag       480
Ile Thr Trp Leu Ser Asn Gly Gln Ser Val Thr Glu Gly Val Ser Glu
145                 150                 155                 160 acc agc ttc ctc tcc aag agt gat cat tcc ttc ttc aag atc agt tac       528
Thr Ser Phe Leu Ser Lys Ser Asp His Ser Phe Phe Lys Ile Ser Tyr
                165                 170                 175 ctc acc ttc ctc cct tct gct gat gag att tat gac tgc aag gtg gag       576
Leu Thr Phe Leu Pro Ser Ala Asp Glu Ile Tyr Asp Cys Lys Val Glu
            180                 185                 190 cac tgg ggc ctg gac cag cct ctt ctg aaa cac tgg gag cct gag att       624
His Trp Gly Leu Asp Gln Pro Leu Leu Lys His Trp Glu Pro Glu Ile
            195                 200                 205 cca gcc cct atg tca gag ctc aca gag act gtg gtc tgc gcc ctg ggg       672
Pro Ala Pro Met Ser Glu Leu Thr Glu Thr Val Val Cys Ala Leu Gly
        210                 215                 220 ttg tct gtg ggc ctc gtg ggc att gtg gtg ggc act gtc ttc atc atc       720
Leu Ser Val Gly Leu Val Gly Ile Val Val Gly Thr Val Phe Ile Ile
225                 230                 235                 240 caa ggc ctg cgt tca gtt ggt gct tcc aga cac caa ggg cca ttg tga       768
Gln Gly Leu Arg Ser Val Gly Ala Ser Arg His Gln Gly Pro Leu
                245                 250                 255
```

<210> SEQ ID NO 41
<211> LENGTH: 255
<212> TYPE: PRT
<213> ORGANISM: Homo sapiens

<400> SEQUENCE: 41

```
Met Ile Leu Asn Lys Ala Leu Leu Leu Gly Ala Leu Ala Leu Thr Thr
1               5                   10                  15

Val Met Ser Pro Cys Gly Gly Glu Asp Ile Val Ala Asp His Val Ala
            20                  25                  30

Ser Cys Gly Val Asn Leu Tyr Gln Phe Tyr Gly Pro Ser Gly Gln Tyr
        35                  40                  45

Thr His Glu Phe Asp Gly Asp Glu Glu Phe Tyr Val Asp Leu Glu Arg
    50                  55                  60

Lys Glu Thr Ala Trp Arg Trp Pro Glu Phe Ser Lys Phe Gly Gly Phe
65                  70                  75                  80

Asp Pro Gln Gly Ala Leu Arg Asn Met Ala Val Ala Lys His Asn Leu
                85                  90                  95

Asn Ile Met Ile Lys Arg Tyr Asn Ser Thr Ala Ala Thr Asn Glu Val
            100                 105                 110

Pro Glu Val Thr Val Phe Ser Lys Ser Pro Val Thr Leu Gly Gln Pro
            115                 120                 125

Asn Thr Leu Ile Cys Leu Val Asp Asn Ile Phe Pro Pro Val Val Asn
        130                 135                 140

Ile Thr Trp Leu Ser Asn Gly Gln Ser Val Thr Glu Gly Val Ser Glu
145                 150                 155                 160

Thr Ser Phe Leu Ser Lys Ser Asp His Ser Phe Phe Lys Ile Ser Tyr
                165                 170                 175

Leu Thr Phe Leu Pro Ser Ala Asp Glu Ile Tyr Asp Cys Lys Val Glu
                180                 185                 190

His Trp Gly Leu Asp Gln Pro Leu Leu Lys His Trp Glu Pro Glu Ile
            195                 200                 205

Pro Ala Pro Met Ser Glu Leu Thr Glu Thr Val Val Cys Ala Leu Gly
    210                 215                 220

Leu Ser Val Gly Leu Val Gly Ile Val Val Gly Thr Val Phe Ile Ile
225                 230                 235                 240

Gln Gly Leu Arg Ser Val Gly Ala Ser Arg His Gln Gly Pro Leu
                245                 250                 255
```

```
<210> SEQ ID NO 42
<211> LENGTH: 786
<212> TYPE: DNA
<213> ORGANISM: Homo sapiens
<220> FEATURE:
<221> NAME/KEY: CDS
<222> LOCATION: (1)..(786)

<400> SEQUENCE: 42 atg tct tgg aaa aag gct ttg cgg atc ccc gga ggc ctt cgg gca gca        48
Met Ser Trp Lys Lys Ala Leu Arg Ile Pro Gly Gly Leu Arg Ala Ala
1               5                   10                  15 act gtg acc ttg atg ctg tcg atg ctg agc acc cca gtg gct gag ggc        96
Thr Val Thr Leu Met Leu Ser Met Leu Ser Thr Pro Val Ala Glu Gly
            20                  25                  30 aga gac tct ccc gag gat ttc gtg tac cag ttt aag ggc atg tgc tac       144
Arg Asp Ser Pro Glu Asp Phe Val Tyr Gln Phe Lys Gly Met Cys Tyr
        35                  40                  45 ttc acc aac ggg aca gag cgc gtg cgt ctt gtg agc aga agc atc tat       192
Phe Thr Asn Gly Thr Glu Arg Val Arg Leu Val Ser Arg Ser Ile Tyr
        50                  55                  60 aac cga gaa gag atc gtg cgc ttc gac agc gac gtg ggg gag ttc cgg       240
Asn Arg Glu Glu Ile Val Arg Phe Asp Ser Asp Val Gly Glu Phe Arg
65                  70                  75                  80
```

-continued

```
gcg gtg acg ctg ctg ggg ctg cct gcc gcc gag tac tgg aac agc cag        288
Ala Val Thr Leu Leu Gly Leu Pro Ala Ala Glu Tyr Trp Asn Ser Gln
             85                  90                  95 aag gac atc ctg gag agg aaa cgg gcg gcg gtg gac agg gtg tgc aga        336
Lys Asp Ile Leu Glu Arg Lys Arg Ala Ala Val Asp Arg Val Cys Arg
                100                 105                 110 cac aac tac cag ttg gag ctc cgc acg acc ttg cag cgg cga gtg gag        384
His Asn Tyr Gln Leu Glu Leu Arg Thr Thr Leu Gln Arg Arg Val Glu
            115                 120                 125 ccc aca gtg acc atc tcc cca tcc agg aca gag gcc ctc aac cac cac        432
Pro Thr Val Thr Ile Ser Pro Ser Arg Thr Glu Ala Leu Asn His His
            130                 135                 140 aac ctg ctg gtc tgc tcg gtg aca gat ttc tat cca gcc cag atc aaa        480
Asn Leu Leu Val Cys Ser Val Thr Asp Phe Tyr Pro Ala Gln Ile Lys
145                 150                 155                 160 gtc cgg tgg ttt cgg aat gac cag gag gag aca gct ggc gtt gtg tcc        528
Val Arg Trp Phe Arg Asn Asp Gln Glu Glu Thr Ala Gly Val Val Ser
                    165                 170                 175 acc ccc ctt att agg aat ggt gac tgg acc ttc cag atc ctg gtg atg        576
Thr Pro Leu Ile Arg Asn Gly Asp Trp Thr Phe Gln Ile Leu Val Met
                180                 185                 190 ctg gaa atg act ccc cag cgt gga gac gtc tac acc tgc cac gtg gag        624
Leu Glu Met Thr Pro Gln Arg Gly Asp Val Tyr Thr Cys His Val Glu
            195                 200                 205 cac ccc agc ctc cag agc ccc atc acc gtg gag tgg cgg gct caa tct        672
His Pro Ser Leu Gln Ser Pro Ile Thr Val Glu Trp Arg Ala Gln Ser
            210                 215                 220 gaa tct gcc cag agc aag atg ctg agt ggc att gga ggc ttc gtg ctg        720
Glu Ser Ala Gln Ser Lys Met Leu Ser Gly Ile Gly Gly Phe Val Leu
225                 230                 235                 240 ggg ctg atc ttc ctc ggg ctg ggc ctt atc atc cat cac agg agt cag        768
Gly Leu Ile Phe Leu Gly Leu Gly Leu Ile Ile His His Arg Ser Gln
                245                 250                 255 aaa ggg ctc ctg cac tga                                                786
Lys Gly Leu Leu His
                260
```

```
<210> SEQ ID NO 43
<211> LENGTH: 261
<212> TYPE: PRT
<213> ORGANISM: Homo sapiens

<400> SEQUENCE: 43

Met Ser Trp Lys Lys Ala Leu Arg Ile Pro Gly Gly Leu Arg Ala Ala
1               5                   10                  15

Thr Val Thr Leu Met Leu Ser Met Leu Ser Thr Pro Val Ala Glu Gly
                20                  25                  30

Arg Asp Ser Pro Glu Asp Phe Val Tyr Gln Phe Lys Gly Met Cys Tyr
            35                  40                  45

Phe Thr Asn Gly Thr Glu Arg Val Arg Leu Val Ser Arg Ser Ile Tyr
        50                  55                  60

Asn Arg Glu Glu Ile Val Arg Phe Asp Ser Asp Val Gly Glu Phe Arg
65                  70                  75                  80

Ala Val Thr Leu Leu Gly Leu Pro Ala Ala Glu Tyr Trp Asn Ser Gln
                85                  90                  95

Lys Asp Ile Leu Glu Arg Lys Arg Ala Ala Val Asp Arg Val Cys Arg
                100                 105                 110

His Asn Tyr Gln Leu Glu Leu Arg Thr Thr Leu Gln Arg Arg Val Glu
            115                 120                 125
```

-continued

```
Pro Thr Val Thr Ile Ser Pro Ser Arg Thr Glu Ala Leu Asn His His
    130              135           140

Asn Leu Leu Val Cys Ser Val Thr Asp Phe Tyr Pro Ala Gln Ile Lys
145              150               155                   160

Val Arg Trp Phe Arg Asn Asp Gln Glu Glu Thr Ala Gly Val Val Ser
            165               170               175

Thr Pro Leu Ile Arg Asn Gly Asp Trp Thr Phe Gln Ile Leu Val Met
            180               185               190

Leu Glu Met Thr Pro Gln Arg Gly Asp Val Tyr Thr Cys His Val Glu
        195               200               205

His Pro Ser Leu Gln Ser Pro Ile Thr Val Glu Trp Arg Ala Gln Ser
    210               215               220

Glu Ser Ala Gln Ser Lys Met Leu Ser Gly Ile Gly Gly Phe Val Leu
225               230               235               240

Gly Leu Ile Phe Leu Gly Leu Gly Leu Ile Ile His His Arg Ser Gln
            245               250               255

Lys Gly Leu Leu His
            260
```

```
<210> SEQ ID NO 44
<211> LENGTH: 1312
<212> TYPE: DNA
<213> ORGANISM: Homo sapiens
<220> FEATURE:
<221> NAME/KEY: CDS
<222> LOCATION: (110)..(874)

<400> SEQUENCE: 44
ttttaatggt cagactctat tacaccccac attctctttt cttttattct tgtctgttct          60
gcctcactcc cgagctctac tgactcccaa cagagcgccc aagaagaaa atg gcc ata         118
                                                      Met Ala Ile
                                                        1 agt gga gtc cct gtg cta gga ttt ttc atc ata gct gtg ctg atg agc         166
Ser Gly Val Pro Val Leu Gly Phe Phe Ile Ile Ala Val Leu Met Ser
    5               10              15 gct cag gaa tca tgg gct atc aaa gaa gaa cat gtg atc atc cag gcc         214
Ala Gln Glu Ser Trp Ala Ile Lys Glu Glu His Val Ile Ile Gln Ala
20              25              30              35 gag ttc tat ctg aat cct gac caa tca ggc gag ttt atg ttt gac ttt         262
Glu Phe Tyr Leu Asn Pro Asp Gln Ser Gly Glu Phe Met Phe Asp Phe
                40              45              50 gat ggt gat gag att ttc cat gtg gat atg gca aag aag gag acg gtc         310
Asp Gly Asp Glu Ile Phe His Val Asp Met Ala Lys Lys Glu Thr Val
            55              60              65 tgg cgg ctt gaa gaa ttt gga cga ttt gcc agc ttt gag gct caa ggt         358
Trp Arg Leu Glu Glu Phe Gly Arg Phe Ala Ser Phe Glu Ala Gln Gly
        70              75              80 gca ttg gcc aac ata gct gtg gac aaa gcc aac ctg gaa atc atg aca         406
Ala Leu Ala Asn Ile Ala Val Asp Lys Ala Asn Leu Glu Ile Met Thr
    85              90              95 aag cgc tcc aac tat act ccg atc acc aat gta cct cca gag gta act         454
Lys Arg Ser Asn Tyr Thr Pro Ile Thr Asn Val Pro Pro Glu Val Thr
100             105             110             115 gtg ctc aca aac agc cct gtg gaa ctg aga gag ccc aac gtc ctc atc         502
Val Leu Thr Asn Ser Pro Val Glu Leu Arg Glu Pro Asn Val Leu Ile
            120             125             130 tgt ttc ata gac aag ttc acc cca cca gtg gtc aat gtc acg tgg ctt         550
Cys Phe Ile Asp Lys Phe Thr Pro Pro Val Val Asn Val Thr Trp Leu
```

-continued
_____

```
            135               140               145
cga aat gga aaa cct gtc acc aca gga gtg tca gag aca gtc ttc ctg      598
Arg Asn Gly Lys Pro Val Thr Thr Gly Val Ser Glu Thr Val Phe Leu
            150               155               160 ccc agg gaa gac cac ctt ttc cgc aag ttc cac tat ctc ccc ttc ctg      646
Pro Arg Glu Asp His Leu Phe Arg Lys Phe His Tyr Leu Pro Phe Leu
            165               170               175 ccc tca act gag gac gtt tac gac tgc agg gtg gag cac tgg ggc ttg      694
Pro Ser Thr Glu Asp Val Tyr Asp Cys Arg Val Glu His Trp Gly Leu
180               185               190               195 gat gag cct ctt ctc aag cac tgg gag ttt gat gct cca agc cct ctc      742
Asp Glu Pro Leu Leu Lys His Trp Glu Phe Asp Ala Pro Ser Pro Leu
                200               205               210 cca gag act aca gag aac gtg gtg tgt gcc ctg ggc ctg act gtg ggt      790
Pro Glu Thr Thr Glu Asn Val Val Cys Ala Leu Gly Leu Thr Val Gly
                215               220               225 ctg gtg ggc atc att att ggg acc atc ttc atc atc aag gga ttg cgc      838
Leu Val Gly Ile Ile Ile Gly Thr Ile Phe Ile Ile Lys Gly Leu Arg
                230               235               240 aaa agc aat gca gca gaa cgc agg ggg cct ctg taa ggcacatgga          884
Lys Ser Asn Ala Ala Glu Arg Arg Gly Pro Leu
                245               250 ggtgatggtg tttcttagag agaagatcac tgaagaaact tctgctttaa tggctttaca   944
aagctggcaa tattacaatc cttgacctca gtgaaagcag tcatcttcag catttttccag  1004 ccctatagcc accccaagtg tggatatgcc tcttcgattg ctccgtactc taacatctag   1064
ctggcttccc tgtctattgc cttttcctgt atctattttc ctctatttcc tatcatttta   1124
ttatcaccat gcaatgcctc tggaataaaa catacaggag tctgtctctg ctatggaatg   1184
ccccatgggg catctcttgt gtacttattg tttaaggttt cctcaaactg tgattttttct  1244 gaacacaata aactattttg atgatcttgg gtggaaaaaa aaaaaaaaaa aaaaaaaaaa   1304
aaaaaaaa                                                            1312
```

<210> SEQ ID NO 45
<211> LENGTH: 254
<212> TYPE: PRT
<213> ORGANISM: Homo sapiens

<400> SEQUENCE: 45

```
Met Ala Ile Ser Gly Val Pro Val Leu Gly Phe Phe Ile Ile Ala Val
1               5               10               15

Leu Met Ser Ala Gln Glu Ser Trp Ala Ile Lys Glu Glu His Val Ile
            20               25               30

Ile Gln Ala Glu Phe Tyr Leu Asn Pro Asp Gln Ser Gly Glu Phe Met
            35               40               45

Phe Asp Phe Asp Gly Asp Glu Ile Phe His Val Asp Met Ala Lys Lys
        50               55               60

Glu Thr Val Trp Arg Leu Glu Glu Phe Gly Arg Phe Ala Ser Phe Glu
65               70               75               80

Ala Gln Gly Ala Leu Ala Asn Ile Ala Val Asp Lys Ala Asn Leu Glu
                85               90               95

Ile Met Thr Lys Arg Ser Asn Tyr Thr Pro Ile Thr Asn Val Pro Pro
            100               105               110

Glu Val Thr Val Leu Thr Asn Ser Pro Val Glu Leu Arg Glu Pro Asn
            115               120               125

Val Leu Ile Cys Phe Ile Asp Lys Phe Thr Pro Pro Val Val Asn Val
```

-continued

```
           130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
                    165                 170                 175

Pro Phe Leu Pro Ser Thr Glu Asp Val Tyr Asp Cys Arg Val Glu His
                    180                 185                 190

Trp Gly Leu Asp Glu Pro Leu Leu Lys His Trp Glu Phe Asp Ala Pro
                195                 200                 205

Ser Pro Leu Pro Glu Thr Thr Glu Asn Val Val Cys Ala Leu Gly Leu
                210                 215                 220

Thr Val Gly Leu Val Gly Ile Ile Ile Gly Thr Ile Phe Ile Ile Lys
225                 230                 235                 240

Gly Leu Arg Lys Ser Asn Ala Ala Glu Arg Arg Gly Pro Leu
                245                 250
```

<210> SEQ ID NO 46
<211> LENGTH: 801
<212> TYPE: DNA
<213> ORGANISM: Homo sapiens
<220> FEATURE:
<221> NAME/KEY: CDS
<222> LOCATION: (1)..(801)

<400> SEQUENCE: 46

```
atg gtg tgt ctg aag ctc cct gga ggc tcc tgc atg aca gcg ctg aca      48
Met Val Cys Leu Lys Leu Pro Gly Gly Ser Cys Met Thr Ala Leu Thr
1               5                   10                  15 gtg aca ctg atg gtg ctg agc tcc cca ctg gct ttg gct ggg gac acc      96
Val Thr Leu Met Val Leu Ser Ser Pro Leu Ala Leu Ala Gly Asp Thr
                20                  25                  30 cga cca cgt ttc ttg tgg cag ctt aag ttt gaa tgt cat ttc ttc aat     144
Arg Pro Arg Phe Leu Trp Gln Leu Lys Phe Glu Cys His Phe Phe Asn
                35                  40                  45 ggg acg gag cgg gtg cgg ttg ctg gaa aga tgc atc tat aac caa gag     192
Gly Thr Glu Arg Val Arg Leu Leu Glu Arg Cys Ile Tyr Asn Gln Glu
        50                  55                  60 gag tcc gtg cgc ttc gac agc gac gtg ggg gag tac cgg gcg gtg acg     240
Glu Ser Val Arg Phe Asp Ser Asp Val Gly Glu Tyr Arg Ala Val Thr
65                  70                  75                  80 gag ctg ggg cgg cct gat gcc gag tac tgg aac agc cag aag gac ctc     288
Glu Leu Gly Arg Pro Asp Ala Glu Tyr Trp Asn Ser Gln Lys Asp Leu
                85                  90                  95 ctg gag cag agg cgg gcc gcg gtg gac acc tac tgc aga cac aac tac     336
Leu Glu Gln Arg Arg Ala Ala Val Asp Thr Tyr Cys Arg His Asn Tyr
                100                 105                 110 ggg gtt ggt gag agc ttc aca gtg cag cgg cga gtt gag cct aag gtg     384
Gly Val Gly Glu Ser Phe Thr Val Gln Arg Arg Val Glu Pro Lys Val
                115                 120                 125 act gtg tat cct tca aag acc cag ccc ctg cag cac cac aac ctc ctg     432
Thr Val Tyr Pro Ser Lys Thr Gln Pro Leu Gln His His Asn Leu Leu
        130                 135                 140 gtc tgc tct gtg agt ggt ttc tat cca ggc agc att gaa gtc agg tgg     480
Val Cys Ser Val Ser Gly Phe Tyr Pro Gly Ser Ile Glu Val Arg Trp
145                 150                 155                 160 ttc cgg aac ggc cag gaa gag aag gct ggg gtg gtg tcc aca ggc ctg     528
Phe Arg Asn Gly Gln Glu Glu Lys Ala Gly Val Val Ser Thr Gly Leu
                165                 170                 175 atc cag aat gga gat tgg acc ttc cag acc ctg gtg atg ctg gaa aca     576
```

-continued

```
Ile Gln Asn Gly Asp Trp Thr Phe Gln Thr Leu Val Met Leu Glu Thr
            180                 185                 190 gtt cct cgg agt gga gag gtt tac acc tgc caa gtg gag cac cca agt          624
Val Pro Arg Ser Gly Glu Val Tyr Thr Cys Gln Val Glu His Pro Ser
        195                 200                 205 gtg acg agc cct ctc aca gtg gaa tgg aga gca cgg tct gaa tct gca          672
Val Thr Ser Pro Leu Thr Val Glu Trp Arg Ala Arg Ser Glu Ser Ala
    210                 215                 220 cag agc aag atg ctg agt gga gtc ggg ggc ttc gtg ctg ggc ctg ctc          720
Gln Ser Lys Met Leu Ser Gly Val Gly Gly Phe Val Leu Gly Leu Leu
225                 230                 235                 240 ttc ctt ggg gcc ggg ctg ttc atc tac ttc agg aat cag aaa gga cac          768
Phe Leu Gly Ala Gly Leu Phe Ile Tyr Phe Arg Asn Gln Lys Gly His
                245                 250                 255 tct gga ctt cag cca aca gga ttc ctg agc tga                              801
Ser Gly Leu Gln Pro Thr Gly Phe Leu Ser
                260                 265

<210> SEQ ID NO 47
<211> LENGTH: 266
<212> TYPE: PRT
<213> ORGANISM: Homo sapiens

<400> SEQUENCE: 47

Met Val Cys Leu Lys Leu Pro Gly Gly Ser Cys Met Thr Ala Leu Thr
1               5                   10                  15

Val Thr Leu Met Val Leu Ser Ser Pro Leu Ala Leu Ala Gly Asp Thr
            20                  25                  30

Arg Pro Arg Phe Leu Trp Gln Leu Lys Phe Glu Cys His Phe Phe Asn
        35                  40                  45

Gly Thr Glu Arg Val Arg Leu Leu Glu Arg Cys Ile Tyr Asn Gln Glu
    50                  55                  60

Glu Ser Val Arg Phe Asp Ser Asp Val Gly Glu Tyr Arg Ala Val Thr
65                  70                  75                  80

Glu Leu Gly Arg Pro Asp Ala Glu Tyr Trp Asn Ser Gln Lys Asp Leu
                85                  90                  95

Leu Glu Gln Arg Arg Ala Ala Val Asp Thr Tyr Cys Arg His Asn Tyr
            100                 105                 110

Gly Val Gly Glu Ser Phe Thr Val Gln Arg Arg Val Glu Pro Lys Val
        115                 120                 125

Thr Val Tyr Pro Ser Lys Thr Gln Pro Leu Gln His His Asn Leu Leu
        130                 135                 140

Val Cys Ser Val Ser Gly Phe Tyr Pro Gly Ser Ile Glu Val Arg Trp
145                 150                 155                 160

Phe Arg Asn Gly Gln Glu Glu Lys Ala Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Arg Ser Gly Glu Val Tyr Thr Cys Gln Val Glu His Pro Ser
        195                 200                 205

Val Thr Ser Pro Leu Thr Val Glu Trp Arg Ala Arg Ser Glu Ser Ala
    210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255
```

```
Ser Gly Leu Gln Pro Thr Gly Phe Leu Ser
        260                 265

<210> SEQ ID NO 48
<211> LENGTH: 1122
<212> TYPE: DNA
<213> ORGANISM: Homo sapiens
<220> FEATURE:
<221> NAME/KEY: CDS
<222> LOCATION: (87)..(872)

<400> SEQUENCE: 48
gatctaaggc caccctctcg gggagggagt tggggaagct gggttggctg ggttggtagc        60
tcctacctac tgtgtggcaa gaaggt atg ggt cat gaa cag aac caa gga gct       113
                               Met Gly His Glu Gln Asn Gln Gly Ala
                                1               5 gcg ctg cta cag atg tta cca ctt ctg tgg ctg cta ccc cac tcc tgg       161
Ala Leu Leu Gln Met Leu Pro Leu Leu Trp Leu Leu Pro His Ser Trp
10               15                  20                  25 gcc gtc cct gaa gct cct act cca atg tgg cca gat gac ctg caa aac       209
Ala Val Pro Glu Ala Pro Thr Pro Met Trp Pro Asp Asp Leu Gln Asn
                30                  35                  40 cac aca ttc ctg cac aca gtg tac tgc cag gat ggg agt ccc agt gtg       257
His Thr Phe Leu His Thr Val Tyr Cys Gln Asp Gly Ser Pro Ser Val
            45                  50                  55 gga ctc tct gag gcc tac gac gag gac cag ctt ttc ttc ttc gac ttt       305
Gly Leu Ser Glu Ala Tyr Asp Glu Asp Gln Leu Phe Phe Phe Asp Phe
        60                  65                  70 tcc cag aac act cgg gtg cct cgc ctg ccc gaa ttt gct gac tgg gct       353
Ser Gln Asn Thr Arg Val Pro Arg Leu Pro Glu Phe Ala Asp Trp Ala
    75                  80                  85 cag gaa cag gga gat gct cct gcc att tta ttt gac aaa gag ttc tgc       401
Gln Glu Gln Gly Asp Ala Pro Ala Ile Leu Phe Asp Lys Glu Phe Cys
90                  95                  100                 105 gag tgg atg atc cag caa ata ggg cca aaa ctt gat ggg aaa atc ccg       449
Glu Trp Met Ile Gln Gln Ile Gly Pro Lys Leu Asp Gly Lys Ile Pro
                110                 115                 120 gtg tcc aga ggg ttt cct atc gct gaa gtg ttc acg ctg aag ccc ctg       497
Val Ser Arg Gly Phe Pro Ile Ala Glu Val Phe Thr Leu Lys Pro Leu
            125                 130                 135 gag ttt ggc aag ccc aac act ttg gtc tgt ttt gtc agt aat ctc ttc       545
Glu Phe Gly Lys Pro Asn Thr Leu Val Cys Phe Val Ser Asn Leu Phe
        140                 145                 150 cca ccc atg ctg aca gtg aac tgg cag cat cat tcc gtc cct gtg gaa       593
Pro Pro Met Leu Thr Val Asn Trp Gln His His Ser Val Pro Val Glu
    155                 160                 165 gga ttt ggg cct act ttt gtc tca gct gtc gat gga ctc agc ttc cag       641
Gly Phe Gly Pro Thr Phe Val Ser Ala Val Asp Gly Leu Ser Phe Gln
170                 175                 180                 185 gcc ttt tct tac tta aac ttc aca cca gaa cct tct gac att ttc tcc       689
Ala Phe Ser Tyr Leu Asn Phe Thr Pro Glu Pro Ser Asp Ile Phe Ser
                190                 195                 200 tgc att gtg act cac gaa att gac cgc tac aca gca att gcc tat tgg       737
Cys Ile Val Thr His Glu Ile Asp Arg Tyr Thr Ala Ile Ala Tyr Trp
                205                 210                 215 gta ccc cgg aac gca ctg ccc tca gat ctg ctg gag aat gtg ctg tgt       785
Val Pro Arg Asn Ala Leu Pro Ser Asp Leu Leu Glu Asn Val Leu Cys
            220                 225                 230 ggc gtg gcc ttt ggc ctg ggt gtg ctg ggc atc atc gtg ggc att gtt       833
Gly Val Ala Phe Gly Leu Gly Val Leu Gly Ile Ile Val Gly Ile Val
        235                 240                 245
```

```
ctc atc atc tac ttc cgg aag cct tgc tca ggt gac tga ttcttccaga         882
Leu Ile Ile Tyr Phe Arg Lys Pro Cys Ser Gly Asp
250                 255                 260 ccagagtttg atgccagcag cttcggccat ccaaacagag gatgctcaga tttctcacat       942
cctgcccagg atctcctctt agggtagaag tctctgggac atccctgggg tgtgtgtgta      1002
gatttcccac ctggggactc tgctgtccct gggcttgcat cccagggatc ccagagtggc      1062
ctgcctatca caaccacatc ccttcccccc acaaggcaat aaatctcatt tctttatatc      1122
```

<210> SEQ ID NO 49
<211> LENGTH: 261
<212> TYPE: PRT
<213> ORGANISM: Homo sapiens

<400> SEQUENCE: 49

```
Met Gly His Glu Gln Asn Gln Gly Ala Ala Leu Leu Gln Met Leu Pro
1               5                   10                  15

Leu Leu Trp Leu Leu Pro His Ser Trp Ala Val Pro Glu Ala Pro Thr
            20                  25                  30

Pro Met Trp Pro Asp Asp Leu Gln Asn His Thr Phe Leu His Thr Val
        35                  40                  45

Tyr Cys Gln Asp Gly Ser Pro Ser Val Gly Leu Ser Glu Ala Tyr Asp
    50                  55                  60

Glu Asp Gln Leu Phe Phe Phe Asp Phe Ser Gln Asn Thr Arg Val Pro
65                  70                  75                  80

Arg Leu Pro Glu Phe Ala Asp Trp Ala Gln Glu Gln Gly Asp Ala Pro
                85                  90                  95

Ala Ile Leu Phe Asp Lys Glu Phe Cys Glu Trp Met Ile Gln Gln Ile
            100                 105                 110

Gly Pro Lys Leu Asp Gly Lys Ile Pro Val Ser Arg Gly Phe Pro Ile
            115                 120                 125

Ala Glu Val Phe Thr Leu Lys Pro Leu Glu Phe Gly Lys Pro Asn Thr
        130                 135                 140

Leu Val Cys Phe Val Ser Asn Leu Phe Pro Pro Met Leu Thr Val Asn
145                 150                 155                 160

Trp Gln His His Ser Val Pro Val Glu Gly Phe Gly Pro Thr Phe Val
                165                 170                 175

Ser Ala Val Asp Gly Leu Ser Phe Gln Ala Phe Ser Tyr Leu Asn Phe
            180                 185                 190

Thr Pro Glu Pro Ser Asp Ile Phe Ser Cys Ile Val Thr His Glu Ile
            195                 200                 205

Asp Arg Tyr Thr Ala Ile Ala Tyr Trp Val Pro Arg Asn Ala Leu Pro
        210                 215                 220

Ser Asp Leu Leu Glu Asn Val Leu Cys Gly Val Ala Phe Gly Leu Gly
225                 230                 235                 240

Val Leu Gly Ile Ile Val Gly Ile Val Leu Ile Ile Tyr Phe Arg Lys
                245                 250                 255

Pro Cys Ser Gly Asp
            260
```

<210> SEQ ID NO 50
<211> LENGTH: 1412
<212> TYPE: DNA
<213> ORGANISM: Homo sapiens
<220> FEATURE:
<221> NAME/KEY: CDS

```
<222> LOCATION: (264)..(1055)

<400> SEQUENCE: 50
atttgtccct gcctacctag ccaatctgtc cctgtttggg acactggact cccgtgagct        60
ggaaggaaca gatttaatat ctaggggctg ggtatcccca catcactcat ttggggggtc       120
aagggacccg ggcaatatag tattctgctc agtgtctgga gatcatctac ccaggctggg       180
gcttctggga caggcgagga cccacggacc ctggaagagc tggtccaggg gactgaactc       240
ccggcatctt tacagagcag agc atg atc aca ttc ctg ccg ctg ctg ctg ggg       293
                        Met Ile Thr Phe Leu Pro Leu Leu Leu Gly
                        1               5                   10 ctc agc ctg ggc tgc aca gga gca ggt ggc ttc gtg gcc cat gtg gaa       341
Leu Ser Leu Gly Cys Thr Gly Ala Gly Gly Phe Val Ala His Val Glu
              15                  20                  25 agc acc tgt ctg ttg gat gat gct ggg act cca aag gat ttc aca tac       389
Ser Thr Cys Leu Leu Asp Asp Ala Gly Thr Pro Lys Asp Phe Thr Tyr
          30                  35                  40 tgc atc tcc ttc aac aag gat ctg ctg acc tgc tgg gat cca gag gag       437
Cys Ile Ser Phe Asn Lys Asp Leu Leu Thr Cys Trp Asp Pro Glu Glu
              45                  50                  55 aat aag atg gcc cct tgc gaa ttt ggg gtg ctg aat agc ttg gcg aat       485
Asn Lys Met Ala Pro Cys Glu Phe Gly Val Leu Asn Ser Leu Ala Asn
60                  65                  70 gtc ctc tca cag cac ctc aac caa aaa gac acc ctg atg cag cgc ttg       533
Val Leu Ser Gln His Leu Asn Gln Lys Asp Thr Leu Met Gln Arg Leu
75                  80                  85                  90 cgc aat ggg ctt cag aat tgt gcc aca cac acc cag ccc ttc tgg gga       581
Arg Asn Gly Leu Gln Asn Cys Ala Thr His Thr Gln Pro Phe Trp Gly
                  95                  100                 105 tca ctg acc aac agg aca cgg cca cca tct gtg caa gta gcc aaa acc       629
Ser Leu Thr Asn Arg Thr Arg Pro Pro Ser Val Gln Val Ala Lys Thr
              110                 115                 120 act cct ttt aac acg agg gag cct gtg atg ctg gcc tgc tat gtg tgg       677
Thr Pro Phe Asn Thr Arg Glu Pro Val Met Leu Ala Cys Tyr Val Trp
          125                 130                 135 ggc ttc tat cca gca gaa gtg act atc acg tgg agg aag aac ggg aag       725
Gly Phe Tyr Pro Ala Glu Val Thr Ile Thr Trp Arg Lys Asn Gly Lys
          140                 145                 150 ctt gtc atg cct cac agc agt gcg cac aag act gcc cag ccc aat gga       773
Leu Val Met Pro His Ser Ser Ala His Lys Thr Ala Gln Pro Asn Gly
155                 160                 165                 170 gac tgg aca tac cag acc ctc tcc cat tta gcc tta acc ccc tct tac       821
Asp Trp Thr Tyr Gln Thr Leu Ser His Leu Ala Leu Thr Pro Ser Tyr
              175                 180                 185 ggg gac act tac acc tgt gtg gta gag cac act ggg gct cct gag ccc       869
Gly Asp Thr Tyr Thr Cys Val Val Glu His Thr Gly Ala Pro Glu Pro
              190                 195                 200 atc ctt cgg gac tgg aca cct ggg ctg tcc ccc atg cag acc ctg aag       917
Ile Leu Arg Asp Trp Thr Pro Gly Leu Ser Pro Met Gln Thr Leu Lys
          205                 210                 215 gtt tct gtg tct gca gtg act ctg ggc ctg ggc ctc atc atc ttc tct       965
Val Ser Val Ser Ala Val Thr Leu Gly Leu Gly Leu Ile Ile Phe Ser
      220                 225                 230 ctt ggt gtg atc agc tgg cgg aga gct ggc cac tct agt tac act cct      1013
Leu Gly Val Ile Ser Trp Arg Arg Ala Gly His Ser Ser Tyr Thr Pro
235                 240                 245                 250 ctt cct ggg tcc aat tat tca gaa gga tgg cac att tcc tag            1055
Leu Pro Gly Ser Asn Tyr Ser Glu Gly Trp His Ile Ser
                  255                 260
```

```
aggcagaatc ctacaacttc cactccaagt gagaaggaga ttcaaactca atgatgctac   1115
catgcctctc caacatcttc aaccccctga cattatcttg gatcctatgg tttctccatc   1175
caattctttg aatttcccag tctcccctat gtaaaactta gcaacttggg ggacctcatt   1235
cctgggacta tgctgtaacc aaattattgt ccaaggctat atttctggga tgaatataat   1295
ctgaggaagg gagttaaaga ccctcctggg gctctcagtg tgccatagag gacagcaact   1355
ggtgattgtt tcagagaaat aaactttggt ggaaatattg ttaaaaaaaa aaaaaaa     1412
```

<210> SEQ ID NO 51
<211> LENGTH: 263
<212> TYPE: PRT
<213> ORGANISM: Homo sapiens

<400> SEQUENCE: 51

```
Met Ile Thr Phe Leu Pro Leu Leu Leu Gly Leu Ser Leu Gly Cys Thr
1               5                   10                  15

Gly Ala Gly Gly Phe Val Ala His Val Glu Ser Thr Cys Leu Leu Asp
            20                  25                  30

Asp Ala Gly Thr Pro Lys Asp Phe Thr Tyr Cys Ile Ser Phe Asn Lys
        35                  40                  45

Asp Leu Leu Thr Cys Trp Asp Pro Glu Glu Asn Lys Met Ala Pro Cys
    50                  55                  60

Glu Phe Gly Val Leu Asn Ser Leu Ala Asn Val Leu Ser Gln His Leu
65                  70                  75                  80

Asn Gln Lys Asp Thr Leu Met Gln Arg Leu Arg Asn Gly Leu Gln Asn
                85                  90                  95

Cys Ala Thr His Thr Gln Pro Phe Trp Gly Ser Leu Thr Asn Arg Thr
            100                 105                 110

Arg Pro Pro Ser Val Gln Val Ala Lys Thr Thr Pro Phe Asn Thr Arg
        115                 120                 125

Glu Pro Val Met Leu Ala Cys Tyr Val Trp Gly Phe Tyr Pro Ala Glu
    130                 135                 140

Val Thr Ile Thr Trp Arg Lys Asn Gly Lys Leu Val Met Pro His Ser
145                 150                 155                 160

Ser Ala His Lys Thr Ala Gln Pro Asn Gly Asp Trp Thr Tyr Gln Thr
                165                 170                 175

Leu Ser His Leu Ala Leu Thr Pro Ser Tyr Gly Asp Thr Tyr Thr Cys
            180                 185                 190

Val Val Glu His Thr Gly Ala Pro Glu Pro Ile Leu Arg Asp Trp Thr
            195                 200                 205

Pro Gly Leu Ser Pro Met Gln Thr Leu Lys Val Ser Val Ser Ala Val
    210                 215                 220

Thr Leu Gly Leu Gly Leu Ile Ile Phe Ser Leu Gly Val Ile Ser Trp
225                 230                 235                 240

Arg Arg Ala Gly His Ser Ser Tyr Thr Pro Leu Pro Gly Ser Asn Tyr
                245                 250                 255

Ser Glu Gly Trp His Ile Ser
            260
```

<210> SEQ ID NO 52
<211> LENGTH: 3485
<212> TYPE: DNA
<213> ORGANISM: Homo sapiens
<220> FEATURE:
<221> NAME/KEY: CDS

```
<222> LOCATION: (77)..(829)

<400> SEQUENCE: 52
cttcttcttt acctccgcct tgttcctgtc ctcaccacac ggactgagac tgatttgatt        60
aaagcaccag agtgta atg gcc ctc aga gca ggg ctg gtc ctg ggg ttc cac       112
                   Met Ala Leu Arg Ala Gly Leu Val Leu Gly Phe His
                   1               5                   10 acc ctg atg acc ctc ctg agc ccg cag gag gca ggg gcc acc aag gct         160
Thr Leu Met Thr Leu Leu Ser Pro Gln Glu Ala Gly Ala Thr Lys Ala
        15                  20                  25 gac cac atg ggc tcc tac gga ccc gcc ttc tac cag tct tac ggc gcc         208
Asp His Met Gly Ser Tyr Gly Pro Ala Phe Tyr Gln Ser Tyr Gly Ala
        30                  35                  40 tcg ggc cag ttc acc cat gaa ttt gat gag gaa cag ctg ttc tct gtg         256
Ser Gly Gln Phe Thr His Glu Phe Asp Glu Glu Gln Leu Phe Ser Val
45                  50                  55                  60 gac ctg aag aaa agc gag gcc gtg tgg cgt ctg cct gag ttt ggt gac         304
Asp Leu Lys Lys Ser Glu Ala Val Trp Arg Leu Pro Glu Phe Gly Asp
                65                  70                  75 ttt gcc cgc ttt gac ccg cag ggc ggg ctg gcc ggc atc gcc gca atc         352
Phe Ala Arg Phe Asp Pro Gln Gly Gly Leu Ala Gly Ile Ala Ala Ile
                80                  85                  90 aaa gcc cat ctg gac atc ctg gtg gag cgc tcc aac cgc agc aga gcc         400
Lys Ala His Leu Asp Ile Leu Val Glu Arg Ser Asn Arg Ser Arg Ala
            95                  100                 105 atc aac gtg cct cca cgg gtg acc gtg ctc ccc aag tct cgg gtg gag         448
Ile Asn Val Pro Pro Arg Val Thr Val Leu Pro Lys Ser Arg Val Glu
        110                 115                 120 ctg ggc cag ccc aac atc ctc atc tgc atc gtg gac aac atc ttc ccc         496
Leu Gly Gln Pro Asn Ile Leu Ile Cys Ile Val Asp Asn Ile Phe Pro
125                 130                 135                 140 cct gtg atc aat atc acc tgg ctg cgc aac ggc caa act gtc act gag         544
Pro Val Ile Asn Ile Thr Trp Leu Arg Asn Gly Gln Thr Val Thr Glu
                145                 150                 155 gga gtg gcc cag acc agc ttc tat tcc cag cct gac cat ttg ttc cgc         592
Gly Val Ala Gln Thr Ser Phe Tyr Ser Gln Pro Asp His Leu Phe Arg
                160                 165                 170 aag ttc cac tac ctg ccc ttc gtg ccc tca gcc gag gac gtc tat gac         640
Lys Phe His Tyr Leu Pro Phe Val Pro Ser Ala Glu Asp Val Tyr Asp
            175                 180                 185 tgc cag gtg gag cac tgg ggc ctg gat gcg cca ctc ctc agg cat tgg         688
Cys Gln Val Glu His Trp Gly Leu Asp Ala Pro Leu Leu Arg His Trp
        190                 195                 200 gag ctc cag gtg cct att cca cca cca gat gcc atg gag acc ctg gtc         736
Glu Leu Gln Val Pro Ile Pro Pro Pro Asp Ala Met Glu Thr Leu Val
205                 210                 215                 220 tgt gcc ctg ggc ctg gcc atc ggc ctg gtg ggc ttc ctc gtg ggc acc         784
Cys Ala Leu Gly Leu Ala Ile Gly Leu Val Gly Phe Leu Val Gly Thr
                225                 230                 235 gtc ctc atc atc atg ggc aca tat gtg tcc agt gtc ccc agg taa            829
Val Leu Ile Ile Met Gly Thr Tyr Val Ser Ser Val Pro Arg
                240                 245                 250 tgatccttct gagagaaatg acttgtggga gacaccctgc agatcctcat gggtttgtga        889
cagcccctgc gtgctcagtg ccctttaagt gcatcccgct gtgctgactt tgagtgggat        949
caacatctgt cctacgggtc ccctcttttt tggccccagt attcatggca gggtttgttg       1009
gacacctact agcttccctt cccattcaac acacacacac attcttgctc tacccaaagc       1069
tctggctggc agcactaaat gctttggtgg tgtttgcact gtgtcctttc caggccttgg       1129
```

-continued

```
ccagttcttc caggggtgag gcatgtggtg ctggggattg gcagccatcc tggggcccac    1189
acaggtgtgt cttgctccat ttggcccatt gtgtgttact ttgtgaatga gccatttcac    1249
atggacttca tgaaatttgc ctcctgagtt caggtttacc ctgaaaggga tgcagattat    1309
cctgttcctc acgacccccct cagctaacaa cagttctgaa gggtgctggg acaggacagg    1369
ctcatgggga ctccactcct gcctgggttt actctgtatg aagaggccac tggtatcctg    1429
ccatgatgtt atctcctttt tctacttttc cctagagtcc catgcatgat aaagagaggc    1489
ccaaggcttg gataaggtgg ccacttccct cagtggagtc agtcatgtta ggtaggaggt    1549
ggtagagtcg gtctgcgagg tatctcgtaa gagggggaggg ccacctagac acactctaaa    1609
tatgtggcct agaagatttt ggtctacttt tctgtgaaca gaatttaaaa catacaaaga    1669
gataaatcac cataccacat agtttatgtc aggaccaaaa tgagcaatac agattacggt    1729
tttcaaacca gaatgcacat aagaactgct tgggatcctt ttaaaagtac aggcattggc    1789
ctggtgcagt ggctcattcc tgtaatccca gcactttggg aggccaaggg gacaggactg    1849
cttgaggcca gaggtggaa accatcttgg gctacataga gagaccccat ctctacaaag    1909
aaagatttaa aaattaacca ggcatggtgg ctcgcacctg tattcccagc cactggggag    1969
gctgaggccg gaggagtgct tgagcccagg agttcaaggc tgcagtgagc caagattgcg    2029
ccactgcact ccagcctagg tgacagagtg agaccctgtc tctaaataaa taaataaata    2089
aaatataaaa ataacagtca tcacccagac ctactgaatt agaatctcgg gagtgcaggg    2149
ggcagcaaca gggaggctgt cttttctgag atggggtctc actctgtcac caggctggag    2209
tgccatggca tgatctcagc tcactgcaac ctccacctcc tgagttcaag ccattctcct    2269
gcctcagcct cctgagtagc tgggactaca ggtgtgcgcc actacactca gctaattttt    2329
gtattttaag tagagacggg gtttcatcat gttggccagg atggcctcca tctcttgacc    2389
tcgtgatcca cccaccttcc ctcccaaagt actggaatta caggcattag ccactgtgcc    2449
cagccgaggc tgtcattttt aaccggctct ggatgactct gatgcagcca tcctggacct    2509
tggctgtggt ctggtaactg gaacccagtg acgtaatcag gtgccatcgg gggtcatggg    2569 aaaggggggat ccccaaggtc tgaggtggac taggaaggct ttctgaagaa cctgggtctg    2629
ttagggcatc agccaatcaa ggtacaagta aatagaggca aaatgagggt ttgaactgtg    2689
agcagttggt cctggaaaag aaagaaacca agagattatg gggactcaat gggcttctta    2749
agagagaata agttgaaatc aatgaccaga agaccctgat ggaagtggag gagaatcatc    2809
tcaggcaaac tttttgtgtg ccagtaacag aaaccctctt tgtgtgatca catgcaaagt    2869
ataggatatt tgcaatatag ccatggggag gagtgcaggg cccaagggta gattttagcc    2929
aggcctccca ggaacagaac tcggatccga aaagcccaga gaagctagag ctgcccctcc    2989
aacactctcg gatccacatg gtctgtgttc tctagacccc cctgcatgtt agcggtgttc    3049
tctctctgtg gactgactgt ccttctcagt gaacatgtcc acccgacagc tcctgagttt    3109
atatcatctc aaccctcaca acccacagag gctgtgtctc ctagtcacag ctttaaatta    3169
ctggaaaaat aaatgactgg ccaaacttgg agcaggtgtc catcccagcc ctgtgtagtt    3229
agagcaggaa tcaagatctc aacacaaatg tggctgccaa gcactcagcc ccggggcgag    3289
gggtcaagtt cttctcagag aaagaggaat aagttggttc tcagaagaca tcacaagata    3349
cgtgtgtacc caacaatctc tgatctctgc tgatctttg cttagacgtt aacttgatgc    3409
atcattggaa aggtgtttct ctcatctctg tcctaaggct tgataaagtc attaaaattg    3469
```

-continued tgttctttttg actaaa                                                                                3485

<210> SEQ ID NO 53
<211> LENGTH: 250
<212> TYPE: PRT
<213> ORGANISM: Homo sapiens

<400> SEQUENCE: 53

Met Ala Leu Arg Ala Gly Leu Val Leu Gly Phe His Thr Leu Met Thr
1               5                   10                  15

Leu Leu Ser Pro Gln Glu Ala Gly Ala Thr Lys Ala Asp His Met Gly
                20                  25                  30

Ser Tyr Gly Pro Ala Phe Tyr Gln Ser Tyr Gly Ala Ser Gly Gln Phe
            35                  40                  45

Thr His Glu Phe Asp Glu Glu Gln Leu Phe Ser Val Asp Leu Lys Lys
        50                  55                  60

Ser Glu Ala Val Trp Arg Leu Pro Glu Phe Gly Asp Phe Ala Arg Phe
65                  70                  75                  80

Asp Pro Gln Gly Gly Leu Ala Gly Ile Ala Ala Ile Lys Ala His Leu
                85                  90                  95

Asp Ile Leu Val Glu Arg Ser Asn Arg Ser Arg Ala Ile Asn Val Pro
            100                 105                 110

Pro Arg Val Thr Val Leu Pro Lys Ser Arg Val Glu Leu Gly Gln Pro
            115                 120                 125

Asn Ile Leu Ile Cys Ile Val Asp Asn Ile Phe Pro Pro Val Ile Asn
        130                 135                 140

Ile Thr Trp Leu Arg Asn Gly Gln Thr Val Thr Glu Gly Val Ala Gln
145                 150                 155                 160

Thr Ser Phe Tyr Ser Gln Pro Asp His Leu Phe Arg Lys Phe His Tyr
                165                 170                 175

Leu Pro Phe Val Pro Ser Ala Glu Asp Val Tyr Asp Cys Gln Val Glu
            180                 185                 190

His Trp Gly Leu Asp Ala Pro Leu Leu Arg His Trp Glu Leu Gln Val
            195                 200                 205

Pro Ile Pro Pro Pro Asp Ala Met Glu Thr Leu Val Cys Ala Leu Gly
        210                 215                 220

Leu Ala Ile Gly Leu Val Gly Phe Leu Val Gly Thr Val Leu Ile Ile
225                 230                 235                 240

Met Gly Thr Tyr Val Ser Ser Val Pro Arg
                245                 250

<210> SEQ ID NO 54
<211> LENGTH: 1388
<212> TYPE: DNA
<213> ORGANISM: Homo sapiens
<220> FEATURE:
<221> NAME/KEY: CDS
<222> LOCATION: (98)..(919)

<400> SEQUENCE: 54
gatttatact cttaatgggt actttctgac tgaattttat gagctcattc tgaagaggct        60
gacgatttta ctatctcatt tttttcctttt ctccagaa atg ggt tct ggg tgg gtc       115
                                         Met Gly Ser Gly Trp Val
                                         1               5 ccc tgg gtg gtg gct ctg cta gtg aat ctg acc cga ctg gat tcc tcc        163
Pro Trp Val Val Ala Leu Leu Val Asn Leu Thr Arg Leu Asp Ser Ser
            10                  15                  20

-continued

```
atg act caa ggc aca gac tct cca gaa gat ttt gtg att cag gca aag        211
Met Thr Gln Gly Thr Asp Ser Pro Glu Asp Phe Val Ile Gln Ala Lys
        25              30              35 gct gac tgt tac ttc acc aac ggg aca gaa aag gtg cag ttt gtg gtc        259
Ala Asp Cys Tyr Phe Thr Asn Gly Thr Glu Lys Val Gln Phe Val Val
        40              45              50 aga ttc atc ttt aac ttg gag gag tat gta cgt ttc gac agt gat gtg        307
Arg Phe Ile Phe Asn Leu Glu Glu Tyr Val Arg Phe Asp Ser Asp Val
55              60              65              70 ggg atg ttt gtg gca ttg acc aag ctg ggg cag cca gat gct gag cag        355
Gly Met Phe Val Ala Leu Thr Lys Leu Gly Gln Pro Asp Ala Glu Gln
        75              80              85 tgg aac agc cgg ctg gat ctc ttg gag agg agc aga cag gcc gtg gat        403
Trp Asn Ser Arg Leu Asp Leu Leu Glu Arg Ser Arg Gln Ala Val Asp
        90              95              100 ggg gtc tgt aga cac aac tac agg ctg ggc gca ccc ttc act gtg ggg        451
Gly Val Cys Arg His Asn Tyr Arg Leu Gly Ala Pro Phe Thr Val Gly
        105             110             115 aga aaa gtg caa cca gag gtg aca gtg tac cca gag agg acc cca ctc        499
Arg Lys Val Gln Pro Glu Val Thr Val Tyr Pro Glu Arg Thr Pro Leu
        120             125             130 ctg cac cag cat aat ctg ctg cac tgc tct gtg aca ggc ttc tat cca        547
Leu His Gln His Asn Leu Leu His Cys Ser Val Thr Gly Phe Tyr Pro
135             140             145             150 ggg gat atc aag atc aag tgg ttc ctg aat ggg cag gag gag aga gct        595
Gly Asp Ile Lys Ile Lys Trp Phe Leu Asn Gly Gln Glu Glu Arg Ala
            155             160             165 ggg gtc atg tcc act ggc cct atc agg aat gga gac tgg acc ttt cag        643
Gly Val Met Ser Thr Gly Pro Ile Arg Asn Gly Asp Trp Thr Phe Gln
        170             175             180 act gtg gtg atg cta gaa atg act cct gaa ctt gga cat gtc tac acc        691
Thr Val Val Met Leu Glu Met Thr Pro Glu Leu Gly His Val Tyr Thr
        185             190             195 tgc ctt gtc gat cac tcc agc ctg ctg agc cct gtt tct gtg gag tgg        739
Cys Leu Val Asp His Ser Ser Leu Leu Ser Pro Val Ser Val Glu Trp
        200             205             210 aga gct cag tct gaa tat tct tgg aga aag atg ctg agt ggc att gca        787
Arg Ala Gln Ser Glu Tyr Ser Trp Arg Lys Met Leu Ser Gly Ile Ala
215             220             225             230 gcc ttc cta ctt ggg cta atc ttc ctt ctg gtg gga atc gtc atc cag        835
Ala Phe Leu Leu Gly Leu Ile Phe Leu Leu Val Gly Ile Val Ile Gln
            235             240             245 cta agg gct cag aaa gga tat gtg agg acg cag atg tct ggt aat gag        883
Leu Arg Ala Gln Lys Gly Tyr Val Arg Thr Gln Met Ser Gly Asn Glu
        250             255             260 gtc tca aga gct gtt ctg ctc cct cag tca tgc taa ggtcctcact            929
Val Ser Arg Ala Val Leu Leu Pro Gln Ser Cys
        265             270 gaagcttctc tctctggagc ctgaagtagt gatgagtagt ctgggccctg ggtgaggtaa     989
aggacattca tgaggtcaat gttctgggaa taactctctt ccctgatcct tggaggagcc     1049
cgaactgatt ctggagctct gtgttctgag atcatgcatc tcccacccat ctgcccttct     1109
cccttctacg tgtacatcat taatccccat tgccaagggc attgtccaga aactcccctg     1169
agaccttact ccttccagcc ccaaatcatt tactttctg tggtccagcc ctactcctat      1229
aagtcatgat ctccaaagct ttctgtcttc caactgcagt ctccacagtc ttcagaagac     1289
aaatgctcag gtagtcactg tttccttttc actgtttta aaaacctttt attgtcaaat      1349
aaaatggaga tacaaaaaat gtaaaaaaaa aaaaaaaa                             1388
```

```
<210> SEQ ID NO 55
<211> LENGTH: 273
<212> TYPE: PRT
<213> ORGANISM: Homo sapiens

<400> SEQUENCE: 55

Met Gly Ser Gly Trp Val Pro Trp Val Val Ala Leu Leu Val Asn Leu
1               5                   10                  15

Thr Arg Leu Asp Ser Ser Met Thr Gln Gly Thr Asp Ser Pro Glu Asp
            20                  25                  30

Phe Val Ile Gln Ala Lys Ala Asp Cys Tyr Phe Thr Asn Gly Thr Glu
        35                  40                  45

Lys Val Gln Phe Val Val Arg Phe Ile Phe Asn Leu Glu Glu Tyr Val
    50                  55                  60

Arg Phe Asp Ser Asp Val Gly Met Phe Val Ala Leu Thr Lys Leu Gly
65                  70                  75                  80

Gln Pro Asp Ala Glu Gln Trp Asn Ser Arg Leu Asp Leu Leu Glu Arg
                85                  90                  95

Ser Arg Gln Ala Val Asp Gly Val Cys Arg His Asn Tyr Arg Leu Gly
            100                 105                 110

Ala Pro Phe Thr Val Gly Arg Lys Val Gln Pro Glu Val Thr Val Tyr
            115                 120                 125

Pro Glu Arg Thr Pro Leu Leu His Gln His Asn Leu Leu His Cys Ser
    130                 135                 140

Val Thr Gly Phe Tyr Pro Gly Asp Ile Lys Ile Lys Trp Phe Leu Asn
145                 150                 155                 160

Gly Gln Glu Glu Arg Ala Gly Val Met Ser Thr Gly Pro Ile Arg Asn
                165                 170                 175

Gly Asp Trp Thr Phe Gln Thr Val Val Met Leu Glu Met Thr Pro Glu
            180                 185                 190

Leu Gly His Val Tyr Thr Cys Leu Val Asp His Ser Ser Leu Leu Ser
            195                 200                 205

Pro Val Ser Val Glu Trp Arg Ala Gln Ser Glu Tyr Ser Trp Arg Lys
    210                 215                 220

Met Leu Ser Gly Ile Ala Ala Phe Leu Leu Gly Leu Ile Phe Leu Leu
225                 230                 235                 240

Val Gly Ile Val Ile Gln Leu Arg Ala Gln Lys Gly Tyr Val Arg Thr
                245                 250                 255

Gln Met Ser Gly Asn Glu Val Ser Arg Ala Val Leu Leu Pro Gln Ser
            260                 265                 270

Cys

<210> SEQ ID NO 56
<211> LENGTH: 4507
<212> TYPE: DNA
<213> ORGANISM: Artificial Sequence
<220> FEATURE:
<223> OTHER INFORMATION: Synthetic

<400> SEQUENCE: 56
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120 agggggttcct gcggccgcgg tcgagtatca agttgctttc tgtcccggca gaggaagcca    180
gatcgctgag ggtccggtct ccagtttgcc tcctgctata tccattggaa gagaaaagtt    240
```

```
tgtgacttgg gcccccaagt tttgagagaa ctgggctttc ggcgcggggg gacagaggag      300
gctcgtgggg aggtgagtgg acctcctgga tcgatttagg aggctcgggt gggactggga      360
ccaatcgcac ctttgttgag ccgtcactca ttatggggag cccctcccaa caaccatagc      420
gaatatttat tgagctccac gcttagcaga tcccccgata agctatgtac agacataatt      480
cgttgtaggt ctcatttcca cattttgtcg tggaggaaac tgaggctcaa aggttaagtc      540
acgtgcccaa gttctcacgg cctataaatt gagggattcg aacccagaca gctgacccca      600
gagccccggc tttttttttcc tttctttttt tttttttttt tttttttttga gacagagtct      660 tgctctgtcg ccccagctac agtgcagtgg tgcgatctct gctcaccgca acctccacct      720
cccgagttca agcaattctg cctcagcctc ccgagtagct gggatcacag gcgcccgcca      780
ccgcgcttgg ctaattttttg tattttttagt acagatgggg tttcaccatg gtggccagcc      840
tggtctcgaa ctcctgacct catgatccac cctcctcggc ctcccaaagt gctgggatta      900
cagccgtgag ccactgtgcc ctgccagagc ccaggctctt aaacattgca cattgtaggt      960
gctttggtgg tggggaatgg tagacctcga aagcagttgg actctggttt tcatttccct     1020
ggctctggta attaacctgg acctcagttt acccaccctc acagtgcaag gctaggtatg     1080
cagtcggtgc ctactttatt ataactgttg ataattattg tcatctctcc ccttctgaca     1140
cctccgccag ctttccccat ctagataact tcgtataatg tatgctatac gaagttatgg     1200
atccatcgat tctgcgatcg ctccggtgcc cgtcagtggg cagagcgcac atcgcccaca     1260
gtccccgaga agttgggggg aggggtcggc aattgaaccg gtgcctagag aaggtggcgc     1320
ggggtaaact gggaaagtga tgtcgtgtac tggctccgcc ttttttcccga gggtggggga     1380 gaaccgtata taagtgcagt agtcgccgtg aacgttcttt ttcgcaacgg gtttgccgcc     1440
agaacacagc tgaagcttcc accatgccca cgctactgcg ggtttatata gacggtcccc     1500
acgggatggg gaaaaccacc accacgcaac tgctggtggc cctgggttcg cgcgacgata     1560
tcgtctacgt acccgagccg atgacttact ggcgggtgct gggggcttcc gagacaatcg     1620
cgaacatcta caccacacaa caccgcctcg accagggtga gatatcggcc ggggacgcgg     1680
cggtggtaat gacaagcgcc cagataacaa tgggcatgcc ttatgccgtg accgacgccg     1740
ttctggctcc tcatatcggg ggggaggctg ggagctcaca tgccccgccc ccggccctca     1800
ccctcatctt cgaccgccat cccatcgccg ccctcctgtg ctaccggcc gcgcggtacc     1860 ttatgggcag catgacccccc caggccgtgc tggcgttcgt ggccctcatc ccgccgacct     1920
tgcccggcac caacatcgtg cttggggccc ttccggagga cagacacatc gaccgcctgg     1980
ccaaacgcca gcgccccggc gagcggctgg acctggctat gctggctgcg attcgccgcg     2040
tttacgggct acttgccaat acggtgcggt atctgcagtg cggcgggtcg tggcgggagg     2100
actggggaca gctttcgggg acggccgtgc cgccccaggg tgccgagccc cagagcaacg     2160
cgggcccacg accccatatc ggggacacgt tatttaccct gtttcgggcc cccgagttgc     2220
tggcccccaa cggcgacctg tataacgtgt ttgcctgggc cttggacgtc ttggccaaac     2280
gcctccgttc catgcacgtc tttatcctgg attacgacca atcgcccgcc ggctgccggg     2340
acgccctgct gcaacttacc tccgggatgg tccagcccca cgtcaccacc cccggctcca     2400
taccgacgat atgcgacctg gcgcgcacgt ttgcccggga gatgggatcg gccattgaac     2460
aagatggatt gcacgcaggt tctccggccg cttgggtgga gaggctattc ggctatgact     2520
gggcacaaca gacaatcggc tgctctgatg ccgccgtgtt ccggctgtca gcgcaggggc     2580
```

-continued

```
gcccggttct ttttgtcaag accgacctgt ccggtgccct gaatgaactg caggacgagg    2640
cagcgcggct atcgtggctg gccacgacgg gcgttccttg cgcagctgtg ctcgacgttg    2700
tcactgaagc gggaagggac tggctgctat tgggcgaagt gccggggcag gatctcctgt    2760
catctcacct tgctcctgcc gagaaagtat ccatcatggc tgatgcaatg cggcggctgc    2820
atacgcttga tccggctacc tgcccattcg accaccaagc gaaacatcgc atcgagcgag    2880
cacgtactcg gatggaagcc ggtcttgtcg atcaggatga tctggacgaa gagcatcagg    2940
ggctcgcgcc agccgaactg ttcgccaggc tcaaggcgcg catgcccgac ggcgaggatc    3000
tcgtcgtgac ccatggcgat gcctgcttgc cgaatatcat ggtggaaaat ggccgctttt    3060
ctggattcat cgactgtggc cggctgggtg tggcggaccg ctatcaggac atagcgttgg    3120
ctacccgtga tattgctgaa gagcttggcg gcgaatgggc tgaccgcttc ctcgtgcttt    3180
acggtatcgc cgctcccgat tcgcagcgca tcgccttcta tcgccttctt gacgagttct    3240
tctgagggtc tctagcataa cttcgtataa tgtatgctat acgaagttat aataaaagat    3300
ccttattttc attggatctg tgtgttggtt ttttgtgtgg gatccgttga ctgagtcgac    3360
ggagcttacc cagcctgcag aagacctcat ccagacccag cagacccctg cctcagaact    3420
tggggaccct gaagacccgg gagaggaggc tgcagatggc tcagacactg tggtcctcag    3480
tctctttccc tgcacccctg agcctgtgaa tcctgaaccg gatgccagtg tttcctctcc    3540
acagggtagg atacctcctc tgggattagc cctctgggat tccatgatga tggaatgtca    3600
ggcctcacat ggaacctgtg tcttgctttc gtttttgttt tgttttgttt tgttgttttt    3660
tgagatggag ttttgctctt gttgcccatg ctggagtgca atggcgtgat ctcagctcac    3720
tgcaacctct gcctcctggg ttcaactgat tctcctgtct cagcctcctg agtagctggg    3780
attacaggct ccgccacta cgcccagcta atttttttgg tatttttagt agagacgggg    3840
tttcaccatg ttggccaggc tggtcttgaa ctcctgacct caggtgatcc gcccacctcg    3900
gcctcccaaa gtgctgggat tacaggcatg agccactgtg cccggcctgt ttttgttttt    3960
tgatacaggg tctcgctctg ttactaaggc tggagtgcag tgatgcaatc atagttcact    4020
gcagcctcaa cttcctgggc tgaagccatc actcagcctc cctaggagct gggactatag    4080
gcatgcaacc acacctggct aatttttttt ttttttttgg gaggctggtc tccacctcct    4140
gggctcaagt gatctgcagg cctccacttc cgaaagtgct gggattacag gtgtgagcca    4200
cagtgcccgg cccttcacac ctgtttttaa ctctttgagg gtagatagct aggagtgaaa    4260
ttactgggtc agatggtcat cctgtttfac ttactgagga actgaggatt tattttgat     4320 tggagtccaa gaatatgcct aatttaggcg gccgatcact agtgaattcg cggccgcagg    4380
aacccctagt gatggagttg gccactccct ctctgcgcgc tcgctcgctc actgaggccg    4440
ggcgaccaaa ggtcgcccga cgcccgggct ttgcccgggc ggcctcagtg agcgagcgag    4500
cgcgcag                                                                4507
```